(12) United States Patent
Momose et al.

(10) Patent No.: US 7,238,716 B2
(45) Date of Patent: Jul. 3, 2007

(54) ALKANOIC ACID DERIVATIVES PROCESS FOR THEIR PRODUCTION AND USE THEREOF

(75) Inventors: Yu Momose, Takarazuka (JP); Tsuyoshi Maekawa, Nara (JP); Nobuyuki Takakura, Nagaokakyo (JP); Hiroyuki Odaka, Kobe (JP); Hiroyuki Kimura, Sakai (JP); Tatsuya Ito, Kashiba (JP)

(73) Assignee: Takeda Pharmaceuticals Company Limited (JP)

( * ) Notice: Subject to any disclaimer, the term of this patent is extended or adjusted under 35 U.S.C. 154(b) by 247 days.

(21) Appl. No.: 10/465,938

(22) PCT Filed: Dec. 28, 2001

(86) PCT No.: PCT/JP01/11611

§ 371 (c)(1),
(2), (4) Date: Jun. 26, 2003

(87) PCT Pub. No.: WO02/053547

PCT Pub. Date: Jul. 11, 2002

(65) Prior Publication Data

US 2004/0058965 A1 Mar. 25, 2004

(30) Foreign Application Priority Data

Dec. 28, 2000 (JP) .............................. 2000-402648

(51) Int. Cl.
*A61K 31/4439* (2006.01)
*C07D 413/12* (2006.01)
(52) U.S. Cl. .................................... 514/340; 546/271.4
(58) Field of Classification Search ............. 546/271.4; 514/340
See application file for complete search history.

(56) References Cited

FOREIGN PATENT DOCUMENTS

| WO | WO 92/20350 | 11/1992 |
|----|-------------|---------|
| WO | WO 98/03505 | 1/1998 |
| WO | WO 99/20275 | 4/1999 |
| WO | WO 99/58510 | 11/1999 |
| WO | WO 00/64876 | 11/2000 |
| WO | WO 01/38325 | 5/2001 |

*Primary Examiner*—Patricia L. Morris
(74) *Attorney, Agent, or Firm*—Finnegan, Henderson, Farabow, Garrett & Dunner, LLP

(57) ABSTRACT

An alkanoic acid derivative useful as a prophylactic or therapeutic agent of diabetes mellitus, hyperlipidemia, impaired glucose tolerance and the like can be provided by a compound represented by the formula

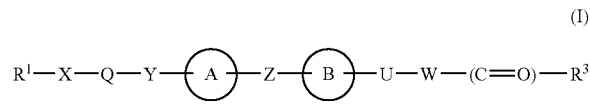

(I)

wherein $R^1$ is an optionally substituted 5-membered aromatic heterocyclic group; X is a bond and the like; Q is a divalent hydrocarbon group having 1 to 20 carbon atoms; Y is a bond and the like; ring A is an aromatic ring optionally further having 1 to 3 substituents; Z is $—(CH_2)_n-Z^1-$ (n is an integer of 1 to 8 and $Z^1$ is an oxygen atom and the like) and the like; ring B is a pyridine ring optionally further having 1 to 3 substituents, and the like; U is a bond and the like; W is a divalent hydrocarbon group having 1 to 20 carbon atoms; and $R^3$ is —OH and the like, provided that, when ring B is a benzene ring optionally further having 1 to 3 substituents, U should be a bond, or a salt thereof.

9 Claims, No Drawings

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
gtgggtaccg aaatgaccat ggttgacaca gag                           33

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
ggggtcgacc aggactctct gctagtacaa gtc                           33

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
ttagaattcg acatggacac caaacatttc ctg                           33

<210> SEQ ID NO 4
<211> LENGTH: 33
<212> TYPE: DNA
<213> ORGANISM: Artificial Sequence
<220> FEATURE:
<223> OTHER INFORMATION: Primer
```

```
<400> SEQUENCE: 4
cccctcgagc taagtcattt ggtgcggcgc ctc                            33

<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5
tcgacagggg accaggacaa aggtcacgtt cgggag                         36

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
tcgactcccg aacgtgacct ttgtcctggt cccctg                         36

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
cccagatctc cccagcgtct tgtcattg                                  28

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
tcaccatggt caagctttta agcgggtc                                  28
```

ALKANOIC ACID DERIVATIVES PROCESS FOR THEIR PRODUCTION AND USE THEREOF

This application is the National Phase filing of International Patent Application No. PCT/JP01/11611, filed 28 Dec. 2001.

TECHNICAL FIELD

The present invention relates to a novel alkanoic acid derivative having an excellent pharmaceutical action such as hypoglycemic action, hypolipidemic action and the like, which is useful as a prophylactic or therapeutic agent of diabetes mellitus, hyperlipidemia, impaired glucose tolerance, inflammatory diseases, arteriosclerosis and the like, as well as a production method thereof.

The present invention also relates to a prophylactic or therapeutic agent of diabetes mellitus, hyperlipidemia, impaired glucose tolerance and the like, which comprises a novel alkanoic acid derivative.

The present invention further relates to a retinoid-related receptor function regulating agent, an insulin sensitizer or the like, which comprises a novel alkanoic acid derivative.

BACKGROUND ART

As alkanoic acid derivatives, the compounds described in the following references are known.
(1) WO 00/64876 describes, as a PPAR ligand-receptor binder, a compound represented by the formula:

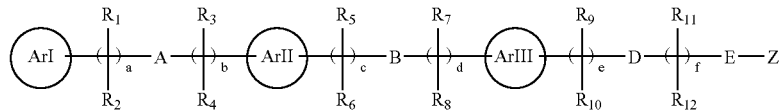

wherein

are each independently aryl and the like; A is —O— and the like; B is —O— and the like; D is —O— and the like; E is a bond or an ethylene group; a, b, c and e are each 0-4; d is 0-5; f is 0-6; $R_1$, $R_3$, $R_5$, $R_7$, $R_9$ and $R_{11}$ are each independently hydrogen and the like; $R_2$, $R_4$, $R_6$, $R_8$, $R_{10}$ and $R_{12}$ are each independently —(CH)$_q$—X; q is 0-3; X is hydrogen and the like; Z is $R_{21}O_2C$— and the like; $R_{21}$ is hydrogen and the like.
(2) WO 99/20275 describes a method of mediating the activity of PPAR-γ receptor using a compound represented by the formula:

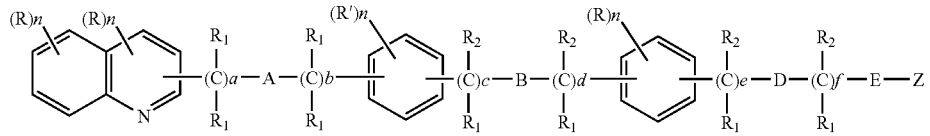

wherein A is a bond, an oxygen atom, a sulfur atom and the like; B is a bond, an oxygen atom, a sulfur atom and the like; D is a bond, an oxygen atom, a sulfur atom and the like; E is a bond and the like; a and n are each 0-2; b is 0-1; c and e are each 0-4; d and f are each 0-5; R is hydrogen and the like; R' is hydrogen and the like; $R_1$ is hydrogen and the like; $R_2$ is —(CH$_2$)$_q$—X and the like; q is 0-3; X is hydrogen and the like; and Z is $R_1O_2C$— and the like.
(3) WO 92/20350 describes, as a substance capable of mimicking the action of physiologically active natural polymer, a compound represented by the formula: Mi-(Mn)n-Mt wherein n is the number of 2 to about 50; Mi, Mn and Mt are

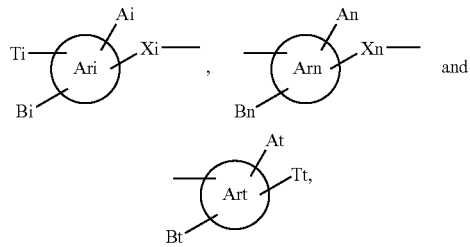

respectively;

wherein

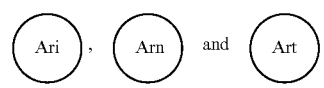

are each independently an aromatic carbocycle or an aromatic heterocycle; Ai, Bi, An, Bn, At, Bt, Ti and Tt are each independently hydrogen or a substituent; and Xi and Xn are each independently a bond and the like.
(4) WO 99/58510 describes, as a substance having a hypoglycemic and hypolipidemic action, a compound represented by the formula:

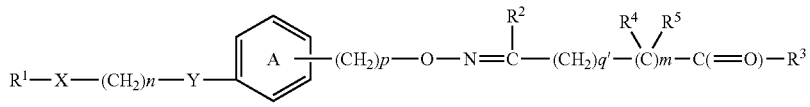

wherein $R^1$ is an optionally substituted hydrocarbon group or an optionally substituted heterocyclic group; X is a bond and the like; n is an integer of 1 to 3; Y is an oxygen atom and the like; ring A is a benzene ring optionally further having 1 to 3 substituents; p is an integer of 1 to 8; $R^2$ is a hydrogen atom and the like; q' is an integer of 0 to 6; m is 0 or 1; $R^3$ is a hydroxy group and the like; and $R^4$ and $R^5$ are the same or different and each is a hydrogen atom and the like.

Peroxisome proliferator-activated receptor gamma (PPARγ), a member of the intranuclear hormone receptor superfamily, which is typically exemplified by steroid hormone receptors and thyroid hormone receptors, plays an important role as a master regulator in the differentiation of adipose cells with its expression induced in the very early stage of adipose cell differentiation. PPARγ forms a dimer with the retinoid X receptor (RXR) by binding to a ligand, and binds to a responsive site of the target gene in the nucleus to directly control (activate) transcription efficiency. In recent years, the possibility that 15-deoxy-$\Delta^{12,14}$ prostaglandin $J_2$, a metabolite of prostaglandin $D_2$, serves as an endogenous ligand for PPARγ, has been suggested, and it has been shown that a class of insulin sensitivity enhancing agent, typically exemplified by thiazolidinedione derivatives, possess ligand activity for PPARγ, and that its potency is proportional to its hypoglycemic action or adipose cell differentiation-promoting action [*Cell*, vol. 83, p. 803 (1995): *The Journal of Biological Chemistry*, vol. 270, p. 12953 (1995); *Journal of Medicinal Chemistry*, vol. 39, p. 655 (1996)]. Furthermore, in recent years, it has been shown that 1) PPARγ is expressed in cultured cells of human liposarcoma origin, whose proliferation is ceased by the addition of a PPARγ ligand [*Proceedings of the National Academy of Sciences of the United States of America*, vol. 94, p. 237 (1997)], 2) nonsteroidal anti-inflammatory drugs, typically exemplified by indomethacin and fenoprofen, have PPARγ ligand activity [*The Journal of Biological Chemistry*, vol. 272, p. 3406 (1997)], 3) PPARγ is expressed at high levels in activated macrophages, with the transcription of a gene involved in inflammation inhibited by the addition of a ligand therefor [*Nature*, vol. 391, p. 79 (1998)], and 4) PPARγ ligands suppress the production of inflammatory cytokines (TNFα, IL-1β, IL-6) by monocytes [*Nature*, vol. 391, p. 82 (1998)], and the like.

From the foregoing, there is a demand for development of a novel compound useful as a prophylactic or therapeutic agent of diabetes mellitus, hyperlipidemia, impaired glucose tolerance, inflammatory diseases, arteriosclerosis etc., and having pharmaceutically excellent properties such as low side effects, and the like.

DISCLOSURE OF THE INVENTION

It is an object of the present invention to provide an alkanoic acid derivative useful as a prophylactic or therapeutic agent of diabetes mellitus, hyperlipidemia, impaired glucose tolerance and the like, and a production method thereof.

The present invention relates to the following (1)-(32) and the like.
(1) A compound represented by the formula

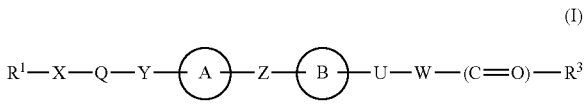

wherein
$R^1$ is an optionally substituted 5-membered aromatic heterocyclic group;
X is a bond, an oxygen atom, a sulfur atom, —CO—, —CS—, —CR$^4$(OR$^5$)— or —NR$^6$— (R$^4$ is a hydrogen atom or an optionally substituted hydrocarbon group, $R^5$ is a hydrogen atom or a hydroxy-protecting group, $R^6$ is a hydrogen atom, an optionally substituted hydrocarbon group or an amino-protecting group);
Q is a divalent hydrocarbon group having 1 to 20 carbon atoms;
Y is a bond, an oxygen atom, a sulfur atom, —SO—, —SO$_2$—, —NR$^7$—, —CONR$^7$— or —NR$^7$CO— ($R^7$ is a hydrogen atom, an optionally substituted hydrocarbon group or an amino-protecting group);
ring A is an aromatic ring optionally further having 1 to 3 substituents;
Z is —(CH$_2$)$_n$-Z- or -Z$^1$-(CH$_2$)$_n$— (n is an integer of 1 to 8, $Z^1$ is an oxygen atom, a sulfur atom, —SO—, —SO$_2$— or —NR$^{16}$— ($R^{16}$ is a hydrogen atom or an optionally substituted hydrocarbon group));
ring B is a pyridine ring, a benzene ring or a naphthalene ring, each of which optionally further has 1 to 3 substituents;
U is a bond, an oxygen atom, a sulfur atom, —SO— or —SO$_2$—;
W is a divalent hydrocarbon group having 1 to 20 carbon atoms; and
$R^3$ is —OR$^8$ ($R^8$ is a hydrogen atom or an optionally substituted hydrocarbon group) or —NR$^9$R$^{10}$ ($R^9$ and $R^{10}$ are the same or different and each is a hydrogen atom, an optionally substituted hydrocarbon group, an optionally substituted heterocyclic group or an optionally substituted acyl group, or $R^9$ and $R^{10}$ may be bonded to form an optionally substituted ring);

provided that, when ring B is a benzene ring optionally further having 1 to 3 substituents, U should be a bond, or a salt thereof.
(2) The compound of the above-mentioned (1), wherein the 5-membered aromatic heterocyclic group represented by $R^1$ is oxazolyl, thiazolyl or triazolyl.
(3) The compound of the above-mentioned (1), wherein X is a bond or —NR$^6$— ($R^6$ is a hydrogen atom, an optionally substituted hydrocarbon group or an amino-protecting group).
(4) The compound of the above-mentioned (1), wherein Q is $C_{1-6}$alkylene or $C_{2-6}$ alkenylene.

(5) The compound of the above-mentioned (1), wherein Y is a bond, an oxygen atom or —NR$^7$— (R$^7$ is a hydrogen atom, an optionally substituted hydrocarbon group or an amino-protecting group).

(6) The compound of the above-mentioned (1), wherein the aromatic ring represented by ring A is a benzene ring, a pyridine ring or an isoxazole ring.

(7) The compound of the above-mentioned (1), wherein n is an integer of 1 to 3 and Z$^1$ is an oxygen atom or a sulfur atom.

(8) The compound of the above-mentioned (1), wherein the ring B is a pyridine ring or a naphthalene ring, each of which optionally further has 1 to 3 substituents.

(9) The compound of the above-mentioned (1), wherein U is a bond.

(10) The compound of the above-mentioned (1), wherein W is a $C_{1-6}$ alkylene or a $C_{2-6}$ alkenylene.

(11) The compound of the above-mentioned (1), wherein R$^3$ is —OR$^8$ (R$^8$ is a hydrogen atom or an optionally substituted hydrocarbon group.

(12) The compound of the above-mentioned (1), wherein R$^1$ is an oxazolyl, a thiazolyl, a pyrazolyl or a triazolyl, each of which optionally has 1 to 3 substituents selected from 1) a $C_{1-10}$ alkyl group optionally having 1 to 3 substituents selected from a $C_{1-6}$ alkoxy group optionally substituted by 1 to 3 halogen atoms, a halogen atom, a nitro group, a hydroxy group and an amino group;

2) a $C_{3-10}$ cycloalkyl group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group;

3) an aromatic heterocyclic group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group; and 4) a $C_{6-14}$ aromatic hydrocarbon group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group;

X is a bond or —NR$^6$— wherein R$^6$ is a hydrogen atom or an alkyl group having 1 to 4 carbon atoms;

Q is a $C_{1-6}$ alkylene or a $C_{2-6}$ alkenylene;

Y is a bond, an oxygen atom or —NR$^7$— wherein R$^7$ is an amino-protecting group;

ring A is a benzene ring, a fused aromatic hydrocarbon ring having 9 to 14 carbon atoms, or a 5- or 6-membered aromatic heterocycle, each of which optionally further has 1 to 3 substitutents selected from an alkyl group having 1 to 4 carbon atoms, a hydroxy group, an alkoxy group having 1 to 4 carbon atoms, an aralkyloxy group having 7 to 10 carbon atoms and a halogen atom;

Z is —(CH$_2$)$_n$-Z$^1$- or -Z$^1$-(CH$_2$)$_n$— wherein n is an integer of 1 to 3 and Z$^1$ is an oxygen atom or a sulfur atom;

ring B is a pyridine ring or a naphthalene ring, each of which optionally further has 1 to 3 substituents selected from an alkyl group having 1 to 4 carbon atoms, an aryl group having 6 to 14 carbon atoms, a hydroxy group, an alkoxy group having 1 to 4 carbon atoms, an aralkyloxy group having 7 to 10 carbon atoms and a halogen atom;

U is a bond or an oxygen atom; and

W is a $C_{1-6}$ alkylene or a $C_{2-6}$ alkenylene;

R$^3$ is —OR$^8$ wherein R$^8$ is a hydrogen atom or an alkyl group having 1 to 4 carbon atoms.

(13) The compound of the above-mentioned (1), which is 2-[2-[4-[(5-methyl-2-phenyl-4-oxazolyl)methoxy]benzyloxy]-3-pyridyl]acetic acid;

2-[2-[[6-[(5-methyl-2-phenyl-4-oxazolyl)methoxy]-3-pyridyl]methoxy]phenyl]acetic acid;

2-[2-[[6-[(5-methyl-2-phenyl-4-oxazolyl)methoxy]-3-pyridyl]methoxy]-3-pyridyl]acetic acid;

2-[2-[[3-[(5-methyl-2-phenyl-4-thiazolyl)methoxy]-5-isoxazolyl]methoxy]phenyl]acetic acid;

2-[2-[[4-[(5-methyl-2-phenyl-4-oxazolyl)methoxy]phenoxy]methyl]-3-pyridyl]acetic acid; or a salt thereof.

(14) A prodrug of the compound of the above-mentioned (1) or a salt thereof.

(15) A pharmaceutical composition comprising the compound of the above-mentioned (1) or a salt thereof or a prodrug thereof.

(16) A prophylactic or therapeutic agent of diabetes mellitus, which comprises the compound of the above-mentioned (1) or a salt thereof or a prodrug thereof.

(17) A prophylactic or therapeutic agent of hyperlipidemia, which comprises the compound of the above-mentioned (1) or a salt thereof or a prodrug thereof.

(18) A prophylactic or therapeutic agent of impaired glucose tolerance, which comprises the compound of the above-mentioned (1) or a salt thereof or a prodrug thereof.

(19) A retinoid-related receptor function regulating agent comprising the compound of the above-mentioned (1) or a salt thereof or a prodrug thereof.

(20) The agent of the above-mentioned (19), which is a ligand for peroxisome proliferator-activated receptor.

(21) The agent of the above-mentioned (19), which is a ligand for retinoid X receptor.

(22) An insulin sensitizer comprising the compound of the above-mentioned (1) or a salt thereof or a prodrug thereof

(23) A method for treating diabetes mellitus in a mammal, which comprises administering the compound of the above-mentioned (1) or a salt thereof or a prodrug thereof to said mammal.

(24) A method for treating hyperlipidemia in a mammal, which comprises administering the compound of the above-mentioned (1) or a salt thereof or a prodrug thereof to said mammal.

(25) A method for treating impaired glucose tolerance in a mammal, which comprises administering the compound of the above-mentioned (1) or a salt thereof or a prodrug thereof to said mammal.

(26) Use of the compound of the above-mentioned (1) or a salt thereof or a prodrug thereof for the production of a prophylactic or therapeutic agent of diabetes mellitus.

(27) Use of the compound of the above-mentioned (1) or a salt thereof or a prodrug thereof for the production of a prophylactic or therapeutic agent of hyperlipidemia.

(28) Use of the compound of the above-mentioned (1) or a salt thereof or a prodrug thereof for the production of a prophylactic or therapeutic agent of impaired glucose tolerance.

(29) A production method of a compound represented by the formula

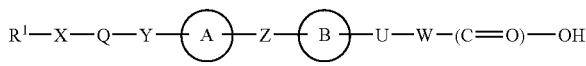
(I-6)

wherein

R$^1$ is an optionally substituted 5-membered aromatic heterocyclic group;

X is a bond, an oxygen atom, a sulfur atom, —CO—, —CS—, —CR$^4$(OR$^5$)— or —NR$^6$— (R$^4$ is a hydrogen atom or an optionally substituted hydrocarbon group, R$^5$ is a hydrogen atom or a hydroxy-protecting group, and R$^6$ is a hydrogen atom, an optionally substituted hydrocarbon group or an amino-protecting group);

Q is a divalent hydrocarbon group having 1 to 20 carbon atoms;

Y is a bond, an oxygen atom, a sulfur atom, —SO—, —SO$_2$—, —NR$^7$—, —CONR$^7$— or —NR$^7$CO— (R$^7$ is a hydrogen atom, an optionally substituted hydrocarbon group or an amino-protecting group);

ring A is an aromatic ring optionally further having 1 to 3 substituents;

Z is —(CH$_2$)$_n$-Z$^1$- or -Z$^1$-(CH$_2$)$_n$— (n is an integer of 1 to 8, and Z$^1$ is an oxygen atom, a sulfur atom, —SO—, —SO$_2$— or —NR$^{16}$— (R$^{16}$ is a hydrogen atom or an optionally substituted hydrocarbon group));

ring B is a pyridine ring, a benzene ring or a naphthalene ring, each of which optionally further has 1 to 3 substituents;

U is a bond, an oxygen atom, a sulfur atom, —SO— or —SO$_2$—; and

W is a divalent hydrocarbon group having 1 to 20 carbon atoms;

provided that, when ring B is a benzene ring optionally further having 1 to 3 substituents, U should be a bond, or a salt thereof, which comprises subjecting a compound represented by the formula

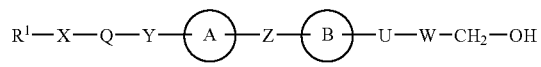
(XII)

wherein each symbol is as defined above, or a salt thereof, to a hydrolysis reaction.

(30) A production method of a compound represented by the formula

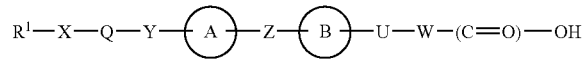
(I-6)

wherein

R$^1$ is an optionally substituted 5-membered aromatic heterocyclic group;

X is a bond, an oxygen atom, a sulfur atom, —CO—, —CS—, —CR$^4$(OR$^5$)— or —NR$^6$— (R$^4$ is a hydrogen atom or an optionally substituted hydrocarbon group, R$^5$ is a hydrogen atom or a hydroxy-protecting group, and R$^6$ is a hydrogen atom, an optionally substituted hydrocarbon group or an amino-protecting group);

Q is a divalent hydrocarbon group having 1 to 20 carbon atoms;

Y is a bond, an oxygen atom, a sulfur atom, —SO—, —SO$_2$—, —NR$^7$—, —CONR$^7$— or —NR$^7$CO— (R$^7$ is a hydrogen atom, an optionally substituted hydrocarbon group or an amino-protecting group);

ring A is an aromatic ring optionally further having 1 to 3 substituents;

Z is —(CH$_2$)$_n$-Z$^1$- or -Z$^1$-(CH$_2$)$_n$— (n is an integer of 1 to 8, and Z$^1$ is an oxygen atom, a sulfur atom, —SO—, —SO$_2$— or —NR$^{16}$— (R$^{16}$ is a hydrogen atom or an optionally substituted hydrocarbon group));

ring B is a pyridine ring, a benzene ring or a naphthalene ring, each of which optionally further has 1 to 3 substituents;

U is a bond, an oxygen atom, a sulfur atom, —SO— or —SO$_2$—; and

W is a divalent hydrocarbon group having 1 to 20 carbon atoms;

provided that, when ring B is a benzene ring optionally further having 1 to 3 substituents, U should be a bond, or a salt thereof, which comprises subjecting a compound represented by the formula

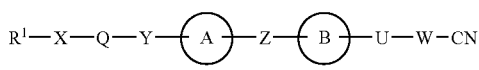
(XIII)

wherein each symbol is as defined above, or a salt thereof, to an oxidation reaction.

(31) A compound represented by the formula (XII)

wherein

R$^1$ is an optionally substituted 5-membered aromatic heterocyclic group;

X is a bond, an oxygen atom, a sulfur atom, —CO—, —CS—, —CR$^4$(OR$^5$)— or —NR$^6$— (R$^4$ is a hydrogen atom or an optionally substituted hydrocarbon group, R$^5$ is a hydrogen atom or a hydroxy-protecting group, and R$^6$ is a hydrogen atom, an optionally substituted hydrocarbon group or an amino-protecting group);

Q is a divalent hydrocarbon group having 1 to 20 carbon atoms;

Y is a bond, an oxygen atom, a sulfur atom, —SO—, —SO$_2$—, —NR$^7$—, —CONR$^7$— or —NR$^7$CO— (R$^7$ is a hydrogen atom, an optionally substituted hydrocarbon group or an amino-protecting group);

ring A is an aromatic ring optionally further having 1 to 3 substituents;

Z is —(CH$_2$)$_n$-Z$^1$- or -Z$^1$-(CH$_2$)$_n$— (n is an integer of 1 to 8, and Z$^1$ is an oxygen atom, a sulfur atom, —SO—, —SO$_2$— or —NR$^{16}$— (R$^{16}$ is a hydrogen atom or an optionally substituted hydrocarbon group));

ring B is a pyridine ring, a benzene ring or a naphthalene ring, each of which optionally further has 1 to 3 substituents;

U is a bond, an oxygen atom, a sulfur atom, —SO— or —SO$_2$—; and

W is a divalent hydrocarbon group having 1 to 20 carbon atoms;

provided that, when ring B is a benzene ring optionally further having 1 to 3 substituents, U should be a bond, or a salt thereof.

(32) A compound represented by the formula

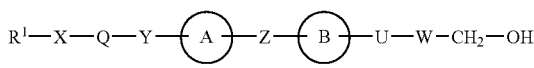

(XIII)

wherein

R$^1$ is an optionally substituted 5-membered aromatic heterocyclic group;

X is a bond, an oxygen atom, a sulfur atom, —CO—, —CS—, —CR$^4$(OR$^5$)— or —NR$^6$— (R$^4$ is a hydrogen atom or an optionally substituted hydrocarbon group, R$^5$ is a hydrogen atom or a hydroxy-protecting group, and R$^6$ is a hydrogen atom, an optionally substituted hydrocarbon group or an amino-protecting group);

Q is a divalent hydrocarbon group having 1 to 20 carbon atoms;

Y is a bond, an oxygen atom, a sulfur atom, —SO—, —SO$_2$—, —NR$^7$—, —CONR$^7$— or —NR$^7$CO— (R$^7$ is a hydrogen atom, an optionally substituted hydrocarbon group or an amino-protecting group);

ring A is an aromatic ring optionally further having 1 to 3 substituents;

Z is —(CH$_2$)$_n$-Z$^1$- or -Z$^1$-(CH$_2$)$_n$— (n is an integer of 1 to 8, and Z$^1$ is an oxygen atom, a sulfur atom, —SO—, —SO$_2$— or —NR$^{16}$— (R$^{16}$ is a hydrogen atom or an optionally substituted hydrocarbon group));

ring B is a pyridine ring, a benzene ring or a naphthalene ring, each of which optionally further has 1 to 3 substituents;

U is a bond, an oxygen atom, a sulfur atom, —SO— or —SO$_2$—; and

W is a divalent hydrocarbon group having 1 to 20 carbon atoms;

provided that, when ring B is a benzene ring optionally further having 1 to 3 substituents, U should be a bond, or a salt thereof.

In the formula (I), as the "5-membered aromatic heterocyclic group" of the "optionally substituted 5-membered aromatic heterocyclic group" represented by R$^1$, for example, a 5-membered monocyclic aromatic heterocyclic group containing, besides carbon atoms, 1 to 4 hetero atoms selected from oxygen atom, sulfur atom and nitrogen atom, as a ring constituting atom, can be mentioned. The monocyclic aromatic heterocyclic group may be condensed with a 6-membered heterocycle containing 1 or 2 nitrogen atoms (e.g., pyridine ring), benzene ring and the like, and such condensed ring is also encompassed in the definition of R$^1$.

Specific examples of the "5-membered monocyclic aromatic heterocyclic group" include furyl (2-furyl, 3-furyl), thienyl (2-thienyl, 3-thienyl), pyrrolyl (1-pyrrolyl, 2-pyrrolyl, 3-pyrrolyl), imidazolyl (1-imidazolyl, 2-imidazolyl, 4-imidazolyl, 5-imidazolyl), pyrazolyl (1-pyrazolyl, 3-pyrazolyl, 4-pyrazolyl), isoxazolyl (3-isoxazolyl, 4-isoxazolyl, 0.5-isoxazolyl), isothiazolyl (3-isothiazolyl, 4-isothiazolyl, 5-isothiazolyl), thiazolyl (2-thiazolyl, 4-thiazolyl, 5-thiazolyl), oxazolyl (2-oxazolyl-4-oxazolyl, 5-oxazolyl), oxadiazolyl (1,2,4-oxadiazol-5-yl, 1,3,4-oxadiazol-2-yl), thiadiazolyl (1,3,4-thiadiazol-2-yl), triazolyl (1,2,4-triazol-1-yl, 1,2,4-triazol-3-yl, 1,2,3-triazol-1-yl, 1,2,3-triazol-2-yl-1,2,3-triazol-4-yl), tetrazolyl (tetrazol-1-yl, tetrazol-5-yl) and the like.

Specific examples of the condensed ring formed by the above-mentioned "5-membered monocyclic aromatic heterocyclic group" include 2-benzoxazolyl, 2-benzothiazolyl, benzimidazol-1-yl, benzimidazol-2-yl, indol-1-yl, indol-3-yl, 1H-indazol-3-yl and the like.

The 5-membered aromatic heterocyclic group represented by R$^1$ is preferably oxazolyl, thiazolyl, pyrazolyl, triazolyl and the like, more preferably oxazolyl, thiazolyl, triazolyl and the like.

The "5-membered aromatic heterocyclic group" represented by R$^1$ may have 1 to 4, preferably 1 to 3, substituents at substitutable positions. As such substituent, for example, "halogen atom", "nitro group", "optionally substituted aliphatic hydrocarbon group", "optionally substituted alicyclic hydrocarbon group", "optionally substituted aromatic hydrocarbon group", "optionally substituted aromatic heterocyclic group", "optionally substituted non-aromatic heterocyclic group", "optionally substituted nonaromatic heterocyclic group", "optionally substituted acyl group", "optionally substituted amino group", "optionally substituted hydroxy group", "optionally substituted thiol group", "optionally esterified or amidated carboxyl group" and the like can be mentioned.

As the "halogen atom", fluorine, chlorine, bromine and iodine can be mentioned, with preference given to fluorine and chlorine.

As the aliphatic hydrocarbon group of the "optionally substituted aliphatic hydrocarbon group", a straight chain or branched aliphatic hydrocarbon group having 1 to 15 carbon atoms, such as alkyl group, alkenyl group, alkynyl group and the like can be mentioned.

Preferable examples of the alkyl group include an alkyl group having 1 to 10 carbon atoms, such as methyl, ethyl, propyl, isopropyl, butyl, isobutyl, sec-butyl, t-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like.

Preferable examples of the alkenyl group include an alkenyl group having 2 to 10 carbon atoms, such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like.

Preferable examples of the alkynyl group include an alkynyl group having 2 to 10 carbon atoms, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like.

As the substituent of the "optionally substituted aliphatic hydrocarbon group", for example, a cycloalkyl group having 3 to 10 carbon atoms, an aryl group having 6 to 14 carbon atoms (e.g., phenyl, naphthyl etc.), an aromatic heterocyclic group (e.g., thienyl, furyl, pyridyl, oxazolyl, thiazolyl etc.), a non-aromatic heterocyclic group (e.g., tetrahydrofuryl, morpholino, thiomorpholino, piperidino, pyrrolidinyl, piperazinyl etc.), an aralkyl group having 7 to 9 carbon atoms, an amino group, an amino group mono- or di-substituted by alkyl group having 1 to 4 carbon atoms or acyl group having 2 to 8 carbon atoms (e.g., alkanoyl group etc.), an amidino group, an acyl group having 2 to 8 carbon atoms (e.g., alkanoyl group etc.), a carbamoyl group, a carbamoyl group mono- or di-substituted by alkyl group having 1 to 4 carbon atoms, a sulfamoyl group, a sulfamoyl group mono- or di-substituted by alkyl group having 1 to 4 carbon atoms, a carboxyl group, an alkoxycarbonyl group having 2 to 8 carbon atoms, a hydroxy group, a $C_{1-6}$ alkoxy group optionally substituted by 1 to 3 halogen atoms (e.g., fluorine, chlorine, bromine, iodine etc.), a $C_{2-5}$ alkenyloxy group optionally substituted by 1 to 3 halogen atoms (e.g., fluorine, chlorine, bromine, iodine etc.), a cycloalkyloxy group having 3 to 7 carbon atoms, an aralkyloxy group having 7 to 9 carbon atoms, an aryloxy group having 6 to 14 carbon atoms (e.g., phenyloxy, naphthyloxy etc.), a thiol group, a $C_{1-6}$ alkylthio group optionally substituted by 1 to 3 halogen atoms (e.g., fluorine, chlorine, bromine, iodine etc.), an aralkylthio group having 7 to 9 carbon atoms, an arylthio group having 6 to 14 carbon atoms (e.g., phenylthio, naphthylthio etc.), a sulfo group, a cyano group, an azide group, a nitro group, a nitroso group, a halogen atom (e.g., fluorine, chlorine, bromine, iodine) and the like can be mentioned. The number of substituent is, for example, 1 to 3.

As the alicyclic hydrocarbon group of the "optionally substituted alicyclic hydrocarbon group", saturated or unsaturated alicyclic hydrocarbon group having 3 to 12 carbon atoms, such as cycloalkyl group, cycloalkenyl group, cycloalkadienyl group and the like, can be mentioned.

Preferable examples of the cycloalkyl group include cycloalkyl group having 3 to 10 carbon atoms, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

Preferable examples of the cycloalkenyl group include cycloalkenyl group having 3 to 10 carbon atoms, such as 2-cyclopenten-1-yl, 3-cyclopenten-1-yl 2-cyclohexen-1-yl, 3-cyclohexen-1-yl and the like.

Preferable examples of the cycloalkadienyl group include cycloalkadienyl group having 4 to 10 carbon atoms, such as 2,4-cyclopentadien-1-yl, 2,4-cyclohexadien-1-yl, 2,5-cyclohexadien-1-yl and the like.

Preferable examples of the aromatic hydrocarbon group of the "optionally substituted aromatic hydrocarbon group" include aromatic hydrocarbon group having 6 to 14 carbon atoms (i.e., aryl group, such as phenyl, naphthyl, anthryl, phenanthryl, acenaphthylenyl, biphenylyl and the like). Of these, phenyl, 1-naphthyl, 2-naphthyl and the like are preferable.

As the aromatic heterocyclic group of the "optionally substituted aromatic heterocyclic group", for example, a monocyclic, bicyclic or tricyclic aromatic heterocyclic group containing, besides carbon atoms, 1 to 5 hetero atoms selected from oxygen atom, sulfur atom and nitrogen atom, as a ring constituting atom, and the like can be mentioned.

Preferable examples of the monocyclic aromatic heterocyclic group include furyl, thienyl, pyrrolyl, oxazolyl, isoxazolyl, thiazolyl, isothiazolyl, imidazolyl, pyrazolyl, oxadiazolyl (1,2,3-oxadiazolyl, 1,2,4-oxadiazolyl, 1,3,4-oxadiazolyl), furazanyl, thiadiazolyl (1,2,3-thiadiazolyl, 1,2,4-thiadiazolyl, 1,3,4-thiadiazolyl), triazolyl (1,2,3-triazolyl, 1,2,4-triazolyl), tetrazolyl, pyridyl, pyrimidinyl, pyridazinyl, pyrazinyl, triazinyl and the like.

Preferable examples of the bicyclic or tricyclic aromatic heterocyclic group include benzofuranyl, isobenzofuranyl, benzo[b]thienyl, indolyl, isoindolyl, 1H-indazolyl, benzimidazolyl, benzoxazolyl, benzothiazoly, 1H-benzotriazolyl, quinolyl, isoquinolyl, cinnolyl, quinazolyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, indolizinyl, pyrrolo[1,2-b]pyridaziriyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, and the like.

As the non-aromatic heterocyclic group of the "optionally substituted non-aromatic heterocyclic group", for example, a $C_{2-10}$ non-aromatic heterocyclic group containing, besides carbon atoms, 1 to 3 hetero atoms selected from oxygen atom, sulfur atom and nitrogen atom, as a ring constituting atom, and the like can be mentioned. Preferable examples of the non-aromatic heterocyclic group include oxiranyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino, thiomorpholino and the like.

As the substituent of the aforementioned "optionally substituted alicyclic hydrocarbon group", "optionally substituted aromatic hydrocarbon group", "optionally substituted aromatic heterocyclic group" and "optionally substituted non-aromatic heterocyclic group", for example, a $C_{1-6}$ alkyl group optionally substituted by 1 to 3 halogen atoms (e.g., fluorine, chlorine, bromine, iodine etc.), a $C_{2-6}$ alkenyl group optionally substituted by 1 to 3 halogen atoms (e.g., fluorine, chlorine, bromine, iodine etc.), a cycloalkyl group having 3 to 10 carbon atoms, an aromatic hydrocarbon group having 6 to 14 carbon atoms (namely, aryl group) (e.g., phenyl, naphthyl etc.), an aromatic heterocyclic group (e.g., thienyl, furyl, pyridyl, oxazolyl, thiazolyl etc.), a non-aromatic heterocyclic group (e.g., tetrahydrofuryl, morpholino, thiomorpholino, piperidino, pyrrolidinyl, piperazinyl etc.), an aralkyl group having 7 to 9 carbon atoms, an amino group, an amino group mono- or di-substituted by alkyl group having 1 to 4 carbon atoms or acyl group having 2 to 8 carbon atoms (e.g., alkanoyl group etc.), an amidino group, an acyl group having 2 to 8 carbon atoms (e.g., alkanoyl group etc.), a carbamoyl group, a carbamoyl group mono- or di-substituted by alkyl group having 1 to 4 carbon atoms, a sulfamoyl group, a sulfamoyl group mono- or di-substituted by alkyl group having 1 to 4 carbon atoms, a carboxyl group, an alkoxycarbonyl group having 2 to 8 carbon atoms, a hydroxy group, a $C_{1-6}$ alkoxy group optionally substituted by 1 to 3 halogen atoms (e.g., fluorine, chlorine, bromine, iodine etc.), a $C_{2-5}$ alkenyloxy group optionally substituted by 1 to 3 halogen atoms (e.g., fluorine, chlorine, bromine, iodine etc.), a cycloalkyloxy group having 3 to 7 carbon atoms, an aralkyloxy group having 7 to 9 carbon atoms, an aryloxy group having 6 to 14 carbon atoms (e.g., phenyloxy, naphthyloxy etc.), a thiol group, a $C_{1-6}$ alkylthio group optionally substituted by 1 to 3 halogen atoms (e.g., fluorine, chlorine, bromine, iodine etc.), an aralkylthio group having 7 to 9 carbon atoms, an arylthio group having 6 to 14 carbon atoms (e.g., phenylthio, naphthylthio etc.), a sulfo group, a cyano group, an azide group, a nitro group, a nitroso group, a halogen atom (e.g., fluorine, chlorine, bromine, iodine) and the like can be mentioned. The number of substituent is, for example, 1 to 3.

As the acyl group of the "optionally substituted acyl group", an acyl group having 1 to 13 carbon atoms, which is, besides formyl, specifically a group represented by the formula: $-COR^{11}$, $-SO_2R^{11}$, $-SOR^{11}$ or $-PO_3R^{11}R^{12}$ wherein $R^{11}$ and $R^{12}$ are the same or different and each is a hydrocarbon group or an aromatic heterocyclic group, and the like can be mentioned.

As the hydrocarbon group represented by $R^{11}$ or $R^{12}$, for example, aliphatic hydrocarbon group, alicyclic hydrocarbon group, alicyclic-aliphatic hydrocarbon group, aromatic-aliphatic hydrocarbon group, aromatic hydrocarbon group can be mentioned. These hydrocarbon groups preferably have 1 to 15 carbon atoms.

As used herein, as the aliphatic hydrocarbon group, alicyclic hydrocarbon group and aromatic hydrocarbon group, those exemplified as the aforementioned substituent for $R^1$ can be mentioned.

As the alicyclic-aliphatic hydrocarbon group, for example, one wherein the aforementioned alicyclic hydrocarbon group and aliphatic hydrocarbon group are bonded (e.g., cycloalkyl-alkyl group, cycloalkenyl-alkyl group etc.) can be mentioned. Of these, an alicyclic-aliphatic hydrocarbon group having 4 to 9 carbon atoms is preferable. Preferable examples of alicyclic-aliphatic hydrocarbon group include cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl and the like.

As the aromatic-aliphatic hydrocarbon group, for example, an aromatic-aliphatic hydrocarbon group having 7 to 13 carbon atoms (e.g., aralkyl group having 7 to 13 carbon atoms, arylalkenyl group having 8 to 13 carbon atoms, etc.) and the like can be mentioned. Preferable examples of the aromatic-aliphatic hydrocarbon group include phenylalkyl having 7 to 9 carbon atoms such as benzyl, phenethyl, 1-phenylethyl, 1-phenylpropyl, 2-phenylpropyl, 3-phenylpropyl and the like; naphthylalkyl having 11 to 13 carbon atoms such as α-naphthylmethyl, α-naphthylethyl, β-naphthylmethyl, β-naphthylethyl and the like; phenylalkenyl having 8 to 10 carbon atoms such as styryl and the like; naphthylalkenyl having 12 or 13 carbon atoms such as 2-(2-naphthylvinyl) and the like; and the like.

The hydrocarbon group represented by $R^{11}$ or $R^{12}$ is preferably an alkyl group having 1 to 10 carbon atoms, an alkenyl group having 2 to 10 carbon atoms, a cycloalkyl group having 3 to 10 carbon atoms, a cycloalkenyl group having 3 to 10 carbon atoms, an aryl group having 6 to 14 carbon atoms and the like.

As the aromatic heterocyclic group represented by $R^{11}$ or $R^{12}$, for example, a 5 to 7-membered monocyclic aromatic heterocyclic group containing, besides carbon atoms, 1 to 4 hetero atoms selected from oxygen atom, sulfur atom and nitrogen atom, as a ring constituting atom, and a condensed ring group thereof can be mentioned. As the condensed ring group, for example, a group wherein such 5 to 7-membered monocyclic aromatic heterocyclic group and a 6-membered ring containing 1 or 2 nitrogen atoms (e.g., pyridine), a benzene ring or a 5-membered ring containing one sulfur atom are condensed, and the like can be mentioned.

Preferable examples of the aromatic heterocyclic group include pyridyl (2-pyridyl, 3-pyridyl, 4-pyridyl), pyrimidinyl, (2-pyrimidinyl, 4-pyrimidinyl, 5-pyrimidinyl, 6-pyrimidinyl), pyridazinyl (3-pyridazinyl, 4-pyridazinyl), pyrazinyl (2-pyrazinyl), pyrrolyl (1-pyrrolyl, 2-pyrrolyl, 3-pyrrolyl), imidazolyl (1-imidazolyl, 2-imidazolyl, 4-imidazolyl, 5-imidazolyl), pyrazolyl (1-pyrazolyl, 3-pyrazolyl, 4-pyrazolyl), isoxazolyl (3-isoxazolyl, 4-isoxazolyl, 5-isoxazolyl), isothiazolyl-(3-isothiazolyl, 4-isothiazolyl, 5-isothiazolyl), thiazolyl (2-thiazolyl, 4-thiazolyl, 5-thiazolyl), oxazolyl (2-oxazolyl, 4-oxazolyl, 5-oxazolyl), oxadiazolyl (1,2,4-oxadiazol-5-yl, 1,3,4-oxadiazol-2-yl), thiadiazolyl (1,3,4-thiadiazol-2-yl), triazolyl (1,2,4-triazol-1-yl, 1,2,4-triazol-3-yl, 1,2,3-triazol-1-yl, 1,2,3-triazol-2-yl, 1,2,3-triazol-4-yl), tetrazolyl (tetrazol-1-yl, tetrazol-5-yl), quinolyl (2-quinolyl, 3-quinolyl, 4-quinolyl), quinazolyl (2-quinazolyl, 4-quinazolyl), quinoxalyl (2-quinoxalyl), benzoxazolyl-(2-benzoxazolyl), benzothiazolyl (2-benzothiazolyl), benzimidazolyl (benzimidazol-1-yl, benzimidazol-2-yl), indolyl (indol-1-yl, indol-3-yl), indazolyl (1H-indazol-3-yl), pyrrolopyrazinyl (1H-pyrrolo[2,3-b]pyrazin-2-yl), pyrrolopyridinyl (1H-pyrrolo[2,3-b]pyridin-6-yl), imidazopyridinyl (imidazo[1,2-a]pyridin-2-yl, 1H-imidazo[4,5-b]pyridin-2-yl, 1H-imidazo[4,5-c]pyridin-2-yl), imidazopyrazinyl (1H-imidazo[4,5-b]pyrazin-2-yl), oxophthalazinyl (1-oxo-2-(1H)-phthalazinyl) and the like. Of these, thienyl, furyl, pyridyl and the like are preferable.

Preferable examples of the acyl group include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, isonicotinoyl and the like.

The acyl group may have 1 to 3 substituents at substitutable positions thereof. As such substituent, for example, a $C_{1-6}$ alkyl group optionally substituted by 1 to 3 halogen atoms (e.g., fluorine, chlorine, bromine, iodine etc.), a $C_{1-6}$ alkoxy group optionally substituted by 1 to 3 halogen atoms (e.g., fluorine, chlorine, bromine, iodine etc.), a halogen atom (e.g., fluorine, chlorine, bromine, iodine etc.), nitro, hydroxy, amino and the like can be mentioned.

As the "optionally substituted amino group", for example, an amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms or acyl group having 1 to 13 carbon atoms and the like can be mentioned. As these groups, those exemplified as the aforementioned substituent for $R^1$ can be mentioned. The acyl group having 1 to 13 carbon atoms is preferably alkanoyl group having 2 to 10 carbon atoms, arylcarbonyl group having 7 to 13 carbon atoms and the like.

Preferable examples of the substituted amino group include methylamino, dimethylamino, ethylamino, diethylamino, propylamino, dibutylamino, diallylamino, cyclohexylamino, acetylamino, propionylamino, benzoylamino, phenylamino, N-methyl-N-phenylamino and the like.

As the "optionally substituted hydroxy group", for example, a hydroxy group optionally substituted by optionally Substituted alkyl group having 1 to 10 carbon atoms, optionally substituted alkenyl group having 2 to 10 carbon atoms, optionally substituted aralkyl group having 7 to 13 carbon atoms, optionally substituted acyl group having 7 to 13 carbon atoms or optionally substituted aryl group having 6 to 14 carbon atoms can be mentioned. As these alkyl group, alkenyl group, acyl group and aryl group, those exemplified as the aforementioned substituent for $R^1$ can be mentioned. As the "aralkyl group having 7 to 13 carbon atoms", those exemplified as the aforementioned hydrocarbon group represented by $R^{11}$ and $R^{12}$ can be mentioned.

As the substituent that the aforementioned alkyl group, alkenyl group, aralkyl group, acyl group and aryl group may have, for example, a halogen atom (e.g., fluorine, chlorine, bromine, iodine etc.), an alkoxy group having 1 to 3 carbon atoms and the like can be mentioned. The number of substituent is, for example; 1 or 2.

As the substituted hydroxy group, for example, alkoxy group, alkenyloxy group, aralkyloxy group, acyloxy group, aryloxy group and the like, each optionally substituted, can be mentioned.

Preferable examples of the alkoxy group include an alkoxy group having 1 to 10 carbon atoms, such as methoxy, ethoxy, propoxy, isopropoxy, butoxy, isobutoxy, sec-butoxy, t-butoxy, pentyloxy, isopentyloxy, neopentyloxy, hexyloxy, heptyloxy, nonyloxy, cyclobutoxy, cyclopentyloxy, cyclohexyloxy and the like.

Preferable examples of the alkenyloxy group include an alkenyloxy group having 2 to 10 carbon atoms, such as allyloxy, crotyloxy, 2-pentenyloxy, 3-hexenyloxy, 2-cyclopentenylmethoxy, 2-cyclohexenylmethoxy and the like.

Preferable examples of the aralkyloxy group include an aralkyloxy group having 7 to 10 carbon atoms, such as phenyl-$C_{1-4}$ alkyloxy (e.g., benzyloxy, phenethyloxy etc.) and the like.

Preferable examples of the acyloxy group include an acyloxy group having 2 to 13 carbon atoms, more preferably an alkanoyloxy having 2 to 4 carbon atoms (e.g., acetyloxy, propionyloxy, butyryloxy, isobutyryloxy etc.) and the like.

Preferable examples of the aryloxy group include, an aryloxy group having 6 to 14 carbon atoms, such as phenoxy, naphthyloxy and the like.

The above-mentioned alkoxy group, alkenyloxy group, aralkyloxy group, acyloxy group and aryloxy group may have 1 or 2 substituents at substitutable positions thereof. As such substituent, for example, a halogen atom (e.g., fluorine, chlorine, bromine, iodine etc.), a $C_{1-6}$ alkoxy group optionally substituted by 1 to 3 halogen atoms (e.g., fluorine, chlorine, bromine, iodine etc.), hydroxy group, nitro group, amino group and the like can be mentioned. As the substituted aryloxy group, for example, 4-chlorophenoxy, 2-methoxyphenoxy and the like can be mentioned.

As the "optionally substituted thiol group", for example, a thiol group optionally substituted by alkyl group having 1 to 10 carbon atoms, cycloalkyl group having 3 to 10 carbon atoms, aralkyl group having 7 to 13 carbon atoms, acyl group having 2 to 13 carbon atoms, an aryl group having 6 to 14 carbon atoms, heteroaryl group and the like can be mentioned. As these alkyl group, cycloalkyl group, acyl group and aryl group, those exemplified as the aforementioned substituent for $R^1$ can be mentioned. As the aralkyl group, those exemplified as the aforementioned hydrocarbon group represented by $R^{11}$ and $R^{12}$ can be mentioned. Preferable examples of the heteroaryl group include pyridyl (e.g., 2-pyridyl, 3-pyridyl etc.), imidazolyl (e.g., 2-imidazolyl etc.), triazolyl (e.g., 1,2,4-triazol-5-yl etc.) and the like.

As the substituted thiol group, for example, alkylthio, cycloalkylthio, aralkylthio, acylthio, arylthio, heteroarylthio and the like can be mentioned.

Preferable examples of the alkylthio group include an alkylthio group having 1 to 10 carbon atoms, such as methylthio, ethylthio, propylthio, isopropylthio, butylthio, isobutylthio, sec-butylthio, t-butylthio, pentylthio, isopentylthio, neopentylthio, hexylthio, heptylthio, nonylthio and the like.

Preferable examples of the cycloalkylthio group include a cycloalkylthio group having 3 to 10 carbon atoms, such as cyclobutylthio, cyclopentylthio, cyclohexylthio and the like.

Preferable examples of the aralkylthio group include an aralkylthio group having 7 to 10 carbon atoms such as phenyl-$C_{1-4}$ alkylthio (e.g., benzylthio, phenethylthio etc.) and the like.

Preferable examples of the acylthio group include acylthio group having 2 to 13 carbon atoms, more preferably alkanoylthio group having 2 to 4 carbon atoms (e.g., acetylthio, propionylthio, butyrylthio, isobutyrylthio etc.) and the like.

Preferable examples of the arylthio group include an arylthio group having 6 to 14 carbon atoms, such as phenylthio, naphthylthio and the like.

Preferable examples of the heteroarylthio group include pyridylthio (e.g., 2-pyridylthio, 3-pyridylthio), imidazolylthio (e.g., 2-imidazolylthio), triazolylthio (e.g., 1,2,4-triazol-5-ylthio) and the like.

As the esterified carboxyl group of the optionally esterified carboxyl group, for example, alkoxycarbonyl group having 2 to 5 carbon atoms (e.g., methoxycarbonyl, ethoxycarbonyl, propoxycarbonyl, butoxycarbonyl etc.), aralkyloxycarbonyl group having 8 to 10 carbon atoms (e.g., benzyloxycarbonyl etc.), $C_{7-15}$ aryloxycarbonyl group optionally substituted by 1 or 2 alkyl group having 1 to 3 carbon atoms (e.g., phenoxycarbonyl, p-tolyloxycarbonyl etc.) and the like can be mentioned.

As the amidated carboxyl group of the optionally amidated carboxyl group, a group represented by the formula: —CON($R^{13}$)($R^{14}$) wherein $R^{13}$ and $R^{14}$ are the same or different and each is hydrogen atom, optionally substituted hydrocarbon group or optionally substituted heterocyclic group, can be mentioned.

Here, as the hydrocarbon group of the "optionally substituted hydrocarbon, group" represented by $R^{13}$ and $R^{14}$, those exemplified for the aforementioned $R^{11}$ and $R^{12}$ can be mentioned. As the heterocyclic group of the "optionally substituted heterocyclic group" represented by $R^{13}$ and $R^{14}$, aromatic heterocyclic group and non-aromatic heterocyclic group exemplified as the substituent for $R^1$ can be mentioned.

The hydrocarbon group and heterocyclic group may have 1 to 3 substituents at substitutable positions thereof. As such substituent, for example, halogen atom (e.g., fluorine, chlorine, bromine, iodine etc.), $C_{1-6}$ alkyl group optionally substituted by 1 to 3 halogen atoms (e.g., fluorine, chlorine, bromine, iodine etc.), $C_{1-6}$ alkoxy group optionally substituted by 1 to 3 halogen atoms (e.g., fluorine, chlorine, bromine, iodine etc.), nitro group, hydroxy group, amino group and the like can be mentioned.

The substituent for $R^1$ is preferably
1) $C_{1-10}$ (preferably $C_{1-4}$) alkyl group optionally having 1 to 3 substituents selected from $C_{1-6}$ alkoxy group optionally substituted by 1 to 3 halogen atoms (e.g., fluorine, chlorine, bromine, iodine etc.), halogen atom (e.g., fluorine, chlorine, bromine, iodine etc.), nitro group, hydroxy group and amino group;
2) $C_{3-10}$ (preferably $C_{3-7}$) cycloalkyl group optionally having 1 to 3 substituents selected from $C_{1-6}$ alkyl group optionally substituted by 1 to 3 halogen atoms (e.g., fluorine, chlorine, bromine, iodine etc.), $C_{1-6}$ alkoxy group optionally substituted by 1 to 3 halogen atoms (e.g., fluorine, chlorine, bromine, iodine etc.), halogen atom (e.g., fluorine, chlorine, bromine, iodine etc.), nitro group, hydroxy group and amino group;
3) aromatic heterocyclic group (preferably furyl, thienyl, pyridyl, pyrazinyl etc.) optionally having 1 to 3 substituents selected from $C_{1-6}$ alkyl group optionally substituted by 1 to 3 halogen atoms (e.g., fluorine, chlorine, bromine, iodine etc.), $C_{1-6}$ alkoxy group optionally substituted by 1 to 3 halogenatoms (e.g., fluorine, chlorine, bromine, iodine etc.), halogen atom (e.g., fluorine, chlorine, bromine, iodine etc.), nitro group, hydroxy group and amino group;

14) $C_{6-14}$ aromatic hydrocarbon group (preferably, phenyl, naphthyl etc.) optionally having 1 to 3 substituents selected from $C_{1-6}$ alkyl group optionally substituted by 1 to 3 halogen atoms (e.g., fluorine, chlorine, bromine, iodine etc.), $C_{1-6}$ alkoxy group optionally substituted by 1 to 63 halogen atoms (e.g., fluorine, chlorine, bromine, iodine etc.), halogen atom (e.g., fluorine, chlorine, bromine, iodine etc.), nitro group, hydroxy group and amino group, and the like.

The number of substituent for $R^1$ is, for example, 1 to 3, preferably 1 or 2.

The substituent for $R^1$ is more preferably an alkyl group having 1 to 4 carbon atoms, furyl, thienyl, phenyl, naphthyl and the like.

$R^1$ is preferably oxazolyl, thiazolyl, pyrazolyl or triazolyl, each of which optionally has 1 to 3 substituents selected from
1) $C_{1-10}$ (preferably $C_{1-4}$) alkyl group optionally having 1 to 3 substituents selected from $C_{1-6}$ alkoxy group optionally substituted by 1 to 3 halogen atoms (e.g., fluorine, chlorine, bromine, iodine etc.), halogen atom (e.g., fluorine, chlorine, bromine, iodine etc.), nitro group, hydroxy group and amino group;
2) $C_{3-10}$ (preferably $C_{3-7}$) cycloalkyl group optionally having 1 to 3 substituents selected from $C_{1-6}$ alkyl group optionally substituted by 1 to 3 halogen atoms (e.g., fluorine, chlorine, bromine, iodine etc.), $C_{1-6}$ alkoxy group optionally substituted by 1 to 3 halogen atoms (e.g., fluorine, chlorine, bromine, iodine etc.), halogen atom (e.g., fluorine, chlorine, bromine, iodine etc.), nitro group, hydroxy group and amino group;
3) aromatic heterocyclic group (preferably furyl, thienyl, pyridyl, pyrazinyl etc.) optionally having 1 to 3 substituents selected from $C_{1-6}$ alkyl group optionally substituted by 1 to 3 halogen atoms (e.g., fluorine, chlorine, bromine, iodine etc.), $C_{1-6}$ alkoxy group optionally substituted by 1 to 3 halogen atoms (e.g., fluorine, chlorine, bromine, iodine etc.), halogen atom (e.g., fluorine, chlorine, bromine, iodine etc.), nitro group, hydroxy group sand amino group; and
4) $C_{6-14}$ aromatic hydrocarbon group (preferably phenyl, naphthyl etc.) optionally having 1 to 3 substituents selected from $C_{1-6}$ alkyl group optionally substituted by 1 to 3 halogen atoms (e.g., fluorine, chlorine, bromine, iodine etc.), $C_{1-6}$ alkoxy group optionally substituted by 1 to 3 halogen atoms (e.g., fluorine, chlorine, bromine, iodine etc.), a halogen atom (e.g., fluorine, chlorine, bromine, iodine etc.), nitro group, hydroxy group and amino group.

$R^1$ is more preferably oxazolyl, thiazolyl or triazolyl, each of which optionally has 1 or 2 substituents selected from alkyl group having 1 to 3 carbon atoms, cycloalkyl group having 3 to 7 carbon atoms, furyl, thienyl, phenyl and naphthyl.

In the formula (I), X is a bond, an oxygen atom, a sulfur atom, —CO—, —CS—, —CR$^4$(R$^5$)— or —NR$^6$— (R$^4$ is a hydrogen atom or an optionally substituted hydrocarbon group, R$^5$ is a hydrogen atom or a hydroxy-protecting group, and R$^6$ is a hydrogen atom, an optionally substituted hydrocarbon group or an amino-protecting group). X is preferably a bond, —CR$^4$(OR$^5$)— or —NR$^6$— (the symbols are as defined above), more preferably a bond or —NR$^6$— (R$^6$ is as defined above). Particularly preferably, X is a bond or —NR$^6$— wherein R$^6$ is a hydrogen atom or an alkyl group having 1 to 4 carbon atoms.

As the "optionally substituted hydrocarbon group" represented by R$^4$ and R$^6$, those exemplified for the aforementioned R$^{13}$ and R$^{14}$ can be mentioned. The "optionally substituted hydrocarbon group" is preferably an alkyl group having 1 to 4 carbon atoms, such as methyl, ethyl, propyl, isopropyl, butyl, isobutyl, sec-butyl, t-butyl and the like, which may be substituted. The alkyl group may have 1 to 3 substituents at substitutable positions thereof. As such substituent, for example, halogen atom (e.g., fluorine, chlorine, bromine, iodine), alkoxy group, having 1 to 4 carbon atoms (e.g., methoxy, ethoxy, propoxy, isopropoxy, butoxy, isobutoxy, sec-butoxy, t-butoxy etc.), hydroxy, nitro, amino, acyl group having 1 to 4 carbon atoms (e.g., alkanoyl group having 1 to 4 carbon atoms such as formyl, acetyl, propionyl etc.), and the like can be mentioned.

R$^4$ and R$^6$ are each preferably a hydrogen atom or an alkyl group having 1 to 4 carbon atoms.

As the hydroxy-protecting group represented by R$^5$, for example, $C_{1-6}$ alkyl (e.g., methyl, ethyl, propyl, isopropyl, butyl, tert-butyl etc.), phenyl, trityl, $C_{7-10}$ aralkyl (e.g., benzyl etc.), formyl, $C_{1-6}$ alkyl-carbonyl (e.g., acetyl, propionyl etc.), benzoyl, $C_{7-10}$ aralkyl-carbonyl (e.g., benzylcarbonyl etc.), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl etc.), $C_{2-6}$ alkenyl (e.g., 1-allyl etc.) and the like can be mentioned. These groups may be substituted by 1 to 3 halogen atoms (e.g., fluorine, chlorine, bromine, iodine etc.), $C_{1-6}$ alkyl (e.g., methyl, ethyl, propyl etc.), $C_{1-6}$ alkoxy (e.g., methoxy, ethoxy, propoxy etc.) or nitro and the like.

As the amino-protecting group represented by R$^6$, for example, formyl, $C_{1-6}$ alkyl-carbonyl (e.g., acetyl, propionyl etc.), $C_{1-6}$ alkoxy-carbonyl (e.g., methoxycarbonyl, ethoxycarbonyl, tert-butoxycarbonyl etc.), benzoyl, $C_{7-10}$ aralkyl-carbonyl (e.g., benzylcarbonyl etc.), $C_{7-14}$ aralkyloxy-carbonyl (e.g., benzyloxycarbonyl, 9-fluorenylmethoxycarbonyl etc.), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl etc.), $C_{2-6}$ alkenyl (e.g., 1-allyl etc.) and the like can be mentioned. These groups may be substituted by 1 to 3 halogen atoms (e.g., fluorine, chlorine, bromine, iodine etc.), $C_{1-6}$-alkoxy (e.g., methoxy, ethoxy, propoxy etc.) or nitro and the like.

As the "divalent hydrocarbon group having 1 to 20 carbon atoms" represented by Q in the formula (I), for example, "divalent acyclic hydrocarbon group", "divalent cyclic hydrocarbon group", a divalent group obtained by combining one or more kinds of "divalent acyclic hydrocarbon groups" and one or more kinds of "divalent cyclic hydrocarbon groups" can be mentioned.

Here, as the "divalent acyclic hydrocarbon group", for example, alkylene having 1 to 20 carbon atoms, alkenylene having 2 to 20 carbon atoms, alkynylene having 2 to 20 carbon atoms and the like can be mentioned.

As the "divalent cyclic hydrocarbon group", a divalent group obtained by removing optional two hydrogen atoms from cycloalkane having 5 to 20 carbon atoms, cycloalkene having 5 to 20 carbon atoms or aromatic hydrocarbon having 6 to 18 carbon atoms (e.g., benzene, naphthalene, indene, anthracene etc.), and the like can be mentioned. Examples thereof include 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene, 1,4-cycloheptylene, 3-cyclohexen-1,4-ylene, 3-cyclohexen-1,2-ylene, 2,5-cyclohexadien-1,4-ylene, 1,2-phenylene, 1,3-phenylene, 1,4-phenylene, 1,4-naphthylene, 1,6-naphthylene, 2,6-naphthylene, 2,7-naphthylene, 1,5-indenylene, 2,5-indenylene and the like.

Q is preferably a divalent hydrocarbon group having 1 to 6 carbon atoms. Particularly,
(1) $C_{1-6}$ alkylene (e.g., —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$(CH(CH_3))_2$—, —$(CH_2)_2C(CH_3)_2$—; —$(CH_2)_3C(CH_3)_2$— etc.);
(2) $C_{2-6}$ alkenylene (e.g., —CH=CH—, —$CH_2$—CH=CH—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— etc.);
(3) $C_{2-6}$ alkynylene (e.g., —C≡C—, —$CH_2$—C≡C—, —$CH_2$—C≡C—$CH_2$—$CH_2$— etc.) and the like are preferable.

Q is particularly preferably $C_{1-6}$ alkylene or $C_{2-6}$ alkenylene, of which —$CH_2$—, —$(CH_2)_2$—, —$(CH_2)_3$—, —$(CH_2)_4$—, —CH=CH— and the like are preferable.

In the formula (I), Y is a bond, an oxygen atom, a sulfur atom, —SO—, —$SO_2$—, —$NR^7$—, —$CONR^7$— or —$NR^7CO$— ($R^7$ is a hydrogen atom, an optionally substituted hydrocarbon group or an amino-protecting group). Y is preferably a bond, an oxygen atom, a sulfur atom, —$NR^7$— or —$NR^7CO$— ($R^7$ is as defined above), more preferably a bond, oxygen atom or —$NR^7$— ($R^7$ is as defined above). Particularly preferably, Y is a bond or oxygen atom.

As the "optionally substituted hydrocarbon group" represented by $R^7$, those exemplified for the aforementioned $R^{13}$ and $R^{14}$ can be mentioned. As the amino-protecting group represented by $R^7$, those exemplified for the aforementioned $R^6$ can be mentioned. Of these, $C_{1-6}$ alkoxycarbonyl and the like are preferable. $R^7$ is preferably a hydrogen atom.

As the "aromatic ring" of the "aromatic ring optionally further having 1 to 3 substituents" represented by ring A in the formula (I), for example, benzene ring, fused aromatic hydrocarbon ring, 5- or 6-membered aromatic heterocycle, fused aromatic heterocycle and the like can be mentioned.

Here, as the "fused aromatic hydrocarbon ring", for example, fused aromatic hydrocarbon having 9 to 14 carbon atoms and the like can be mentioned. Specifically, naphthalene, indene, fluorene, anthracene and the like can be mentioned.

As the "5- or 6-membered aromatic heterocycle", for example, a 5- or 6-membered aromatic heterocycle containing, besides carbon atoms, 1 to 3 hetero atoms selected from nitrogen atom, sulfur atom and oxygen atom, and the like can be mentioned. Specifically, thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazle, 1,2,4-thiadiazole, 1,3,4-thiadiazole, furazan and the like can be mentioned.

As the "fused aromatic heterocycle", for example, a 9- to 14-membered (preferably 9- or 10-membered) fused aromatic heterocycle containing, besides carbon atoms, 1 to 4 hetero atoms selected from nitrogen atom, sulfur atom and oxygen atom, and the like can be mentioned. Specifically, benzofuran, benzothiophene, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalazine, naphthyridine, quinazolin, cinnoline, carbazole, β-carboline, acridine, phenazine, phthalimide and the like can be mentioned.

The "aromatic ring" is preferably a benzene ring, a fused aromatic hydrocarbon ring having 9 to 14 carbon atoms (preferably naphthalene etc.), a 5- or 6-membered aromatic heterocycle (preferably pyridine, oxazole, isoxazole, thiazole, oxadiazole etc.) and the like. The "aromatic ring" is more preferably a benzene ring, a pyridine ring or an isoxazole ring.

When the aromatic ring represented by ring A in the formula (I) is a benzene ring or a pyridine ring, the relationship between Y and Z, which are substituents on the ring A, is preferably meta position and para position, more preferably para position.

That is, when the aromatic ring represented by ring A in the formula (I) is a benzene ring,

is preferably

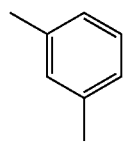 or 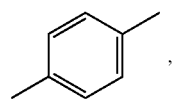

more preferably

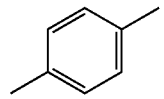

In addition, when the aromatic ring represented by ring A is a pyridine ring,

is preferably

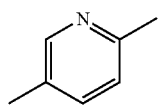, 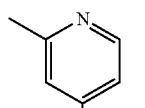 or 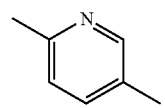, more preferably

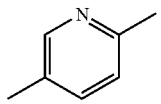 or 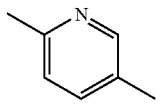.

As the "substituent" of the "aromatic ring optionally further having 1 to 3 substituents" represented by ring A, optionally substituted aliphatic hydrocarbon group (preferably alkyl group), optionally substituted hydroxy group, halogen atom, optionally substituted acyl group, nitro group, optionally substituted amino group and the like can be mentioned. As these substituents, those exemplified as the substituent for $R^1$ can be used. The substituent of the ring A is preferably an alkyl group having 1 to 4 carbon atoms, hydroxy group, an alkoxy group having 1 to 4 carbon atoms, an aralkyloxy group having 7 to 10 carbon atoms (preferably benzyloxy) or a halogen atom (preferably fluorine, chlorine).

Accordingly, ring A is preferably a benzene ring, a fused aromatic hydrocarbon ring having 9 to 14 carbon atoms or a 5- or 6-membered aromatic heterocycle, each of which optionally further has 1 to 3 substituents selected from alkyl group having 1 to 4 carbon atoms, hydroxy group, alkoxy group having 1 to 4 carbon atoms, aralkyloxy group having 7 to 10 carbon atoms and halogen atom.

In the formula (I), Z is —(CH$_2$)$_n$-Z$^1$- or -Z$^1$-(CH$_2$)$_n$— (n is an integer of 1 to 8 and $Z^1$ is an oxygen atom, a sulfur atom, —SO—, —SO$_2$— or —NR$^{16}$— ($R^{16}$ is a hydrogen atom or an optionally substituted hydrocarbon group).

As the "optionally substituted hydrocarbon group" represented by $R^{16}$, those exemplified for the aforementioned $R^{13}$ and $R^{14}$ can be mentioned.

The "n" is preferably an integer of 1 to 3.

$Z^1$ is preferably an oxygen atom or a sulfur atom.

Z is preferably —(CH$_2$)$_n$-Z$^1$- or -Z$^1$-(CH$_2$)$_n$— (more preferably —(CH$_2$)$_n$-Z$^1$-), n is an integer of 1 to 3, and $Z^1$ is an oxygen atom or a sulfur atom, In the formula (I), ring B is a pyridine ring, benzene ring or naphthalene ring, each of which optionally further has 1 to 3 substituents.

When ring B in the formula (I) is a pyridine ring optionally further having 1 to 3 substituents, the relationship between Z and U, which are substituents on the ring B, may be any of ortho position, meta position and para position, preferably ortho position or meta position.

That is, when ring B is a pyridine ring,

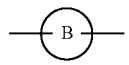

is preferably

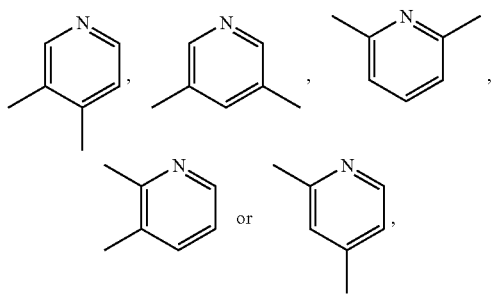

more preferably

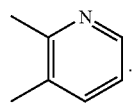

When ring B in the formula (I) is a benzene ring optionally further having 1 to 3 substituents, the relationship between Z and U, which are substituents on the ring B, is preferably ortho position or meta position, particularly preferably ortho position.

That is, when ring B is a benzene ring,

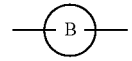

is preferably

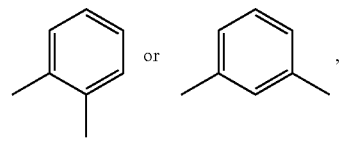

more preferably

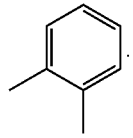

when ring B is a naphthalene ring,

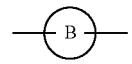

is preferably

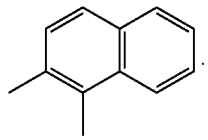

The ring B is preferably a pyridine ring or a naphthalene ring, each of which optionally further has 1 to 3 substituents, more preferably a pyridine ring optionally further having 1 to 3 substituents.

As the "substituent" in the ring B, for example, an optionally substituted aliphatic hydrocarbon group (preferably alkyl group), an optionally substituted aromatic hydrocarbon group, an optionally substituted hydroxy group, a halogen atom, an optionally substituted acyl group, a nitro group, an optionally substituted amino group and the like can be mentioned. As these substituents, those exemplified as the substituent for $R^1$ can be used. The substituent for ring B is preferably an alkyl group having 1 to 4 carbon atoms, an aryl group having 6 to 14 carbon atoms (preferably phenyl group), a hydroxy group, an alkoxy group having 1 to 4 carbon atoms, an aralkyloxy group having 7 to 10 carbon atoms (preferably benzyloxy) or a halogen atom (preferably fluorine, chlorine, bromine).

Accordingly ring B is particularly preferably a pyridine ring or a naphthalene ring, each of which optionally further has 1 to 3 substituents selected from alkyl group having 1 to 4 carbon atoms, aryl group having 6 to 14 carbon atoms, hydroxy group, alkoxy group having 1 to 4 carbon atoms, aralkyloxy group having 7 to 10 carbon atoms and halogen atom.

In the formula (I), U is a bond, an oxygen atom, a sulfur atom, —SO— or —$SO_2$—. U is preferably a bond, an oxygen atom or a sulfur atom, more preferably a bond or an oxygen atom, particularly preferably a bond. When ring B in the formula (I) is a benzene ring optionally further having 1 to 3 substituents, U represents a bond. As used herein, the substituent is preferably an alkyl group having 1 to 4 carbon atoms, an aryl group having 6 to 14 carbon atoms, a hydroxy group, an alkoxy group having 1 to 4 carbon atoms, an aralkyloxy group having 7 to 10 carbon atoms or a halogen atom.

As the "divalent hydrocarbon group having 1 to 20 carbon atoms" represented by W in the formula (I), those exemplified for the aforementioned Q can be mentioned.

W is preferably $C_{1-6}$ alkylene or $C_{2-6}$ alkenylene, more preferably —$CH_2$—, —$(CH_2)_2$—, —$(CH_2)_3$—, —$(CH_2)_4$—, —CH=CH— and the like. Particularly, —$CH_2$— is preferable.

In the formula (I), $R^3$ is —$OR^8$ ($R^8$ is a hydrogen atom or an optionally substituted hydrocarbon group) or —$NR^9R^{10}$ ($R^9$ and $R^{10}$ are the same or different and each is a hydrogen atom, an optionally substituted hydrocarbon group, an optionally substituted heterocyclic group or an optionally substituted acyl group, or $R^9$ and $R^{10}$ may be bonded to form an optionally substituted ring).

As the "optionally substituted hydrocarbon group" represented by $R^8$, the "optionally substituted hydrocarbon group" exemplified for the aforementioned $R^{13}$ and $R^{14}$ can be mentioned.

The "optionally substituted hydrocarbon group" is preferably "alkyl group having 1 to 4 carbon atoms", "$C_{6-10}$ aryl group optionally having 1 to 3 substituents selected from alkyl group having 1 to 4 carbon atoms and halogen atom (e.g., fluorine, chlorine, bromine, iodine)", and the like.

As used herein, as the "alkyl group having 1 to 4 carbon atoms", for example, methyl, ethyl, propyl, butyl, isobutyl, sec-butyl, t-butyl and the like can be mentioned. Particularly, methyl and ethyl are preferable. As the "halogen atom", chlorine is preferable. As the "$C_{6-10}$ aryl group", phenyl and naphthyl can be mentioned. Particularly, phenyl is preferable.

As the "optionally substituted hydrocarbon group" and "optionally substituted heterocyclic group" represented by $R^9$ and $R^{10}$, those exemplified for $R^{13}$ and $R^{14}$ can be mentioned.

As the "optionally substituted acyl group" represented by $R^9$ and $R^{10}$, the "optionally substituted acyl group" exemplified as the substituent for $R^1$ can be mentioned.

As the ring of the "optionally substituted ring" formed by $R^9$ and $R^{10}$ bonded to each other, for example, a 5- to 7-membered cyclic amino group, preferably 1-pyrrolidinyl, 1-piperidinyl, 1-hexamethyleneiminyl, 4-morpholino, 4-thiomorpholino, 1-piperazinyl and the like can be mentioned. As the substituent of the "optionally substituted ring", those exemplified as the substituent for the aforementioned "optionally substituted alicyclic hydrocarbon group" and the like can be mentioned. The number of substituent is, for example, 1 to 3.

$R^3$ is preferably —$OR^8$ (the symbol is as defined above), and $R^8$ is preferably a hydrogen atom or an alkyl group having 1 to 4 carbon atoms. $R^3$ is particularly preferably —OH.

Preferable examples of the compound represented by the formula (I) include the following compound.

A compound wherein $R^1$ is an oxazolyl, a thiazolyl, a pyrazolyl or a triazolyl, each of which optionally has 1 to 3 substituents selected from 1) a $C_{1-10}$ alkyl group optionally having 1 to 3 substituents selected from a $C_{1-6}$ alkoxy group optionally substituted by 1 to 3 halogen atoms, a halogen atom, a nitro group, a hydroxy group and an amino group;

2) a $C_{3-10}$ cycloalkyl group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group;

3) an aromatic heterocyclic group (preferably furyl, thienyl, pyridyl, pyrazinyl etc.) optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group; and 4) a $C_{6-14}$ aromatic hydrocarbon group (preferably, phenyl, naphthyl etc.) optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group;

X is a bond or —$NR^6$—, wherein $R^6$ is a hydrogen atom or an alkyl group having 1 to 4 carbon atoms;

Q is a $C_{1-6}$ alkylene or a $C_{2-6}$ alkenylene;

Y is a bond, an oxygen atom or —$NR^7$—, wherein $R^7$ is an amino-protecting group (preferably $C_{1-6}$ alkoxy carbonyl etc.) (Y is preferably a bond or an oxygen atom);

ring A is a benzene ring, a fused aromatic hydrocarbon ring having 9 to 14 carbon atoms (preferably naphthalene etc.), or a 5- or 6-membered aromatic heterocycle (preferably pyridine, oxazole, isoxazole, thiazole, oxadiazole etc.), each of which optionally further has 1 to 3 substituents selected from an alkyl group having 1 to 4 carbon atoms, a hydroxy group, an alkoxy group having 1 to 4 carbon atoms, an aralkyloxy group having 7 to 10 carbon atoms and a halogen atom;

Z is —$(CH_2)_n$-$Z^1$- or -$Z^1$-$(CH_2)_n$— wherein n is an integer of 1 to 3 and $Z^1$ is a oxygen atom or a sulfur atom;

ring B is a pyridine ring or a naphthalene ring, each of which optionally further has 1 to 3 substituents selected from an alkyl group having 1 to 4 carbon atoms, an aryl group having 6 to 14 carbon atoms, a hydroxy group, an alkoxy group having 1 to 4 carbon atoms, an aralkyloxy group having 7 to 10 carbon atoms and a halogen atom;

U is a bond or an oxygen atom;

W is a $C_{1-6}$ alkylene or a $C_{2-6}$ alkenylene; and $R^3$ is —$OR^8$ wherein $R^8$ is a hydrogen atom or an alkyl group having 1 to 4 carbon atoms.

Particularly preferable examples of the compound represented by the formula (I) include the following compounds:

2-[2-[4-[(5-methyl-2-phenyl-4-oxazolyl)methoxy]benzyloxy]-3-pyridyl]acetic acid;

2-[2-[[6-[(5-methyl-2-phenyl-4-oxazolyl)methoxy]-3-pyridyl]methoxy]phenyl]acetic acid;

2-[2-[[6-[(5-methyl-2-phenyl-4-oxazolyl)methoxy]-3-pyridyl]methoxy]-3-pyridyl]acetic acid;

2-[2-[[3-[(5-methyl-2-phenyl-4-thiazolyl)methoxy]-5-isoxazolyl]methoxy]phenyl]acetic acid; and 2-[2-[[4-[(5-methyl-2-phenyl-4-oxazolyl)methoxy]phenoxy]methyl]-3-pyridyl]acetic acid.

The salt of a compound of the formula (I) (hereinafter also to be referred to as Compound (I)) is preferably a pharmacologically acceptable salt, and is exemplified by salts with inorganic bases, salts with organic bases, salts with inorganic acids, salts with organic acids, and salts with basic or acidic amino acids, and the like.

Preferred examples of the salts with inorganic bases, include alkali metal salts such as sodium salts, potassium salts and the like; alkaline earth metal salts such as calcium salts, magnesium salts and the like; aluminum salts, ammonium salts, and the like.

Preferred examples of the salts with organic bases include salts with trimethylamine, triethylamine, pyridine, picoline, ethanolamine, diethanolamine, triethanolamine, dicyclohexylamine, N,N-dibenzylethylenediamine, etc.

Preferred examples of the salts with inorganic acids include salts with hydrochloric acid, hydrobromic acid, nitric acid, sulfuric acid, phosphoric acid, etc.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of the salts with basic amino acids include salts with arginine, lysine, ornithine, etc.

Preferred examples of the salts with acidic amino acids include salts with aspartic acid, glutamic acid, etc.

Of the aforementioned salts, sodium salts, potassium salts, hydrochlorides, etc. are preferred.

A prodrug of Compound (I) refers to a compound capable of being converted to Compound (I) by reactions with an enzyme, gastric juice, or the like, under physiological conditions in vivo, specifically a compound capable of being converted to Compound (I) upon enzymatic oxidation, reduction, hydrolysis, or the like, or a compound capable of being converted to Compound (I) upon hydrolysis or the like by gastric juice or the like. Examples of the prodrugs of Compound (I) include compounds derived by acylation, alkylation or phosphorylation of the amino group of Compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, tetrahydropyranylation, pyrrolidylmethylation, pivaloyloxymethylation or tert-butylation of the amino group of Compound (I), etc.); compounds derived by acylation, alkylation, phosphorylation or boration of the hydroxy group of Compound (I) (e.g., compounds derived by acetylation, palmitoylation, propanoylation, pivaloylation, succinylation, fumarylation, alanylation, dimethylaminomethylcarbonylation or tetrahydropyranylation of the hydroxy group of Compound (I), etc.); and compounds derived by esterification or amidation of the carboxyl group of Compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation of the carboxyl group of Compound (I), etc.), etc. These compounds can be produced from Compound (I) by per se known methods.

The prodrug of Compound (I) may be one capable of being converted to Compound (II) under physiological conditions, as described in "Iyakuhin No Kaihatsu (Development of Drugs)", vol. 7, Molecular Designing, published by Hirokawa Shoten, 1990, pages 163-198.

In addition, Compound (I) may be labeled with an isotope (e.g. $^3$H, $^{14}$C, $^{35}$S, $^{125}$I, etc.) and the like.

Furthermore, Compound (I) may be anhydrides or hydrates.

Compounds (I) and salts thereof (hereinafter also simply referred to as "compound of the present invention") are of low toxicity and can be used as a prophylactic or therapeutic agent of the various diseases mentioned below in mammals (e.g., humans, mice, rats, rabbits, dogs, cats, bovines, horses, swine, monkeys, etc.), as such or in the form of pharmaceutical compositions prepared by admixing with a pharmacologically acceptable carrier, etc.

Here, the pharmacologically acceptable carriers are exemplified by various organic or inorganic carrier substances in common use as materials for pharmaceutical preparations, and they are formulated as excipients, lubricants, binders, and disintegrants for solid preparations; and as solvents, solubilizers, suspending agents, isotonizing agents, buffers, soothing agents for liquid preparations, etc. In addition, other additives for pharmaceutical preparations, such as antiseptics, antioxidants, coloring agents, sweetening agents and the like, may also be used as necessary.

Preferred examples of the excipients include lactose saccharose, D-mannitol, D-sorbitol, starch, gelatinized starch, dextrin, crystalline cellulose, low substituted hydroxypropylcellulose, carboxymethylcellulose sodium, gum arabic, dextrin pullulan, light silcic anhydride, synthetic aluminum silicate, magnesium metasilicate aluminate and the like.

Preferred examples of the lubricants include magnesium stearate, calcium stearate, talc, colloidal silica and the like.

Preferred examples of the binders include gelatinized starch, sucrose, gelatin, gum arabic, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like.

Preferred examples of the disintegrants include lactose, saccharose, starch, carboxymethylcellulose, carboxymethylcellulose calcium, croscarmellose sodium, carboxymethyl starch sodium, light silicic anhydride, low-substituted hydroxypropylcellulose and the like.

Preferred examples of the solvents include water for injection, physiological saline, Ringer's solution, alcohol, propylene glycol, polyethylene glycol, sesame oil, corn oil, olive oil, cottonseed oil and the like.

Preferred examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agents include surfactants such as stearyltriethanolamine, sodium lauryl sulfate, laurylamino propionate, lecithin, benzalkonium chloride, benzethonium chloride, monostearic glycerol and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates; polyoxyethylene hydrogenated castor oil and the like.

Preferred examples of the isotonizing agents include sodium chloride, glycerol, D-mannitol, D-sorbitol, glucose and the like.

Preferred examples of the buffers include buffer solutions of phosphates, acetates, carbonates, citrates and the like, etc.

Preferred examples of the soothing agents include benzyl alcohol and the like.

Preferred examples of the antiseptics include p-oxybenzoic acid esters, chlorobutanol, benzyl alcohol, phenethyl alcohol, dehydroacetic acid, sorbic acid and the like.

Preferred examples of the antioxidants include sulfites, ascorbates and the like.

Preferred examples of the coloring agents include food colors such as water soluble tar colors for food (e.g., Food Color Red Nos. 2 and 3, Food Color Yellow Nos. 4 and 5, Food Color Blue Nos. 1 and 2, etc.), water insoluble lake colors (e.g., aluminum salts of the aforementioned water soluble tar colors for food, etc.), natural colors (e.g., β-carotene, chlorophyll, red oxide, etc.) and the like.

Preferred examples of the sweetening agents include saccharin sodium, dipotassium glycyrrhetinate, aspartame, stevia and the like.

Examples of the dosage forms of the above pharmaceutical composition include oral preparations such as tablets, capsules (including soft capsules and microcapsules), granules, powders, syrups, emulsions, suspensions and the like; and parenteral preparations such as injections (e.g., subcutaneous injections, intravenous injections, intramuscular injections, intraperitoneal injections, etc.), external preparations (e.g., preparations for nasal administration, dermal preparations, ointments, etc.), suppositories (e.g., rectal suppositories, vaginal suppositories, etc.), pellets, drip infusions, sustained-release preparations (e.g., sustained-release microcapsules, etc.), eye drops and the like. These preparations can each be safely administered, orally or parenterally.

The pharmaceutical composition can be prepared by conventional methods in the fields of pharmaceutical manufacturing techniques, for example, methods described in the Japanese Pharmacopoeia, and the like. Specific production methods for such preparations are hereinafter described in detail.

An oral preparation, for instance, is produced by adding to the active ingredient, for example, an excipient (e.g., lactose, saccharose, starch, D-mannitol, etc.), a disintegrant (e.g., carboxymethylcellulose calcium, etc.), a binder (e.g., gelatinized starch, gum arabic, carboxymethylcellulose, hydroxypropylcellulose, polyvinylpyrrolidone, etc.), a lubricant (e.g., talc, magnesium stearate, polyethyleneglycol 6000, etc.), and the like, compression molding the obtained mixture, then, if necessary coating by a method known per se using a coating base for the purpose of taste masking, enteric coating or sustained release.

Examples of the coating base include a sugar coating base, a water-soluble film coating base, an enteric film coating base, a sustained-release film coating base and the like.

As the sugar coating base, saccharose is employed. Further, one or two or more species selected from talc, precipitated calcium carbonate, gelatin, gum arabic, pullulan, carnauba wax and the like may be used in combination.

Examples of the water-soluble film coating base include cellulose polymers such as hydroxypropylcellullose, hydroxypropylmethylcellulose, hydroxyethylcellulose, methylhydroxyethylcellulose and the like; synthetic polymers such as polyvinylacetal diethylaminoacetate, aminoalky methacrylate copolymer E [Eudragit E (trademark), Rohm Pharma], polyvinylpyrrolidone and the like; polysaccharides such as pullulan and the like, and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L[Eudragit L (trademark), Rohm Pharma], methacrylic acid copolymer LD [Eudragit L-30D55 (trademark), Rohm Pharma], methacrylic acid copolymer S [Eudragit S (trademark), Rohm Pharma] and the like; natural products such as shellac and the like, and the like.

Examples of the sustained-release film coating base include cellulose polymers such as ethylcellulose and the like; acrylic acid polymers such as aminoalkyl methacrylate copolymer RS [Eudragit RS (trademark), Rohm Pharma], an ethyl acrylate-methyl methacrylate copolymer suspension [Eudragit NE (trademark), Rohm Pharma] and the like, and the like.

Two or more of the above coating bases may be used in admixture in an appropriate ratio. On the occasion of coating, a shading agent such as titanium oxide, red ferric oxide and the like may be used.

Injections are produced by dissolving, suspending or emulsifying the active ingredient in an aqueous solvent (e.g. distilled water, physiological saline, Ringer's solution, etc.) or an oleaginous solvent (e.g., vegetable oils such as olive oil, sesame oil, cotton seed oil, corn oil; propylene glycol, etc.) and the like, together with a dispersant (e.g. polysorbate 80, polyoxyethylene hydrogenated castor oil 60, etc.), polyethylene glycol, carboxymethylcellulose, sodium alginate, etc.), a preservative (e.g. methylparaben, propylparaben, benzyl alcohol, chlorobutanol, phenol, etc.), an isotonizing agent (e.g. sodium chloride, glycerol, D-mannitol, D-sorbitol, glucose, etc.) and the like. If desired, additives such as a solubilizer (e.g. sodium salicylate, sodium acetate, etc.), a stabilizer (e.g. human serum albumin, etc.), a soothing agent (e.g. benzyl alcohol, etc.) and the like, may be used.

The compound of the present invention can be used as an insulin sensitizer, an insulin sensitivity enhancing agent, a retinoid-related receptor function regulating agent, a ligand for peroxisome proliferator-activated receptors, and a ligand for retinoid X receptor, etc. The term "function regulating agent" used here stands for both an agonist and an antagonist.

The compound of the present invention has a hypoglycemic action, a hypolipidemic action, a hypoinsulinemic action, an insulin resistance improving action, an insulin sensitivity enhancing action, and a retinoid-related receptor function regulating activity. The function regulating agent may be a partial agonist or a partial antagonist.

The term "retinoid-related receptor" used here is classified as nuclear receptors, and is a DNA-binding transcription factor whose ligand is a signal molecule such as oil-soluble vitamins, etc., and may be any of a monomer receptor, a homodimer receptor and a heterodimer receptor.

Here, examples of the monomer receptor include retinoid O receptor (hereinafter, also abbreviated as ROR) α (GenBank Accession No. L14611), RORβ (GenBank Accession No.L14160), RORγ (GenBank Accession No. U16997); Rev-erb α (GenBank Accession No. M24898), Rev-erb β (GenBank Accession No. L31785); ERRα (GenBank Accession No. X51416), ERRβ (GenBank Accession No. X51417); Ftz-FI α (GenBank Accession No. S65876), Ftz-FI β (GenBank Accession No. M81385); TIx (GenBank Accession No. S77482); GCNF (GenBank Accession No. U14666) and the like.

Examples of the homodimer receptor include homodimers formed by retinoid X receptor (hereinafter, also abbreviated as RXR) α (GenBank Accession No. X52773), RXRβ (GenBank Accession No. M84820), RXRγ (GenBank Accession No. U38480); COUPα (GenBank Accession No. X12795), COUPβ (GenBank Accession No. M64497)

COUPγ (GenBank Accession No. X12794); TR2α (GenBank Accession No. M29960), TR2α (GenBank Accession No. L27586); or HNF4α (GenBank Accession No. X76930), HNF4γ (GenBank Accession No. Z49826), etc.

Examples of the heterodimer receptor include heterodimers which are formed by the above-mentioned retinoid X receptor (RXRα, RXRβ or RXRγ) and one receptor selected from retinoid A receptor (hereinafter, also abbreviated as RAR) α (GenBank Accession No. X06614), RARβ (GenBank Accession No. Y00291), RARγ (GenBank Accession No. M24857); thyroid hormone receptor (hereinafter, also abbreviated as TR) α (GenBank Accession No. M24748), TRβ (GenBank Accession No. M26747); vitamin D receptor (VDR) (GenBank Accession No. J03258): peroxisome proliferator-activated receptor (hereinafter, also abbreviated as PPAR) α (GenBank Accession No. L02932), PPARβ (PPAR δ) (GenBank Accession No. U10375), PPARγ (GenBank Accession No. L40904); LXRα (GenBank Accession No. U22662); LXRβ (GenBank Accession No. U14534); FXR (GenBank Accession No. U18374); MB67 (GenBank Accession No. L29263); ONR (GenBank Accession No. X75163); NURα (GenBank Accession No. L13740), NURβ (GenBank Accession No. X75918) and NURγ (GenBank Accession No. U12767).

The compound of the present invention has an excellent ligand activity particularly to retinoid X receptors (RXRα, RXRβ, RXRγ) and to peroxisome proliferator-activated receptors (PPARα, PPARβ (PPARδ), PPARγ) among the above-mentioned retinoid-related receptors.

Further, the compound of the present invention has an excellent ligand activity to peroxisome proliferator-activated receptors in heterodimer receptors formed from a retinoid X receptor and a peroxisome proliferator-activated receptor, and preferably in heterodimer receptors formed from RXRα and PPARγ.

Accordingly, the retinoid-related receptor ligand of the present invention can be used advantageously as a ligand for peroxisome proliferator-activated receptors or a ligand for retinoid X receptors.

The compound of the present invention can be used as, for example, a prophylactic or therapeutic agent of diabetes mellitus (e.g., type 1 diabetes mellitus, type 2 diabetes mellitus, gestational diabetes mellitus, etc.); a prophylactic or therapeutic agent of hyperlipidemia (e.g., hypertriglyceridemia, hypercholesterolemia, hypo-high-density-lipoproteinemia, postprandial hyperlipidemia, etc.); an insulin sensitizer; an insulin sensitivity enhancing agent; a prophylactic or therapeutic agent of impaired glucose tolerance (IGT); and an agent for preventing progress from impaired glucose tolerance to diabetes mellitus.

Regarding diagnostic criteria of diabetes mellitus, new diagnostic criteria were reported by the Japan Diabetes Society in 1999.

According to this report, diabetes mellitus is a condition wherein the fasting blood glucose level (glucose concentration in venous plasma) is not less than 126 mg/dl, the 2-hour value (glucose concentration in venous plasma) of the 75 g oral glucose tolerance test (75 g OGTT) is not less than 200 mg/dl, or the non-fasting blood glucose level (glucose concentration in venous plasma) is not less than 200 mg/dl. In addition, a condition which does not fall within the scope of the above definition of diabetes mellitus, and which is not a "condition wherein the fasting blood glucose level (glucose concentration in venous plasma) is less than 110 mg/dl or the 2-hour value (glucose concentration in venous plasma) of the 75 g oral glucose tolerance test (75 g OGTT) is less than 140 mg/dl" (normal type), is called the "borderline type".

In addition, regarding diagnostic criteria for diabetes mellitus, new diagnostic criteria were reported by ADA (American Diabetes Association) in 1997 and by WHO in 1998.

According to these reports, diabetes mellitus is a condition wherein the fasting blood glucose level (glucose concentration in venous plasma) is not less than 126 mg/dl, and the 2-hour value (glucose concentration in venous plasma) of the 75 g oral glucose tolerance test is not less than 200 mg/dl In addition, according to the above reports, impaired glucose tolerance is a condition wherein the fasting blood glucose level (glucose concentration in venous plasma) is less than 126 mg/dl, and the 2-hour value (glucose concentration in venous plasma) of the 75 g oral glucose tolerance test is not less than 1400 mg/dl and less than 200 mg/dl. Furthermore, according to the ADA report, a condition wherein the fasting blood glucose level (glucose concentration in venous plasma) is not less than 110 mg/dl and less than 126 mg/dl, is called IFG (impaired fasting glucose). On the other hand, according to the WHO report, a condition of IFG (impaired fasting glucose) as such wherein the 2-hour value (glucose concentration in venous plasma) of the 0.75 g oral glucose tolerance test is less than 140 mg/dl, is called IFG (impaired fasting glycemia).

The compound of the present invention can also be used as a prophylactic or therapeutic agent of diabetes mellitus, borderline type, impaired glucose tolerance, IFG (impaired fasting glucose) and IFG (impaired fasting glycemia) as defined by the above new diagnostic criteria. Furthermore, the compound of the present invention can also be used to prevent progress from the borderline type, impaired glucose tolerance, IFG (impaired fasting glucose) or IFG (impaired fasting glycemia) to diabetes mellitus.

The compound of the present invention can be used also as a prophylactic or therapeutic agent of, for example, diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, inferior limb infection, etc.), diabetic gangrene, xerostomia, lowered sense of hearing, cerebrovascular disease, peripheral circulatory disturbance, etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disease, etc.), muscular dystrophy, myocardiac infarction, angina pectoris, cerebrovascular disease (e.g., cerebral infarction, cerebral apoplexy), insulin resistant syndrome, syndrome X, hyperinsulinemia, hyperinsulinemia-induced sensory disorder, tumor (e.g., leukemia, breast cancer, prostate cancer, skin cancer, etc.), irritable intestinal syndrome, acute or chronic diarrhea, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, pancreatitis, inflammatory colonic disease, ulcerative colitis, etc.), visceral obesity syndrome, etc.

The compound of the present invention possess a total cholesterol lowering action and enhance a plasma anti-arteriosclerosis index [(HDL cholesterol/total cholesterol)× 100], and therefore, can be used as a prophylactic or therapeutic agent of arteriosclerosis (e.g., atherosclerosis, etc.) and the like.

Also, the compound of the present invention can be used for ameliorating conditions such as bellyache, nausea, vomiting, dysphoria in epigastrium, and the like, each of which is accompanied by gastrointestinal ulcer, acute or chronic gastritis, biliary dyskinesia, or cholecystitis, etc., and the like.

Further, the compound of the present invention can control (enhance or inhibit) appetite and food intake, and therefore, can be used, for example, as an agent for treating leanness and cibophobia (the weight increase in administration subjects suffering from leanness or cibophobia) or as an agent for treating obesity.

The compound of the present invention can be also used as a prophylactic or therapeutic agent of TNF-α mediated inflammatory diseases. The TNF-α mediated inflammatory diseases mean inflammatory diseases which occur in the presence of TNF-α and can be treated by way of a TNF-α inhibitory action. Examples of such inflammatory diseases include diabetic complications (e.g., retinopathy, nephropathy, neuropathy, macroangiopathy, etc.), rheumatoid arthritis, spondylitis deformans, osteoarthritis, lumbago, gout, postoperative or traumatic inflammation, remission of swelling, neuralgia, pharyngolaryngitis, cystitis, hepatitis, pneumonia, gastric mucosal injury (including aspirin-induced gastric mucosal injury), etc.

The compound of the present invention have an apoptosis inhibitory activity, and can be used as a prophylactic or therapeutic agent of diseases mediated by promotion of apoptosis. Examples of the diseases mediated by promotion of apoptosis include viral diseases (e.g., AIDS, fulminant hepatitis, etc.) neurodegenerative diseases (e.g., Alzheimers disease, Parkinson's disease, amyotropic lateral sclerosis, retinitis pigmentosa, cerebellar degeneration, etc.), myelodysplasia (e.g., aplastic anemia, etc.), ischemic diseases. (e.g., myocardial infarction, cerebral apoplexy, etc.), hepatic diseases (e.g., alcoholic hepatitis, hepatitis B, hepatitis C, etc.), joint-diseases (e.g., osteoarthritis, etc.), atherosclerosis, etc.

Also, the compound of the present invention can be used for reducing visceral fats, inhibiting accumulation of visceral fats, ameliorating glycometabolism, ameliorating lipidmetabolism, ameliorating insulin resistance, inhibiting production of oxidized LDL, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism, etc.

Also, the compound of the present invention can be used, for secondary prevention and for inhibition in progress, of the various diseases described above (e.g., cardiovascular events such as myocardial infarction, etc.).

The compound of the present invention can be used in combination with midazolam, ketoconazole, etc.

Although the doses of the compound of the present invention vary depending on administration subject, administration route, target disease, clinical condition, etc., the compound of the present invention is administered at a usual dosage per administration of about 0.005 to 50 mg/kg body weight, preferably 0.01 to 2 mg/kg body weight, more preferably 0.025 to 0.5 mg/kg body weight, for oral administration to an adult diabetic patient, for instance. These doses are preferably administered 1 to 3 times a day.

The compound of the present invention can be used in combination with a drug such as a therapeutic agent for diabetes mellitus, a therapeutic agent for diabetic complications, an antihyperlipidemic agent, a hypotensive agent, an antiobesity agent, a diuretic agent, a chemotherapeutic agent, an immunotherapeutic agent and the like (hereinafter, abbreviated as a concomitant drug). The concomitant drug may be a low molecular weight compound, or a high molecular protein, polypeptide, antibody, or vaccine and the like. On such occasions, the timing of administration of the compound of the present invention and that of the concomitant drug is not limited. They may be administered simultaneously or at staggered times to the administration subject. The dose of the concomitant drug can be appropriately selected based on the dose which is clinically employed. The proportion of the compound of the present invention and the concomitant drug can be appropriately selected according to the administration subject, administration route, target disease, clinical condition, combination, and other factors. In cases where the administration subject is human, for instance, the concomitant drug may be used in an amount of 0.01 to 100 parts by weight per part by weight of the compound of the present invention.

Examples of the therapeutic agent for diabetes mellitus include insulin preparations (e.g., animal insulin preparations extracted from the bovine or swine pancreas; human insulin preparations synthesized by a genetic engineering technique using *Escherichia coli* or a yeast; insulin zinc; insulin zinc protamine; insulin fragment or derivative thereof (e.g., INS-1 etc.) etc.), insulin sensitizers (e.g., pioglitazone hydrochloride, troglitazone, rosiglitazone or its maleate, GI-262570, JTT-501, MCC-555, YM-440, KRP-297, CS-011, FK-614, etc.), α-glucosidase inhibitors (e.g., voglibose, acarbose, miglitol, emiglitate, etc.), biguamides (e.g., phenformin, metformin, buformin, etc.), insulin secretagogues [sulfonylureas (e.g., tolbutamide, glibenclamide, gliclazide, chlorpropamide, tolazamide, acetohexamide, glyclopyramide, glimepiride, glipizide, glybuzole, etc.), repaglinide, nateglinide, mitiglinide or its calcium salt hydrate, GLP-1, etc.], dipeptidylpeptidase IV inhibitors (e.g., NVP-DPP-278, PT-100, etc.), β3 agonists (e.g., CL-316243, SR-58611-A, UL-TG-307, SB-226552, AJ-9677, BMS-196085, AZ-40140, etc.), amyrin agonist (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLUT (sodium-glucose cotransporter) inhibitors (e.g. T-1095, etc.), and the like.

Examples of the therapeutic agent for diabetic complications include aldose reductase inhibitors (e.g., tolrestat, epalrestat, zenarestat, zopolrestat, minalrestat, fidarestat (SNK-860), CT-112, etc.), neurotrophic factors (e.g., NGF, NT-3, BDNF, etc.), production and secretion promoters of neurotrophic factors, PKC inhibitors (e.g., LY-333531, etc.), AGE inhibitors (e.g., ALT946, pimagedine, pyratoxathine, N-phenacylthiazolium bromide (ALT766), EXO-226, etc.), active oxygen scavengers (e.g. thioctic acid, etc.), cerebral vasodilators (e.g., tiapuride, mexiletine, etc.).

Examples of the antihyperlipidemic agent include statin compounds which are cholesterol synthesis inhibitors (e.g., cerivastatin, pravastatin, simvastatin, lovastatin, atorvastatin, fluvastatin, itavastatin or their salts (e.g., sodium salt, etc.), etc.), squalene synthase inhibitors or fibrate compounds (e.g., bezafibrate, clofibrate, simfibrate, clinofibrate, etc.) having a triglyceride lowering action, and the like.

Examples of the hypotensive agent include angiotensin converting enzyme inhibitors (e.g., captopril, enalapril, delapril, etc.), angiotensin II antagonists (e.g., candesartan cilexetil, losartan, eprosartan, valsartan, termisartan, irbesartan, tasosartan, etc.), calcium antagonist (e.g., manidipine, nifedipine, nicardipine, amlodipine, efonidipine, etc.), clonidine, and the like.

Examples of the antiobesity agent include antiobesity drugs acting on the central nervous system (e.g. dexfenfluramine, fenfluramine, phentermine, sibutramine, anfepramon, dexamphetamine, mazindol, phenylpropanolamine, clobenzorex, etc.), pancreatic lipase inhibitors (e.g. orlistat, etc.), β3 agonists (e.g. CL-316243, SR-58611-A, UL-TG-307, SB-226552, AJ-9677, BMS-196085, AZ-40140, etc.), anorectic peptides (e.g. leptin, CNTF (Ciliary Neurotrophic Factor), etc.), cholecystokinin agonists (e.g. lintitript, FPL-15849, etc.), and the, like.

Examples of the diuretic agent include xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonate dehydratase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetamide, furosemide, and the like.

Examples of the chemotherapeutic agent include alkylating agents (e.g., cyclophosphamide, ifosfamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, Taxol, etc.), cisplatin, carboplatin, etoposide, and the like. Among these, 5-fluorouracil derivatives such as Furtulon, Neo-Furtulon and the like are preferable.

Examples of the immunotherapeutic agent include microorganism- or *bacterium*-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating agents (e.g., granulocyte colony stimulating factor, erythropoietin, etc.), and the like. Among these, IL-1, IL-2, IL-12 and the like are preferable.

As the concomitant drug, moreover, agents whose effects of ameliorating cachexia have been confirmed in animal models or clinically, namely cyclooxygenase inhibitors (e.g., indomethacin, etc.). (Cancer Research, vol. 49, pp. 5935-5939, 1989), progesterone derivatives (e.g., megestrol acetate) (Journal of Clinical Oncology, vol. 12, pp. 213-225, 1994), glucocorticoids (e.g. dexamethasone, etc.), metoclopramide pharmaceuticals, tetrahydrocannabinol pharmaceuticals (the above references are applied to both), fat metabolism ameliorating agents (e.g., eicosapentanoic acid, etc.) (British Journal of Cancer, vol. 68, pp 314-318, 1993), growth hormones, IGF-1, and antibodies to the cachexia-inducing factor TNF-α, LIF, IL-6 or oncostatin M, and the like can also be mentioned.

As the concomitant drug, moreover, neuranagenesis promoter (e.g., Y-128, VX-853, prosaptide, etc.), antidepressant (e.g., desipramine, amitriptyline, imipramine, etc.), antiepileptic (e.g., lamotrigine, etc.), antiarrhythmic (e.g., mexiletine, etc.), ligand for acetylcholine receptor (e.g., ABT-594, etc.), endothelin receptor antagonist (e.g., ABT-627, etc.), monoamine uptake inhibitor (e.g., tramadole, etc.), anesthetic analgesic (e.g., morphine, etc.), GABA receptor agonist. (e.g., gabapentin, etc.), α2 receptor agonist (e.g., clonidine, etc.), topical analgesic (e.g., capsaicin, etc.), protein kinase C inhibitor (e.g., LY-333531, etc.), antianxiety drugs (e.g., benzodiazepine, etc.), phosphodiesterase inhibitor (e.g., sildenafil citrate, etc.), dopamine agonist (e.g., apomorphine, etc.), the therapeutic agent for osteoporosis (e.g., alfacalcidol, calcitriol, elcaltonin, calcitonin salmon, estriol, ipriflavone, pamidronate disodium, alendronate sodium hydrate, incadronate disodium, etc.), the antidementia agent (e.g., tacrine, donepezil, rivastigmine, galantamine, etc.), the therapeutic agent for incontinentia or pollakiuria (e.g., flavoxate hydrochloride, oxybutynin hydrochloride, propiverine hydrochloride, etc.), and the like can be mentioned.

The concomitant drug is preferably an insulin preparation, an insulin sensitizer, an α-glucosidase inhibitor, a biguamide, an insulin secretagogue (preferably sulfonylurea), etc.

The above concomitant drugs can be used in combination of two or more species in an appropriate ratio. In the case of using two or more concomitant drugs, for example, preferable combinations include the followings.

1) an insulin sensitizer and an insulin preparation;

2) an insulin sensitizer and an insulin secretagogue;

3) an insulin sensitizer and an α-glucosidase inhibitor;

4) an insulin sensitizer and a biguanide;

5) an insulin sensitizer, an insulin preparation and a biguanide;

6) an insulin sensitizer, an insulin preparation and an insulin secretagogue;

7) an insulin sensitizer, an insulin preparation and an α-glucosidase inhibitor;

8) an insulin sensitizer, an insulin secretagogue and a biguanide;

9) an insulin sensitizer, an insulin secretagogue and an α-glucosidase inhibitor; and 10) an insulin sensitizer, a biguanide and an α-glucosidase inhibitor.

When the compound of the present invention is used in combination with a concomitant drug, the amount of each drug can be reduced within a safe range by taking their adverse effects into consideration. Particularly, the dose of an insulin sensitizer, an insulin secretagogue and a biguamide can be reduced as compared with the normal dose. Accordingly, an adverse effect which may be caused by these agents can be safely prevented. In addition, the dose of an agent for diabetic complications, an anti-hyperlipidemic agent and a hypotensive agent can be reduced whereby an adverse effect which may be caused by these agents can be effectively prevented.

In the following, the production method of the compound of the present invention is explained.

The compound of the present invention can be produced by a method known peruse, such as the following Method A to Method J or a method analogous thereto. In each of the following production methods, the starting compound may be used as a salt, and as such salt, those exemplified as the salt of the aforementioned Compound (I) can be used.

The compound (I-1) of the formula (I) wherein Z is —$(CH_2)n$-$Z^2$-(n is as defined above and $Z^2$ is an oxygen atom, a sulfur atom or —$NR^{16}$— ($R^{16}$ is as defined above)) can be produced by, for example, the following Method A.

[Method A]

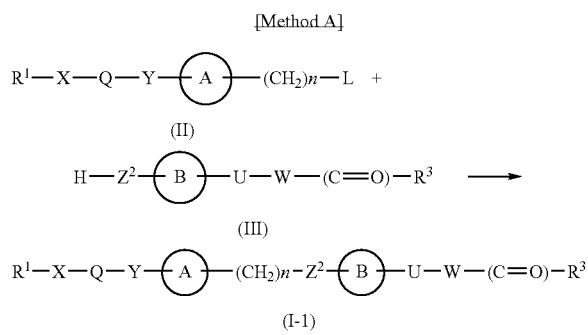

wherein L is a leaving group and other symbols are as defined above.

As the leaving group represented by L, for example, hydroxy group, halogen atom, —OSOR$^{15}$ (R$^{15}$ is an alkyl group having 1 to 4 carbon atoms, or aryl group having 6 to 10 carbon atoms which may be substituted by an alkyl group having 1 to 4 carbon atoms and the like can be mentioned.

Here, the alkyl group having 1 to 4 carbon atoms in the "alkyl group having 1 to 4 carbon atoms" and "aryl group having 6 to 10 carbon atoms which may be substituted by an alkyl group having 1 to 4 carbon atoms" for R$^{15}$ is exemplified by methyl, ethyl, propyl; isopropyl, butyl, isobutyl, sec-butyl, and t-butyl, with preference given to methyl. The aryl group having 6 to 10 carbon atoms in the "aryl group having 6 to 10 carbon atoms which may be substituted by an alkyl group having 1 to 4 carbon atoms" for R$^{15}$ is exemplified by phenyl and naphthyl, with preference given to phenyl.

In this method Compound (I-1) is produced by a reaction of Compound (II) and Compound (III).

When L is a hydroxy group, this reaction is carried out by a method known per se, e.g., the method described in *Synthesis*, page 1 (1981), or a method analogous thereto. Namely, this reaction is normally carried out in the presence of an organic phosphorus compound and an electrophilic agent in a solvent which does not interfere with the reaction.

Examples of the organic phosphorus compound include triphenylphosphine, tributylphosphine and the like.

Examples of the electrophilic agent include diethyl azodicarboxylate, diisopropyl azodicarboxylate, azodicarbonyldipiperazine and the like.

The amount of the organic phosphorus compound and electrophilic agent used is preferably about 1 to about 5 mole equivalents relative to Compound (III).

Examples of the solvent which does not interfere with the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; and sulfoxides such as dimethyl sulfoxide and the like, and the like. These solvents may be used in a mixture of two or more kinds in appropriate ratios.

The reaction temperature is normally about −50 to about 150° C., preferably about −10 to about 100° C.

The reaction time is normally about 0.5 to about 20 hours.

When L is a halogen atom or —OSO$_2$R$^{15}$, this reaction is carried out by a conventional method in the presence of a base in a solvent which does not interfere with the reaction.

Examples of the base include alkali metal salts such as potassium hydroxide, sodium hydroxide, sodium hydrogencarbonate, potassium carbonate and the like; amines such as pyridine, triethylamine N,N-dimethylaniline, 1,8-diazabicyclo[5.4.0]undec-7-ene and the like; metal hydrides such as potassium hydride, sodium hydride and the like; and alkali metal alkoxides such as sodium methoxide, sodium ethoxide, potassium t-butoxide and the like The amount of these bases used is preferably about 1 to about 5 mole equivalents relative to Compound (III).

Examples of the solvent which does not interfere with the reaction include aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; and sulfoxides such as dimethyl sulfoxide and the like, and the like. These solvents may be used in a mixture of two or more kinds in appropriate ratios.

The reaction temperature is normally about −50 to about 150° C. preferably about −10 to about 100° C.

The reaction time is normally about 0.5 to about 20 hours.

Compound (I) thus obtained may be isolated and purified by known means of separation and purification such as concentration, concentration under reduced pressure, solvent extraction, crystallization, recrystallization, redissolution, chromatography and the like Compound (II), which is used as the starting compound in Method A above, can be produced by a method described in, for example, EP-A 710659, EP-A 629624 (JP-A 7 (1995)-53555), WO 98/03505 or WO 99/58510, etc., or a method analogous thereto.

Compound (III) used as the starting compound in the above-mentioned Method A can be produced according to, for example, a method described in *The Journal of Organic Chemistry*, vol. 55, pp. 5867-5877 (1990), *Bulletin de la Societe Chimique de France*, pp. 901-904 (1988), *Chemical Abstracts*, vol. 94, 174782n, *Chemical Abstracts*, vol. 95, 186786a and the like, or a method analogous thereto.

A compound of the formula (I) wherein R$^3$ is OR$^8$, U is a bond and W is —CH═CH— or —(CH$_2$)$_2$— [Compound (I-2) or (I-3), respectively] can be also produced according to the following Method B.

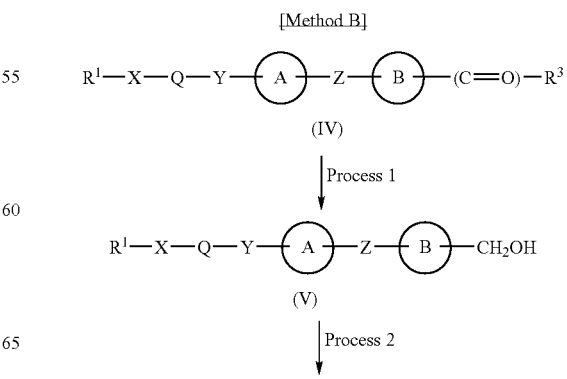

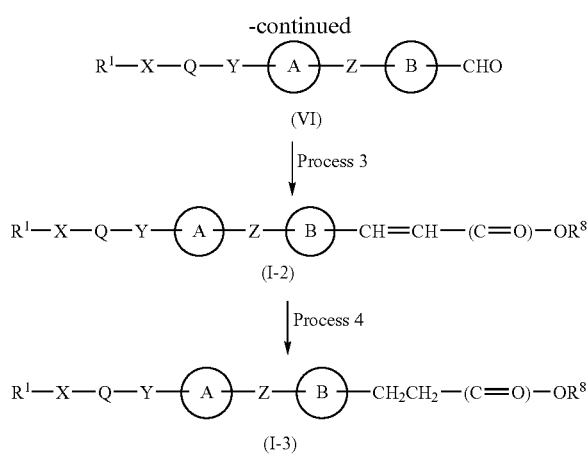

wherein each symbol is as defined above.

(Process 1)

In this Process, Compound (IV) is subjected to a reduction reaction to produce Compound (V). This reaction is carried out by a conventional method in the presence of a reducing agent in a solvent which does not interfere with the reaction.

Examples of the reducing agent include sodium borohydride, lithium borohydride, lithium aluminum hydride, and diisobutyl aluminum hydride and the like.

The amount of the reducing agent used is preferably about 0.5 to about 10 mole equivalents relative to Compound (IV).

Examples of the solvent which does not interfere with the reaction include aromatic hydrocarbons such as benzene, toluene, xylene and the like; halogenated hydrocarbons such as chloroform, dichloromethane and the like; ethers such as tetrahydrofuran, dioxane, diethyl ether and the like; water; and alcohols such as methanol, ethanol, isopropanol and the like, and the like. These solvents may be used in a mixture of two or more kinds in appropriate ratios.

The reaction temperature is normally about −50 to about 150° C., preferably about −10 to about 100° C.

The reaction time is normally about 0.5 to about 20 hours.

Compound (V) thus obtained may be isolated and purified by known means of separation and purification such as concentration, concentration under reduced pressure, solvent extraction, crystallization, recrystallization, redissolution, chromatography and the like. Alternatively, Compound (V) may be used as a reaction mixture for the next Process without isolation.

Compound (IV), which is used as the starting compound in Process 1, can be produced by, for example, Method A above. In addition, Compound (IV) can also be produced by the method described in, for example, *Journal of Heterocyclic Chemistry*, vol. 24, p. 1669 (1987); *Journal of Organic Chemistry*, vol. 62, p. 2649 (1997); *Bioorganic & Medicinal Chemistry Letters*, vol. 6, p. 1047 (1996), etc., or a method analogous thereto.

(Process 2)

In this Process, Compound (V) is subjected to an oxidation reaction to produce Compound (VI). This reaction is carried out by a conventional method in the presence of an oxidizing agent in a solvent which does not interfere with the reaction.

Examples of the oxidizing agent include metal oxidizing agents such as manganese dioxide, pyridinium chlorochromate, pyridinium dichromate, and ruthenium oxide and the like, and the like.

The amount of the oxidizing agent used is preferably about 1 to about 10 mole equivalents relative to Compound (V).

Examples of the solvent which does not interfere with the reaction include aromatic hydrocarbons such as benzene, toluene, xylene and the like; ethers such as tetrahydrofuran, dioxane, diethyl ether and the like; and halogenated hydrocarbons such as chloroform, dichloromethane and the like, and the like. These solvents may be used in a mixture of two or more kinds in appropriate ratios.

The reaction temperature is normally about −50 to about 150° C., preferably about −10 to about 100° C.

The reaction time is normally about 0.5 to about 20 hours.

In addition, Compound (VI) can also be produced by adding a reaction reagent such as sulfur trioxide-pyridine complex or oxalyl chloride and the like to Compound (V) in dimethyl sulfoxide or a solvent mixture of dimethyl sulfoxide and a halogenated hydrocarbon (e.g., chloroform, dichloromethane etc.), and then reacting it with an organic base such as triethylamine, N-methylmorpholine and the like.

The amount of the reaction reagent used is preferably about 1 to about 10 mole equivalents relative to Compound (V).

The amount of the organic base used is preferably about 1 to about 10 mole equivalents relative to Compound (V).

The reaction temperature is normally about −50 to about 150° C., preferably about −10 to about 100° C. The reaction time is normally about 0.5 to about 20 hours.

Compound (VI) thus obtained may be isolated and purified by known means of separation and purification such as concentration, concentration under reduced pressure, solvent extraction, crystallization, recrystallization, redissolution, chromatography and the like. Alternatively, Compound (VI) may be used as a reaction mixture for the next Process without isolation.

(Process 3)

In this process, Compound (I-2) is produced by reacting Compound (VI) with an organic phosphorus reagent. This reaction is carried out by a conventional method in the, presence of a base in a solvent which does not interfere with the reaction.

Examples of the organic phosphorus reagent include methyl dimethylphosphonoacetate, ethyl diethylphosphonoacetate, ethyl dimethylphosphonoacetate and the like.

The amount of the organic phosphorus reagent used is preferably about 1 to about 10 mole equivalents relative to Compound (VI).

Examples of the base include alkali metal salts such as potassium hydroxide, sodium hydroxide, sodium hydrogencarbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; and alkali metal alkoxides such as sodium methoxide, sodium ethoxide, potassium t-butoxide and the like.

The amount of these bases used is preferably about 1 to about 5 mole equivalents relative to Compound (VI).

Examples of the solvent which does not interfere with the reaction include aromatic hydrocarbons such as benzene, toluene, xylene and the like; ethers such as tetrahydrofuran, dioxane, diethyl ether and the like; halogenated hydrocarbons such as chloroform, dichloromethane and the like;

amides such as N,N-dimethylformamide and the like; sulfoxides such as dimethyl sulfoxide and the like, and the like. These solvents may be used in a mixture of two or more kinds in appropriate ratios.

The reaction temperature is normally about −50 to about 150° C., preferably about −10 to about 100° C.

The reaction time is normally about 0.5 to about 20 hours.

Compound (I-2) thus obtained may be isolated and purified by known means of separation and purification such as concentration, concentration under reduced pressure, solvent extraction, crystallization, recrystallization, redissolution, chromatography and the like. Alternatively, Compound (I-2) may be used as a reaction mixture for the next Process without isolation.

(Process 4)

In this Process, Compound (I-2) is subjected to a hydrogenation reaction to produce Compound (I-3). This reaction is carried out by a conventional method under a hydrogen atmosphere or in the presence of a proton source such as formic acid and the like and a metal catalyst, in a solvent which does not interfere with the reaction.

Examples of the metal catalyst include transition metal catalysts such as palladium-carbon, palladium black, platinum oxide, Raney nickel, Wilkinson's catalyst and the like, and the like.

The amount of these transition metal catalysts used is preferably about 0.01 to about 10 mole equivalents relative to Compound (I-2).

Examples of the solvent which does not interfere with the reaction include aromatic hydrocarbons such as benzene, toluene, xylene and the like; ethers such as tetrahydrofuran, dioxane, diethyl ether, and the like; halogenated hydrocarbons such as chloroform, dichloromethane and the like; amides such as N,N-dimethylformamide and the like; alcohols such as methanol, ethanol, isopropanol and the like, and the like. These solvents may be used in a mixture of two or more kinds in appropriate ratios.

The reaction temperature is normally about −50 to about 150° C., preferably about −10 to about 100° C.

The reaction time is normally about 0.5 to about 20 hours.

Compound (I-3) thus obtained may be isolated and purified by known means of separation and purification such as concentration, concentration under reduced pressure, solvent extraction, crystallization, recrystallization, redissolution, chromatography and the like.

Compound (I-4) of the formula (I) wherein Y is $Y^1$ (oxygen atom, sulfur atom or —$NR^7$— ($R^7$ is as defined above)) can be also produced according to, for example, the following Method C.

[Method C]

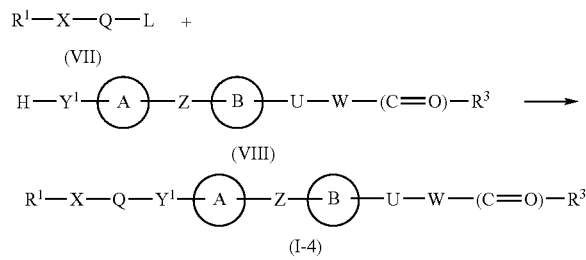

wherein each symbol is as defined above.

In this method, Compound (I-4) is produced by reacting Compound (VII) with Compound (VIII). This reaction is carried out in the same manner as the reaction of Compound (II) and Compound (III) in Method A.

Compound (I-4) thus obtained may be isolated and purified by known means of separation and purification such as concentration, concentration under reduced pressure, solvent extraction, crystallization, recrystallization, redissolution, chromatography and the like.

Compound (VII), which is used as the starting compound in Method C above, can be produced by a method described in, for example, *Journal of Medicinal Chemistry*, vol. 35, p. 2617 (1992); *Chemical and Pharmaceutical Bulletin*, vol. 34, p. 2840 (1986); WO 98/03505, etc., or an analogous method thereof.

Compound (I-6) of the formula (I) wherein $R^3$ is OH can be also produced according to, for example, the following Method D.

[Method D]

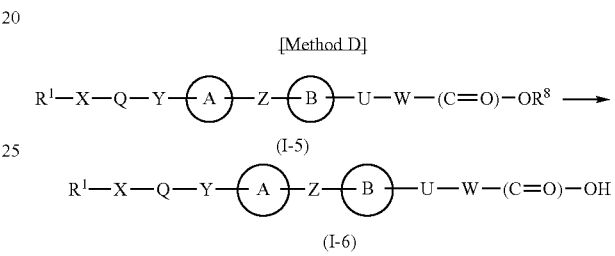

wherein the symbols have the same meanings as above.

In this method, Compound (I-6) is produced by subjecting Compound (I-5) to a hydrolysis reaction. This reaction is carried out by a conventional method in the presence of an acid or a base in an aqueous solvent.

Examples of the acid include hydrochloric acid, sulfuric acid, acetic acid, hydrobromic acid and the like.

Examples of the base include alkali metal carbonates such as potassium carbonate, sodium carbonate and the like; alkali metal alkoxides such as sodium methoxide and the like; and alkali metal hydroxides such as potassium hydroxide, sodium hydroxide, lithium hydroxide and the like, and the like.

The amount of the acid or base used is normally in excess to Compound (I-5). Preferably, the amount of the acid used is about 2 to about 50 equivalents relative to Compound (I-5), and the amount of the base used is about 1.2 to about 5 equivalents relative to Compound (I-5).

Examples of the aqueous solvents include solvent mixtures of water and one or more solvents selected from alcohols such as methanol, ethanol and the like; ethers such as tetrahydrofuran, dioxane, diethyl ether and the like; dimethyl sulfoxide, acetone and the like, and the like.

The reaction temperature is normally about −20 to about 150° C., preferably about −10 to about 100° C.

The reaction time is normally about 0.1 to about 20 hours.

Compound (I-6) thus obtained may be isolated and purified by known means of separation and purification such as concentration, concentration under reduced pressure, solvent extraction, crystallization, recrystallization, redissolution, chromatography and the like.

Compound (I-5), which is used as the starting compound in Method D above, is produced by, for example, Methods A through C above.

For example, Compound (I-7) of the formula (I) wherein $R^3$ is —$NR^9R^{10}$ can also be produced by Method E below.

[Method E]

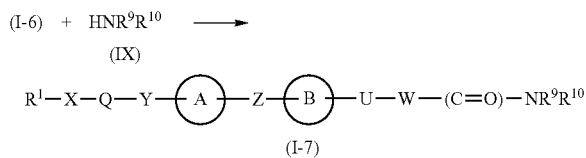

wherein the symbols have the same meanings as above.

In this method, Compound (I-7) is produced by subjecting Compound (I-6) to an amidation reaction. This reaction is carried out by a method known per se, e.g., a method wherein Compound (I-6) and Compound (IX) are directly condensed by means of a condensing agent (e.g., dicyclohexylcarbodiimide, etc.), a method wherein a reactive derivative of Compound (I-6) and Compound (IX) are reacted as appropriate, or the like. Here, the reactive derivative of Compound (I-6) is exemplified by acid anhydrides, acid halides (acid chlorides, acid bromides), imidazolides, or mixed acid anhydrides (e.g., anhydrides with methyl carbonate, ethyl carbonate, or isobutyl carbonate, etc.) and the like.

When an acid halide is used, for example, the reaction is carried out in the presence of a base in a solvent which does not interfere with the reaction.

Examples of the base include triethylamirie, N-methylmorpholine, N,N-dimethylaniline, sodium hydrogencarbonate, sodium carbonate, potassium carbonate and the like.

Examples of the solvent which does not interfere with the reaction include halogenated hydrocarbons such as chloroform, dichloromethane and the like; aromatic hydrocarbons such as benzene, toluene and the like; ethers such as tetrahydrofuran, dioxane, diethyl ether and the like; ethyl acetate, water, and the like. These solvents may be used in a mixture of two or more kinds in appropriate ratios.

The amount of Compound (IX) used is 0.1 to 10 mole equivalents, preferably 0.3 to 3 mole equivalents, relative to Compound (I-6).

The reaction temperature is normally −30 to 100° C.

The reaction time is normally 0.5 to 20 hours.

In addition, when a mixed acid anhydride is used, Compound (I-6) and a chlorocarbonic acid ester (e.g., methyl chlorocarbonate, ethyl chlorocarbonate, isobutyl chlorocarbonate, etc.) are reacted in the presence of a base (e.g., triethylamine, N-methylmorpholine, N,N-dimethylaniline, sodium hydrogencarbonate, sodium carbonate, potassium carbonate, etc.), and are further reacted with Compound (IX).

The amount of Compound (IX) used is normally 0.1 to 10 mole equivalents, preferably 0.3 to 3 mole equivalents, relative to Compound (I-6).

The reaction temperature is normally −30° C. to 100° C.

The reaction time is normally 0.5 to 20 hours.

Compound (I-7) thus obtained may be isolated and purified by known means of separation and purification such as concentration, concentration under reduced pressure, solvent extraction, crystallization, recrystallization, redissolution, chromatography and the like.

Compound (I-6), which is used as the starting compound in Method E above, is produced by, for example, Methods A through D above.

Of the Compound (VIII) used as the starting compound in Method C, Compound (VIII-1) wherein Z is —$(CH_2)n$-$Z^2$- (symbols in the formula are as defined above) can be produced by, for example, the following Method F.

[Method F]

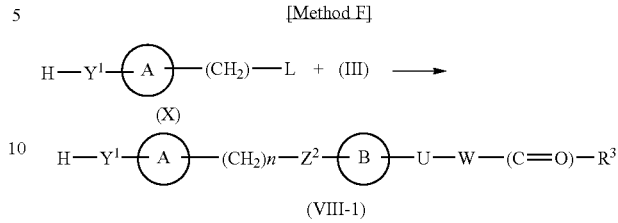

wherein each symbol is as defined above.

In this method, Compound (VIII-1) is produced by a reacting Compound (X) with Compound (III). This reaction is carried out in the same manner as in the reaction of Compound (II) and Compound (III) in Method A. The —$Y^1H$ moiety of Compound (X) may be protected with a suitable protecting group before condensation reaction, and after the reaction, may be deprotected. As such protecting group, for example, benzyl group, methoxymethyl group or silyl group (trimethylsilyl group, tert-butyldimethylsilyl group etc.) and the like can be mentioned.

Of the Compounds (IV) used as the starting compound in Method B, Compound (IV-1) wherein Z is —$(CH_2)n$-$Z^2$- (symbols in the formula are as defined above) can be produced by, for example, the following Method G.

[Method G]

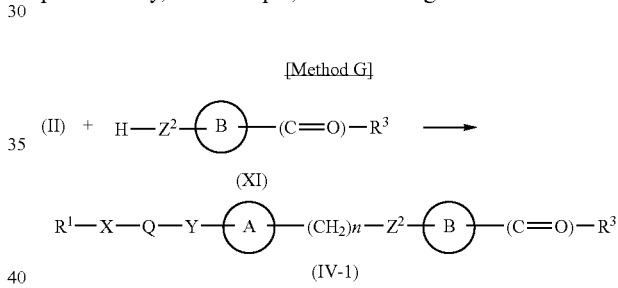

wherein each symbol is as defined above.

In this method, Compound (II) is reacted with Compound (XI) to produce Compound (IV-1). This reaction is carried out in the same manner as in the reaction of Compound (II) and Compound (III) in Method A.

[Method H]

The aforementioned Compound (I-6) can be also produced by, for example, subjecting a compound represented by the formula

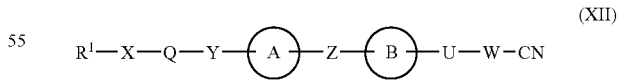

wherein each symbol is as defined above, or a salt thereof, to hydrolysis reaction.

Here, the hydrolysis reaction is carried out in the same manner as in the aforementioned hydrolysis reaction of Compound (I-5).

Of Compound (XII) used as the starting compound in the above-mentioned Method H, Compound (XIIa) wherein U is a bond and W is —$CH_2$— can be produced by, for example, the following Method I.

[Method I]

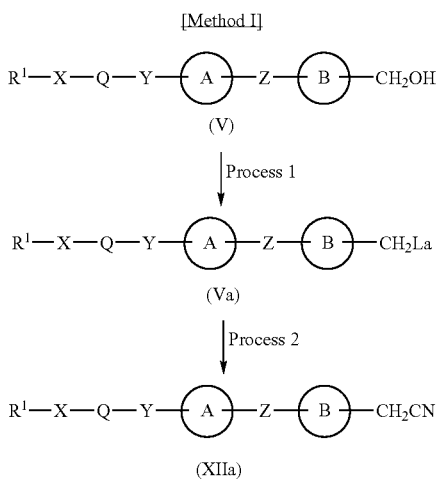

wherein La is a leaving group and other symbols are as defined above.

As the leaving group represented by La, a halogen atom and —OSOR$^{15}$ (R$^{15}$ is as defined above) exemplified as the aforementioned L can be mentioned.

(Process 1)

In this Process, Compound (V) is reacted with a halogenating agent or a sulfonylating agent to produce Compound (Va).

As the halogenating agent, for example, hydrochloric acid, thionyl chloride, phosphorus tribromide and the like are used. In this case, Compound (Va) wherein La is a halogen (e.g., chlorine, bromine etc.) can be produced.

The reaction between Compound (V) and a halogenating agent is generally carried out in a solvent that does not adversely affect the reaction.

As the solvent that does not adversely affect the reaction, for example, halogenated hydrocarbons such as dichloromethane, chloroform; carbon tetrachloride and the like; aromatic hydrocarbons such as benzene, toluene, xylene and the like; ethers such as diethyl ether, diisopropyl ether, tert-butylmethyl ether, tetrahydrofuran, dioxane, dimethoxyethane and the like; esters such as methyl acetate, ethyl acetate, n-butyl acetate, tert-butyl acetate and the like can be mentioned. These solvents may be used in a mixture of two or more kinds in appropriate ratios. In addition, an excess amount of a halogenating agent may be used as a solvent.

The amount of the halogenating agent to bemused is generally 1 to 10 mole equivalents relative to Compound (V).

The reaction temperature is generally −20 to 100° C.

The reaction time is generally 0.5-24 hrs.

As the sulfonylating agent, for example, methanesulfonyl chloride, benzenesulfonyl chloride, p-toluenesulfonyl chloride and the like can be used. In this case, Compound (Va) wherein La is, for example, methanesulfonyloxy, benzenesulfonyloxy, p-toluenesulfonyloxy and the like is produced.

The reaction between Compound (V) and a sulfonylating agent is generally carried out in the presence of a base in a solvent that does not adversely affect the reaction.

As the solvent that does not adversely affect the reaction, for example, halogenated hydrocarbons such as dichloromethane, chloroform, carbon tetrachloride and the like; aromatic hydrocarbons such as benzene, toluene, xylene and the like; ethers such as diethyl ether, diisopropyl ether, tert-butylmethyl ether, tetrahydrofuran, dioxane, dimethoxyethane and the like; esters such as methyl acetate, ethyl acetate, n-butyl acetate, tert-butyl acetate and the like, and the like can be mentioned. These solvents may be used in a mixture of two or more kinds in appropriate ratios.

The amount of the sulfonylating agent to be used is generally 1 to 10 mole equivalents relative to Compound (V).

As the base, for example, amines such as triethylamine, N-methylmorpholine and the like; alkali metal salt such as sodium hydrogencarbonate, potassium hydrogencarbonate, potassium carbonate and the like, and the like can be mentioned.

The amount of the base to be used is generally 1 to 10 mole equivalents relative to Compound (V).

The reaction temperature is generally −20 to 100° C.

The reaction time is generally 0.5-24 hrs.

Compound (Va) thus obtained may be isolated and purified by known means of separation and purification such as concentration, concentration under reduced pressure, solvent extraction, crystallization, recrystallization, redissolution, chromatography and the like. Alternatively, Compound (Va) may be used as a reaction mixture containing Compound (Va) for the next reaction without isolation.

(Process 2)

In this Process, Compound (Va) is reacted with a cyanating agent to produce Compound (XIIa).

As the cyanating agent, for example, sodium cyanide, potassium cyanide and the like can be mentioned.

This reaction is generally carried out in a solvent that does not adversely affect the reaction.

As the solvent that does not adversely affect the reaction, for example, aromatic hydrocarbons such as benzene, toluene, xylene and the like; ethers such as diethyl ether, diisopropyl ether, tert-butylmethyl ether, tetrahydrofuran, dioxane, dimethoxyethane and the like; esters such as methyl acetate, ethyl acetate, n-butyl acetate, tert-butyl acetate and the like; amides such as dimethylformamide, dimethylacetamide and the like; sulfoxides such as dimethyl sulfoxide and the like; water and the like can be mentioned. These solvents may be used in a mixture of two or more kinds in appropriate ratios.

The amount of the cyanating agent to be used is generally 1 to 10 mole equivalents relative to Compound (Va).

The reaction temperature is generally −20 to 100° C.

The reaction time is generally 0.5-24 hrs.

This reaction may be carried out in the presence of a phase transfer catalyst (e.g., benzyl tributyl ammonium chloride, crown ethers (18-crown-6-ether, 15-crown-5-ether etc.). The amount of the phase transfer catalyst to be used is, for example, 0.5 to 10 mole equivalents relative to Compound (Va).

Compound (XIIa) thus obtained may be isolated and purified by known means of separation and purification such as concentration, concentration under reduced pressure, solvent extraction, crystallization, recrystallization, redissolution, chromatography and the like. Alternatively, Compound (XIIa) may be used as a reaction mixture containing Compound (XIIa) for the next reaction without isolation.

[Method J]

Compound (I-6) can be also produced by, for example, subjecting a compound represented by the formula

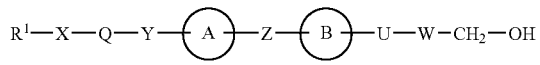

(XIII)

wherein each symbol is as defined above, or a salt thereof to an oxidation reaction.

The oxidation reaction is carried out according to a conventional method in the presence of an oxidizing agent in a solvent that does not adversely affect the reaction.

As the oxidizing agent, for example, manganese derivatives (e.g., manganese dioxide, potassium permanganate 0.5 etc.), chromic acid derivatives (e.g., chromium(VI) oxide, dichromate, chromate, chromyl chloride, chromic acid ester etc.), nitric acid, nickel peroxide and the like can be used. As the oxidizing agent, a mixture of sodium hypochlorite, sodium chlorite and the like, may be used with 2,2,6,6-tetramethyl-1-piperidinyloxy radical as a catalyst for oxidation.

The amount of the oxidizing agent to be used is, for example, 1 to 10 mole equivalents relative to Compound (XIII).

As the solvent that does not adversely affect the reaction, for example, halogenated hydrocarbons such as dichloromethane, chloroform, carbon tetrachloride and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; nitriles such as acetonitrile, propionitrile and the like; esters such as methyl acetate, ethyl acetate, n-butyl acetate, tert-butyl acetate and the like; amides such as dimethylformamide, dimethylacetamide and the like, and the like can be mentioned. These solvents may be used in a mixture of two or more kinds in appropriate ratios, and may be mixed with water and a buffer solution (e.g., phosphate buffer etc.) before use.

The reaction temperature is generally −10 to 100° C., preferably 0 to 40° C.

The reaction time is generally 0.1-20 hrs, preferably 0.1-10 hrs.

This reaction may be carried out in the presence of an acid or a base.

As the acid, for example, mineral acids (e.g., hydrochloric acid, hydrobromic acid, sulfuric acid etc.), carboxylic acids (e.g., formic acid, acetic acid, propionic acid etc.) and the like can be mentioned.

As the base, for example, alkali metal salts such as sodium hydroxide, potassium hydroxide, potassium carbonate, sodium carbonate, potassium hydrogencarbonate, sodium hydrogencarbonate and the like; alkali metal alkoxides such as potassium methoxide, potassium ethoxide, sodium methoxide, sodium ethoxide, potassium t-butoxide, sodium t-butoxide and the like; amines such as trimethylamine, triethylamine, ethyldiisopropylamine, N-methylmorpholine and the like; aromatic amines such as pyridine, lutidine, picoline and the like; and the like can be mentioned. In some cases, these acids and bases may be used as a solvent.

The amount of the acid or base to be used is, for example, 1 to 200 mole equivalent relative to Compound (XIII).

Compound (I-6) thus obtained may be isolated and purified by known means of separation and purification such as concentration, concentration under reduced pressure, solvent extraction, crystallization, recrystallization, redissolution, chromatography and the like.

Of Compound (XIII) used as the starting compound in the above-mentioned Method J, Compound (XIIIa) wherein U is a bond and W is —CH$_2$— can be produced by, for example, subjecting a compound represented by the formula

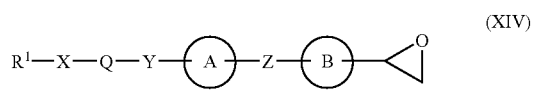

(XIV)

wherein each symbol is as defined above, or a salt thereof, to a reduction reaction.

The reduction reaction is carried out according to a conventional method in the presence of a reducing agent in a solvent that does not adversely affect the reaction.

As the reducing agent, for example, reducing agent of metal hydride compounds such as sodium bis(2-methoxyethoxy)aluminum hydride, duisobutylaluminum hydride and the like; metal hydride complex compounds such as sodium borohydride, sodium cyanoborohydride, lithium aluminum hydride and the like; and the like can be mentioned. Of these, diisobutylaluminum hydride is preferable.

The amount of the reducing agent to be used is, for example, about 0.1—about 20 mole equivalents, relative to Compound (XIV).

As the solvent that does not adversely affect the reaction, for example, alcohols such as methanol, ethanol, propanol, 2-propanol, butanol, isobutanol, tert-butanol and the like; aromatic hydrocarbons such as benzene, toluene, xylene and the like; aliphatic hydrocarbons, such as hexane, heptane and the like; ethers such as diethyl ether, diisopropyl ether, tert-butylmethyl ether, tetrahydrofuran, dioxane, dimethoxyethane and the like; nitriles such as acetonitrile propionitrile and the like; esters such as methyl acetate, ethyl acetate, n-butylbacetate, tert-butyl acetate and the like; amides such as dimethylformamide, dimethylacetamide and the like can be used. These solvents may be used in a mixture of two or more kinds in appropriate ratios, and may be mixed with water and a buffet solution (e.g., phosphate buffer etc.) before use. Of these solvents, tetrahydrofuran, dimethoxyethane and the like are preferable.

The reaction temperature is generally −70 to 150° C., preferably −20-100° C.

The reaction time is generally 0.1-100 hrs, preferably 0.1-40 hrs.

The reduction reaction can be also carried out in the presence of a metal catalyst such as palladium-carbon, palladium black, palladium chloride, platinum oxide, platinum black, platinum-palladium, Raney-nickel, Raney-cobalt and the like, and a proton source, in a solvent that does not adversely affect the reaction.

The amount of the metal catalyst to be used is, for example, 0.01-1000 mole equivalents, preferably 0.05-100 mole equivalents relative to Compound (XIV).

As the proton source, hydrogen gas, formic acid, amine formate, phosphinate, hydrazine and the like can be Mentioned.

As the solvent that does not adversely affect the reaction, those used for the aforementioned reduction reaction using the reducing agent can be mentioned.

The reaction temperature and reaction time are the same as those in the aforementioned reduction reaction using a reducing agent.

Compound (XIIIa) thus obtained may be isolated and purified by known means of separation and purification such as concentration, concentration under reduced pressure, solvent extraction, crystallization, recrystallization, redissolution, chromatography and the like. Alternatively, Compound (XIIIa) may be used as a reaction mixture containing Compound (XIIIa) for the next reaction without isolation.

The above-mentioned Compound (XIV) can be produced by subjecting Compound (VI) to an epoxidation reaction.

The epoxidation reaction is carried out using, for example, a compound represented by the formula: $R^{17}R^{18}CH_3SO_mLb$ (XV) wherein $R^{17}$ and $R^{18}$ are the same or different and each is alkyl group, Lb is a halogen atom and m is 0 or 1, and a base.

As the alkyl group represented by $R^{17}$ or $R^{18}$, for example, alkyl group having 1 to 6 carbon atoms such as methyl, ethyl, propyl, isopropyl, butyl, isobutyl, pentyl, hexyl and the like can be mentioned. Of these, methyl is preferable.

As the halogen atom represented by Lb, for example, chlorine, bromine, fluorine, iodine and the like can be mentioned. Of these, bromine and iodine are preferable.

The amount of Compound (XV) to be used is, for example, 1-100 mole equivalents, preferably 1-10 mole equivalents relative to Compound (VI).

As the base, for example, alkali metal hydrides such as potassium hydride, sodium hydride and the like; alkali metal salts such as sodium hydroxide, potassium hydroxide, potassium carbonate, sodium carbonate, potassium hydrogencarbonate, sodium hydrogencarbonate and the like; alkali metal alkoxides such as potassium methoxide, potassium ethoxide, sodium methoxide, sodium ethoxide, potassium t-butoxide, sodium t-butoxide and the like; amines such as trimethylamine, triethylamine, ethyldiisopropylamine, N-methylmorpholine and the like; amides such as lithium diethylamide, lithium diisopropylamide and the like; and the like can be mentioned. Of these, potassium t-butoxide, sodium t-butoxide, sodium hydroxide, potassium hydroxide and the like are preferable.

The amount of the base to be used is, for example, 1-100 mole equivalents, preferably 1-10 mole equivalents, relative to Compound (VI).

This reaction is generally carried out in a solvent that does not adversely affect the reaction. As such solvent, for example, alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; nitriles such as acetonitrile, propionitrile and the like; esters such as methyl acetate, ethyl acetate, n-butyl acetate, tert-butyl acetate and the like; amides such as dimethylformamide, dimethylacetamide and the like; sulfoxides such as dimethyl sulfoxide and the like; and the like can be mentioned. These solvents may be used in a mixture of two or more kinds in appropriate ratios, and may be mixed with water and a buffer solution (e.g., phosphate buffer etc.) before use. Of these solvents, acetonitrile, tetrahydrofuran, dimethyl sulfoxide and the like are preferable.

The reaction temperature is generally −50 to 150° C., preferably −20° C. to 100° C.

The reaction time is generally 0.1-20 hrs, preferably 0.1-10 hrs.

Compound (XIV) thus obtained may be isolated and purified by known means of separation and purification such as concentration, concentration under reduced pressure, solvent extraction, crystallization, recrystallization, redissolution, chromatography and the like. Alternatively, Compound (XIV) may be used as a reaction mixture containing Compound (XIV) for the next reaction without isolation.

Compound (XV) used as the starting compound in the above-mentioned reaction is obtained as, for example, a commercially available product.

Compound (VI) may be once converted to hydrogensulfite and then subjected to an epoxidation reaction, wherein the use of hydrogensulfite of Compound (VI) for the epoxidation reaction results in the production of Compound (XIV) in a higher yield.

The hydrogensulfite of Compound (VI) can be produced by, for example, reacting Compound (VI) with an alkali metal hydrogensulfite. As the alkali metal hydrogensulfite, for example, sodium hydrogensulfite and the like can be mentioned.

The amount of the alkali metal hydrogensulfite to be used is, generally 1-20 mole equivalents, preferably 1-10 mole equivalents, relative to Compound (VI).

This reaction is generally carried out in a solvent that does not adversely affect the reaction. As such solvent, for example, alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; nitrites such as acetonitrile, propionitrile and the like; esters such as methyl acetate, ethyl acetate, n-butyl acetate, tert-butyl acetate and the like; and the like can be mentioned. These solvents may be used in a mixture of two or more kinds in appropriate ratios, and may be mixed with water and a buffer solution (e.g., phosphate buffer etc.) before use. Of these solvents tetrahydrofuran, isopropyl ether, ethyl acetate and the like are preferable.

The reaction temperature is generally −10 to 100° C., preferably 0 to 50° C.

The reaction time is generally 0.1-30 hrs, preferably 0.5-20 hrs.

The hydrogensulfite of Compound (VI) thus obtained may be isolated and purified by known means of separation and purification such as concentration, concentration under reduced pressure, solvent extraction, crystallization, recrystallization, redissolution, chromatography and the like. Alternatively, hydrogensulfite of Compound (VI) may be used as a reaction mixture containing the hydrogensulfite for the next reaction without isolation.

When the hydrogensulfite of Compound (VI) can be used, this may be converted to Compound (VI) and then subjected to an epoxidation reaction.

The reaction for obtaining Compound (VI) can be generally carried out in the presence of an acid or a base.

Here, as the acid, for example, mineral acids (e.g., hydrochloric acid, hydrobromic acid, sulfuric acid etc.), carboxylic acids (e.g., formic acid, acetic acid, propionic acid etc.) and the like can be mentioned. Of these, acetic acid, formic acid and the like are preferable.

As the base, for example, alkali metal salts such as potassium hydroxide, sodium hydroxide, potassium carbonate, sodium carbonate, potassium hydrogencarbonate, sodium hydrogencarbonate and the like; amines such as trimethylamine, triethylamine, ethyldiisopropylamine, N-methylmorpholine and the like; and the like can be mentioned. Of these, sodium carbonate, sodium hydroxide and the like are preferable.

The amount of the acid or base to be used is for example, 1-100 mole equivalents, preferably 1-50 mole equivalents, relative to hydrogensulfite of Compound (VI).

The reaction is generally carried out in a solvent that does not adversely affect the reaction. As such solvent, for example, alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; nitrites such as acetonitrile, propionitrile and the like; esters such as methyl acetate, ethyl acetate, n-butyl acetate, tert-butyl acetate and the like; amides such as dimethylformamide, dimethylacetamide and the like; sulfoxides such as dimethyl sulfoxide and the like; and the like can be mentioned. These solvents may be used in a mixture of two or more kinds in appropriate ratios, and may be mixed with water and a buffer solution (e.g., phosphate buffer etc.) before use. Of these solvents, tetrahydrofuran, isopropyl ether, ethyl acetate and the like are preferable.

The reaction temperature is generally 0 to 100° C., preferably 10 to 50° C.

The reaction time is generally 0.1-100 hrs, preferably 0.1-10 hrs.

Compound (VI) can be produced by, for example, subjecting a compound represented by the formula:

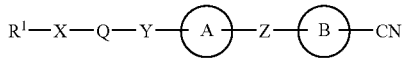

(XVI)

wherein each symbol is as defined above, or a salt thereof, to a reduction reaction.

The reduction reaction is carried out according to a conventional method in the presence of a reducing agent in a solvent that does not adversely affect the reaction.

As the reducing agent, for example, the reducing agents of metal hydride compounds such as sodium bis(2-methoxyethoxy)aluminum hydride, sodium triethoxyaluminum hydride, diisobutylaluminum hydride, triethoxy lithium aluminum hydride, lithium tri-(tert-butoxy)aluminum hydride and the like, and the like can be mentioned. Of these, diisobutylaluminum hydride is preferable.

The amount of the reducing agent to be used is, for example, 0.1-100 equivalents, preferably 1-5 equivalents, relative to Compound (XVI).

As the solvent that does not adversely affect the reaction, for example, halogenated hydrocarbons such as dichloromethane, dichloroethane, chloroform and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; and the like can be mentioned. Of these, aromatic hydrocarbons such as toluene, xylene and the like are preferable.

The reaction temperature is generally –100° C. to 50° C., preferably –90° C. to 30° C.

The reaction time is generally 0.1-10 hrs, preferably 0.1-5 hrs.

The reduction reaction can be also carried out in the presence of a metal catalyst such as palladium-carbon, palladium black, palladium chloride, platinum oxide, platinum black, platinum-palladium, Raney-nickel, Raney-cobalt and the like, and a proton source, in a solvent that does not adversely affect the reaction.

The amount of the metal catalyst to be used is for example 0.01-1000 mole equivalents, preferably 0.05-100 mole equivalents, more preferably 0.1-10 mole equivalents, relative to Compound (XVI).

As the proton source, hydrogen gas, mineral acids (e.g., hydrochloric acid, hydrobromic acid, sulfuric acid etc.), carboxylic acids (e.g., formic acid, acetic acid, propionic acid etc.), phosphinate (e.g., sodium phosphinate, potassium phosphinate etc.), amine formate, hydrazine and the like can be mentioned. Two or more kinds of these proton sources may be used in combination. As the proton source, a combination of mineral acids (e.g., hydrochloric acid, hydrobromic acid, sulfuric acid etc.) or carboxylic acids (e.g., formic acid, acetic acid, propionic acid etc.) and phosphinate (e.g., sodium phosphinate, potassium phosphinate etc.) is particularly preferable.

The amount of the acid and phosphinate to be used is, generally 0.1-100 mole equivalents, preferably 1-50 mole equivalents, relative to Compound (XVI), respectively.

The reduction reaction is preferably carried out using a metal catalyst selected from Raney-nickel and Raney-cobalt, and a proton source which is a combination of mineral acids (e.g., hydrochloric acid, hydrobromic acid, sulfuric acid etc.) or carbbxylic acids (e.g., formic acid, acetic acid, propionic acid etc.) and phosphinate (e.g., sodium phosphinate, potassium phosphinate etc.).

As the solvent that does not adversely affect the reaction, for example, alcohols such as methanol, ethanol, prbpanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; aromatic amines such as pyridine, picoline, lutidine, quinoline and the like; and the like can be mentioned. These solvents may be used in a mixture of two or more kinds in appropriate ratios, and may be mixed with water and a buffer solution (e.g., phosphate buffer etc.) before use. Of these, pyridine is preferable.

When mineral acids, carboxylic acids and the like are used as a proton source, these may be used as a solvent.

The reaction temperature is generally 0 to 100° C., preferably 20 to 80° C.

The reaction time is generally 0.1-100 hrs, preferably 0.5-10 hrs.

Compound (XVI) can be produced by, for example, the following method.

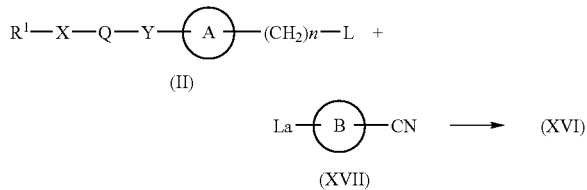

wherein each symbol is as defined above.

This reaction is, for example, carried out in the presence of a base in a solvent that does not adversely affect the reaction.

As the base, for example, alkali metal hydride such as potassium hydride, sodium hydride and the like; alkali metal salt such as potassium hydroxide, sodium hydroxide, potassium carbonate, sodium carbonate, potassium hydrogencarbonate, sodium hydrogencarbonate and the like; alkali metal alkoxide such as potassium methoxide, sodium methoxide, potassium ethoxide, sodium ethoxide, potassium-t-butoxide, sodium-t-butoxide and the like; amines such as trimethylamine, triethylamine, ethyldiisopropylamine, N-methylmorpholine and the like; and the like can be mentioned. Of these, sodium hydride, sodium hydroxide, sodium-t-butoxide and the like are preferable.

The amount of the base to be used is, for example, 1-100 mole equivalents, preferably 1-10 mole equivalents, relative to Compound (II).

As the solvent that does not adversely affect the reaction, for example alcohols such as methanol, ethanol, propanol, 2-propanol, butanol, isobutanol, tert-butanol and the like; aromatic hydrocarbons such as benzene, toluene, xylene and the like; aliphatic hydrocarbons such as hexane, heptane and the like; ethers such as diethyl ether, diisopropyl ether, tert-butylmethyl ether, tetrahydrofuran, dioxane, dimethoxyethane and the like; nitrites such as acetonitrile, propionitrile and the like; esters such as methyl acetate, ethyl acetate, n-butyl acetate, tert-butyl acetate and the like; amides such as N,N-dimethylformamide dimethylacetamide and the like; sulfoxides such as dimethyl sulfoxide and the like; and the like can be mentioned. These solvents may be used in a mixture of two or more kinds in appropriate ratios, and may be mixed with water and a buffer solution (e.g., phosphate buffer etc.) before use. Of these solvents, dimethylformamide and the like are preferable.

The amount of Compound (XVII) to be used is, for example, 0.1-10 mole equivalents, preferably 0.3-3 mole equivalents, relative to Compound (II).

The reaction temperature is generally 0 to 100° C., preferably 10 to 50° C.

The reaction time is generally 0.1-100 hrs.

Compound (XVI) thus obtained may be isolated and purified by known means of separation and purification such as concentration, concentration under reduced pressure, solvent extraction, crystallization, recrystallization, redissolution, chromatography and the like. Alternatively, Compound (XVI) may be used as a reaction mixture containing Compound (XVI) for the next reaction without isolation.

Compound (XVII) can be produced according to a method known per se.

When the starting compound has amino group, carboxy group, hydroxy group or carbonyl group as a substituent in each reaction described above, these groups may have a protecting group in common use in peptide chemistry and other fields. The desired compound can be obtained by removing the protecting group after the reaction, if necessary.

As the amino-protecting group, those exemplified for the aforementioned $R^6$ can be mentioned.

Examples of the carboxy-protecting groups include $C_{1-6}$ alkyls (e.g., methyl, ethyl, propyl, isopropyl, butyl, tert-butyl, etc.), $C_{7-11}$ aralkyls (e.g., benzyl, etc.), phenyl, trityl, silyls (e.g., trimethylsilyl, triethylsilyl, dimethylphenylsilyl, tert-butyldimethylsilyl, tert-butyldiethylsilyl, etc.), $C_{2-6}$ alkenyls (e.g., 1-allyl, etc.), and the like. These groups may be substituted by 1 to 3 halogen atoms (e.g., fluorine, chlorine, bromine, iodine, etc.), $C_{1-6}$ alkoxys (e.g., methoxy, ethoxy, propoxy, etc.), nitro, or the like.

As the hydroxy-protecting group, those exemplified for the aforementioned $R^5$ can be mentioned.

Examples of the carbonyl-protecting groups include cyclic acetals (e.g., 1,3-dioxane, etc.), acyclic acetals (e.g., di-$C_{1-6}$ alkylacetals, etc.), and the like.

In addition, these protecting groups can be removed according to a method known per se, e.g., the method described in *Protective Groups in Organic Synthesis*, published by John Wiley and Sons (1980) and the like. For example, there may be used methods employing an acid, a base, ultraviolet rays, hydrazine, phenylhydrazine, sodium N-methyldithiocarbamate, tetrabutylammonium fluoride palladium acetate, a trialkylsilylkhalide (e.g., trimethylsilyl iodide, trimethylsilyl bromide, etc.), or the like, the reduction method, and the like.

When Compound (I) contains an optical isomer, a stereoisomer, a regioisomer, or a rotational isomer, these isomers are also contained as Compound (I) and can each be obtained as a single substance by means of a method known per se of synthesis or separation. For example, when an optical isomers are present in Compound (I), the optical isomers separated from said compound are also included in Compound (I).

Optical isomers can be produced by a method known per se. Specifically, optical isomers are obtained by using an optically active synthetic intermediate, or optically resolving a racemate of the final product by a conventional method.

Examples of the methods of optical resolution include methods known per se, such as the fractional recrystallization method, the chiral column method, the diastereomer method, and the like.

1) Fractional Recrystallization Method

A method wherein salts are formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.], which salts are separated by fractional recrystallization and, if desired, subjected to a neutralization process, to yield free optical isomers.

2) Chiral Column Method

A separating method wherein a racemate or a salt thereof is applied to a separation column for optical isomer (chiral column). In the case of liquid chromatography, for example, optical isomers are separated by adding a mixture of the optical isomers to a chiral column such as ENANTIO-OVM (produced by Tosoh Corporation) or CHIRAL series produced by DAICEL CHEMICAL IND., and the like and developing it in water, various buffers (e.g., phosphate buffer), an organic solvent (e.g., ethanol, methanol, isopropanol, acetonitrile, trifluoroacetic acid, diethylamine, etc.), or a solvent mixture thereof. In the case of gas chromatography, for example, a chiral column such as CP-Chirasil-DeX CB (produced by GL Science) and the like is used to separate optical isomers.

3) Diastereomer Method

A method wherein a racemate mixture and an optically active reagent are chemically reacted to yield a diastereomer mixture, which is then subjected to ordinary means of separation (e.g., fractional recrystallization, chromatography method, etc.) and the like to obtain single substances, which are subjected to a chemical treatment such as hydrolysis to cut off the optically active reagent moiety, whereby the desired optical isomer is obtained. For example, when Compound (I) has hydroxy or primary or secondary amino in the molecule thereof, said compound, an optically active organic acid (e.g., MTPA [α-methoxy-α-(trifluoromethyl)phenylacetic acid], (−)-menthoxyacetic acid, etc.) and the like may be subjected to a condensing reaction to yield a diastereomer of an ester or amide, respectively. On the other hand, when Compound (I) has a carboxyl group, said compound and an optically active amine or alcohol reagent may be subjected to a condensing reaction to yield a diastereomer of an amide or ester, respectively. The diastereomer thus separated is converted to an optical isomer of the original compound by subjecting it to an acid hydrolysis or basic hydrolysis reaction.

The present invention is hereinafter described in more detail by means of, but is not limited to, the following Test Examples, Reference Examples, Examples and Preparation Examples.

In addition, % in the Reference Examples and Examples below means percent by weight, unless mentioned otherwise. Room temperature means the temperature of 1 to 30° C.

Abbreviations for bases, amino acids and others used in the present specification are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise mentioned.

The sequence numbers in the sequence listing in the present specification show the following respective sequences.
[SEQ ID NO:1]
Shows the base sequence of the primer PAG-U used in Reference Example 1.
[SEQ ID NO:2]
Shows the base sequence of the primer PAG-L used in Reference Example 1.
[SEQ ID NO:3]
Shows the base sequence of the primer XRA-U used in Reference Example 2.
[SEQ ID NO:4]
Shows the base sequence of the primer XRA-L used in Reference Example 2.
[SEQ ID NO:5]
Shows the base sequence of PPRE-U used in Reference Example 4.
[SEQ ID NO:6]
Shows the base sequence of PPRE-L used in Reference Example 4.
[SEQ ID NO:7]
Shows the base sequence of the primer TK-U used in Reference Example 4.
[SEQ ID NO:8]
Shows the base sequence of the primer TK-L used in Reference Example 4.

EXAMPLES

Test Example 1

Hypoglycemic and Hypolipidemic Actions in Mice

Test compounds were mixed in a powdery diet (CE-2, Japan Clea) at the concentration of 0.01% (compounds of Examples 7, 26, 29, 32) or 0.005% (compounds of Examples 1, 11, 15, 18, 24, 36, 37, 41, 48, 50, 51, 52, 58, 62, 79, 83, 88, 90, 91, 92, 93, 97, 107, 110, 115, 119, 122, 125, 129 and 130), and freely given to KKAY mice (11 to 12 weeks old, 5 mice in a group), a model of type 2 diabetes mellitus, for four days. During this period, water was given freely. Blood was sampled from orbital venous plexus, and glucose and triglyceride levels in plasma separated from blood were determined enzymatically using L type Wako Glu2 (Wako Pure Chemical Industries, Ltd.) or L type Wako TG.H (Wako Pure Chemical Industries, Ltd.), respectively. The results are given in Table 1.

In the Table, "hypoglycemic action (%)" means a percent reduction (%) of the glucose level in the test compound administration group when that of the test compound non-administration group is taken as 100%. In addition, the "hypolipidemic action (%)" means a percent reduction (%) of the triglyceride level in the test compound administration group when that of the test compound non-administration group is taken as 100%.

TABLE 1

| test compound (Example number) | hypoglycemic action (%) | hypolipidemic action (%) |
| --- | --- | --- |
| 1 | 21 | 33 |
| 7 | 48 | 62 |
| 11 | 56 | 84 |
| 15 | 49 | 60 |
| 18 | 41 | 34 |
| 24 | 49 | 67 |
| 26 | 53 | 88 |
| 29 | 58 | 67 |
| 32 | 40 | 53 |
| 36 | 55 | 71 |
| 37 | 50 | 61 |
| 41 | 48 | 93 |
| 48 | 53 | 50 |
| 50 | 54 | 77 |
| 51 | 55 | 79 |
| 52 | 56 | 61 |
| 58 | 57 | 75 |
| 62 | 47 | 44 |
| 79 | 54 | 96 |
| 83 | 48 | 43 |
| 88 | 47 | 90 |
| 90 | 30 | 40 |
| 91 | 50 | 67 |
| 92 | 58 | 83 |
| 93 | 45 | 53 |
| 97 | 34 | 83 |
| 107 | 40 | 39 |
| 110 | 51 | 74 |
| 115 | 52 | 87 |
| 119 | 40 | 33 |
| 122 | 52 | 67 |
| 125 | 41 | 40 |
| 129 | 45 | 93 |
| 130 | 55 | 63 |

These results indicated that the compounds of the present invention possess potent hypoglycemic and hypolipidemic actions. Therefore, the present compounds are useful as prophylactic or therapeutic agents of diabetes mellitus, hyperlipidemia (especially hypertriglyceridemia), impaired glucose tolerance, etc.

Test Example 2

Total Cholesterol Lowering Action and Plasma Anti-arteriosclerosis Index Enhancing Action in Mice Test compounds were mixed in a powdery diet (CE-2, Japan Clea) the concentration of 0.01% (compounds of Examples 7, 26, 29 and 32) or 0.005% (compounds of Examples 1, 11, 15, 18, 24, 36, 37, 41, 48, 50, 51, 52, 58, 62, 79, 88, 91, 92, 93, 97, 107, 110, 129 and 130), and freely given to KKA$^y$ mice (11 to 12 weeks old, 5 mice per group), a model of type-2 diabetes mellitus, for four days. During this period, water was given freely. Blood was sampled from orbital venous plexus and components were analyzed using the plasma separated from the blood. Total cholesterol levels were determined by using L type Wako Cholesterol (Wako Pure Chemical Industries, Ltd). Precipitation reagent for HDL cholesterol (Wako Pure Chemical Industries, Ltd.) was added to a part of the plasma to precipitate non-HDL lipoprotein, and cholesterol (HDL cholesterol) in the resulting supernatant was determined. The plasma anti-arteriosclerosis index [(HDL cholesterol/total cholesterol)×100] was calculated by using these cholesterol levels. The results are given in Table 2.

In the Table, "Total cholesterol lowering action (%)" represents the percent reduction (%) of total cholesterol level in the test compound administration group, when the total cholesterol level in the test compound non-administration group is taken as 100%. "Plasma anti-arteriosclerosis index-enhancing action (%)" represents the percent increase (%) of plasma anti-arteriosclerosis index in the test compound administration group, when the plasma anti-arteriosclerosis index in the test compound non-administration group is taken as 100%.

TABLE 2

| test compound (Example number) | total cholesterol lowering action (%) | plasma anti-arteriosclerosis index-enhancing action (%) |
|---|---|---|
| 1 | 7 | 11 |
| 7 | 17 | 15 |
| 11 | 23 | 18 |
| 15 | 25 | 4 |
| 18 | 23 | 12 |
| 24 | 10 | 17 |
| 26 | 20 | 16 |
| 29 | 21 | 20 |
| 32 | 2 | 10 |
| 36 | 19 | 34 |
| 37 | 15 | 19 |
| 41 | 25 | 28 |
| 48 | 17 | 20 |
| 50 | 20 | 15 |
| 51 | 24 | 22 |
| 52 | 26 | 15 |
| 58 | 20 | 21 |
| 62 | 9 | 15 |
| 79 | 39 | 42 |
| 88 | 10 | 22 |
| 91 | 6 | 16 |
| 92 | 15 | 23 |
| 93 | 16 | 17 |
| 97 | 27 | 27 |
| 107 | 13 | 9 |
| 110 | 21 | 24 |
| 129 | 14 | 25 |
| 130 | 16 | 15 |

These results indicated that the compounds of the present invention possess total cholesterol lowering and plasma anti-arteriosclerosis index-enhancing actions. Therefore, the present compounds are proved to be useful as prophylactic or therapeutic agents of arteriosclerosis and the like, by improving plasma lipoprotein profiles of hypercholesterolemia or hypo-HDL-cholesterolemia.

Test Example 3

(PPARγ-RXRα Heterodimer Ligand Activity)

A PPARγ:RXRα:4ERPP/CHO-K1 cells obtained in Reference Example 5 described later were cultured in HAM F12 medium (produced by NISSUI SEIYAKU) containing 10% Fetal bovine serum (produced by Life Technologies, Inc., USA) and then inoculated to a 96-well white plate (produced by Corning Costar Corporation, USA) at the density of $2\times10^4$ cells/well, and cultured in a $CO_2$ gas incubator at 37° C. overnight.

After washing the 96 well white plate with PBS (Phosphate-buffered saline), 90 μl of HAM F12 medium containing 0.1% fatty acid-free bovine serum albumin (BSA) and 10 μl of test compound were added, which was cultured in a $CO_2$ gas incubator at 37° C. for 48 hours. After removing the medium, 40 μl of PIKKAGENE 7.5 (produced by Wako Pure Chemical Industries, Ltd.) was added. After stirring, the luciferase activity was determined using Lumistar (produced by BMG Labtechnologies GmbH, Germany).

A fold induction was calculated based on the luciferase activity of each test compound by taking the luciferase activity in the test compound non administration group as 1. The values of the test compound, concentration and the fold induction were analyzed using PRISM 2.01 (produced by GraphPad Software Inc. USA) to calculate the $EC_{50}$ values, the effective concentration of a test compound for 50% of the maximum fold induction. The results are shown in Table 3.

TABLE 3

| test compound (Example number) | $EC_{50}$ (μM) |
|---|---|
| 1 | 0.29 |
| 7 | 0.036 |
| 11 | 0.062 |
| 15 | 0.20 |
| 18 | 2.90 |
| 24 | 0.16 |
| 26 | 0.035 |
| 29 | 0.025 |
| 32 | 0.077 |
| 36 | 0.033 |
| 37 | 0.61 |
| 41 | 0.015 |
| 48 | 0.018 |
| 50 | 0.18 |
| 51 | 1.20 |
| 52 | 0.23 |
| 58 | 0.12 |
| 60 | 0.0061 |
| 62 | 0.020 |
| 66 | 0.94 |
| 71 | 0.33 |
| 78 | 0.19 |
| 79 | 0.0092 |
| 81 | 0.062 |
| 83 | 0.11 |
| 85 | 0.26 |
| 88 | 0.0071 |
| 90 | 0.052 |
| 91 | 0.0017 |
| 92 | 0.37 |
| 93 | 0.39 |
| 97 | 0.026 |
| 99 | 0.16 |
| 101 | 0.043 |
| 103 | 0.24 |
| 107 | 0.087 |
| 110 | 0.042 |
| 115 | 0.070 |
| 119 | 0.22 |
| 122 | 0.017 |
| 124 | 0.042 |
| 125 | 0.13 |
| 126 | 1.70 |
| 129 | 0.059 |

TABLE 3-continued

| test compound (Example number) | EC$_{50}$ (μM) |
|---|---|
| 130 | 0.011 |
| 132 | 0.11 |

These results indicated that the compounds of the present invention have potent PPARγ-RXRα heterodimer ligand activity.

Reference Example 1

(Human PPARγ Gene Cloning)

A human PPARγ gene was cloned using a heart cDNA (produced by Toyobo Co., Ltd., trade name: QUICK-Clone cDNA) as a template by means of a PCR method employing a primer set shown below which was prepared with reference to the base sequence of PPARγ gene reported by Greene et al (*Gene Expr.*, 1995, Vol. 4(4-5), page 281-299).
PAG-U: 5'-GTG GGT ACC GAA ATG ACC ATG GTT GAC ACA GAG-3' (Sequence ID Number: 1)
PAG-L: 5'-GGG GTC GAC CAG GAC TCT CTG CTA GTA CAA GTC-3' (Sequence ID Number: 2)

The PCR reaction was performed by Hot Start method using AmpliWax PCR Gem 100 (produced by TAKARA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of human heart cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution, mixture described above, added was one unit of AmpliWax PCR Gem 100 (produced by TAKARA SHUZO CO., LTD.), which was treated at 70° C. for 5 minutes and then in ice for 5 minutes. Then the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector (produced by TAKARA SHUZO CO., LTD.) to obtain a plasmid pTBT-hPPARγ.

Reference Example 2

(Human RXRα Gene Cloning)

A human RXRα gene was cloned using a kidney cDNA (produced by Toyobo Co., Ltd., trade name: QUICK-Clone cDNA) as a template by means of a PCR method employing a primer set shown below which was prepared with reference to the base sequence of RXRα gene reported by Mangelsdorf, D. J. et al (*Nature*, 1990, Vol. 345 (6272), page 224-229).

XRA-U: 5'-TTA GAA TTC GAC ATG GAC ACC AAA CAT TTC CTG-3' (Sequence ID Number: 3)

XRA-L: 5'-CCC CTC GAG CTA AGT CAT TTG GTG CGG CGC CTC-3' (Sequence ID Number: 4)

The PCR reaction was performed by Hot Start method using AmpliWax PCR Gem 100 (produced by TAKAEA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of human kidney cDNA (1 ng/ml) as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture for PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector (produced by TAKARA SHUZO CO., LTD.) to obtain a plasmid pTBT-hRXRα.

Reference Example 3

(Construction of Plasmids for Expressing Human PPARγ, RXRα)

A 7.8 kb. FspI-NotI fragment of plasmid pVgRXR (produced by Invitrogen, USA) was ligated to a 0.9 kb FspI-NotI fragment containing RXRα gene of plasmid pTBT-hRXRα obtained in Reference Example 2 to prepare plasmid pVgRXR2. Then, pVgRXR2 was digested with BstXI and then treated with T4DNA polymerase (produced by TAKARA SHUZO CO., LTD.) to obtain a blunt terminal. Then digestion at KpnI gave a 6.5 kb DNA fragment.

On the other hand, plasmid pTBT-hPPARγ obtained in Reference Example 1 was digested with Sal I and then treated with T4DNA polymerase (produced by TAKARA SHUZO CO., LTD.) to obtain a blunt terminal. Then digestion at KpnI gave a 1.4 kb DNA fragment containing human PPARγ gene.

The both DNA fragments were ligated to construct plasmid pVgRXR2-hPPARγ.

Reference Example 4

(Construction of Reporter Plasmids)

A DNA fragment containing PPAR-responding element (PPRE) of an acyl-CoA oxidase was prepared using the following 5'-terminal phosphorylated synthetic DNA.

```
PPRE-U: 5'-pTCGACAGGGGACCAGGACAAAGGTCACGTTCGGGAG-3'  (Sequence ID Number: 5)

PPRE-L: 5'-pTCGACTCCCGAACGTGACCTTTGTCCTGGTCCCCTG-3'  (Sequence ID Number: 6)
```

First, PPRE-U and PPRE-L were annealed and inserted to Sal I site of plasmid pBlue Script SK+. By determining the base sequence of the inserted fragment, plasmid pBSS-PPRE4 in which 4 PPREs were ligated in tandem was selected.

A HSV thymidine kinase minimum promoter (TK promoter) region was cloned using pRL-TK vector (produced by Promega, USA) as a template by means of a PCR method employing a primer set shown below which was prepared with reference to the base sequence of the promoter region of thymidine kinase gene reported by Luckow, B. et al (*Nucleic Acids Res.*, 1987, Vol. 15(13), p. 5490)

```
TK-U:   5'-CCCAGATCTCCCCAGCGTCTTGTCATTG-3'  (Sequence ID Number: 7)

TK-L:   5'-TCACCATGGTCAAGCTTTTAAGCGGGTC-3'  (Sequence ID Number: 8)
```

The PCR reaction was performed by Hot Start method using AmpliWax PCR Gem 100 (TAKARA SHUZO CO., LTD.). First, 2 µl of 10×LA PCR Buffer, 3 µl of 2.5 µM dNTP solution, 2.5 µl each of 12.5 µM primer solutions and 10 µl of sterilized distilled water were mixed to obtain a bottom layer solution mixture. 1 µl of pRL-TK vector (produced by Promega, USA) as a template, 3 µl of 10×LA PCR Buffer, 1 µl of 2.5 mM dNTP solution, 0.5 µl of TaKaRa LA Taq DNA polymerase (produced by TAKARA SHUZO CO., LTD.) and 24.5 µl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture for PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 140 b DNA fragment containing TK promoter was recovered from the gel, and then inserted into pT7 Blue-T vector (produced by TAKARA SHUZO CO., LTD.). By digesting the plasmid thus obtained with the restriction enzymes Bgl II and NcoI, a fragment containing TK promoter was obtained, which was ligated to the Bgl II-NcoI fragment of plasmid pGL3-Basic vector (produced by Promega, USA) to obtain plasmid pGL3-TK.

A 4.9 kb NheI-XhoI fragment of plasmid pGL3-TK thus obtained was ligated to a 200 b NheI-XhoI fragment of plasmid pBSS-PPRE4 to obtain plasmid pGL3-4ERPP-TK.

This plasmid pGL3-4ERPP-TK thus obtained was digested with BamHI (produced by TAKARA SHUZO CO., LTD.) and then treated with T4DNA polymerase (produced by TAKARA SHUZO CO., LTD.) to form a blunt terminal, whereby obtaining a DNA fragment.

On the other hand, pGFP-C1 (produced by Toyobo Co., Ltd.) was digested with Bsu36I (NEB) and then treated with T4DNA polymerase (produced by TAKARA SHUZO CO., LTD.) to form a blunt terminal whereby obtaining a 1.6 kb of a DNA fragment.

The both DNA fragments were ligated to construct a reporter plasmid pGL3-4ERPP-TK neo.

Reference Example 5

(Introduction of Human PPARγ and RXRα Expressing Plasmid and Reporter Plasmid into CHO-K1 Cell and Establishment of Expressed Cell)

After a CHO-K1 cell cultured in a 750 ml tissue culture flask (produced by Corning-Costar Corporation, USA) containing HAM F12 medium (produced by NISSUI SEIYAKU) supplemented with 10% Fetal Bovine Serum (produced by Life Technologies, Inc., USA) was scraped by treating with 0.5 g/L trypsin-0.2 g/L EDTA (ethylenediaminetetraacetic acid) (produced by Life Technologies, Inc., USA), the cell was washed with PBS (phosphate buffered saline) (produced by Life Technologies, Inc., USA), centrifuged (1000 rpm, 5 minutes), and then suspended in PBS. Subsequently, a DNA was introduced into the cell under the condition shown below using GENE PULSER (produced by Bio-Rad Laboratories, USA).

Namely, to a cuvette having a 0.4 cm gap, added were $8 \times 10^6$ cells and 10 µg of plasmid pVgRXR2-hPPARγ obtained in Reference Example 3 and 10 µg of reporter plasmid pGL3-4ERPP-TK neo obtained in Reference Example 4, which was subjected to electroporation at the voltage of 0.25 kV under the capacitance of 960 µF. Subsequently, the cell was transferred into a HAM F12 medium containing 10% Fetal Bovine. Serum and cultured for 24 hours. Then the cell was scraped again and centrifuged, and then suspended in HAM F12 medium containing 10% Fetal Bovine Serum supplemented with 500 µg/ml of GENETICIN (produced by Life Technologies, Inc., USA) and 250 µg/ml of ZEOCIN (produced by Invitrogen, USA). The suspension was diluted to the density of $10^4$ cells/ml, and inoculated to a 96-well plate (produced by Corning Costar Corporation, USA), which was cultured in a $CO_2$ gas incubator at 37° C., whereby obtaining a GENETICIN- and ZEOCIN-resistant transformant.

Subsequently, after the transformant cell line thus obtained was cultured in a 24-well plate (produced by Corning Costar Corporation, USA), selected was a cell line, PPARγ:RXRα:4ERPP/CHO-K1 cell, in which the luciferase was expressed and induced by addition of 10 μM pioglitazone hydrochloride.

Reference Example 6

A mixture of 2,5-dihydroxybenzaldehyde (9.81 g), ethyl iodide (13.29 g), anhydrous potassium carbonate (14.72 g) and N,N-dimethylformamide (100 mL) was stirred at room temperature for 1 hr. The reaction mixture was poured into water and extracted with ethyl acetate. The organic layer was washed with saturated brine, dried over anhydrous magnesium sulfate, and concentrated. The obtained residue was subjected to silica gel column a chromatography to give crystals (4.20 g, 36%) of 2-ethoxy-5-hydroxybenzaldehyde from a fraction eluted with ethyl acetate-hexane (1:4, v/v). Recrystallization from ethyl acetate-hexane gave pale-yellow prism crystals. melting point: 108-109° C.

Reference Example 7

A mixture of 2-ethoxy-5-hydroxybenzaldehyde (3.72 g), benzyl bromide (5.75 g), anhydrous potassium carbonate (3.10 g) and N,N-dimethylformamide (50 mL) was stirred at 90° C. for 3 hrs. The reaction mixture was poured into water and extracted with ethyl acetate. The organic layer was washed with saturated brine, dried over anhydrous magnesium sulfate, and concentrated. The obtained residue was subjected to silica gel column chromatography to give crystals (5.06 g, 88%) of 5-benzyloxy-2-ethoxybenzaldehyde from a fraction eluted with ethyl acetate-hexane (1:4, v/v). Redrystallization from ethyl, acetate-hexane gave colorless prism crystals. melting point: 81-82° C.

Reference Example 8

A mixture of methyl methylthiomethyl sulfoxide. (0.30 g) and finely triturated sodium hydroxide (0.015 g) was stirred at 70° C. for 30 min. To the reaction mixture was added 5-benzyloxy-2-ethoxybenzaldehyde (0.30 g), and the mixture was further stirred at 70° C. for 1.5 hrs. To the reaction mixture was added ethyl acetate, and the organic layer was washed successively with 1N hydrochloric acid and saturated brine, dried over anhydrous magnesium sulfate, and concentrated. A mixture of the obtained residue and 10% hydrogen chloride-methanol (15 mL) was heated under reflux for 15 hrs. To the reaction mixture was added ethyl acetate. The organic layer was washed successively with saturated aqueous sodium hydrogencarbonate and saturated brine, dried over anhydrous magnesium sulfate, and concentrated. The obtained residue was subjected to silica gel column chromatography to give methyl 2-(2-ethoxy-5-hydroxyphenyl)acetate as a colorless oil (0.11 g, 44%) from a fraction eluted with ethyl acetate-hexane (1:4, v/v).

$^1$H-NMR (CDCl$_3$) δ: 1.35 (3H, t, J=7.0 Hz), 3.59 (2H, s), 3.70 (3H, s), 3.96 (2H, t, J=7.0 Hz), 4.81 (1H, s), 6.65-6.76 (3H, m).

Reference Example 9

To a mixture of triethyl phosphonoacetate (1.93 g), 5-benzyloxy-2-ethoxybenzaldehyde (2.00 g) and N,N-di methylformamide (50 mL) was added sodium hydride. (60%, oil, 0.38 g) under ice-cooling. The reaction mixture was stirred at room temperature for 3 hrs. Water was added to the reaction mixture and the mixture was extracted with ethyl acetate. The organic layer was washed successively with water and saturated brine, dried over anhydrous magnesium sulfate, and concentrated. The obtained crystals were washed with hexane to give crystals (2.01 g, 79%) of ethyl (E)-3-(5-benzyloxy-2-ethoxyphenyl)-2-propenoate. Recrystallization from ethyl acetate-hexane gave colorless prism crystals. melting point: 124-125° C.

Reference Example 10

A mixture of ethyl (E)-3-(5-benzyloxy-2-ethoxyphenyl)-2-propenoate (1.85 g), 5% palladium carbon (3.0 g), ethanol (50 mL) and tetrahydrofuran (30 mL) was subjected to catalytic hydrogenation at room temperature and 1 atm. After filtering off the catalyst, the solvents were evaporated under reduced pressure. The obtained residue was subjected to silica gel column chromatography to give ethyl 3-(2-ethoxy-5-hydroxyphenyl)propionate as a colorless oil (1.30 g, 96%) from a fraction eluted with ethyl acetate-hexane (1:4, v/v).

$^1$H-NMR (CDCl$_3$) δ: 1.24 (3H, t, J=7.0 Hz), 1.39 (3H, t, J=7.0 Hz), 2.55-2.63 (2H, m), 2.85-2.93 (2H, m), 3.97 (2H, q, J=7.0 Hz), 4.13 (2H, q, J=7.0 Hz), 4.66 (1H, s), 6.59-6.72 (3H, m).

Reference Example 11

To a mixture of dimethyl sulfoxide (70 mL) and tetrahydrofuran (200 mL) was added sodium hydride (60%, oil, 1.29 g) at room temperature. After stirring at 50° C. for 1.5 hrs., the reaction mixture was cooled to room temperature. Thereto was added ethyl triphenyl phosphonium bromide (9.76 g) and the mixture was stirred at room temperature for 30 min. To this mixture was dropwise added further a solution (10 mL) of 2-benzyloxy-4-methoxymethoxybenzaldehyde (5.50 g) in dimethyl sulfoxide. The mixture was heated under reflux for 1 hr. Water was added to the reaction mixture, and the mixture was neutralized by adding 1N hydrochloric acid (33 mL) and extracted with ethyl acetate. The organic layer was washed successively with water and saturated brine dried over anhydrous magnesium sulfate, and concentrated. The obtained residue was subjected to silica gel column chromatography to give an oil (4.94 g) from a fraction eluted with ethyl acetate-hexane (9, v/v). A mixture of this oil, 5% palladium carbon (10.0 g) and tetrahydrofuran (300 mL) was subjected to catalytic hydrogenation at room temperature and 1 atm. After filtering off the catalyst, the solvent was evaporated under reduced pressure. The obtained residue was subjected to silica gel column chromatography to give 2-hydroxy-4-methoxymethoxy-1-propylbenzene as a colorless oil (3.3 g, 83%) from a fraction eluted with ethyl acetate-hexane (1:6, v/v).

$^1$H-NMR (CDCl$_3$) δ: 0.96 (3H, t, J=7.2 Hz), 1.51-1.66 (2H, m), 2.51 (2H, t, J=7.6 Hz), 3.47 (3H, s), 4.76 (1H, s), 5.13 (2H, s), 6.50-6.59 (2H, m), 7.00 (1H, d, J=8.0 Hz).

Reference Example 12

To a mixture of 2-hydroxy-4-methoxymethoxy-1-propylbenzene (1.50 g), methyl bromoacetate (1.39 g) and N,N-dimethylformamide (20 mL) was added sodium hydride (60%, oil, 1.50 g) under ice-cooling. The reaction mixture was stirred at room temperature for 13 hrs. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give methyl 2-(5-methoxymethoxy-2-propylphenoxy)acetate as a colorless oil (1.60 g, 78%) from a fraction eluted with ethyl acetate-hexane (1:6, v/v).

$^1$H-NMR (CDCl$_3$) δ: 0.94 (3H, t, J=7.2 Hz), 1.51-1.66 (2H, m), 2.58 (2H, t, J=7.6 Hz), 3.47 (3H, s), 3.80 (3H, s), 4.62 (2H, s), 5.12 (2H, s), 6.43 (1H, d, J=2.4 Hz), 6.62 (1H, dd, J=8.4, 2.4 Hz), 7.04 (1H, d, J=8.4 Hz).

Reference Example 13

A mixture of methyl 2-(5-methoxymethoxy-2-propylphenoxy)acetate (1.60 g) and 10% hydrogen chloride-methanol (50 mL) was stirred at room temperature for 3 hrs. The reaction mixture was concentrated, and ethyl acetate was added to the residue. The mixture was washed successively with saturated aqueous sodium hydrogencarbonate and saturated brine, dried over anhydrous magnesium sulfate, and concentrated to give methyl 2-(5-hydroxy-2-propylphenoxy)acetate as a colorless oil (1.17 g, 87%).

$^1$H-NMR (CDCl$_3$) δ: 0.93 (3H, t, J=7.4 Hz), 1.49-1.68 (2H, m), 2.56 (2H, t, J=7.6 Hz), 3.80 (3H, s), 4.61 (2H, s), 5.02 (1H, brs), 6.25 (1H; d, J=2.6 Hz), 6.38 (1H, dd, J=8.2, 2.6 Hz), 6.97 (1H, d, J=8.2 Hz).

Reference Example 14

To a mixture of 2-benzyloxy-5-hydroxybenzaldehyde (16.68 g) and N,N-dimethylformamide (100 mL) was added sodium hydride (60%, oil, 3.07 g) under ice-cooling, and the mixture was stirred at room temperature for 30 min. Chloromethyl methyl ether (11.8 g) was dropwise added to the reaction mixture. The reaction mixture was further stirred at room temperature for 3 hrs. The reaction mixture was poured into water and extracted with ethyl acetate. The organic layer was washed with saturated brine, dried over anhydrous magnesium sulfate, and concentrated. The obtained residue was subjected to silica gel column chromatography to give 2-benzyloxy-5-methoxymethoxybenzaldehyde as a colorless oil (10.32 g, 52%) from a fraction eluted with ethyl acetate-hexane (1:4, v/v).

$^1$H-NMR (CDCl$_3$) δ: 3.47 (3H, s), 5.14 (2H, s), 5.16 (2H, s), 6.97-7.01 (1H, m), 7.19-7.25 (1H, m), 7.34-7.43 (5H, m), 7.42-7.51 (1H, m), 10.50 (1H, s).

Reference Example 15

To a mixture of 2-benzyloxy-5-methoxymethoxybenzaldehyde (10.03 g), ethanol (50 mL) and tetrahydrofuran (100 mL) was added sodium tetrahydroborate (1.43 g) under ice-cooling, and the mixture was stirred at room temperature for 1 hr. To the reaction mixture was added water and the mixture was extracted with ethyl acetate. The organic layer was washed successively with water and saturated brine, dried over anhydrous magnesium sulfate, and concentrated to give (2-benzyloxy-5-methoxymethoxyphenyl)methanol as a colorless oil (10.08 g, 97%).

$^1$H-NMR (CDCl$_3$) δ: 2.31 (1H, t, J=6.6 Hz), 3.49 (3H, s), 4.71 (2H, d, J=6.6 Hz), 5.09 (2H, s), 5.13 (2H, s), 6.85-6.98 (2H, m), 7.04-7.06 (1H, m), 7.33-7.43 (5H, m).

Reference Example 16

A mixture of (2-benzyloxy-5-methoxymethoxyphenyl)methanol (8.0 g), triphenylphosphine (7.66 g), carbon tetrabromide (9.68 g) and N,N-dimethylformamide (100 mL) was stirred at room temperature for 1.5 hrs. To the reaction mixture was added water and the mixture was extracted with ethyl acetate. The organic layer was washed successively with water and saturated brine, dried over anhydrous magnesium sulfate, and concentrated. The obtained residue was subjected to silica gel column chromatography to give crystals (4.49 g, 46%) of 1-benzyloxy-2-bromomethyl-4-methoxymethoxybenzene from a fraction eluted with ethyl acetate-hexane (1:4, v/v). Recrystallization from ethyl acetate-hexane gave colorless prism crystals. melting point: 55-57° C.

Reference Example 17

To a mixture of 1-benzyloxy-2-bromomethyl-4-methoxymethoxybenzene (0.30 g) and dimethyl sulfoxide (3 mL) was added an aqueous solution (0.3 mL) of sodium cyanide (0.05 g) at room temperature and the mixture was stirred for 13 hrs. To the reaction mixture was added water and the mixture was extracted with ethyl acetate. The organic layer was washed successively with water and saturated brine, dried over anhydrous magnesium sulfate, and concentrated to give 2-(2-benzyloxy-5-methoxymethoxyphenyl)acetonitrile as a colorless oil (0.23 g, 92%).

$^1$H-NMR (CDCl$_3$) δ: 3.48 (3H, s), 3.69 (2H, s), 5.07 (2H, s), 5.12 (2H, s), 6.86 (1H, d, J=9.0 Hz), 6.97 (1H, dd, J=9.0, 2.6 Hz), 7.09 (1H, d, J=2.6 Hz), 7.32-7.45 (5H, m).

Reference Example 18

A mixture of 2-(2-benzyloxy-5-methoxymethoxyphenyl)acetonitrile (2.95 g), 5% palladium carbon (2.0 g) and tetrahydrofuran (100 mL) was subjected to catalytic hydrogenation at room temperature and 4.8 atm. After filtering off the catalyst, the solvent was evaporated under reduced pressure to give crystals (1.88 g, 94%) of 2-(2-hydroxy-5-methoxymethoxyphenyl)acetonitrile. Recrystallization from ethyl acetate-hexane gave pale-brown prism crystals. melting point: 68-69° C.

Reference Example 19

To a mixture of 4-(4-chloromethylphenoxymethyl)-5-methyl-2-phenyloxazole (1.95 g), 2-(2-hydroxy-5-methoxymethoxyphenyl)acetonitrile (1.0 g) and N,N-dimethylformamide (50 mL) was added sodium hydride (60%, oil, 0.23 g) under ice-cooling, and the mixture was stirred at 80° C. for 1 hr. The reaction mixture was poured into water and extracted with ethyl acetate. The organic, layer was washed successively with water, 2N aqueous sodium hydroxide solution and saturated brine, and dried over anhydrous magnesium sulfate. After concentration of the organic layer, the residue was subjected to silica gel column chromatography to give crystals (1.40 g, 57%) of 2-[5-methoxymethoxy-2-[4-[(5-methyl-2-phenyl-4-oxazolyl)methoxy]benzyloxy]phenyl]acetonitrile from a fraction eluted with ethyl acetate-hexane (1:3, v/v). Recrystallization from ethyl acetate-hexane gave colorless prism crystals. melting point: 123-124° C.

Reference Example 20

A mixture of 2-[5-methoxymethoxy-2-[4-[(5-methyl-2-phenyl-4-oxazolyl)methoxy]benzyloxy]phenyl]acetonitrile (1.83 g), 10% sulfuric acid (5 mL) and tetrahydrofuran (50 mL) was heated under reflux for 3 hrs. Water was added to the reaction mixture and the mixture was extracted with ethyl acetate. The organic layer was washed successively with saturated aqueous sodium hydrogencarbonate and saturated brine, dried over anhydrous magnesium sulfate, and concentrated to give crystals (1.13 g, 68%) of 2-[5-hydroxy-2-[4-[(5-methyl-2-phenyl-4-oxazolyl)methoxy]benzyloxy]phenyl]acetonitrile. Recrystallization from ethyl acetate-hexane gave colorless prism crystals. melting point: 185-186° C.

Reference Example 21

A mixture of 2-[5-hydroxy-2-[4-[(5-methyl-2-phenyl-4-oxazolyl)methoxy]benzyloxy]phenyl]acetonitrile (0.40 g), benzyl bromide (0.48 g), anhydrous potassium carbonate (0.14 g) and N,N-dimethylformamide (5 mL) was stirred at 90° C. for 3 hrs. The reaction mixture was poured into water and extracted with ethyl acetate. The organic layer was washed successively with water and saturated brine, dried over anhydrous magnesium sulfate, and concentrated. The obtained residue was subjected to silica gel column chromatography to give crystals (0.27 g, 55%) of 2-[5-benzyloxy-2-[4-[(5-methyl-2-phenyl-4-oxazolyl)methoxy]benzyloxy]phenyl]acetonitrile from a fraction eluted with ethyl acetate-hexane (1:4, v/v). Recrystallization from ethyl acetate-hexane gave colorless prism crystals. melting point: 130-131° C.

Reference Example 22

A mixture of methyl methylthiomethyl sulfoxide (11.7 g), 40% solution of benzyltrimethylammonium hydroxide in methanol (7.5 mL), 5-chloro-2-methoxymethoxybenzaldehyde (9.43 g) and tetrahydrofuran (150 mL) was heated under reflux for 20 hrs. Water was added to the reaction mixture and the mixture was extracted with ethyl acetate. The organic layer was washed with saturated brine, dried over anhydrous magnesium sulfate, and concentrated. A mixture of the obtained residue and 10% hydrogen chloride-methanol (100 mL) was heated under reflux for 15 hrs. The reaction mixture was concentrated, and ethyl acetate was added to the residue. The organic layer was washed successively with water and saturated brine, dried over anhydrous magnesium sulfate, and concentrated. The obtained residue was subjected to silica gel column chromatography to give crystals (7.24 g, 91%) of methyl 2-(5-chloro-2-hydroxyphenyl)acetate from a fraction eluted with ethyl acetate-hexane (1:4, v/v). Recrystallization from ethyl acetate-hexane gave colorless prism crystals. melting point: 84-85° C.

Reference Example 23

To a mixture of 4-(4-chloromethylphenoxymethyl)-5-methyl-2-phenyloxazole (4.52 g), methyl 5-hydroxy-3-pyridinecarboxylate (2.0 g), and N,N-dimethylformamide (30 mL) was added sodium hydride (60%, oil, 0.58 g) under ice-cooling, and the mixture was stirred at room temperature for 3 hrs. The reaction mixture was poured into water, and the precipitated crystals were collected by filtration. The crystals were subjected to silica gel column chromatography to give crystals (2.41 g, 0.43%) of methyl 5-[4-[(5-methyl-2-phenyl-4-oxazolyl)methoxy]benzyloxy]-3-pyridinecarboxylate from a fraction eluted with ethyl acetate-hexane (1:1, v/v). Recrystallization from ethyl acetate-hexane gave colorless prism crystals. melting point: 138-139° C.

Reference Example 24

To a mixture of methyl 5-[4-[(5-methyl-2-phenyl-4-oxazolyl)methoxy]benzyloxy]-3-pyridinecarboxylate (2.09 g), sodium tetrahydroborate (0.93 g) and tetrahydrofuran (100 mL) was dropwise added methanol (10 mL) at 50° C., and the mixture was stirred at 50° C. for 1 hr. To the reaction mixture was added water and the mixture was extracted with ethyl acetate. The organic layer was washed with saturated brine, dried over anhydrous magnesium sulfate, and concentrated to give crystals (1.85 g, 94%) of [5-[4-[(5-methyl-2-phenyl-4-oxazolyl)methoxy]benzyloxy]-3-pyridyl]methanol. Recrystallization from ethyl acetate-hexane gave colorless prism crystals. melting point: 128-130° C.

Reference Example 25

To a mixture of [5-[4-[(5-methyl-2-phenyl-4-oxazolyl)methoxy]benzyloxy]-3-pyridyl]methanol (1.68 g), triethylamine (0.85 g) and ethyl acetate (100 mL) was dropwise added methanesulfonyl chloride (0.96 g) at room temperature, and the mixture was stirred at room temperature for 15 hrs. The reaction mixture was washed successively with water, saturated aqueous sodium hydrogencarbonate, 1N hydrochloric acid and saturated brine, dried over anhydrous magnesium sulfate, and concentrated to give pale-yellow crystals. To a mixture of the crystals and dimethyl sulfoxide (20 mL) was added an aqueous solution (2 mL) of sodium cyanide (0.41 g) at room temperature and the mixture was stirred at room temperature for 2 days. To the reaction mixture was added water and the mixture was extracted with ethyl acetate. The organic layer was washed successively with water and saturated brine, dried over anhydrous magnesium sulfate, and concentrated. The obtained residue was subjected to silica gel column chromatography to give crystals (0.76 g, 44%) of 2-[5-[4-[(5-methyl-2-phenyl-4-oxazolyl)methoxy]benzyloxy]-3-pyridyl]acetonitrile from a fraction eluted with ethyl acetate-hexane (2:1, v/v). Recrystallization from ethyl acetate-hexane gave pale-yellow prism crystals. melting point: 137-138° C.

Reference Example 26

To a mixture of 4-(4-chloromethylphenoxymethyl)-5-methyl-2-phenyloxazole (4.52 g), 2-(2-hydroxy-1-naphthyl)acetonitrile (0.58 g) and N,N-dimethylformamide (30 mL) was added sodium hydride (60%, oil, 0.14 g) under ice-cooling, and the mixture was stirred at room temperature for 1 hr. To the reaction mixture was added water and the mixture was extracted with ethyl acetate. The organic layer was washed successively with water and saturated brine, dried over anhydrous magnesium sulfate, and concentrated. The obtained residue was subjected to silica gel column chromatography to give crystals (1.11 g, 76%) of 2-[2-[4-[(5-methyl-2-phenyl-4-oxazolyl)methoxy]benzyloxy]-1-naphthyl]acetonitrile from a fraction eluted with ethyl acetate-hexane (1:2, v/v). Recrystallization from ethyl acetate-hexane gave pale-yellow prism crystals. melting point: 178-179° C.

Reference Example 27

To a solution of 2-(5-methyl-2-phenyl-4-oxazolyl-methoxy)pyridine-5-carbaldehyde (13.0 g) in tetrahydrofuran (150 ml)-methanol (10 ml) was gradually added sodium borohydride (835 mg) at 0° C. After stirring for 30 min., water was added to the reaction mixture, and the mixture was extracted with ethyl acetate. The organic layer was washed with water, dried over anhydrous magnesium sulfate, and concentrated to give crystals of 2-(5-methyl-2-phenyl-4-oxazolylmethoxy)pyridine-5-methanol. Recrystallization from acetone-isopropyl ether gave colorless prism crystals (12.4 g, yield 95%). melting point: 121-122° C.

Reference Example 28

To a mixture of 2-(5-methyl-2-phenyl-4-oxazolyl-methoxy)pyridine-5-methanol (12.2 g) and toluene (200 ml) was added thionyl chloride (5.39 g), and the mixture was stirred at room temperature for 1 hr. Iced water was added to the reaction mixture, and after neutralization with saturated aqueous sodium hydrogencarbonate, the mixture was extracted with ethyl acetate. The organic layer was washed with water, dried over anhydrous magnesium sulfate, and concentrated. The residue was subjected to silica gel column chromatography to give crystals (11.7 g, yield 90%) of 5-chloromethyl-2-(5-methyl-2-phenyl-4-oxazolylmethoxy)pyridine from a fraction eluted with ethyl acetate-hexane (1:3, v/v). Recrystallization from ethyl acetate-hexane gave colorless prism crystals. melting point: 86-87° C.

Reference Example 29

A mixture of 4-chloromethyl-5-methyl-2-phenyloxazole (13.4 g), methyl 5-hydroxypyridine-3-carboxylate (9.84 g), anhydrous potassium carbonate (8.90 g) and N,N-dimethylformamide (100 mL) was stirred overnight at 80° C. The reaction mixture was poured into water and extracted with ethyl acetate. The organic layer was washed with water, dried over anhydrous magnesium sulfate, and concentrated. The obtained residue was subjected to silica gel column chromatography to give crystals (12.42 g, 59%) of methyl 5-(5-methyl-2-phenyl-4-oxazolyl)methoxy-3-pyridinecarboxylate from a fraction eluted with ethyl acetate-hexane (1:2, v/v). Recrystallization from ethyl acetate-hexane gave colorless prism crystals. melting point: 119-120° C.

Reference Example 30

To a mixture of methyl 5-(5-methyl-2-phenyl-4-oxazolyl)methoxy-3-pyridinecarboxylate (10.70 g) and tetrahydrofuran (100 mL) was added lithium aluminum hydride (1.02 g) under ice-cooling, and the mixture was stirred at room temperature for 10 min. To the mixture was added sodium sulfate 10 hydrate (8.38 g), and the mixture was further stirred at room temperature for 30 min. The insoluble materials were removed by filtration, and the filtrate was concentrated. The obtained residue was subjected to silica gel column chromatography to give crystals (8.93 g, 91%) of [5-(5-methyl-2-phenyl-4-oxazolylmethoxy)-3-pyridyl]methanol from a fraction eluted with ethyl acetate-hexane (1:1, v/v). Recrystallization from ethyl acetate-hexane gave colorless prism crystals. melting point: 111-112° C.

Reference Example 31

A mixture of 4-(4-chloromethylphenoxymethyl)-5-methyl-2-phenyloxazole-(2.76 g), 2,4-dihydroxybenzophenone (2.00 g), anhydrous potassium carbonate (1.29 g) and acetone (50 mL) was heated under reflux for 0.15 hrs. The reaction mixture was poured into water and extracted with ethyl acetate. The organic layer was washed with saturated brine, dried over anhydrous magnesium sulfate, and concentrated to give crystals (1.72 g, 40%) of 4-[4-(4-benzoyl-3-hydroxyphenoxymethyl)phenoxymethyl]-5-methyl-2-phenyloxazole. Recrystallization from ethyl acetate-hexane gave pale-yellow prism crystals. melting point: 160-161° C.

Reference Example 32

To a mixture of 4-methoxy-3-(5-methyl-2-phenyl-4-oxazolylmethoxy)benzaldehyde (3.23 g), tetrahydrofuran (15 ml) and methanol (15 mL) was added sodium borohydride (0.378 g) at room temperature and the mixture was stirred at room temperature for 30 min. The reaction mixture was poured into water and extracted with ethyl acetate. The organic layer was washed with saturated brine, dried over an hydrous magnesium sulfate, and concentrated to give crystals of [[4-methoxy-3(5-methyl-2-phenyl-4-oxazolyl)methoxy]phenyl]methanol. Recrystallization from tetrahydrofuran-hexane gave pale-yellow plate crystals (3.22 g, 99%). melting point: 144-145° C.

Reference Example 33

To a mixture of 4-[[2-(2-furyl)-5-methyl-4-oxazolyl]methoxy]benzaldehyde (37.8 g), tetrahydrofuran (140 ml) and methanol (60 mL) was added sodium borohydride (2.53 g) under ice-cooling, and the mixture was stirred at room temperature for 1 hr. The reaction mixture was poured into iced water, and the precipitated solid was collected by filtration, and dried with air to give crystals (34.6 g, 91%) of [4-[[2-(2-furyl)-5-methyl-4-oxazolyl]methoxy]phenyl]methanol. Recrystallization from ethyl acetate-hexane gave colorless prism crystals. melting point: 91-92° C.

Reference Example 34

To a mixture of [4-[[2-(2-furyl)-5-methyl-4-oxazolyl]methoxy]phenyl]methanol (34.5 g), tetrahydrofuran (100 mL) and toluene (300 mL) was added thionyl chloride (17.3 g) under ice-cooling, and the mixture was stirred at room temperature for 1 hr. The reaction mixture was concentrated and the residue was dissolved in ethyl acetate. The mixture was washed successively with saturated aqueous sodium hydrogencarbonate and water, dried over anhydrous magnesium sulfate, and concentrated. The residue was washed with diisopropyl ether to give colorless crystals (31.1 g, 85%) of 4-(4-chloromethylphenoxymethyl)-2-(2-furyl)-5-methylthiazole. Recrystallization from ethyl acetate-diisopropyl ether gave colorless prism crystals. melting point: 115-116° C.

Reference Example 35

To a mixture of 4-[(2-phenyl-4-thiazolyl)methoxy]benzaldehyde (6.35 g), tetrahydrofuran (30 ml) and methanol (20 mL) was added sodium borohydride (0.45 g) under ice-cooling, and the mixture was stirred at room temperature for 30 min. Dilute hydrochloric acid and water were added to acidify the reaction mixture. The precipitated solid was collected by filtration, and dried with air to give crystals (5.76 g, 90%) of [4-[(2-phenyl-4-thiazolyl)methoxy]phenyl]methanol. Recrystallization from ethyl acetate-hexane gave colorless needle crystals. melting point: 145-146° C.

Reference Example 36

To a mixture of [4-[(2-phenyl-4-thiazolyl)methoxy]phenyl]methanol (4.35 g), tetrahydrofuran (50 mL) and toluene (50 mL) was added a solution (5 mL) of thionyl chloride (1.5 mL) in toluene under ice-cooling, and the mixture was stirred at room temperature for 2 hrs. The reaction mixture was concentrated and the residue was dissolved in ethyl acetate. The mixture was washed successively with saturated aqueous sodium hydrogencarbonate and saturated brine, dried over anhydrous magnesium sulfate, and concentrated to give colorless crystals (4.10 g, 89%) of 4-(4-chloromethylphenoxymethyl)-2-phenylthiazole. melting point: 98-99° C.

Reference Example 37

A mixture of 4-chloromethyl-5-methyl-2-phenylthiazole (5.40 g), 4-hydroxybenzaldehyde (2.91 g), anhydrous potassium carbonate (4.95 g) and N,N-dimethylformamide (50 mL) was stirred at 80° C. for 3 hrs. The reaction mixture was poured into water, and the precipitated solid was collected by filtration, and dried with air to give crystals (6.85 g, 93%) of 4-[(5-methyl-2-phenyl-4-thiazolyl)methoxy]benzaldehyde. Recrystallization from ethyl aceetate-hexane gave colorless prism crystals. melting point: 18-119° C.

Reference Example 38

To a mixture of 4-[(5-methyl-2-phenyl-4-thiazolyl)methoxy]benzaldehyde (6.00 g), tetrahydrofuran (30 ml) and methanol (20 mL) was added sodium borohydride (0.38 g) under ice-cooling, and the mixture was stirred at room temperature for 30 min. Dilute hydrochloric acid and water were added to acidify the reaction mixture, and the precipitated solid was collected by filtration, and dried with air to give crystals (5.68 g, 94%) of [4-[(5-methyl-2-phenyl-4-thiazolyl)methoxy]phenyl]methanol. Recrystallization from ethyl acetate-hexane gave colorless prism crystals. melting point: 94-95° C.

Reference Example 39

To a mixture of [4-[(5-methyl-2-phenyl-4-thiazolyl)methoxy]phenyl]methanol (4.50 g), tetrahydrofuran (50 mL) and toluene (50 mL) was added a solution (5 mL) of thionyl chloride (1.5 mL) in toluene under ice-cooling, and the mixture was stirred at room temperature for 2 hrs. The reaction mixture was concentrated and the residue was dissolved in ethyl acetate. The mixture was washed successively with saturated aqueous sodium hydrogencarbonate and saturated brine, dried over anhydrous magnesium sulfate, and concentrated to give colorless crystals (4.50 g, 94%) of 4-(4-chloromethylphenoxymethyl)-5-methyl-2-phenylthiazole. melting point: 100-101° C.

Reference Example 40

A mixture of 4-(4-chloromethylphenoxymethyl)-5-methyl-2-phenyloxazole (11.13 g), 2-hydroxy-1-naphthaldehyde (5.96 g), anhydrous potassium carbonate (5.03 g) and N,N-dimethylformamide (50 mL) was stirred at room temperature for 2 days. The reaction mixture was poured into water, and the precipitated solid was collected by filtration, and dried with air to give crystals (13.83 g, 89%) of 2-[4-[(5-methyl-2-phenyl-4-oxazolyl)methoxy]benzyloxy]-1-naphthaldehyde. Recrystallization from ethyl acetate-hexane gave pale-yellow prism crystals. melting point: 141-142° C.

Reference Example 41

A mixture of 5-methoxy-2-methoxymethoxybenzaldehyde (9.25 g), methyl methylthiomethyl sulfoxide (11.7 g), 40% solution of benzyltrimethylammonium hydroxide in methanol (10 mL) and tetrahydrofuran (200 mL) heated under reflux for 20 hrs. Water was added to the reaction mixture and the mixture was extracted with ethyl acetate. The organic layer was washed with saturated brine, dried over anhydrous magnesium sulfate, and concentrated. A mixture of the obtained residue and 10% hydrogen chloride-methanol (80 mL) was heated under reflux for 15 hrs. The reaction mixture was concentrated, and ethyl acetate was added to the residue. The organic layer was washed successively with water and saturated brine, dried over anhydrous magnesium sulfate, and concentrated. The obtained residue was subjected to silica gel column chromatography to give crystals (4.88 g, 53%) of methyl 2-(2-hydroxy-5-methoxyphenyl)acetate from a fraction eluted with ethyl acetate-hexane (1:4, v/v). Recrystallization from ethyl acetate-hexane gave colorless prism crystals. melting point: 69-70° C.

Reference Example 42

A mixture of 2-benzyloxy-5-hydroxybenzaldehyde (8.93 g), ethyl iodide (7.31 g), anhydrous potassium carbonate (5.40 g) and N,N-dimethylformamide (50 mL) was stirred at room temperature for 15 hrs. The reaction mixture was poured into water and extracted with ethyl acetate. The organic layer was washed with saturated brine, dried over anhydrous magnesium sulfate, and concentrated. The obtained residue was subjected to silica gel column chromatography to give 2-benzyloxy-5-ethoxybenzaldehyde as a colorless oil (9.25 g, 92%) from a fraction eluted with ethyl acetate-hexane (1:9, v/v).

$^1$H-NMR (CDCl$_3$) δ: 1.39 (3H, t, J=7.0 Hz), 4.02 (2H, q, J=7.0 Hz), 5.14 (2H, s), 6.96-7.13 (2H, m), 7.30-7.42 (6H, m), 10.50 (1H, s).

Reference Example 43

A mixture of methyl methylthiomethyl sulfoxide (1.94 g) and finely triturated sodium hydroxide (0.01 g) was stirred at 70° C. for 30 min. 2-Benzyloxy-5-ethoxybenzaldehyde (2.0 g) and methanol (10 mL) were added to the reaction mixture, and the mixture was further heated under reflux for 24 hrs. To the reaction mixture was added ethyl acetate, and the organic layer was washed successively with 1N hydrochloric acid and saturated brine, dried over anhydrous magnesium sulfate, and concentrated. A mixture of the obtained residue and 10% hydrogen chloride-methanol (100 mL) was heated under reflux for 24 hrs. The reaction mixture was concentrated, and then ethyl acetate was added to the residue. The organic layer was washed successively with saturated aqueous sodium hydrogencarbonate and saturated brine, dried over anhydrous magnesium sulfate, and concentrated. The obtained residue was subjected to silica gel column chromatography to give methyl 2-(2-benzyloxy-5- ethoxyphenyl)acetate as a yellow oil (1.60 g, 69%) from a fraction eluted with ethyl acetate-hexane (1:3, v/v).

$^1$H-NMR (CDCl$_3$) δ: 1.38 (3H, t, J=7.0 Hz), 3.63 (3H, s), 3.65 (2H, s), 3.98 (2H, q, J=7.0 Hz), 5.02 (2H, s), 6.73-6.87 (3H, m), 7.26-7.42 (5H, m).

Reference Example 44

A mixture of methyl 2-(2-benzyloxy-5-ethoxyphenyl)acetate (1.60 g), 5% palladium carbon (3.0 g) and tetrahydrofuran (50 mL) was subjected to catalytic hydrogenation at room temperature and 1 atm. After filtering off the catalyst, the solvent was evaporated under reduced pressure. Hexane was added to the obtained crystals and the mixture was filtrated to give crystals (0.82 g) of methyl 2-(2-hydroxy-5-ethoxyphenyl)acetate. Recrystallization from diisopropyl ether-hexane gave pale-yellow prism crystals. melting point: 83-84° C.

Reference Example 45

To a mixture of triethyl phosphonoacetate (3.86 g), 2-benzyloxy-5-ethoxybenzaldehyde (2.00 g) and N,N-dimethylformamide (100 mL) was added sodium hydride (60%, oil, 0.75 g) under ice-cooling. The reaction mixture was stirred at room temperature for 3 hrs. Water was added to the reaction mixture and the mixture was extracted with ethyl acetate. The organic layer was washed successively with water and saturated brine, dried over anhydrous magnesium sulfate, and concentrated. The obtained residue was subjected to silica gel column chromatography to give ethyl (E)-3-(2-benzyloxy-5-ethoxyphenyl)-2-propenoate as a colorless oil (4.58 g, 90%) from a fraction eluted with ethyl acetate-hexane (1:6, v/v).

$^1$H-NMR (CDCl$_3$) δ: 1.33 (3H, t, J=7.0 Hz), 1.39 (3H, t, J=7.0 Hz), 3.99 (2H, q, J=7.0 Hz), 4.25 (2H, q, J=7.0 Hz), 5.10 (2H, s), 6.48 (1H, d, J=16.0 Hz), 6.85-6.91 (2H, m), 7.06-7.08 (1H, m), 7.25-7.44 (5H, m), 8.06 (1H, d, J=16.0 Hz),

Reference Example 46

A mixture of ethyl (E)-3-(2-benzyloxy-5-ethoxyphenyl)-2-propenoate (4.58 g), 5% palladium carbon (6.0, g) and tetrahydrofuran (100 mL) was subjected to catalytic hydrogenation at room temperature and 1 atm. After filtering off the catalyst, the solvent was evaporated under reduced pressure. The obtained residue was subjected to silica gel column chromatography to give ethyl 3-(5-ethoxy-2-hydroxyphenyl)propionate as a colorless oil (3.15 g, 94%) from a fraction eluted with ethyl acetate-hexane (1:6, v/v).

$^1$H-NMR (CDCl$_3$) δ: 1.23 (3H, t, J=7.0 Hz), 1.37 (3H, t, J=7.0 Hz), 2.66-2.73 (2H, m), 2.82-2.89 (2H, m), 3:96 (2H, q, J=7.0 Hz), 4.14 (2H, q, J=7.0 Hz), 6.64-6.69 (2H, m), 6.77-6.84 (2H, m).

Reference Example 47

To a mixture of [4-[(5-methyl-2-phenyl-4-oxazolyl)methoxy]phenyl]methanol (10.0 g), 2-chloro-3-cyanopyridine (4.27 g) and N,N-dimethylformamide (100 mL) was added sodium hydride (60%, oil, 1.48 g) under ice-cooling. The reaction mixture was stirred at room temperature for 15 hrs. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (10.98 g, 90%) of 3-cyano-2-[4-[(5-methyl-2-phenyl-4-oxazolyl)methoxy]benzyloxy]pyridine from a fraction eluted with ethyl acetate-hexane (1:3, v/v). Recrystallization from ethyl acetate-hexane gave colorless needle crystals. melting point: 119-120° C.

Reference Example 48

To a mixture of 3-cyano-2-[4-[(5-methyl-2-phenyl-4-oxazolyl)methoxy]benzyloxy]pyridine (8.42 g) and anhydrous toluene (300 mL) was dropwise added a solution (1M, 46.6 mL) of diisobutylaluminum hydride in hexane at −78° C. The reaction mixture was allowed to warm to room temperature over 1 hr with stirring. A saturated aqueous ammonium chloride solution (70 L) was dropwise added to the mixture, and the mixture was further stirred at room temperature for 30 min. Ethyl acetate (300 mL) was added to the mixture and, after stirring the mixture at room temperature for 30 min., insoluble materials were filtered off. The filtrate, was washed with saturated brine, dried over anhydrous magnesium sulfate, and concentrated. The obtained residue was subjected to silica gel column chromatography to give crystals (6.49 g, 76%) of 2-[4-[(5-methyl-2-phenyl-4-oxazolyl)methoxy]benzyloxy]-3-pyridinecarbaldehyde from a fraction eluted with ethyl acetate-hexane (1:4, v/v). Recrystallization from ethyl acetate-hexane gave colorless prism crystals. melting point: 97-98° C.

Reference Example 49

To a mixture of 2-[4-[(5-methyl-2-phenyl-4-oxazolyl)methoxy]benzyloxy]-3-pyridinecarbaldehyde (0.40 g), ethanol (10 mL) and tetrahydrofuran (10 mL) was added sodium borohydride (0.04 g) at 0° C., and the mixture was stirred at room temperature for 1 hr. Water was added to the reaction mixture, and the precipitated solid was collected by filtration, and dried with air to give crystals (0.35 g, 88%) of [2-[4-[(5-methyl-2-phenyl-4-oxazolyl)methoxy]benzyloxy]-3-pyridyl]methanol. Recrystallization from ethyl acetate-hexane gave colorless prism crystals. melting point: 139-140° C.

Reference Example 50

To a mixture of [2-[4-[(5-methyl-2-phenyl-4-oxazolyl)methoxy]benzyloxy]-3-pyridyl]methanol (1.50 g), triethylamine (0.75 g) and ethyl acetate (150 mL) was dropwise added methanesulfonyl chloride (0.85 g) at room temperature and the mixture was stirred at room temperature for 15 hrs. The reaction mixture was washed successively with water, saturated aqueous sodium hydrogencarbonate and saturated brine, dried over anhydrous magnesium sulfate, and concentrated to give an oil. A mixture of this oil, sodium cyanide (0.72 g), benzyltributylammonium chloride (0.59 g), acetonitrile (20 mL) and water (10 ml) was stirred at room temperature for 15 hrs. The reaction mixture was concentrated, and ethyl acetate was added to the residue. The organic layer was washed with saturated brine, dried over anhydrous magnesium sulfate, and concentrated. The obtained residue was subjected to silica gel column chromatography to give crystals (0.55 g, 36%) of 2-[2-[4-[(5-methyl-2-phenyl-4-oxazolyl)methoxy]benzyloxy]-3-pyridyl]acetonitrile from a fraction eluted with ethyl acetate-hexane (1:4, v/v). Recrystallization from ethyl acetate-hexane gave colorless prism crystals. melting point: 149-150° C.

Reference Example 51

To a mixture of 4-(4-chloromethylphenoxymethyl)-5-methyl-2-phenyloxazole (0.97 g) methyl 3-hydroxypyridine 2-carboxylate (0.40 g), and N,N-dimethylformamide (30 mL) was added sodium hydride (60%, oil, 0.12 g) under ice-cooling. The reaction mixture was stirred at room temperature for 15 hrs. Water was added to the reaction mixture and the mixture was extracted with ethyl acetate. The organic layer was washed successively with water and saturated brine, dried over anhydrous magnesium sulfate, and concentrated. The obtained residue was subjected to silica gel column chromatography to give methyl 3-[4-[(5-methyl-2-phenyl-4-oxazolyl)methoxy]benzyloxy]pyridine-2-carboxylate as a colorless oil (0.32 g, 29%) from a fraction eluted with ethyl acetate-hexane (2:3, v/v).

$^1$H-NMR (CDCl$_3$) δ: 2.44 (3H, s), 3.98 (3H, s), 5.00 (2H, s), 5.16 (2H, s), 7.01-7.06 (2H, m), 7.36-7.47 (7H, m), 7.99-8.04 (2H, m), 8.28 (1H, t, J=3.2 Hz).

Reference Example 52

To a mixture of methyl 3-[4-[(5-methyl-2-phenyl-4-oxazolyl)methoxy]benzyloxy]-2-pyridinecarboxylate (0.30 g), sodium borohydride (0.13 g) and tetrahydrofuran (10 mL) was dropwise added methanol (2 mL) at 50° C., and the mixture was stirred at 50° C. for 1 hr. To the reaction mixture was added water and the mixture was extracted with ethyl acetate. The organic layer was washed with saturated brine, dried over anhydrous magnesium sulfate, and concentrated to give crystals (0.23 g, 82%) of [3-[4-[(5-methyl-2-phenyl-4-oxazolyl)methoxy]benzyloxy]-2-pyridyl]methanol. Recrystallization from ethyl acetate-hexane gave colorless prism crystals. melting point: 118-119° C.

Reference Example 53

To a mixture of [3-[4-[(5-methyl-2-phenyl-4-oxazolyl)methoxy]benzyloxy]-2-pyridyl]methanol (0.74 g), triethylamine (0.36 g) and ethyl acetate (50 mL) was dropwise added methanesulfonyl chloride (0.41 g) at room temperature and the mixture was stirred at room temperature for 14 hrs. The reaction mixture was washed successively with water saturated aqueous sodium hydrogencarbonate, 1N hydrochloric acid and saturated brine, dried over anhydrous magnesium sulfate, and concentrated to give a yellow oil. To a mixture of this yellow oil and dimethyl sulfoxide (20 mL) was added an aqueous solution (2 mL) of sodium cyanide (0.18 g) at room temperature and the mixture was stirred at room temperature for 2 days. Water was added to the reaction mixture and the mixture was extracted with ethyl acetate. The organic layer was washed successively with water and saturated brine, dried over anhydrous magnesium sulfate, and concentrated. The obtained residue was subjected to silica gel column chromatography to give crystals (0.60 g, 81%) of 2-[3-[4-[(5-methyl-2-phenyl-4-oxazolyl)methoxy]benzyloxy]-2-pyridyl]acetonitrile from a fraction eluted with ethyl acetate-hexane (1:1, v/v). Recrystallization from ethyl acetate-hexane gave pale-brown prism crystals. melting point: 138-139° C.

Reference Example 54

To a mixture of (5-methyl-2-phenyl-4-oxazolyl)methanol (9.46 g) and N,N-dimethylformamide (0.50 mL) was added sodium hydride (60%, oil, 2.40 g) at room temperature and the reaction mixture was stirred at room temperature until generation of hydrogen ended. The mixture was added to a solution of methyl 2-chloropyridine-4-carboxylate (8.58 g) in tetrahydrofuran (50 ml) at room temperature and the resulting mixture was further stirred at room temperature for 1 hr. Water was added to the reaction mixture and the mixture was extracted with ethyl acetate. The organic layer was washed successively with water and saturated brine, dried over anhydrous magnesium sulfate, and concentrated. The obtained residue was subjected to silica gel column chromatography to give crystals of methyl 2-(5-methyl-2-phenyl-4-oxazolyl)methoxy-4-pyridinecarboxylate from a fraction eluted with ethyl acetate-hexane (1:3, v/v). Recrystallization from ethyl acetate-hexane gave colorless needle crystals (2.19 g, 14%). melting point: 106-107° C.

Reference Example 55

To a mixture of methyl 2-(5-methyl-2-phenyl-4-oxazolyl)methoxy-4-pyridinecarboxylate (1.95 g) and tetrahydrofuran (20 mL) was added lithium aluminum hydride (0.228 g) under ice-cooling, and the mixture was stirred at room temperature for 30 min. Sodium sulfate 10 hydrate (1.93 g) was added to the mixture and the mixture was stirred at room temperature for 30 min. The insoluble materials were removed by filtration, and the filtrate was concentrated. The obtained crystals were recrystallized from ethyl acetate-hexane to give [2-(5-methyl-2-phenyl-4-oxazolylmethoxy)-4-pyridyl]methanol as colorless plate crystals (1.37 g, 77%). melting point: 100-101° C.

Reference Example 56

To thionyl chloride (4 mL) was added [2-(5-methyl-2-phenyl-4-oxazolylmethoxy)-4-pyridyl]methanol (1.19 g) under ice-cooling, and the mixture was stirred at room temperature for 1 hr. The reaction mixture was concentrated, and saturated aqueous sodium hydrogencarbonate was added to the residue. The mixture was extracted with ethyl acetate. The organic layer was washed with saturated brine, dried over anhydrous magnesium sulfate, and concentrated. The obtained residue was subjected to silica gel column chromatography to give crystals of 4-chloromethyl-2-(5-methyl-2-phenyl-4-oxazolylmethoxy)pyridine from a fraction eluted with ethyl acetate-hexane (1:3, v/v). Recrystallization from ethyl acetate-hexane gave colorless needle crystals (0.68 g, 54%). melting point: 104-105° C.

Reference Example 57

To a mixture of (5-methyl-2-phenyl-4-oxazolyl)methanol (8.51 g) and tetrahydrofuran (100 mL) was added sodium hydride (60%, oil, 1.80 g) at room temperature and the reaction mixture was stirred at room temperature until generation of hydrogen ended. The mixture was added to a solution of methyl 6-chloropyridine-2-carboxylate (7.72 g) in tetrahydrofuran (75 ml) at room temperature and the obtained mixture was further stirred at 40° C. for 5 hrs. Water was added to the reaction mixture and the mixture was extracted with ethyl acetate. The organic layer was washed successively with water and saturated brine, dried over anhydrous magnesium sulfate, and concentrated. The obtained residue was subjected to silica gel column chromatography to give crystals of methyl 6-(5-methyl-2-phenyl-4-oxazolyl)methoxy-2-pyridinecarboxylate from a fraction eluted with ethyl acetate-hexane (1:3, v/v). Recrystallization from ethyl acetate-hexane gave pale-yellow plate crystals (7.41 g, 51%). melting point: 97-98° C.

Reference Example 58

To a mixture of methyl 6-(5-methyl-2-phenyl-4-oxazolyl)methoxy-2-pyridinecarboxylate (6.49 g) and tetrahydrofuran (60 mL) was added lithium aluminum hydride (0.759 g) under ice-cooling, and the mixture was stirred at room temperature for 30 min. To the mixture was added sodium sulfate 10 hydrate (6.44 g) and further stirred at room temperature for 30 min. The insoluble materials were removed by filtration, and the filtrate was concentrated to give crystals. The obtained crystals were added to thionyl chloride (20 mL) under ice-cooling, and the mixture was stirred at room temperature for 1 hr. The reaction mixture was concentrated, saturated aqueous sodium hydrogencarbonate was added to the residue and the mixture was extracted with ethyl acetate. The organic layer was washed with saturated brine, dried over anhydrous magnesium sulfate, and concentrated. The obtained residue was subjected to silica gel column chromatography to give crystals of 2-chloromethyl-6-(5-methyl-2-phenyl-4-oxazolylmethoxy)pyridine from a fraction eluted with ethyl acetate-hexane (1:3, v/v). Recrystallization from ethyl acetate-hexane gave colorless plate crystals (2.74 g, 44%). melting point: 85-86° C.

Reference Example 59.

A mixture of 4-(4-chloromethylphenoxymethyl)-5-methyl-2-phenyloxazole (1.79 g), methyl 2-(5-hydroxy-2-propylphenoxy)acetate (1.17 g), anhydrous potassium carbonate (0.72 g) and N,N-dimethylformamide (50 mL) was stirred at 90° C. for 2 hrs. The reaction mixture was poured into water and extracted with ethyl acetate. The organic layer was washed with saturated brine, dried over anhydrous magnesium sulfate, and concentrated. The obtained residue was subjected to silica gel column chromatography to give crystals (1.60 g, 61%) of methyl 2-[5-[4-[(5-methyl-2-phenyl-4-oxazolyl)methoxy]benzyloxy]-2-propylphenoxy]acetate from a fraction eluted with ethyl acetate-hexane (1:6, v/v). Recrystallization from ethyl acetate-hexane gave colorless prism crystals. melting point: 100-101° C.

Reference Example 60

To a mixture of methyl 2-[5-[4-[(5-methyl-2-phenyl-4-oxazolyl)methoxy]benzyloxy]-2-propylphenoxy]acetate (1.16 g), tetrahydrofuran (4 mL) and methanol (4 mL) was added 1N aqueous sodium hydroxide solution (4.5 mL) and the mixture was stirred at room temperature for 2 hrs. 1N Hydrochloric acid and water were added to acidify the reaction mixture, and the mixture was extracted with ethyl acetate. The organic layer was washed with saturated brine, dried over anhydrous magnesium sulfate, and concentrated to give crystals (1.01 g, 90%) of 2-[5-[4-[(5-methyl-2-phenyl-4-oxazolyl)methoxy]benzyloxy]-2-propylphenoxy] acetic acid. Recrystallization from ethyl acetate-hexane gave colorless prism crystals. melting point: 162-163° C.

Reference Example 61

To a mixture of 4-[4-(4-benzoyl-3-hydroxyphenoxymethyl)phenoxymethyl]-5-methyl-2-phenyloxazole (1.52 g) and N,N-dimethylformamide (20 mL) was added sodium hydride (60%, oil, 0.14 g) under ice-cooling, and the mixture was stirred at room temperature for 1 hr. Methyl bromoacetate (0.57 g) was added to the mixture and the mixture was stirred at 80° C. for 2 hrs., The reaction mixture was poured into water, and extracted with ethyl acetate. The organic layer was washed with saturated brine, and dried over anhydrous magnesium sulfate. After concentration of the organic layer, the residue was subjected to silica gel column chromatography to give methyl 2-[2-benzoyl-5-[4-[(5-methyl-2-phenyl-4-oxazolyl)methoxy]benzyloxy]phenoxy]acetate as an oil (1.65 g, 94%) from a fraction eluted with ethyl acetate-hexane (1:2, v/v).

$^1$H-NMR(CDCl$_3$)δ: 2.45 (3H, s), 3.68 (3H, s), 4.50 (2H, s), 5.02 (2H, s), 5.03 (2H, s), 6.45 (1H, d, J=2.2 Hz), 6.69 (1H, dd. J=8.4, 2.2 Hz), 7.03-7.08 (2H, m), 7.35-7.57 (9H, m), 7.80-7.84 (2H, m), 7.99-8.05 (2H, m).

Reference Example 62

To a mixture of methyl 2-[2-benzoyl-5-[4-[(5-methyl-2-phenyl-4-oxazolyl)methoxy]benzyloxy]phenoxy]acetate (0.55 g), tetrahydrofuran (1.5 mL) and methanol (1.5 mL) was added a 1N aqueous sodium hydroxide solution (1.5 mL) and the mixture was stirred at room temperature for 3 hrs. 1N Hydrochloric acid and water were added to acidify the reaction mixture, and the mixture was extracted with ethyl acetate. The organic layer was washed with saturated brine, dried over anhydrous magnesium sulfate, and concentrated to give 2-[2-benzoyl-5-[4[(5-methyl-2-phenyl-4-oxazolyl)methoxy]benzyloxy]phenoxy]acetic acid as a colorless amorphous compound (0.41 g, 76%).

$^1$H-NMR(CDCl$_3$)δ: 2.45 (3H, s), 4.76 (2H, s), 5.03 (2H, s), 5.08 (2H, s), 6.63-6.70(2H, m), 7.04-7.08 (2H, m), 7.34-7.66 (9H, m), 7.79-7.83 (2H, m), 7.98-8.04 (2H, m).

Reference Example 63

A mixture of 2-hydroxy-4-methoxymethoxybenzaldehyde (17.1 g), benzyl bromide (19.33 g), anhydrous potassium carbonate (13.0 g) and N,N-dimethylformamide (200 mL) was stirred at room temperature for 15 hrs. The reaction mixture was poured into water and extracted with ethyl acetate. The organic layer was washed with saturated brine, dried over anhydrous magnesium sulfate and concentrated. The obtained residue was subjected to silica gel column chromatography to give 2-benzyloxy-4-methoxymethoxybenzaldehyde as a colorless oil (25.3 g, 99%) from a fraction eluted with ethyl acetate-hexane (1:4, v/v).

$^1$H-NMR(CDCl$_3$)δ: 3.48 (3H, s), 5.17 (2H, s), 5.21 (2H, s), 6.66-6.72 (2H, m), 7.34-7.47 (5H, m), 7.80-7.84 (1H, m), 10.40 (1H, s).

Reference Example 64

To a mixture of triethyl phosphonoacetate (10.9 g), 2-benzyloxy-4-methoxymethoxybenzaldehyde (12.0 g) and N,N-dimethylformamide (150 mL) was added sodium hydride (60%, oil, 2.12 g) under ice-cooling. The reaction mixture was stirred at room temperature for 13 hrs. Water was added to the reaction mixture and the mixture was extracted with ethyl acetate. The organic layer was washed successively with water and saturated brine, dried over anhydrous magnesium sulfate, and concentrated. The obtained residue was subjected to silica gel column chromatography to give ethyl (E)-3-(2-benzyloxy-4-methoxymethoxyphenyl)-2-propenoate as a colorless oil (14.80 g, 98%) from a fraction eluted with ethyl acetate-hexane (1:4, v/v).

$^1$H-NMR(CDCl$_3$)δ: 1.32 (3H, t, J=7.0 Hz), 3.45 (3H, s), 4.23 (2H, q, J=7.4 Hz), 5.15 (2H, s), 5.16 (2H, s), 6.44 (1H, d, J=16.0 Hz), 6.62-6.68 (2H, m), 7.24-7.49 (6H, m), 8.01 (1H, d, J=16.0 Hz).

Reference Example 65

A mixture of ethyl (E)-3-(2-benzyloxy-4-methoxymethoxyphenyl)-2-propenoate (14.80 g), 5% palladium carbon (20.0 g) and ethanol (300 mL) was subjected to catalytic hydrogenation at room temperature and 1 atm. After filtering off the catalyst, the solvent was evaporated under reduced pressure to give ethyl 3-(2-hydroxy-4-methoxymethoxyphenyl)propionate as a colorless oil (9.17 g, 84%).

$^1$H-NMR(CDCl$_3$)δ: 1.24 (3H, t, J=7.0 Hz), 2.63-2.71 (2H, m), 2.79-2.86 (2H, m), 3.46 (3H, s), 4.15 (2H, q, J=7.0 Hz), 5.13 (2H, s), 6.53-6.62 (2H, m), 6.97 (1H, d, J=8.0 Hz), 7.43 (1H, brs).

Reference Example 66

A mixture of ethyl 3-(2-hydroxy-4-methoxymethoxyphenyl)propionate (6.00 g), ethyl iodide (5.52 g), anhydrous potassium carbonate (3.26 g) and N,N-dimethylformamide (50 mL) was stirred at room temperature for 13 hrs. The reaction mixture was poured into water and extracted with ethyl acetate. The organic layer was washed with saturated brine, dried over anhydrous magnesium sulfate, and concentrated to give an oil. A mixture of the obtained oil, 10% aqueous sulfuric acid solution (10 mL) and ethanol (300 mL) was stirred with heating under reflux for 6 hrs. The reaction mixture was concentrated under reduced pressure and the residue was diluted with water, and then basified with a saturated aqueous sodium hydrogencarbonate. The mixture was extracted with ethyl acetate. The organic layer was washed with saturated brine, dried over anhydrous magnesium sulfate, and concentrated. The obtained residue was subjected to silica gel column chromatography to give ethyl 3-(2-ethoxy-4-hydroxyphenyl)propionate as a colorless oil (3.58 g, 64%) from a fraction eluted with ethyl acetate-hexane (1:6, v/v).

$^1$H-NMR(CDCl$_3$)δ: 1.23 (3H, t, J=7.0 Hz), 1.41 (3H, t, J=7.0 Hz), 2.52-2.61 (2H, m), 2.81-2.89 (2H, m), 3.98 (2H, q, J=7.0 Hz), 4.12 (2H, q, J=7.0 Hz), 5.00 (1H, brs), 6.26-6.37 (2H, m), 6.96 (1H, d, J=8.2 Hz).

Reference Example 67

To a mixture of [3-[(5-methyl-2-phenyl-4-oxazolyl)methoxy]phenyl]methanol (1.92 g), methyl 5-hydroxynicotinate (1.0 g), tributylphosphine (1.98 g) and tetrahydrofuran (100 mL) was added 1,1'-(azodicarbonyl)dipiperidine (2.47 g) at room temperature and the mixture was stirred for 15 hrs. The precipitated crystals were removed by filtration. The filtrate was concentrated and the residue was subjected to silica gel column chromatography to give crystals (2.21 g, 79%) of methyl 5-[3-[(5-methyl-2-phenyl-4-oxazolyl)methoxy]benzyloxy]nicotinate from a fraction eluted with ethyl acetate-hexane (1:3, v/v). Recrystallization from ethyl acetate-hexane gave colorless prism crystals. melting point: 96-97° C.

Reference Example 68

To a mixture of methyl-5-[3-[(5-methyl-2-phenyl-4-oxazolyl)methoxy]benzyloxy]nicotinate (0.50 g) and tetrahydrofuran (10 mL) was added lithium aluminum hydride (0.045 g) under ice-cooling, and the mixture was stirred at room temperature for 3 hrs. Sodium sulfate 1.0 hydrate (0.39 g) was added to the mixture and the mixture was further stirred at room temperature for 30 min. The insoluble materials were removed by filtration, and the filtrate was concentrated to give crystals (0.47 g, 98%) of [5-[3-[(5-methyl-2-phenyl-4-oxazolyl)methoxy]benzyloxy]-3-pyridyl]methanol. Recrystallization from ethyl acetate-hexane gave colorless needle crystals. melting point: 145-146° C.

Reference Example 69

To a solution of methyl 3-hydroxyisoxazole-5-carboxylate (3.51 g) in N,N-dimethylformamide (100 mL) was added sodium hydride (60%, oil, 1.07 g) at 0° C. After stirring for 30 min., 4-chloromethyl-5-methyl-2-phenylthiazole (5.00 g) was added. After stirring at 60° C. for 2 hrs, the reaction mixture was poured into water and extracted with ethyl acetate. The organic layer was washed successively with water and saturated brine, dried over anhydrous magnesium sulfate, and concentrated. The residue was subjected to silica gel column chromatography to give methyl 3-(5-methyl-2-phenyl-4-thiazolylmethoxy)-5-isoxazolecarboxylate (5.42 g, 74%) as colorless crystals from a fraction eluted with ethyl acetate-hexane (1:4, v/v). Recrystallization from ethyl acetate-hexane gave colorless prism crystals. melting point: 89-90° C.

Reference Example 70

A mixture of [5-[3-[(5-methyl-2-phenyl-4-oxazolyl)methoxy]benzyloxy]-3-pyridyl]methanol (4.60 g), thionyl chloride (1.7 mL) and toluene (50 mL) was stirred at 100° C. for 1 hr. The reaction mixture was concentrated, and then ethyl acetate was added. The mixture was washed successively with saturated aqueous sodium hydrogencarbonate and saturated brine, and then the ethyl acetate layer was dried over anhydrous magnesium sulfate and concentrated. Sodium cyanide (0.91 g), 18-crown-6 (0.35 g) and acetonitrile (50 mL) were added to the residue and the mixture was heated under reflux for 2.5 hrs. The reaction mixture was poured into water and extracted with ethyl acetate. The ethyl acetate layer was washed with saturated brine, dried over anhydrous magnesium sulfate and concentrated. The residue was subjected to silica gel column chromatography to give 2-[5-[3-[(5-methyl-2-phenyl-4-oxazolyl)methoxy]benzyloxy]-3-pyridyl]acetonitrile as a pale-brown oil (3.06 g, 65%) from a fraction eluted with tetrahydrofuran-hexane (1:1, v/v).

$^1$H-NMR (CDCl$_3$) δ: 2.44 (3H, s), 3.73 (2H, s), 5.01 (2H, s), 5.13 (2H, s), 6.96-7.14 (3H, m), 7.22-7.52 (5H, m), 7.74-8.07 (2H, m), 8.18 (1H, d, J=2.0 Hz), 8.35 (1H, d, J=2.6 Hz).

Reference Example 71

To a solution of methyl 3-hydroxyisoxazole-5-carboxylate (5.01 g) in N,N-dimethylformamide (70 mL) was added sodium hydride (60%, oil, 1.40 g) at 0° C. and, after stirring the mixture for 15 min., 4-chloromethyl-5-methyl-2-phenyloxazole (7.26 g) was added. After stirring the mixture at 60° C. for 2 hrs., the reaction mixture was poured into water and extracted with ethyl acetate. The ethyl acetate layer was washed with saturated brine, dried over anhydrous magnesium sulfate and concentrated. The residue was subjected to silica gel column chromatography to give methyl 3-(5-methyl-2-phenyl-4-oxazolylmethoxy)-5-isoxazolecarboxylate (7.96 g, yield 72%) as colorless crystals from a fraction eluted with tetrahydrofuran-hexane (1:1, v/v). The crystals were recrystallized from tetrahydrofuran-hexane. melting point: 123-124° C.

Reference Example 72

To a solution of methyl 3-(5-methyl-2-phenyl-4-oxazolylmethoxy)-5-isoxazolecarboxylate (7.86 g) in tetrahydrofuran (150 mL) was slowly added diisobutylaluminum hydride (1.0 M tetrahydrofuran solution, 60 mL) at 0° C. and the mixture was stirred at room temperature for 30 min. The reaction mixture was poured into dilute hydrochloric acid and extracted with ethyl acetate. The ethyl acetate layer was washed with saturated brine, dried over anhydrous magnesium sulfate and concentrated to give 3-(5-methyl-2-phenyl-4-oxazolylmethoxy)-5-isoxazolylmethanol (5.93 g, yield 86%) as colorless crystals. The crystals were recrystallized from ethyl acetate-hexane. melting point: 99-100° C.

Reference Example 73

To a solution of 3-(5-methyl-2-phenyl-4-oxazolylmethoxy)-5-isoxazolylmethanol (2.86 g) in toluene (50 ml) was slowly added thionyl chloride (0.80 mL) at room temperature and the mixture was stirred under reflux for 30 min. After cooling, the reaction mixture was poured into saturated aqueous sodium hydrogencarbonate and extracted with ethyl acetate. The ethyl acetate layer was washed with saturated brine, dried over anhydrous magnesium sulfate and concentrated to give 5-chloromethyl-3-(5-methyl-2-phenyl-4-oxazolylmethoxy)isoxazole (2.70 g, yield 89%) as colorless crystals. The crystals were recrystallized from ethyl acetate-hexane. melting point: 105-106° C.

Reference Example 74

To a mixture of 5-formyl-2-hydroxybenzoic acid (15.34 g) and N,N-dimethylformamide (150 mL) was added sodium hydride (60%, oil, 9.24 g) under ice-cooling. The reaction mixture was stirred at room temperature for 30 min., and then chloromethyl methyl ether (29.7 g) was added to the reaction mixture under ice-cooling. The reaction mixture was further stirred at room temperature for 15 hrs. The reaction mixture was poured into water and extracted with ethyl acetate. The organic layer was washed successively with water and saturated brine, dried over anhydrous magnesium sulfate and concentrated. The obtained residue was subjected to silica gel column chromatography to give methoxymethyl 5-formyl-2-methoxymethoxybenzoate as a colorless oil (14.23 g, 61%) from a fraction eluted with ethyl acetate-hexane (2:3, v/v).

$^1$H-NMR (CDCl$_3$) δ: 3.52 (3H, s), 3.57 (3H, s), 5.36 (2H, s), 5.48 (2H, s), 7.32-7.37 (1H, m), 7.96-8.04 (1H, m), 8.33-8.37 (1H, m), 9.93 (1H, s).

To a mixture of dimethyl sulfoxide (100 mL) and tetrahydrdfuran (300 mL) was added sodium hydride (60%, oil, 3.58 g) at room temperature. The reaction mixture was stirred at 50° C. for 1.5 hrs. The reaction mixture was allowed to warm to room temperature, and then ethyl triphenylphosphonium bromide (27.03 g) was added. The mixture was stirred at room temperature for 30 min. To the reaction mixture was added a solution (50 mL) of methoxymethyl 5-formyl-2-methoxymethoxybenzoate (14.23 g) in dimethyl sulfoxide and the mixture was heated under reflux for 1 hr. Water was added to the reaction mixture, and the mixture was neutralized with 1N hydrochloric acid and extracted with ethyl acetate. The organic layer was washed with saturated brine, dried over anhydrous magnesium sulfate, and concentrated. The obtained residue was subjected to silica gel column chromatography to give a colorless oil from a fraction eluted with ethyl acetate-hexane (1:8, v/v).

A mixture of the obtained oil, 5% palladium carbon (7.0 g) and tetrahydrofuran (300 mL) was subjected to catalytic hydrogenation at room temperature and 1 atm. After filtering off the catalyst, the solvent was evaporated under reduced pressure to give methyl 2-methoxymethoxy-5-propylbenzoate as an oil (6.06 g, 45%).

$^1$H-NMR (CDCl$_3$) δ: 0.93 (3H, t, J=7.2 Hz), 1.52-1.72 (2H, m), 2.55 (2H, t, J=7.6 Hz), 3.52 (3H, s), 3.89 (3H, s), 5.22 (2H, s), 7.10 (1H, d, J=8.4 Hz), 7.25 (1H, dd, J=8.4, 2.2 Hz), 7.59 (1H, d, J=2.2 Hz).

To a mixture of methyl 2-methoxymethoxy-5-propylbenzoate (6.06 g) and tetrahydrofuran (200 mL) was added lithium aluminum hydride (0.96 g) under ice-cooling, and the mixture was stirred at room temperature for 1 hr. To the mixture was added sodium sulfate 10 hydrate (8.18 g) and the mixture was further stirred at room temperature for 30 min. The insoluble materials were removed by filtration, and the filtrate was concentrated to give (2-methoxymethoxy-5-propylphenyl)methanol as an oil (4.98 g, 93%).

$^1$H-NMR (CDCl$_3$) δ: 0.93 (3H, t, J=7.2 Hz), 1.55-1.71 (2H, m), 2.28 (1H, t, J=6.4 Hz), 2.53 (2H, t, J=7.4 Hz), 3.49 (3H, s), 4.68 (2H, d, J=6.4 Hz), 5.21 (2H, s), 6.98-7.11 (3H, m).

A mixture of (2-methoxymethoxy-5-propylphenyl)methanol (4.98 g), activated manganese dioxide (15.0 g) and ethyl acetate (300 ml) was stirred at room temperature for 15 hrs. Manganese dioxide was removed by filtration and the filtrate was concentrated. The obtained residue was subjected to silica gel column chromatography to give 2-methoxymethoxy-5-propylbenzaldehyde as an oil (4.19 g, 85%) from a fraction eluted with ethyl acetate-hexane (1:4, v/v).

$^1$H-NMR (CDCl$_3$) δ: 0.92 (3H, t, J=7.2 Hz), 1.52-1.68 (2H, m), 2.56 (2H, t, J=7.4 Hz), 3.52 (3H, s), 5.28 (2H, s), 7.13 (1H, d, J=8.8 Hz), 7.35 (1H, dd, J=8.8, 2.2 Hz), 7.65 (1H, d, J=2.2 Hz), 10.49 (1H, s).

A mixture of 2-methoxymethoxy-5-propylbenzaldehyde (4.15 g), methyl methylthiomethyl sulfoxide (4.94 g), 40% solution of benzyltrimethylammonium hydroxide in methanol (4 mL) and tetrahydrofuran (100 mL) was heated under reflux for 24 hrs.

Water was added to the reaction mixture, and the mixture was extracted with ethyl acetate. The organic layer was washed with saturated brine, dried over anhydrous magnesium sulfate and concentrated. A mixture of the obtained residue and 10% hydrogen chloride-methanol (100 mL) was heated under reflux for 15 hrs. The reaction mixture was concentrated, and ethyl acetate was added to the residue. The organic layer was washed successively with water and saturated brine, dried over anhydrous magnesium sulfate and concentrated. The obtained residue was subjected to silica gel column chromatography to give crystals (1.65 g, 40%) of methyl 2-(2-hydroxy-5-propyl)phenylacetate from a fraction eluted with ethyl acetate-hexane (1:6, v/v). Recrystallization from isopropyl ether-hexane gave colorless prism crystals. melting point: 74-75° C.

Reference Example 75

To a mixture of (2-phenyl-4-oxazolyl)methanol (15.60 g) and tetrahydrofuran (300 mL) was added sodium hydride (60%, oil, 4.28 g) under ice-cooling, and the mixture was stirred at room temperature for 1 hr. Chloromethyl methyl ether (9.34 g) was added to the reaction mixture under ice-cooling, and the mixture was stirred at room temperature for 15 hrs. To the reaction mixture was added water and the mixture was extracted with ethyl acetate. The organic layer was washed successively with water and saturated brine, dried over anhydrous magnesium sulfate and concentrated. The obtained residue was subjected to silica gel column chromatography to give 4-methoxymethoxymethyl-2-phenyloxazole as a colorless oil (10.86 g, 56%) from a fraction eluted with ethyl acetate-hexane (1:8, v/v).

$^1$H-NMR (CDCl$_3$) δ: 3.44 (3H, s), 4.60 (2H, s), 4.76 (2H, s), 7.41-7.49 (3H, m), 7.68 (1H, s), 8.01-8.08 (2H, m).

To a mixture of 4-methoxymethoxymethyl-2-phenyloxazole (10.86 g) and diethyl ether (300 mL) was dropwise added a solution (1.6 M, 37 mL) of n-butyl lithium in hexane at −78° C., and the mixture was stirred at −78° C. for 1.5 hrs. A solution (10 mL) of N,N-dimethylformamide (6.50 g) in diethyl ether was added to the reaction mixture and the reaction mixture was allowed to warm to room temperature with stirring for 2 hrs. Dilute hydrochloric acid was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (6.45 g, 53%) of 4-methoxymethoxymethyl-2-phenyl-5-oxazolecarbaldehyde from a fraction eluted with ethyl acetate-hexane (1:6, v/v). Recrystallization from ethyl acetate-hexane gave colorless prism crystals. melting point: 51-52° C.

To a mixture of dimethyl sulfoxide (80 mL) and tetrahydrofuran (200 mL) was added sodium hydride (6.0%, oil, 1.81 g) at room temperature and the mixture was stirred at 50° C. for 1.5 hrs. After allowing the reaction mixture to cool to room temperature, ethyl triphenylphosphonium bromide (13.66 g) was added and the mixture was stirred at room temperature for 30 min. A solution (20 mL) of 4-methoxymethoxymethyl-2-phenyl-5-oxazolecarbaldehyde (7.0 g) in dimethyl sulfoxide was added to the reaction mixture and the mixture was heated under reflux for 1 hr. Water was added to the reaction mixture, and the mixture was neutralized with 1N hydrochloric acid and extracted with ethyl acetate. The organic layer was washed with saturated brine, dried over anhydrous magnesium sulfate, and concentrated. The obtained residue was subjected to silica gel column chromatography to give an oil from a fraction eluted with ethyl acetate-hexane (1:6, v/v). A mixture of the obtained oil, 5% palladium carbon (2.0 g) and tetrahydrofuran (200 mL) was subjected to catalytic hydrogenation at room temperature and 1 atm. After filtering off the catalyst, the solvent was evaporated under reduced pressure to give 4-methoxymethoxymethyl-2-phenyl-5-propyloxazole as a colorless oil (2.65 g, 36%).

$^1$H-NMR (CDCl$_3$) δ: 1.00 (3H, t, J=7.2 Hz), 1.64-1.83 (2H, m), 2.73 (2H, t, J=7.2 Hz), 3.43 (3H, s), 4.52 (2H, s), 4.74 (2H, s), 7.39-7.49 (3H, m), 7.98-8.05 (2H, m).

A mixture of 4-methoxymethoxymethyl-2-phenyl-5-propyloxazole (2.64 g), 10% sulfuric acid (10 mL) and tetrahydrofuran (100 mL) was heated under reflux for 24 hrs. To the reaction mixture was added ethyl acetate, and the mixture was washed successively with water and saturated brine, dried over anhydrous magnesium sulfate and concentrated to give (2-phenyl-5-propyl-4-oxazolyl)methanol as a colorless oil (2.10 g, 96%).

$^1$H-NMR (CDCl$_3$) δ: 0.99 (3H, t, J=7.4 Hz), 1.63-1.82 (2H, m), 2.71 (2H, t, J=7.4. Hz), 3.00 (1H, brs), 4.60 (2H, s), 7.39-7.50 (3H, m), 7.95-8.04 (2H, m).

Reference Example 76

To a mixture of 2-phenyl-5-propyl-4-oxazolylmethanol (1.38 g) and toluene (100 mL) was added thionyl chloride (1.38 g) under ice-cooling, and the mixture was stirred at room temperature for 1 hr. The reaction mixture was concentrated and the residue was dissolved in ethyl acetate. The mixture was washed successively with saturated aqueous sodium hydrogencarbonate and saturated brine, dried over anhydrous magnesium sulfate, and concentrated to give 4-chloromethyl-2-phenyl-5-propyloxazole as a colorless oil (2.26 g, 99%).

$^1$H-NMR (CDCl$_3$) δ: 1.01 (3H, t, J=7.2 Hz), 1.66-1.85 (2H, m), 2.73 (2H, t, J=7.2 Hz), 4.56 (2H, s), 7.42-7.46 (3H, m), 7.99-8.04 (2H, m).

Reference Example 77

A mixture of 4-chloromethyl-2-phenyl-5-propyloxazole (2.26 g), 4-hydroxybenzaldehyde (1.33 g), anhydrous potassium carbonate (1.76 g) and N,N-dimethylformamide (50 mL) was stirred at 60° C. for 4 hrs. The reaction mixture was poured into water, and the precipitated solid was collected by filtration and dried with air to give crystals (2.75 g, 89%) of 4-[(2-phenyl-5-propyl-4-oxazolyl)methoxy]benzaldehyde. Recrystallization from ethyl acetate-hexane gave colorless prism crystals. melting point: 76-77° C.

Reference Example 78

To a mixture of 4-[(2-phenyl-5-propyl-4-oxazolyl)methoxy]benzaldehyde (2.40 g), tetrahydrofuran (30 ml) and ethanol (10 mL) was added sodium borohydride (0.28 g) at room temperature and the mixture was stirred at room temperature for 1 hr. To, the reaction mixture was added water and the mixture was extracted with ethyl acetate. The organic layer was washed with saturated brine, dried over anhydrous magnesium sulfate, and concentrated. The obtained residue was subjected to silica gel column chromatography to give crystals (1.60 g, 66%) of [4-[(2-phenyl-5-propyl-4-oxazolyl)methoxy]phenyl]methanol from a fraction eluted with ethyl acetate-hexane (1:1, v/v). Recrystallization from ethyl acetate-hexane gave colorless prism crystals. melting point: 79-80° C.

Reference Example 79

To a mixture of [6-(5-methyl-2-phenyl-4-oxazolyl)methoxy]-3-pyridylmethanol (4.01 g), 2-chloro-3-cyanopyridine (1.79 g) and N,N-dimethylformamide (50 mL) was added sodium hydride (60%, oil, 0.62 g) under ice-cooling. The reaction mixture was stirred at room temperature for 3 hrs. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (4.72 g, 92%) of 2-[[6-[(5-methyl-2-phenyl-4-oxazolyl)methoxy]-3-pyridyl]methoxy]nicotinonitrile from a fraction eluted with ethyl acetate-hexane (1:4, v/v). Recrystallization from ethyl acetate-hexane gave colorless prism crystals. melting point: 117-118° C.

Reference Example 80

To a mixture of 2'-[[6-[(5-methyl-2-phenyl-4-oxazolyl)methoxy]-3-pyridyl]methoxy]nicotinonitrile (4.53 g) and anhydrous toluene (100 mL) was dropwise added a solution (0.95 M, 26.3 mL) of diisobutylaluminum hydride in hexane at −78° C. The reaction mixture was allowed to warm to room temperature with stirring for 1 hr. An aqueous solution (50 mL) of saturated ammonium chloride was dropwise added to the mixture and the mixture was further stirred at room temperature for 15 min. To the mixture was added ethyl acetate and the mixture was stirred at room temperature for 30 min., and then the insoluble materials were filtered off. The filtrate was washed with saturated brine, dried over anhydrous magnesium sulfate, and concentrated. The obtained residue was subjected to silica gel column chromatography to give 2-[[6-[(5-methyl-2-phenyl-4-oxazolyl)methoxy]-3-pyridyl]methoxy]nicotinaldehyde as a colorless oil (3.17 g, 69%) from a fraction eluted with ethyl acetate-hexane (1:2, v/v).

$^1$H-NMR (CDCl$_3$) δ: 2.48 (3H, s), 5.31 (2H, s), 5.48 (2H, s), 6.85 (1H, d, J=8.4 Hz), 7.01-7.07 (1H, m), 7.39-7.46 (3H, m), 7.73 (1H, dd, J=8.4, 2.6 Hz), 8.01-8.05 (2H, m), 8.14 (1H, dd, J=7.2, 2.0 Hz), 8.31 (1H, d, J=2.6 Hz), 8.40 (1H, dd, J=4.6, 2.0 Hz), 10.38 (1H, d, J=0.8 Hz).

Reference Example 81

To a mixture of 2-[[6-[(5-methyl-2-phenyl-4-oxazolyl)methoxy]-3-pyridyl]methoxy]nicotinaldehyde (3.16 g), tetrahydrofuran (50 ml) and ethanol (50 mL) was added sodium borohydride (0.30 g) at 0° C. and the mixture was stirred at room temperature for 30 min. Water was added to the reaction mixture, and the precipitated solid was collected by filtration, and dried with air to give crystals (2.70 g, 85%) of [2-[[6-[(5-methyl-2-phenyl-4-oxazolyl)methxy]-3-pyridyl]methoxy]-3-pyridyl]methanol. Recrystallization from ethyl acetate-hexane gave colorless prism crystals. melting point: 142-143° C.

Reference Example 82

To a mixture of [2-[[6-[(5-methyl-2-phenyl-4-oxazolyl)methoxy]-3-pyridyl]methoxy]-3-pyridyl]methanol (2.55 g), triethylamine (1.27 g) and ethyl acetate (200 mL) was dropwise added methanesulfonyl chloride (1.44 g) under ice-cooling and the mixture was stirred at room temperature for 3 hrs. The reaction mixture was washed successively with water, saturated aqueous sodium hydrogencarbonate and saturated brine, dried over anhydrous magnesium sulfate, and concentrated to give an oil. To a mixture of this oil and dimethyl sulfoxide (30 mL) was added an aqueous solution (3 mL) of sodium cyanide (0.77 g) at room temperature and the mixture was stirred at room temperature for 15 hrs. To the reaction mixture was added water and the mixture was extracted with ethyl acetate. The organic layer was washed with saturated brine, dried over anhydrous magnesium sulfate, and concentrated. The obtained residue was subjected to silica gel column chromatography to give crystals (1.85 g, 71%) of 2-[2-[[6-[(5-methyl-2-phenyl-4-oxazolyl)methoxy]-3-pyridyl]methoxy]-3-pyridyl]acetonitrile from a fraction eluted with ethyl acetate-hexane (1:2, v/v). Recrystallization from ethyl acetate-hexane gave colorless prism crystals. melting point: 110-111° C.

Reference Example 83

To a mixture of 2-(2-furyl)-5-methyl-4-oxazolylmethanol (10.8 g), methyl 2-chloro-4-pyridinecarboxylate (10.3 g) and a solution of tetrahydrofuran (100 mL) and N,N-dimethylformamide (100 mL) was added sodium hydride (60%, oil, 2.88 g) at 0° C. and the mixture was stirred at room temperature for 2 hrs. The reaction mixture was poured into water and extracted with ethyl acetate. The ethyl acetate layer was washed with saturated brine, dried over anhydrous magnesium sulfate and concentrated. The residue was subjected to silica gel column chromatography to give ethyl 2-[2-(2-furyl)-5-methyl-4-oxazolylmethoxy]-4-pyridinecarboxylate (2.86 g, yield 15%) as colorless crystals from a fraction eluted with ethyl acetate-hexane (1:3, v/v). The crystals were recrystallized from ethyl acetate-hexane. melting point: 80-81.

Reference Example 84

To a solution of ethyl 2-[2-(2-furyl)-5-methyl-4-oxazolylmethoxy]-4-pyridinecarboxylate (2.63 g) in tetrahydrofuran (30 mL) was added lithium aluminum hydride (304 mg) at 0° C. and the mixture was stirred at room temperature for 30 min. Sodium sulfate 10 hydrate (2.58 g) was added to the reaction mixture and the mixture was stirred at room temperature for 30 min. The precipitate was filtered off by filtration and the filtrate was concentrated. A mixture of the residue, thionyl chloride (10 mL) and toluene (5 mL) was stirred at room temperature for 1 hr. The reaction mixture was concentrated, and then saturated aqueous sodium hydrogencarbonate was added to the mixture, and the mixture was extracted with ethyl acetate. The ethyl acetate layer was washed with saturated brine, dried over anhydrous magnesium sulfate and concentrated. The residue was subjected to silica gel column chromatography to give 4-chloromethyl-2-[2-(2-furyl)-5-methyl-4-oxazolylmethoxy]pyridine (1.02 g, yield 42%) as colorless crystals from a fraction eluted with ethyl acetate-hexane (1:3, v/v). The crystals were recrystallized from ethyl acetate-hexane. melting point: 107-108° C.

Reference Example 85

To a mixture of 3-methoxy-4-[(5-methyl-2-phenyl-4-oxazolyl)methoxy]benzyl alcohol (4.00 g), 2-chloro-3-cyanopyridine (1.62 g) and N,N-dimethylformamide (40 mL) was added sodium hydride (60%, oil, 515 mg) under ice-cooling. The reaction mixture was stirred at room temperature for 15 hrs. Water was added to the reaction mixture and the mixture was extracted with ethyl acetate. The organic layer was washed with saturated brine, dried over anhydrous magnesium sulfate, and concentrated. The obtained crystals were recrystallized from ethyl acetate-hexane to give 2-[3-methoxy-4-[(5-methyl-2-phenyl-4-oxazolyl)methoxy]benzyloxy]nicotinonitrile as pale-yellow crystals (4.50 g, 90%). melting point: 117-118° C.

Reference Example 86

To a mixture of 2-[3-methoxy-4-[(5-methyl-2-phenyl-4-oxazolyl)methoxy]benzyloxy]nicotinonitrile (4.25 g) and toluene (150 mL) was dropwise added a solution (0.95 M, 23.0 mL) of diisobutylaluminum hydride in hexane at −78° C. After stirring for 1 hr the reaction mixture was warmed to room temperature and the mixture was further stirred for 1 hr. A saturated aqueous ammonium chloride solution (35 mL) was dropwise added to the mixture and the mixture was stirred at room temperature for 30 min. To the mixture was added ethyl acetate and the insoluble materials were filtered off. The filtrate was washed with saturated brine, dried over anhydrous magnesium sulfate and concentrated. The obtained residue was subjected to silica gel column chromatography to give 2-[3-methoxy-4-[(5-methyl-2-phenyl-4-oxazolyl)methoxy]benzyloxy]nicotinaldehyde as crystals from a fraction eluted with ethyl acetate-hexane (1:2, v/v). Recrystallization from ethyl acetate-hexane gave colorless crystals (710 mg, 17%). melting point: 99-100° C.

Reference Example 87

To a mixture of 2-[3-methoxy-4-[(5-methyl-2-phenyl-4-oxazolyl)methoxy]benzyloxy]nicotinaldehyde (620 mg), tetrahydrofuran (10 ml) and ethanol (10 mL) was added sodium borohydride (54 mg) at 0° C., and the mixture was stirred at room temperature for 1 hr. To the reaction mixture was added water and the mixture was extracted with ethyl acetate. The organic layer was washed with saturated brine, dried over anhydrous magnesium sulfate and concentrated to give crystals (615 mg, 99%) of [2-[3-methoxy-4-[(5-methyl-2-phenyl-4-oxazolyl)methoxy]benzyloxy]-3-pyridyl]methanol. The crystals were recrystallized from ethyl acetate-hexane. melting point: 143-144° C.

Reference Example 88

To a mixture of [2-[-3-methoxy-4-[(5-methyl-2-phenyl-4-oxazolyl)methoxy]benzyloxy]-3-pyridyl]methanol (540 mg), triethylamine (0.350 mL) and ethyl acetate (50 mL) was dropwise added methanesulfonyl chloride (0.145 mL) under ice-cooling and the mixture was stirred at room temperature for 0.5 hr. To the reaction mixture was added water and the mixture was extracted with ethyl acetate. The organic layer was washed with saturated brine, dried over anhydrous magnesium sulfate and concentrated to give an oil. To a mixture of this oil and dimethyl sulfoxide (10 mL) was added a solution of sodium cyanide (160 mg) in water (1 mL) at room temperature and the mixture was stirred at room temperature for 2 hrs. To the reaction mixture was added water and the mixture was extracted with ethyl acetate. The organic layer was washed with saturated brine, dried over anhydrous magnesium sulfate and concentrated. The obtained crystals were recrystallized from ethyl acetate-hexane to give crystals (438 mg, 79%) of 2-[2-[3-methoxy-4-[(5-methyl-2-phenyl-4-oxazolyl)methoxy]benzyloxy]-3-pyridyl]acetonitrile. melting point: 108-109° C.

Reference Example 89

To a mixture of [4-[[2-(2-furyl)-5-methyl-4-oxazolyl]methoxy]phenyl]methanol (4.14 g), 2-chloro-3-cyanopyridine (1.91 g) and N,N-dimethylformamide (50 mL) was added sodium hydride (60%, oil, 0.66 g) under ice-cooling. The reaction mixture was stirred at room temperature for 3 hrs. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (4.65 g, 87%) of 2-[4-[[2-(2-furyl)-5-methyl-4-oxazolyl]methoxy]benzyloxy]nicotinonitrile from a fraction eluted with ethyl acetate-hexane (1:2, v/v). Recrystallization from ethyl acetate-hexane gave colorless prism crystals. melting point: 135-136° C.

Reference Example 90

To a mixture of 2-[4-[[2-(2-furyl)-5-methyl-4-oxazolyl]methoxy]benzyloxy]nicotinonitrile (4.50 g) and anhydrous toluene (150 mL) was dropwise added a solution (0.95 M, 25.5 mL) of diisobutylaluminum hydride in hexane at −78° C. The reaction mixture was allowed to warm to room temperature with stirring for 1 hr. A saturated aqueous ammonium chloride solution (50 mL) was dropwise added to the mixture and the mixture was further stirred at room temperature for 15 min. To this mixture was added ethyl acetate and the mixture was stirred at room temperature for 30 min., and then insoluble materials were filtered off. The filtrate was washed with saturated brine, dried over anhydrous magnesium sulfate and concentrated. The obtained residue was subjected to silica gel column chromatography to give crystals (2.60 g, 57%) of 2-[4-[[2-(2-furyl)-5-methyl-4-oxazolyl]methoxy]benzyloxy]nicotinaldehyde from a fraction eluted with ethyl acetate-hexane (1:3, v/v). Recrystallization from ethyl acetate-hexane gave colorless prism crystals. melting point: 109-110° C.

Reference Example 91

To a mixture of 2-[4-[[2-(2-furyl)-5-methyl-4-oxazolyl]methoxy]benzyloxy]nicotinaldehyde (2.43 g), tetrahydrofuran (30 ml) and ethanol (30 mL) was added sodium borohydride (0.23 g) at 0° C. and the mixture was stirred at room temperature for 30 min. Water was added to the reaction mixture, and the precipitated solid was collected by filtration and dried with air to give crystals (2.34 g, 96%), of [2-[4-[[2-(2-furyl)-5-methyl-4-oxazolyl]methoxy]benzyloxy]-3-pyridyl]methanol. Recrystallization from ethyl acetate-hexane gave colorless prism crystals. melting point: 119-120° C.

Reference Example 92

To a mixture of [2-[4-[[2-(2-furyl)-5-methyl-4-oxazolyl]methoxy]benzyloxy]-3-pyridyl]methanol (2.12 g), triethylamine (1.09 g) and ethyl acetate (150 mL) was dropwise added methanesulfonyl chloride (1.24 g) under ice-cooling and the mixture was stirred at room temperature for 3 hrs. The reaction mixture was washed successively with water, saturated aqueous sodium hydrogencarbonate and saturated brine, dried over anhydrous magnesium sulfate, and concentrated to give an oil. To a mixture of this oil and dimethyl sulfoxide (30 mL) was added an aqueous solution (3 mL) of sodium cyanide (0.66 g) at room temperature and the mixture was stirred at room temperature for 3 hrs. To the reaction mixture was added water and the mixture was extracted with ethyl acetate. The organic layer was washed with saturated brine, dried over anhydrous magnesium sulfate and concentrated. The obtained residue was subjected to silica gel column chromatography to give crystals (1.63 g, 75%) of 2-[2-[4-[[2-(2-furyl)-5-methyl-4-oxazolyl]methoxy]benzyloxy]-3-pyridyl]acetonitrile from a fraction eluted with ethyl acetate-hexane (1:1, v/v). Recrystallization from ethyl acetate-hexane gave colorless prism crystals. melting point: 141-142° C.

Reference Example 93

To admixture of [4-[(5-methyl-2-phenyl-4-thiazolyl)methoxy]phenyl]methanol (4.50 g), 2-chloro-3-cyanopyridine (1.91 g) and N,N-dimethylformamide (50 mL) was added sodium hydride (60%, oil, 0.66 g) under ice-cooling. The reaction mixture was stirred at room temperature for 3 hrs. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (4.38 g, 77%) of 2-[4-[(5-methyl-2-phenyl-4-thiazolyl)methoxy]benzyloxy]nicotinonitrile from a fraction eluted with ethyl acetate-hexane (1:3, v/v). Recrystallization from ethyl acetate-hexane gave colorless prism crystals. melting point: 120-121° C.

Reference Example 94

To a mixture of 2-[4-[(5-methyl-2-phenyl-4-thiazolyl)methoxy]benzyloxy]nicotinonitrile (4.18 g) and anhydrous toluene (150 mL) was dropwise added a solution (0.95 M, 23.4 mL) of diisobutylaluminum hydride in hexane at −78° C. The reaction mixture was allowed to warm to room temperature with stirring for 1 hr. A saturated aqueous ammonium chloride solution (50 mL) was dropwise added to the mixture and the mixture was further stirred at room temperature for 15 min. Ethyl acetate was added to the mixture and, after stirring the mixture at room temperature for 30 min., insoluble materials were filtered off. The filtrate was washed with saturated brine, dried over anhydrous magnesium sulfate and concentrated. The obtained residue was subjected to silica gel column chromatography to give crystals (2.35 g, 56%) of 2-[4-[(5-methyl-2-phenyl-4-thiazolyl)methoxy]benzyloxy]nicotinaldehyde from a fraction eluted with ethyl acetate-hexane (1:3, v/v). Recrystallization from ethyl acetate-hexane gave colorless prism crystals. melting point: 101-102° C.

Reference Example 95

To a mixture of 2-[4-[(5-methyl-2-phenyl-4-thiazolyl)methoxy]benzyloxy]nicotinaldehyde (2.16 g), tetrahydrofuran (30 ml) and ethanol (30 mL) was added sodium borohydride (0.20 g) at 0° C., and the mixture was stirred at room temperature for 30 min. Water was added to the reaction mixture, and the precipitated solid was collected by filtration, and dried with air to give crystals (2.12 g, 97%) of [2-[4-[(5-methyl-2-phenyl-4-thiazolyl)methoxy]benzyloxy]-3-pyridyl]methanol. Recrystallization from ethyl acetate-hexane gave colorless prism crystals. melting point: 111-112° C.

Reference Example 96

To a mixture of [2-[4-[(5-methyl-2-phenyl-4-thiazolyl)methoxy]benzyloxy]-3-pyridyl]methanol (2.00 g), triethylamine (0.97 g) and ethyl acetate (150 mL) was dropwise added methanesulfonyl chloride (1.10 g) under ice-cooling and the mixture was stirred at room temperature for 2 hrs. The reaction mixture was washed successively with water, saturated aqueous sodium hydrogencarbonate and saturated brine, dried over anhydrous magnesium sulfate, and concentrated to give an oil. To a mixture of this oil and dimethyl sulfoxide (30 mL) was added an aqueous solution (3 mL) of sodium cyanide (0.59 g) at room temperature and the mixture was stirred at room temperature for 3 hrs. Water was added to the reaction mixture, and the precipitated crystals were collected by filtration. The obtained crystals were subjected to silica gel column chromatography to give crystals (1.40 g, 68%) of 2-[2-[4-[(5-methyl-2-phenyl-4-thiazolyl)methoxy]benzyloxy]-3-pyridyl]acetonitrile from a fraction eluted with ethyl acetate-hexane (1:2, v/v). Recrystallization from tetrahydrofuran-hexane gave colorless prism crystals. melting point: 161-162° C.

Reference Example 97

A mixture of [4-[(E)-2-(5-methyl-2-phenyl-4-oxazolyl)ethenyl]phenyl]methanol (0.90 g), 5% palladium carbon (0.90 g) and tetrahydrofuran (100 mL) was subjected to catalytic hydrogenation at room temperature and 1 atm. After filtering off the catalyst, the solvent was evaporated under reduced pressure to give crystals. (0.74 g, 81%) of [4-[2-(5-methyl-2-phenyl-4-oxazolyl)ethyl]phenyl]methanol. Recrystallization from ethyl acetate-hexane gave colorless prism crystals. melting point: 67-68° C.

Reference Example 98

To a mixture of diethyl malonate (115.8 g) and tetrahydrofuran (300 mL) was added sodium hydride (60%, oil, 24.12 g) under ice-cooling. After stirring the mixture at room temperature for 30 min., a solution (100 mL) of 4-chloromethyl-5-methyl-2-phenyloxazole (50.0 g) in tetrahydrofuran was added to the reaction mixture under ice-cooling, and the mixture was heated under reflux for 1 hr. Water was added to the reaction mixture, and the mixture was concentrated. Ethyl acetate was added to the residue and the mixture was washed with saturated brine, dried over anhydrous magnesium sulfate and concentrated to give an oil. A mixture of this oil, 6N hydrochloric acid (300 mL) and acetic acid (150 ml) was heated under reflux for 20 hrs. The reaction mixture was concentrated, and ethyl acetate was added to the residue. The mixture was washed with saturated brine, dried over anhydrous magnesium sulfate and concentrated. The residue was subjected to silica gel column chromatography to give crystals (22.4 g, 40%) of 3-(5-methyl-2-phenyl-4-oxazolyl)propionic acid from a fraction eluted with ethyl acetate-hexane (1:4, v/v). Recrystallization from ethyl acetate-hexane gave colorless prism crystals. melting point: 124-125° C.

Reference Example 99

To a mixture of 3-(5-methyl-2-phenyl-4-oxazolyl)propionic acid (20.0 g), N,N-dimethylformamide (0.5 mL) and tetrahydrofuran; (300 mL) was dropwise added oxalyl chloride (13.18 g) under ice-cooling, and the mixture was stirred at room temperature for 1.5 hrs. The reaction mixture was concentrated, and the obtained residue was dissolved in tetrahydrofuran (100 mL). This solution was dropwise added to a mixture of 25% aqueous ammonia (200 mL) and tetrahydrofuran (100 mL) at room temperature. The reaction mixture was stirred at room temperature for 1.5 hrs and extracted with ethyl acetate. The organic layer was washed with saturated brine, dried over anhydrous magnesium sulfate, and concentrated to give crystals (15.4 g, 77%) of 3-(5-methyl-2-phenyl-4-oxazolyl)propanamide. Recrystallization from chloroform-ethanol gave colorless prism crystals. melting point: 149-150° C.

Reference Example 100

A mixture of 3-(5-methyl-2-phenyl-4-oxazolyl)propanamide (10.0 g) and 1,3-dichloro-2-propanone (5.35 g) was stirred at 130° C. for 2 hrs. An aqueous potassium carbonate solution was added to alkalize the reaction mixture and the mixture was extracted with ethyl acetate. The organic layer was washed with saturated brine, and dried over anhydrous magnesium sulfate. The residue was subjected to silica gel column chromatography to give crystals (2.30 g, 18%) of 4-[2-(4-chloromethyl-2-oxazolyl)ethyl]-5-methyl-2-phenyloxazole from a fraction eluted with ethyl acetate-hexane (1:4, v/v). Recrystallization from ethyl acetate-hexane gave colorless prism crystals. melting point: 71-72° C.

Reference Example 101

A mixture of 3-(5-methyl-2-phenyl-4-oxazolyl)propanamide (10.44 g), 2,4-bis(4-methoxyphenyl)-1,3-dithia-2,4- diphosphetan-2,4-disulfide (14.64 g) and tetrahydrofuran (300 mL) was stirred at room temperature for 2 hrs. To the reaction mixture was added ethyl acetate, and the mixture was washed successively with water and saturated brine, dried over anhydrous magnesium sulfate and concentrated. The obtained residue was subjected to silica gel column chromatography to give crystals (10.7 g, 96%) of 3-(5-methyl-2-phenyl-4-oxazolyl)propanethioamide from a fraction eluted with ethyl acetate-hexane (1:3, v/v). Recrystallization from ethyl acetate-hexane gave colorless prism crystals. melting point: 167-168° C.

Reference Example 102

A mixture of 3-(5-methyl-2-phenyl-4-oxazolyl)propanethioamide (5.47 g), 1,3-dichloro-2-propanone (3.10 g) and ethanol (100 mL) was heated under reflux for 1 hr. The reaction mixture was concentrated, and ethyl acetate was added to the residue. The organic layer was washed successively with saturated aqueous sodium hydrogencarbonate and saturated brine, dried over anhydrous magnesium sulfate, and concentrated. The obtained residue was subjected to silica gel column chromatography to give crystals (3.50 g, 49%) of 4-[2-(4-chloromethyl-2-thiazolyl)ethyl]-5-methyl-2-phenyloxazole from a fraction eluted with ethyl acetate-hexane (1:3, v/v). Recrystallization from ethyl acetate-hexane gave colorless prism crystals. melting point: 89-90° C.

Reference Example 103

To a mixture of 3-(5-methyl-2-phenyl-4-oxazolyl)propanamide (5.0 g) and N,N-dimethylformamide (100 ml) was added phosphoryl chloride (3.33 g) at room temperature and the mixture was stirred at room temperature for 1 hr. To the reaction mixture was added water and the mixture was extracted with ethyl acetate. The organic layer was washed successively with water and saturated brine, dried over anhydrous magnesium sulfate, and concentrated to give crystals (4.10 g, 89%) of 3-(5-methyl-2-phenyl-4-oxazolyl)propionitrile. Recrystallization from ethyl acetate-hexane gave colorless prism crystals. melting point: 63-64° C.

A mixture of 3-(5-methyl-2-phenyl-4-oxazolyl)propionitrile (8.20 g), hydroxylammonium chloride (4.02 g), potassium carbonate (4.01 g) and 70% ethanol (100 mL) was heated under reflux for 24 hrs. The reaction mixture was concentrated and water was added to the residue. The obtained crystals were collected by filtration and washed with isopropyl ether. To a mixture of the obtained crystal, potassium carbonate (2.13 g) and acetone (50 mL) was added chloroacetyl chloride (3.48 g) under ice-cooling. The reaction mixture was stirred at room temperature for 15 hrs. Water was added to the reaction mixture, and the precipitated crystals were collected by filtration and washed with isopropyl ether. A mixture of the obtained crystals and xylene (150 mL) was subjected to azeotropic dehydration for 4 hrs. The reaction mixture was concentrated, and ethyl acetate was added to the residue. The organic layer was washed successively with water and saturated brine, dried over anhydrous magnesium sulfate, and concentrated. The obtained residue was subjected to silica gel column chromatography to give crystals (2.56 g, 23%) of 5-chloromethyl-3-[2-(5-methyl-2-phenyl-4-oxazolyl)ethyl]-1,2,4-oxadiazole from a fraction eluted with ethyl acetate-hexane (1:4, v/v). Recrystallization from ethyl acetate-hexane gave colorless prism crystals. melting point: 71-72° C.

Reference Example 104

To a mixture of [4-[(5-methyl-2-phenyl-4-oxazolyl)methoxy]phenyl]methanol (4.28 g), 2-chloro-3-cyanopyridine (2.10 g) and N,N-dimethylformamide (5.0 mL) was added sodium hydride (60%, oil, 0.66 g) under ice-cooling. The reaction mixture was stirred at 80° C. for 1 hr. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (1.90 g, 33%) of 6-methyl-2-[4-[(5-methyl-2-phenyl-4-oxazolyl)methoxy]benzyloxy]nicotinonitrile from a fraction eluted with ethyl acetate-hexane (1:2, v/v). Recrystallization from ethyl acetate-hexane gave pale-yellow prism crystals. melting point: 116-117° C.

Reference Example 105

To a mixture of 6-methyl-2-[4-[(5-methyl-2-phenyl-4-oxazolyl)methoxy]benzyloxy]nicotinonitrile (1.70 g) and anhydrous toluene (80 mL) was dropwise added a solution (0.95 M, 9.5 mL) of diisobutylaluminum hydride in hexane at −78° C. The reaction mixture was allowed to warm to room temperature with stirring for 1 hr. A saturated aqueous ammonium chloride solution (30 mL) was dropwise added to the mixture and the mixture was further stirred at room temperature for 30 min. Ethyl acetate was added to the mixture and, after stirring the mixture at room temperature for 30 min., insoluble materials were filtered off. The filtrate was washed with saturated brine, dried over anhydrous magnesium sulfate, and concentrated. The obtained residue was subjected to silica gel column chromatography to give crystals (0.98 g, 58%) of 6-methyl-2-[4-[(5-methyl-2-phenyl-4-oxazolyl)methoxy]benzyloxy]nicotinaldehyde from a fraction eluted with ethyl acetate-hexane (1:6, v/v). Recrystallization from ethyl acetate-hexane gave colorless prism crystals. melting point: 114-115° C.

Reference Example 106

To a solution of methyl 3-(5-methyl-2-phenyl-4-thiazolylmethoxy)-5-isoxazolecarboxylate (5.27 g) in tetrahydrofuran (100 ml) was slowly added diisobutylaluminum hydride (0.95 M hexane solution, 60 ml) at 0° C. and the mixture was stirred at 0° C. for 1 hr. Sodium sulfate 10 hydrate (17.01 g) was added to the reaction mixture and the mixture was further stirred at room temperature for 30 min. The insoluble materials were removed by filtration, and the filtrate was concentrated to give [3-(5-methyl-2-phenyl-4-thiazolylmethoxy)-5-isoxazolyl]methanol (3.88 g, 80%) as colorless crystals. The crystals were recrystallized from ethyl acetate-hexane. melting point: 84-85° C.

Reference Example 107

To a mixture of potassium t-butoxide (0.47 g) and dimethoxyethane (8 mL) was added a solution (8 mL) of toluenesulfonylmethylisocyanide (0.43 g) in dimethoxyethane at −78° C. Furthermore, a solution (8 mL) of 6-methyl-2-[4-[(5-methyl-2-phenyl-4-oxazolyl)methoxy]benzyloxy]nicotinaldehyde (0.84 g) in dimethoxyethane was added to the reaction mixture. The reaction mixture was stirred at −78° C. for 1 hr. Methanol (10 mL) was added to the reaction mixture at room temperature and the mixture was heated under reflux for 30 min. To the reaction mixture was added water and the mixture was extracted with ethyl acetate. The organic layer was washed successively with saturated aqueous sodium hydrogencarbonate and saturated brine, dried over anhydrous magnesium sulfate, and concentrated. The obtained residue was subjected to silica gel, column chromatography to give crystals (0.67 g, 79%) of 2-[6-methyl-2-[4-[(5-methyl-2-phenyl-4-oxazolyl)methoxy]benzyloxy]-3-pyridyl]acetonitrile from a fraction eluted with ethyl acetate-hexane (1:6, v/v). Recrystallization from ethyl acetate-hexane gave colorless prism crystals. melting point: 122-123° C.

Reference Example 108

To a mixture of 4-methoxy-3-(5-methyl-2-phenyl-4-oxazolylmethoxy)benzaldehyde (3.23 g), tetrahydrofuran (15 ml) and methanol (15 ml) was added sodium borohydride (0.378 g) at room temperature and the mixture was stirred at room temperature for 30 min. The reaction mixture was poured into water and extracted with ethyl acetate. The organic layer was washed with saturated brine, dried over anhydrous magnesium sulfate, and concentrated to give crystals of 4-methoxy-3-(5-methyl-2-phenyl-4-oxazolylmethoxy)benzyl alcohol. Recrystallization from tetrahydrofuran-hexane gave pale-yellow plate crystals (3.22 g, 99%). melting point: 144-145° C.

Reference Example 109

A mixture of ethyl 3-methyl-1H-pyrazole-4-carboxylate (7.95 g), 2-chloropyridine (5 ml), sodium hydride (0.60%, oil, 2.32 g) and N,N-dimethylformamide (150 ml) was stirred overnight at 180° C. The reaction mixture was poured into water and extracted with ethyl acetate. The ethyl acetate layer was washed with saturated brine, dried over anhydrous magnesium sulfate and concentrated. The residue was subjected to silica gel column chromatography to give ethyl 3-methyl-1-(2-pyridyl)-1H-pyrazole-4-carboxylate (8.31 g, yield 73%) as colorless crystals from a fraction eluted with ethyl acetate-hexane (1:9, volume ratio). The crystals were recrystallized from ethyl acetate-hexane. melting point: 79-80° C.

Reference Example 110

To a solution of ethyl 3-methyl-1-(2-pyridyl)-1H-pyrazole-4-carboxylate (15.00 g) in tetrahydrofuran (150 mL) was added lithium aluminum hydride (1.93 g) at 0° C., and the mixture was stirred at room temperature for 1 hr. Sodium sulfate 10 hydrate (21.03 g) and hexane (100 mL) were added to the reaction mixture, and the mixture was stirred at room temperature for 1 hr. The precipitate was removed by filtration and the filtrate was concentrated. The obtained crystals were collected by filtration to give [3-methyl-1-(2-pyridyl)-1H-pyrazol-4-yl]methanol (11.38 g). The crystals were recrystallized from acetone-hexane. melting point: 116-117° C.

Reference Example 111

A mixture of 3-methyl-1-(2-pyridyl)-1H-pyrazol-4-ylmethanol (3.00 g), thionyl chloride (2.5 mL) and toluene (50 mL) was stirred at 70° C. for 2 hrs. The reaction mixture was concentrated under reduced pressure, and saturated aqueous sodium hydrogencarbonate was added to the residue. The mixture was extracted with ethyl acetate, and the ethyl acetate layer was washed with saturated brine, dried over anhydrous magnesium sulfate and concentrated to give 4-chloromethyl-3-methyl-1-(2-pyridyl)-1H-pyrazole (3.10 g, yield 94%) as a colorless oil.

NMR (CDCl$_3$) δ: 2.44 (3H, s), 4.58 (2H, s), 7.46-7.60 (1H, m), 8.18-8.42 (2H, m), 8.50-8.60 (1H, m), 9.43 (1H, s).

Reference Example 112

To a mixture of 4-[3-methyl-1-(2-pyridyl)-1H-pyrazol-4-ylmethoxy]benzaldehyde (3.50 g), methanol (5 mL) and tetrahydrofuran (25 mL) was added sodium borohydride (0.25 g) at 0° C. and the mixture was stirred at room temperature for 30 min. The reaction mixture was concentrated under reduced pressure, and dilute hydrochloric acid was added to the residue. The mixture was extracted with ethyl acetate and the ethyl acetate layer was washed with saturated brine, dried over anhydrous magnesium sulfate and concentrated. The residue was subjected to silica gel column chromatography to give 4-[3-methyl-1-(2-pyridyl)-1H-pyrazol-4-lymethoxy]benzyl alcohol (3.41 g, yield 97%) as colorless crystals from a fraction eluted with ethyl acetate-hexane (1:2, volume ratio). The crystals were recrystallized from ethyl acetate-hexane. melting point: 83-84° C.

Reference Example 113

To a mixture of [3-(5-methyl-2-phenyl-4-thiazolylmethoxy)-5-isoxazolyl]methanol (1.80 g), 2-chloro-3-cyanopyridine (0.83 g) and N,N-dimethylformamide (80 mL) was added sodium hydride (60%, oil, 0.26 g) under ice-cooling. The reaction mixture was stirred at room temperature for 5 hrs. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (2.08 g, 86%) of 2-[[3-[(5-methyl-2-phenyl-4-thiazolyl)methoxy]-5-isoxazolyl]methoxy]nicotinonitrile from a fraction eluted with ethyl acetate-hexane (1:2, v/v). Recrystallization from ethyl acetate-hexane gave colorless prism crystals. melting point: 135-136° C.

Reference Example 114

To a mixture of 2-[[3-[(5-methyl-2-phenyl-4-thiazolyl)methoxy]-5-isoxazolyl]methoxy]nicotinonitrile (1.90 g) and anhydrous toluene (100 mL) was dropwise added a solution (0.95 M, 16.3 mL) of diisobutylaluminum hydride in hexane at −78° C. The reaction mixture was allowed to warm to room temperature with stirring for 1.5 hrs. A saturated aqueous ammonium chloride solution (30 mL) was dropwise added to the mixture and the mixture was further stirred at room temperature for 30 min. Ethyl acetate was added to the mixture and, after stirring the mixture at room temperature for 30 min., an insoluble materials were filtered off. The filtrate was washed with saturated brine, dried over anhydrous magnesium sulfate, and concentrated. The obtained residue was subjected to silica gel column chromatography to give crystals (0.80 g, 42%) of 2-[[3-[(5-methyl-2-phenyl-4-thiazolyl)methoxy]-5-isoxazolyl]methoxy]nicotinaldehyde from a fraction eluted with ethyl acetate-hexane (1:2, v/v). Recrystallization from ethyl acetate-hexane gave colorless prism crystals. melting point: 123-124° C.

Reference Example 115

To a mixture of potassium t-butoxide (0.40 g) and dimethoxyethane (10 mL) was added a solution (10 mL) of toluenesulfonylmethylisocyanide (0.37 g) in dimethoxyethane at −78° C. Further, a solution (10 mL) of 2-[[3-[(5-methyl-2-phenyl-4-thiazolyl)methoxy]-5-isoxazolyl]methoxy]nicotinaldehyde (0.70 g) in dimethoxyethane was added to the reaction mixture. The reaction mixture was stirred at −78° C. for 1 hr. Methanol (10 mL) was added to the reaction mixture at room temperature and the mixture was heated under reflux for 30 min. To the reaction mixture was added water and the mixture was extracted with ethyl acetate. The organic layer was washed successively with saturated aqueous sodium hydrogencarbonate and saturated brine, dried over anhydrous magnesium sulfate, and concentrated. The obtained residue was subjected to silica gel column chromatography to give crystals (0.45 g, 63%) of 2-[2-[[3-[(5-methyl-2-phenyl-4-thiazolyl)methoxy]-5-isoxazolyl]methoxy]-3-pyridyl]acetonitrile from a fraction eluted with ethyl acetate-hexane (1:2, v/v). Recrystallization from ethyl acetate-hexane gave colorless prism crystals. melting point: 103-104° C.

Reference Example 116

To a mixture of 2-(5-methyl-2-phenyl-4-oxazolyl)ethanol (5.64 g), methyl 3-hydroxy-5-isoxazolecarboxylate (8.00 g), tributylphosphine (15.9 g) and tetrahydrofuran (200 mL) was added a solution (100 mL) of 1,1'-(azodicarbonyl)dipiperidine (19.9 g) in tetrahydrofuran at room temperature and the mixture was stirred for 15 hrs. The precipitated crystals were removed by filtration and the filtrate was concentrated. The residue was subjected to silica gel column chromatography to give crystals (9.50 g, 73%) of methyl 3-[2-(5-methyl-2-phenyl-4-oxazolyl)ethoxy]-5-isoxazolecarboxylate from a fraction eluted with ethyl acetate-hexane (1:3, v/v). Recrystallization from ethyl acetate-hexane gave colorless prism crystals. melting point: 90-91° C.

Reference Example 117

To a mixture of methyl 3-[2-(5-methyl-2-phenyl-4-oxazolyl)ethoxy]-5-isoxazolecarboxylate (9.2 g) and tetrahydrofuran (200 mL) was added lithium aluminum hydride (1.06 g) under ice-cooling, and the mixture was stirred at room temperature for 30 min. Dilute hydrochloric acid was added to acidify the mixture and the mixture was extracted with ethyl acetate. The organic layer was washed with saturated brine, dried over anhydrous magnesium sulfate, and concentrated. The obtained residue was subjected to silica gel column chromatography to give crystals (4.90 g, 58%) of [3-[2-(5-methyl-2-phenyl-4-oxazolyl)ethoxy]-5-isoxazolyl]methanol from a fraction eluted with ethyl acetate-hexane (1:2, v/v). Recrystallization from ethyl acetate-hexane gave colorless prism crystals. melting point: 115-116° C.

Reference Example 118

To a mixture of 2-(5-methyl-2-phenyl-4-oxazolyl)ethanol (9.90 g), methyl 6-chloronicotinate (8.36 g) and N,N-dimethylformamide (100 mL) was added sodium hydride (60%, oil, 2.40 g) under ice-cooling. The reaction mixture was stirred at room temperature for 3 hrs. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give a mixture of methyl 6-[2-(5-methyl-2-phenyl-4-oxazolyl)ethoxy]nicotinate and [2-(5-methyl-2-phenyl-4-oxazolyl)ethyl] 6-[2-(5-methyl-2-phenyl-4-oxazolyl)ethoxy]nicotinate from a fraction eluted with ethyl acetate-hexane (1:4, v/v). To a mixture of the obtained mixture (8.41 g) and tetrahydrofuran (200 mL) was added lithium aluminum hydride (1.85 g) under ice-cooling, and the mixture was stirred at room temperature for 1 hr. Sodium sulfate 10 hydrate (15.7 g) was added to the mixture and hexane and ethyl acetate were added, and the mixture was stirred at room temperature for 30 min. The insoluble materials were removed by filtration, and the filtrate was concentrated. The obtained residue was subjected to silica gel column chromatography to give crystals (4.08 g, 27%) of [6-[2-[(5-methyl-2-phenyl-4-oxazolyl)ethoxy]-3-pyridyl]methanol from a fraction eluted with ethyl acetate-hexane (1:3, v/v). Recrystallization from ethyl acetate-hexane gave colorless prism crystals. melting point: 112-113° C.

Reference Example 119

A mixture of 2-methyl-5-(5-methyl-2-phenyl-4-oxazolylmethoxy)pyridine (18.04 g), 3-chloroperbenzoic acid (18.85 g) and tetrahydrofuran (100 mL) was stirred overnight at room temperature and concentrated. The residue was subjected to silica gel column chromatography to give a colorless oil from a fraction eluted with tetrahydrofuran. A solution of the obtained colorless oil in acetic anhydride (100 mL) was slowly added to acetic anhydride (200 mL) heated to 130° C. and the mixture was stirred for 2 hrs. and concentrated. The residue was dissolved in ethyl acetate, washed with saturated aqueous sodium hydrogencarbonate and then with saturated brine, dried (MgSO$_4$) and concentrated. The residue was subjected to silica gel column chromatography to give [5-(5-methyl-2-phenyl-4-oxazolylmethoxy)-2-pyridylmethyl] acetate (18.09 g, yield 83%) as a colorless oil from a fraction eluted with ethyl acetate-hexane (1:2, volume ratio).

NMR (CDCl$_3$) δ: 2.13 (3H, s), 2.45 (3H, s), 5.05 (2H, s), 5.16 (2H, s), 7.26-7.50 (5H, m), 7.94-8.05 (2H, m), 8.38-8.43 (1H, m).

Reference Example 120

A mixture of [5-(5-methyl-2-phenyl-4-oxazolylmethoxy)-2-pyridylmethyl]acetate (18.0 g), 1N aqueous sodium hydroxide solution (75 mL) and methanol (100 mL) was stirred at room temperature for 3 hrs. and concentrated. The residue was dissolved in ethyl acetate, washed with water and then with saturated brine, dried over anhydrous magnesium sulfate and concentrated. The obtained colorless crystals were collected by filtration to give 5-(5-methyl-2-phenyl-4-oxazolylmethoxy)-2-pyridylmethanol (14.29 g, yield 91%). The crystals were recrystallized from ethyl acetate-hexane. melting point: 125-126° C.

Reference Example 121

To a mixture of (5-methyl-2-phenyl-4-thiazolyl)methanol (5.0 g), 6-chloro-3-cyanopyridine (3.38 g) and N,N-dimethylformamide (100 mL) was added sodium hydride (60%, oil, 1.07 g) under ice-cooling. The reaction mixture was stirred at room temperature for 1 hr. Water was added to the reaction mixture and the mixture was extracted with ethyl acetate. The organic layer was washed with saturated brine, dried over anhydrous magnesium sulfate, and concentrated. The obtained residue was subjected to silica gel column chromatography to give crystals (5.55 g, 74%) of 6-[(5-methyl-2-phenyl-4-thiazolyl)methoxy]nicotinonitrile from a fraction eluted with ethyl acetate-hexane (1:2, v/v). Recrystallization from ethyl acetate-hexane gave colorless prism crystals. melting point: 124-125° C.

Reference Example 122

To a mixture of 6-[(5-methyl-2-phenyl-4-thiazolyl)methoxy]nicotinonitrile (5.45 g) and anhydrous toluene (150 mL) was dropwise added a solution (0.95 M, 41.0 mL) of diisobutylaluminum hydride in hexane at −78° C. The reaction mixture was allowed to warm to room temperature with stirring for 1.5 hrs. A saturated aqueous ammonium chloride solution (100 mL) was dropwise added to the mixture, and the mixture was further stirred at room temperature for 30 min. Ethyl acetate was added to the mixture and the mixture was stirred at room temperature for 30 min. Insoluble materials were filtered away. The filtrate was washed with saturated brine, dried over anhydrous magnesium sulfate, and concentrated. The obtained residue was subjected to silica gel column chromatography to give crystals (4.30 g, 78%) of 6-[(5-methyl-2-phenyl-4-thiazolyl)methoxy]nicotinaldehyde from a fraction eluted with ethyl acetate-hexane (1:4, v/v). Recrystallization from ethyl acetate-hexane gave colorless prism crystals. melting point: 120-121° C.

Reference Example 123

To a mixture of 6-[(5-methyl-2-phenyl-4-thiazolyl)methoxy]nicotinaldehyde (4.20 g), tetrahydrofuran (50 ml) and ethanol (50 mL) was added sodium borohydride (0.51 g) at room temperature and the mixture was stirred at room temperature for 30 min. To the reaction mixture was added water and the mixture was extracted with ethyl acetate. The organic layer was washed with saturated brine, dried over anhydrous magnesium sulfate and concentrated to give crystals (4.10 g, 97%) of [6-[(5-methyl-2-phenyl-4-thiazolyl)methoxy]-3-pyridyl]methanol. Recrystallization from ethyl acetate-hexane gave colorless prism crystals. melting point: 70-71° C.

Reference Example 124

To a mixture of [2-(2-furyl)-5-methyl-4-oxazolyl]methanol (5.18 g), 6-chloro-3-cyanopyridine (4.00 g) and N,N-dimethylformamide (100 mL) was added sodium hydride (60%, oil, 1.27 g) under ice-cooling. The reaction mixture was stirred at room temperature for 1 hr. Water was added to the reaction mixture and the mixture was extracted with ethyl acetate. The organic layer was washed successively with water and saturated brine, dried over anhydrous magnesium sulfate, and concentrated. The obtained residue was subjected to silica gel column chromatography to give crystals (6.97 g, 86%) of 6-[[2-(2-furyl)-5-methyl-4-oxazolyl]methoxy]nicotinonitrile from a fraction eluted with ethyl acetate-hexane (1:2, v/v). Recrystallization from ethyl acetate-hexane gave colorless prism crystals. melting point: 105-106° C.

Reference Example 125

To a mixture of 6-[[2-(2-furyl)-5-methyl-4-oxazolyl]methoxy]nicotinonitrile (6.77 g) and anhydrous toluene (150 mL) was dropwise added a solution (0.95 M, 55.8 mL) of diisobutylaluminum hydride in hexane at −78° C. The reaction mixture was allowed to warm to room temperature with stirring for 1 hr. A saturated aqueous ammonium chloride solution (100 mL) was dropwise added to the mixture and the mixture was further stirred at room temperature for 30 min. Ethyl acetate was added to the mixture and the mixture was stirred at room temperature for 30 min. Insoluble materials were filtered off. The filtrate was washed with saturated brine, dried over anhydrous magnesium sulfate, and concentrated. The obtained residue was subjected to silica gel column chromatography to give crystals (3.25 g, 47%) of 6-[[2-(2-furyl)-5-methyl-4-oxazolyl]methoxy]nicotinaldehyde from a fraction eluted with ethyl acetate-hexane (1:2, v/v). Recrystallization from ethyl acetate-hexane gave colorless prism crystals. melting point: 139-140° C.

Reference Example 126

To a mixture of 6-[[2-(2-furyl)-5-methyl-4-oxazolyl]methoxy]nicotinaldehyde (3.10 g), tetrahydrofuran (50 ml) and ethanol (50 mL) was added sodium borohydride (0.41 g) at room temperature and the mixture was stirred at room temperature for 30 min. To the reaction mixture was added water and the mixture was extracted with ethyl acetate. The organic layer was washed with saturated brine, dried over anhydrous magnesium sulfate, and concentrated to give crystals (2.86 g, 92%) of [6-[[2-(2-furyl)-5-methyl-4-oxazolyl]methoxy]-3-pyridyl]methanol. Recrystallization from ethyl acetate-hexane gave colorless prism crystals. melting point: 120-121° C.

Reference Example 127

A mixture of 4-chloromethyl-5-methyl-2-phenyloxazole (20.18 g), 4-benzyloxyphenol (17.70 g), anhydrous potassium carbonate (12.22 g) and N,N-dimethylformamide (200 mL) was stirred at 90° C. for 15 hrs. The reaction mixture was poured into water, and the precipitated solid was collected by filtration, and dried with air to give crystals (29.03 g, 88%) of 4-[(4-benzyloxyphenoxy)methyl]-5-methyl-2-phenyloxazole. Recrystallization from ethyl acetate-hexane gave colorless leaflet crystals. melting point: 126-127° C. A mixture of the obtained 4-[(4-benzyloxyphenoxy)methyl]-5-methyl-2-phenyloxazole (22.6 g), 5% palladium carbon (10.0 g) and tetrahydrofuran (300 mL) was subjected to catalytic hydrogenation at room temperature and 1 atm. After filtering off the catalyst, the solvent was evaporated under reduced pressure to give crystals (16.3 g, 95%) of 4-[(5-methyl-2-phenyl-4-oxazolyl)methoxy]phenol. Recrystallization from ethyl acetate-hexane gave colorless prism crystals. melting point: 168-169° C.

Reference Example 128

To a mixture of benzyl alcohol (32.0 g), 2-chloro-3-cyanopyridine (37.3 g) and N,N-dimethylformamide (200 mL) was added sodium hydride (60%, oil, 12.92 g) under ice-cooling. The reaction mixture was stirred at room temperature for 3 days. Water was added to the reaction mixture and the mixture was extracted with ethyl acetate. The organic layer was washed successively with water and saturated brine, dried over anhydrous magnesium sulfate and concentrated. The obtained residue was subjected to silica gel column chromatography to give 2-(benzyloxy)nicotinonitrile as an oil (39.13 g, 69%) from a fraction eluted with ethyl acetate-hexane (1:6, v/v).

¹H-NMR (CDCl₃) δ: 5.52 (2H, s), 6.99 (1H, dd, J=7.6, 5.2 Hz), 7.31-7.52 (5H, m), 7.89 (1H, dd, J=7.6, 2.0 Hz), 8.36 (1H, dd, J=5.2, 2.0 Hz).

To a mixture of 2-(benzyloxy)nicotinonitrile (47.50 g) and anhydrous toluene (100 mL) was dropwise added a solution (1 M, 500 mL) of diisobutylaluminum hydride in hexane at −78° C. The reaction mixture was allowed to warm to room temperature with stirring for 1.5 hrs. A saturated aqueous ammonium chloride solution was dropwise added to the mixture and the mixture was stirred at room temperature for 30 min. Ethyl acetate was added to the mixture, and the mixture was further stirred at room temperature for 30 min. Insoluble materials were filtered off. The filtrate was washed with saturated brine, dried over anhydrous magnesium sulfate and concentrated. The obtained residue was subjected to silica gel column chromatography to give 2-(benzyloxy)nicotinaldehyde as an oil (19.71 g, 41%) from a fraction eluted with ethyl acetate-hexane (1:6, v/v).

¹H-NMR (CDCl₃) δ: 5.54 (2H, s), 7.04 (1H, dd, J=7.4, 5.2 Hz), 7.26-7.50 (5H, m), 8.14 (1H, dd, J=7.4-2.0 Hz), 8.40 (1H, dd, J=5.2, 2.0 Hz), 10.45 (1H, s).

To a mixture of potassium t-butoxide (4.52 g) and dimethoxyethane (20 mL) was added a solution (20 mL) of toluenesulfonylmethylisocyanide (4.12 g) in dimethoxyethane at −78° C. Further, a solution (20 mL) of 2-(benzyloxy)nicotinaldehyde (4.12 g) in dimethoxyethane was added to the reaction mixture. The reaction mixture was stirred at −78° C. for 1 hr. Methanol (20 mL) was added to the reaction mixture at room temperature and the mixture was heated under reflux for 30 min. To the reaction mixture was added water and the mixture was extracted with ethyl acetate. The organic layer was washed successively with saturated aqueous sodium hydrogencarbonate and saturated brine, dried over anhydrous magnesium sulfate and concentrated. The obtained residue was subjected to silica gel column chromatography to give 2-(2-benzyloxy-3-pyridyl)acetonitrile as an oil from a fraction eluted with ethyl acetate-hexane (1:8, v/v).

¹H-NMR (CDCl₃) δ: 3.70 (2H, s), 5.44 (2H, s), 6.95 (1H, dd, J=7.4, 5.0 Hz), 7.32-7.49 (5H, m), 7.71 (1H, dd, J=7.4, 1.8 Hz), 8.17 (1H, dd, J=5.0, 1.8 Hz).

A mixture of 2-(2-benzyloxy-3-pyridyl)acetonitrile (1.0 g) and 10% hydrogen chloride-methanol (30 mL) was stirred at room temperature for 3 days. The reaction mixture was concentrated, and saturated aqueous sodium hydrogencarbonate was added to basify the residue. The mixture was concentrated and a mixed solvent of ethyl acetate and tetrahydrofuran (3:1, v/v) was added to the residue. Insoluble materials were removed by filtration. The filtrate was dried over anhydrous magnesium sulfate and concentrated to give crystals (0.42 g, 56%) of methyl 2-(2-oxo-1,2-dihydro-3-pyridyl)acetate. Recrystallization from ethyl acetate-hexane gave colorless prism crystals. melting point: 183-184° C.

Reference Example 129

To a mixture of 4-[(5-methyl-2-phenyl-4-oxazolyl)methoxy]phenol (2.70 g), ethyl 2-chloromethylnicotinate (1.74 g) and N,N-dimethylformamide (100 mL) was added sodium hydride (60%, oil, 0.42 g) under ice-cooling. The reaction mixture was stirred at room temperature for 2 hrs. The reaction mixture was poured into water and extracted with ethyl acetate. The organic layer was washed successively with water and saturated brine, dried over anhydrous magnesium sulfate and concentrated. The obtained residue was subjected to silica gel column chromatography to give ethyl 2-[[4-[(5-methyl-2-phenyl-4-oxazolyl)methoxy]phenoxy]methyl]nicotinate as a colorless oil (2.45 g, 63%) from a fraction eluted with ethyl acetate-hexane (1:4, v/v).

¹H-NMR (CDCl₃) δ: 1.31 (3H, t, J=7.2 Hz), 2.41 (3H, s), 4.34 (2H, q, J=7.2 Hz), 4.93 (2H, s), 5.48 (2H, s), 6.91-6.93 (4H, m), 7.32-7.45 (4H, m), 7.97-8.04 (2H, m), 8.19-8.24 (1H, m), 8.72-8.76 (1H, m).

Reference Example 130

To a mixture of ethyl 2-[[4-[(5-methyl-2-phenyl-4-oxazolyl)methoxy]phenoxy]methyl]nicotinate (2.4 g), sodium borohydride (1.02 g) and tetrahydrofuran (100 ml) was dropwise added methanol (10 mL) at 60° C. The reaction mixture was stirred at 60° C. for 1 hr. Water was added to the reaction mixture and the mixture was extracted with ethyl acetate. The organic layer was washed successively with water and saturated brine, dried over anhydrous magnesium sulfate and concentrated to give 2-[[4-[(5-methyl-2-phenyl-4-oxazolyl)methoxy]phenoxy]methyl]-3-pyridyl]methanol as a colorless oil (2.15 g, 99%).

¹H-NMR (CDCl₃) δ: 2.41 (3H, s), 2.63 (1H, brs), 4.80-4.82 (2H, m), 4.93 (2H, s), 5.25 (2H, s), 6.92-6.95 (4H, m), 7.29 (1H, dd, J=7.8, 4.8 Hz), 7.39-7.47 (3H, m), 7.82 (1H, dd, J=7.8, 1.8 Hz), 7.97-8.04 (2H, m), 8.53 (1H, dd, J=4.8, 1.8 Hz).

Reference Example 131

To a mixture of [2-[[4-[(5-methyl-2-phenyl-4-oxazolyl)methoxy]phenoxy]methyl]-3-pyridyl]methanol (2.10 g), triethylamine (1.05 g) and ethyl acetate (100 mL) was dropwise added methanesulfonyl chloride (1.19 g) under ice-cooling, and the mixture was stirred at room temperature for 2.5 hrs. The reaction mixture was washed successively with water, saturated aqueous sodium hydrogencarbonate and saturated brine, dried over anhydrous magnesium sulfate and concentrated to give an oil. To a mixture of this oil and dimethyl sulfoxide (50 mL) was added an aqueous solution (5 mL) of sodium cyanide (0.51 g) at room temperature and the mixture was stirred at room temperature for 2 hrs. To the reaction mixture was added water and the mixture was extracted with ethyl acetate. The organic layer was washed with saturated brine, dried over anhydrous magnesium sulfate and concentrated. The obtained residue was subjected to silica gel column chromatography to give crystals (1.49 g, 70%) of 2-[2-[[4-[(5-methyl-2-phenyl-4-oxazolyl)methoxy]phenoxy]methyl]-3-pyridyl]acetonitrile from a fraction eluted with ethyl acetate-hexane (1:1, v/v). Recrystallization from ethyl acetate-hexane gave colorless prism crystals. melting point: 134-135° C.

Reference Example 132

To a mixture of [4-[[3-methyl-1-(2-pyridyl)-1H-pyrazol-4-yl]methoxy]phenyl]methanol (2.00 g), 2-chloro-3-cyanopyridine (1.00 g) and N,N-dimethylformamide (20 mL) was added sodium hydride (60%, oil, 0.30 g) under ice-cooling. The reaction mixture was stirred at room temperature for 3 hrs. Water was added to the reaction mixture and the mixture was extracted with ethyl acetate. The organic layer was washed successively with water and saturated brine dried over anhydrous magnesium sulfate and concentrated to give crystals (2.48 g, 92%) of 2-[4-[[3-methyl-1-(2-pyridyl)-1H-pyrazol-4-yl]methoxy]benzyloxy]nicotinonitrile. Recrystallization from acetone-hexane gave colorless prism crystals. melting point: 108-109° C.

Reference Example 133

To a mixture of 2-[4-[[3-methyl-1-(2-pyridyl)-1H-pyrazol-4-yl]methoxy]benzyloxy]nicotinonitrile (2.03 g) and anhydrous toluene (100 mL) was dropwise added a solution (0.95 M, 11.8 mL) of diisobutylaluminum hydride in hexane at −78° C. The reaction mixture was allowed to warm to room temperature with stirring for 1 hr. A saturated aqueous ammonium chloride solution (30 mL) was dropwise added to the mixture and the mixture was further stirred at room temperature for 30 min. Ethyl acetate was added to the mixture and the mixture was stirred at room temperature for 30 min. Insoluble materials were filtered off, and the filtrate was washed with saturated brine, dried over anhydrous magnesium sulfate and concentrated. The obtained residue was subjected to silica gel column chromatography to give crystals (0.61 g, 30%) of 2-[4-[[3-methyl-1-(2-pyridyl)-1H-pyrazol-4-yl]methoxy]benzyloxy]nicotinaldehyde from a fraction eluted with ethyl acetate-hexane (1:3, v/v). Recrystallization from ethyl acetate-hexane gave colorless prism crystals. melting point: 106-1-07° C.

Reference Example 134

To a mixture of potassium t-butoxide (0.30 g) and dimethoxyethane (10 mL) was added a solution (10 mL) of toluenesulfonylmethylisocyanide (0.27 g) in dimethoxyethane at −78° C. Further, a solution (10 mL) of 2-[4-[[3-methyl-1-(2-yridyl)-1H-pyrazol-4-yl]methoxy]benzyloxy]nicotinaldehyde (0.52 g) in dimethoxyethane was added to the reaction mixture. The reaction mixture was stirred at −78° C. for 1 hr. Methanol (10 mL) was added to the reaction mixture at room temperature and the mixture was heated under reflux for 30 min. To the reaction mixture was added water and the mixture was extracted with ethyl acetate. The organic layer was washed successively with saturated aqueous sodium hydrogencarbonate and saturated brine, dried over anhydrous magnesium sulfate and concentrated. The obtained residue was subjected to silica gel column chromatography to give crystals (0.38 g, 72%) of 2-[2-[4-[[3-methyl-1-(2-pyridyl)-1H-pyrazol-4-yl]methoxy]benzyloxy]-3-pyridyl]acetonitrile from a fraction eluted with ethyl acetate-hexane (1:2, v/v). Recrystallization from ethyl acetate-hexane gave colorless prism crystals. melting point: 138-139° C.

Reference Example 135

To a solution of 2-methylamino-4-phenylthiazole (1.76 g) in N,N-dimethylformamide (25 mL) was gradually added sodium hydride (60%, oil, 351 mg) at room temperature and the mixture was stirred for 30 min. Methyl 4-bromobenzoate (2.11 g) was added, and the mixture was further stirred for 1.5 hrs. To the reaction mixture was added water and the mixture was extracted with ethyl acetate. The organic layer was washed with saturated brine, dried over anhydrous magnesium sulfate and concentrated. The residue was subjected to silica gel column chromatography to give methyl 4-[methyl(4-phenyl-2-thiazolyl)aminomethyl]benzoate (2.56 g, 86%) as a yellow oil from a fraction eluted with ethyl acetate-hexane (1:3, v/v).

$^1$H-NMR (CDCl$_3$) δ: 3.08 (3H, s), 3.90 (3H, s), 4.85 (2H, s), 6.75 (1H, s), 7.27-7.43 (5H, m), 7.86 (2H, dd, J=8.4, 1.4 Hz), 8.02 (1H, d, J=8.4 Hz).

Reference Example 136

To a solution of methyl 4-[methyl(4-phenyl-2-thiazolyl)aminomethyl]benzoate (2.06 g) in tetrahydrofuran (30 mL) was dropwise added a solution (0.9 M, 30 mL) of diisobutylaluminum hydride in hexane at 0° C. and the mixture was stirred at room temperature for 2 hrs. Diethyl ether was added to the reaction mixture, sodium sulfate 10 hydrate was further added and the mixture was stirred for 2 hrs. After filtering off insoluble materials, the filtrate was concentrated. The residue was subjected to silica gel column chromatography to give white crystals (1.85 g, 98%) of 4-[methyl(4-phenyl-2-thiazolyl)aminomethyl]benzyl alcohol from a fraction eluted with ethyl acetate-hexane (1:1, v/v). melting point: 88-90° C.

Reference Example 137

To a mixture of [3-(5-methyl-2-phenyl-4-oxazolylmethoxy)-5-isoxazolyl]methanol (2.00 g), 2-chloro-3-cyanopyridine (1.16 g) and N,N-dimethylformamide (60 mL) was gradually added sodium hydride (60%, oil, 335 mg) under ice-cooling. After stirring the reaction mixture at room temperature for 90 min., water was added to the reaction mixture. The mixture was neutralized with 2N hydrochloric acid and extracted with ethyl acetate. The organic layer was washed with water, dried over anhydrous magnesium sulfate and concentrated. The obtained residue was subjected to silica gel column chromatography to give crystals (2.61 g, 96%) of 2-[[3-[(5-methyl-2-phenyl-4-oxazolyl)methoxy]-5-isoxazolyl]methoxy]nicotinonitrile from a fraction eluted with ethyl acetate-hexane (1:1, v/v). Recrystallization from ethyl acetate-hexane gave colorless prism crystals. melting point: 139-140° C.

Reference Example 138

To a mixture of 2-[[3-[(5-methyl-2-phenyl-4-oxazolyl)methoxy]-5-isoxazolyl]methoxy]nicotinonitrile (2.60 g) and anhydrous toluene (100 mL) was dropwise added a solution (0.95 M, 15.5 mL) of diisobutylaluminum hydride in hexane at −78° C. The reaction mixture was allowed to warm to room temperature with stirring for 1.5 hrs. A saturated aqueous ammonium chloride solution (30 mL) was dropwise added to the mixture and the mixture was further stirred at room temperature for 30 min. Ethyl acetate was added to the mixture and the mixture was washed with saturated aqueous ammonium chloride solution and then with saturated brine. The organic layer was dried over anhydrous magnesium sulfate and concentrated. The obtained residue was subjected to silica gel column chromatography to give crystals (1.70 g, 65%) of 2-[[3-[(5-methyl-2-phenyl-4-oxazolyl)methoxy]-5-isoxazolyl]methoxy]nicotinaldehyde from a fraction eluted with ethyl acetate-hexane (1:2, v/v). Recrystallization from ethyl acetate-hexane gave colorless needle crystals. melting point: 90-91° C.

Reference Example 139

To a mixture of 2-[[3-[(5-methyl-2-phenyl-4-oxazolyl)methoxy]-5-isoxazolyl]methoxy]nicotinaldehyde (1.64 g), tetrahydrofuran (20 ml) and ethanol (20 mL) was added sodium borohydride (80 mg) at 0° C., and the mixture was stirred at room temperature for 1 hr. Water was added to the reaction mixture, and the precipitated crystals were collected by filtration and recrystallized from ethyl acetate-isopropyl ether to give colorless needle crystals (1.50 g, 91%) of

[2-[[3-[(5-methyl-2-phenyl-4-oxazolyl)methoxy]-5-isoxazolyl]methoxy]-3-pyridyl]methanol. melting point: 136-137° C.

Reference Example 140

To a mixture of [2-[[3-[(5-methyl-2-phenyl-4-oxazolyl)methoxy]-5-isoxazolyl]methoxy]-3-pyridyl]methanol (1.47 g), triethylamine (760 mg) and ethyl acetate (150 mL) was dropwise added methanesulfonyl chloride (860 mg) under ice-cooling and the mixture was stirred at room temperature or 2 hrs. The reaction mixture was washed with water, dried over anhydrous magnesium sulfate and concentrated to give an oil. To a mixture of this oil and dimethyl sulfoxide (50 mL) was added an aqueous solution (5 mL) of sodium cyanide (280 mg) at room temperature and the mixture was stirred at room temperature for 12 hrs. To the reaction mixture was added water and the mixture was extracted with ethyl acetate. The ethyl acetate layer was washed with water, dried over anhydrous magnesium sulfate and concentrated. The residue was subjected to silica gel column chromatography to give crystals (1.40 g, 68%) of 2-[2-[[3-[(5-methyl-2-phenyl-4-oxazolyl)methoxy]-5-isoxazolyl]methoxy]-3-pyridyl]acetonitrile from a fraction eluted with ethyl acetate-hexane (1:2, v/v). Recrystallization from ethyl acetate-hexane gave colorless prism crystals (1.07 g, 71%). melting point: 110-111° C.

Reference Example 141

To a mixture of 4-[5-methyl-2-(2-naphthyl)-4-oxazolylmethoxy]benzaldehyde (6.00 g), tetrahydrofuran (80 mL) and methanol (20 mL) was gradually added sodium borohydride (330 mg) at room temperature. After stirring for 30 min., water was added to the reaction mixture, and the precipitated crystals were collected by filtration and recrystallized from acetone-methanol to give colorless prism crystals (5.76 g, 95%) of 4-[5-methyl-2-(2-naphthyl)-4-oxazolylmethoxy]benzyl alcohol. melting point: 181-182° C.

Reference Example 142

To a mixture of 4-[5-methyl-2-(2-naphthyl)-4-oxazolylmethoxy]benzyl alcohol (4.00 g), 2-chloro-3-cyanopyridine (2.41 g) and N,N-dimethylformamide (80 mL) was gradually added sodium hydride (60%, oil, 700 mg) under ice-cooling. After stirring the reaction mixture at room temperature for 2 hrs, water was added to the reaction mixture and the mixture was extracted with ethyl acetate. The ethyl acetate layer was washed with water, dried over anhydrous magnesium sulfate and concentrated. Recrystallization from ethyl acetate-isopropyl ether gave colorless prism crystals (4.02 g, 78%) of 2-[4-[5-methyl-2-(2-naphthyl)-4-oxazolylmethoxy]benzyloxy]nicotinonitrile. melting point: 145-146° C.

Reference Example 143

To a mixture of 2-[4-[5-methyl-2-(2-naphthyl)-4-oxazolylmethoxy]benzyloxy]nicotinonitrile (2.30 g) and toluene (50 mL) was dropwise added a solution (0.95 M, 16.2 mL) of diisobutylaluminum hydride in hexane at −78° C. The mixture was stirred at room temperature for 1 hr. A saturated aqueous ammonium chloride solution (30 mL) was dropwise added to the mixture and the mixture was further stirred at room temperature for 30 min. Ethyl acetate was added to the mixture, and the mixture was washed with saturated aqueous ammonium chloride solution and then with saturated brine. The organic layer was dried over anhydrous magnesium sulfate, and concentrated to give crystals (1.50 g, 65%) of the corresponding aldehyde. To a mixture of this crystal (1.50 g), tetrahydrofuran (30 mL) and ethanol (30 mL) was gradually added sodium borohydride (80 mg) at room temperature. After stirring for 1 hr., water was added to the reaction mixture, and the precipitated crystals were collected by filtration. Recrystallization from acetone-hexane gave colorless prism crystals (1.30 g, 86%) of [2-[4-[5-methyl-2-(2-naphthyl)-4-oxazolylmethoxy]benzyloxy]-3-pyridyl]methanol. melting point: 161-162° C.

Reference Example 144

To a mixture of [2-[4-[5-methyl-2-7 (2-naphthyl)-4-oxazolylmethoxy]benzyloxy]-3-pyridyl]methanol (1.25 g), triethylamine (570 mg) and tetrahydrofuran (80 mL) was dropwise added methanesulfonyl chloride (650 mg) under ice-cooling and the mixture was stirred at room temperature for 3 hrs. The reaction mixture was poured into water, and the precipitated crystals were collected by filtration and washed with water and then isopropyl ether. The crystals were dissolved in dimethyl sulfoxide (25 mL) and a solution of sodium cyanide (200 mg) in water (3 mL) was added at room temperature. The mixture was stirred at room temperature for 2 hrs. To the reaction mixture was added water and the mixture was extracted with ethyl acetate. The ethyl acetate layer was washed with water, dried over anhydrous magnesium sulfate and concentrated. The residue was subjected to silica gel column chromatography to give crystals of 2-[2-[4-[5-methyl-2-(2-naphthyl)-4-oxazolylmethoxy]benzyloxy]-3-pyridyl]acetonitrile from a fraction eluted with ethyl acetate-hexane (1:2, v/v). Recrystallization from ethyl acetate-hexane gave colorless prism crystals (770 mg, 60%). melting point: 182-183° C.

Reference Example 145

A mixture of 4-methoxy-3-(5-methyl-2-phenyl-4-oxazolylmethoxy)benzyl alcohol (3.22 g), thionyl chloride (0.73 ml) and toluene (50 ml) was refluxed for 1 hr. The reaction mixture was concentrated and saturated aqueous sodium hydrogencarbonate was added. The mixture was extracted with ethyl acetate. The ethyl acetate layer was washed with saturated brine, dried over anhydrous magnesium sulfate and concentrated. The residue was subjected to silica gel column chromatography to give 4-(5-chloromethyl-2-methoxyphenoxymethyl)-5-methyl-2-phenyloxazole (2.59 g, yield 75%) as colorless crystals from a fraction eluted with ethyl acetate. The crystals were recrystallized from ethyl acetate-hexane. melting point: 129-130° C.

Reference Example 146

To a mixture of [4-[[2-(2-furyl)-5-methyl-4-oxazolyl]methoxy]-3-methoxyphenyl]methanol (5.00 g), 2-chloro-3-cyanopyridine (2.65 g) and N,N-dimethylformamide (150 mL) was added sodium hydride (60%, oil, 0.70 g) at room temperature and the mixture was stirred for 15 hrs. Water was added to the reaction mixture and the precipitated crystals were collected by filtration to give crystals (6.60 g, yield 99%) of 3-cyano-2-[4-[[2-(2-furyl)-5-methyl-4-oxazolyl]methoxy]-3-methoxybenzyloxy]pyridine. Recrystallization from ethyl acetate-hexane gave colorless prism crystals. melting point: 137-138° C.

Reference Example 147

To a mixture of 3-cyano-2-[4-[[2-(2-furyl)-5-methyl-4-oxazolyl]methoxy]-3-methoxybenzyloxy]pyridine (6.30 g) and anhydrous toluene (250 mL) was dropwise added a solution (0.95 M, 47 mL) of diisobutylaluminum hydride in hexane at −78° C. The reaction mixture was allowed to warm to room temperature with stirring for 1 hr. A saturated aqueous ammonium chloride solution (50 mL) was dropwise added to the reaction mixture at 0° C. and ethyl acetate was further added. Insoluble materials were filtered off and the filtrate was extracted with ethyl acetate. The organic layer was washed with saturated brine, dried over anhydrous magnesium sulfate and concentrated. The residue was subjected to silica gel column chromatography to give crystals (1.0 g, yield 16%) of 2-[4-[[2-(2-furyl)-5-methyl-4-oxazolyl]methoxy]-3-methoxybenzyloxy]-3-pyridinecarbaldehyde from a fraction eluted with ethyl acetate-hexane (2:3, v/v). Recrystallization from ethyl acetate-hexane gave colorless prism crystals. melting point: 120-121° C.

Reference Example 148

To a mixture of 4-(3-chloromethylphenoxymethyl)-5-methyl-2-phenyloxazole (3.00 g), 3-mercaptobenzoic acid (1.47 g) and N,N-dimethylformamide (30 mL) was dropwise added triethylamine (2.13 g) at room temperature. The reaction mixture was stirred at room temperature for 1 hr. The reaction mixture was poured into water, acidified with 2N hydrochloric acid, and extracted with ethyl acetate. The organic layer was washed with water, dried over anhydrous magnesium sulfate and concentrated. The residue was subjected to silica gel column chromatography to give crystals (3.70 g, yield 90%) of 3-[3-[(5-methyl-2-phenyl-4-oxazolyl)methoxy]benzylthio]benzoic acid from a fraction eluted with acetone-hexane (1:1, v/v). Recrystallization from ethyl acetate gave colorless prism crystals. melting point: 129-130° C.

Reference Example 149

A mixture of 3-[3-[(5-methyl-2-phenyl-4-oxazolyl)methoxy]benzylthio]benzoic acid (3.20 g), conc. sulfuric acid (1 mL) and methanol (50 mL) was stirred with heating under reflux for 1 hr. The reaction mixture was concentrated, water was added to the residue and the mixture was extracted with ethyl acetate. The organic layer was washed with water, dried over anhydrous magnesium sulfate and concentrated. The residue was subjected to silica gel column chromatography to give methyl 3-[3-[(5-methyl-2-phenyl-4-oxazolyl)methoxy]benzylthio]benzoate as an oil (2.20 g, yield 67%) from a fraction eluted with ethyl acetate-hexane (1:4, v/v).

$^1$H-NMR (CDCl$_3$) δ: 2.42 (3H, s), 3.91 (3H, s), 4.14 (2H, s), 4.96 (2H, s), 6.90-7.01 (3H, m), 7.17-7.34 (2H, m), 7.43-7.46 (4H, m), 7.81-7.85 (1H, m), 7.99-8.04 (3H, m).

Reference Example 150

To a mixture of methyl 3-[3-[(5-methyl-2-phenyl-4-oxazolyl)methoxy]benzylthio]benzoate (2.20 g) and tetrahydrofuran (80 mL) was added lithium aluminum hydride (0.19 g) under ice-cooling, and the mixture was stirred for 2 hrs. The reaction mixture was poured into iced water, acidified with 2N hydrochloric acid and extracted with ethyl acetate. The organic layer was washed with water, dried over anhydrous magnesium sulfate and concentrated. The obtained oil was dissolved in toluene (80 mL). Manganese dioxide (6.0 g) was added to the mixture and the mixture was stirred at room temperature for 2 hrs. The reaction mixture was filtrated and the filtrate was concentrated. The residue was subjected to silica gel column chromatography to give 3-[3-[(5-methyl-2-phenyl-4-oxazolyl)methoxy]benzylthio] benzaldehyde as an oil (1.55 g, yield 76%) from a fraction eluted with ethyl acetate-hexane (1:3, v/v).

$^1$H-NMR (CDCl$_3$) δ: 2.42 (3H, m), 4.16 (2H, s), 4.96 (2H, s), 6.89-6.93 (2H, m), 7.00-7.02 (1H, m), 7.18-7.22 (1H, m), 7.35-7.53 (5H, m), 7.63-7.68 (1H, m), 7.77-7.79 (1H, m), 7.99-8.04 (2H, m), 9.93 (1H, s).

Reference Example 151

A mixture of 3-[3-[(5-methyl-2-phenyl-4-oxazolyl)methoxy]benzylthio]benzaldehyde (0.80 g), diethyl malonate (0.37 g), benzoic acid (0.07 g), piperidine (0.05 g) and toluene (40 mL) was heated under reflux for 4 hrs. with azeotropic dehydration. The reaction mixture was concentrated, water was added to the residue and the mixture was extracted with ethyl acetate. The organic layer was washed successively with saturated aqueous sodium hydrogencarbonate, dilute hydrochloric acid and water, dried over anhydrous magnesium sulfate and concentrated. The residue was subjected to silica gel column chromatography to give an oil from a fraction eluted with acetone-hexane (1:5, v/v). To a mixture of the obtained oil, tetrahydrofuran (20 mL) and ethanol (20 mL) was added sodium borohydride (0.02 g) at 0° C. and the mixture was stirred at 0° C. for 1 hr. The reaction mixture was poured into water, acidified with 2N hydrochloric acid and extracted with ethyl acetate. The organic layer was washed with water, dried over anhydrous magnesium sulfate and concentrated. The residue was subjected to silica gel column chromatography to give diethyl 2-[3-[3-[(5-methyl-2-phenyl-4-oxazolyl)methoxy]benzylthio]benzyl]malonate as an oil (0.71 g, yield 66%) from a fraction eluted with ethyl acetate-hexane (1:4, v/v).

$^1$H-NMR (CDCl$_3$) δ: 1.20 (6H, t, J=7.2 Hz), 2.43 (3H, s), 3.16 (2H, d, J=7.8 Hz), 3.59 (1H, t, J=7.8 Hz), 4.08 (2H, s), 4.15 (4H, q, J=7.2 Hz), 4.96 (2H, s), 6.87-6.92 (2H, m), 6.99-7.04 (2H, m), 7.14-7.25 (4H, m), 7.42-7.45 (3H, m), 7.99-8.05 (2H, m).

Reference Example 152

To a mixture of potassium t-butoxide (0.38 g) and dimethoxyethane (10 mL) was added a solution of toluenesulfonylmethylisocyanide (0.33 g) in dimethoxyethane (5 mL) at −78° C. and the mixture was stirred for 10 min. A solution (10 mL) of 3-[3-[(5-methyl-2-phenyl-4-oxazolyl)methoxy]benzylthio]benzaldehyde (0.70 g) in dimethoxyethane was added to the reaction mixture and the mixture was stirred for 30 min at −78° C. Methanol (25 mL) was added to the reaction mixture at room temperature and the mixture was heated under reflux for 1 hr. The reaction mixture was concentrated, water was added to the residue, and the mixture was extracted with ethyl acetate. The organic layer was washed with saturated brine, dried over anhydrous magnesium sulfate and concentrated. The residue was subjected to silica gel column chromatography to give 2-[3-[3-[(5-methyl-2-phenyl-4-oxazolyl)methoxy]benzylthio]phenyl]acetonitrile as an oil (0.295 g, yield 41%) from a fraction eluted with acetone-hexane (1:5, v/v).

$^1$H-NMR (CDCl$_3$) δ: 2.43 (3H, s), 3.68 (2H, s), 4.11 (2H, s), 4.96 (2H, s), 6.89-7.00 (3H, m), 7.18-7.26 (5H, m), 7.42-7.46 (3H, m), 7.99-8.04 (2H, m).

Reference Example 153

(4-[(5-Methyl-2-phenyl-4-oxazolyl)methoxy]phenyl) methanol (400 g) and then 2-chloro-3-cyanopyridine (206.7 g) were added to dimethylformamide (1.6 L). To the obtained mixture was added triturated sodium hydroxide (59.4 g) and the mixture was stirred at 20-30° C. for 48 hrs. Water (1.6 L) was dropwise added at the same temperature and the mixture was stirred for 2 hrs. The precipitated crystals were collected by filtration, washed with water (1.6 L) and then ice-cooled ethyl acetate (800 ml), and dried (40° C.) under reduced pressure to give 2-({4-[(5-methyl-2-phenyl-4-oxazolyl)methoxy]benzyl}oxy)nicotinonitrile as white crystals.

$^1$H-NMR (DMSO-d$_6$, δ, 300 MHz); 2.42 (3H, s), 4.99 (2H, s), 5.45 (2H, s), 6.93-7.03 (3H, m), 7.41-7.44 (5H, m), 7.84-=7.88 (1H, m), 7.98-8.02 (2H, m), 8.33-8.36 (1H, m).

Reference Example 154

2-({4-[(5-Methyl-2-phenyl-4-oxazolyl)methoxy] benzyl}oxy)nicotinonitrile (5.42 g) was added to toluene (189.6 ml) under an argon stream and cooled to −65° C. To the obtained mixture was dropwise added a 1.5 M solution (20 m) of diisobutylaluminum hydride in toluene and the mixture was stirred at the same temperature for 30 min. and raised to −20° C. A saturated Rochelle salt solution (100 ml) was dropwise added to the obtained mixture and water (50 ml) was further added. After stirring at 40° C. for 10 min., the mixture was partitioned. The aqueous layer was extracted with toluene (20 ml). The organic layers were combined, washed with water and concentrated under reduced pressure. The residue was dissolved in toluene/ethyl acetate=20/1 (50 ml) and silica gel (10.8 g) was added to the mixture. The mixture was stirred for 1 hr. Silica gel was filtrated and washed with toluene/ethyl acetate=20/1 (58 ml). The filtrates were combined and, after concentration under reduced pressure, the residue was dissolved in tetrahydrofuran (31 ml). A solution of sodium hydrogensulfite (1.193 g) in water (3 ml) was added to the obtained solution and the mixture was stirred at room temperature for 3 hrs. The crystallized crystals were collected by filtration washed with ice-cooled tetrahydrofuran and dried under reduced pressure to give sodium hydroxy[2-({4-[(5-methyl-2-phenyl-4-oxazolyl)methoxy]benzyl}oxy)pyridin-3-yl]methanesulfonate as white crystals.

$^1$H-NMR (DMSO-d$_6$, δ, 300 MHz); 2.44 (3H, s), 4.99 (2H, s), 5.25 (2H, s), 5.32 (1H, d, J=6.1 Hz), 5.75 (1H, d, J=6.1 Hz), 6.90-6.94 (1H, m), 7.02 (2H, d, J=8.6 Hz), 7.43 (2H, d, J=8.6 Hz), 7.49-7.52 (3H, m), 7.90-8.02 (4H, m).

Reference Example 155

Under an argon stream, 2-({4-[(5-methyl-2-phenyl-4-oxazolyl)methoxy]benzyl}oxy)nicotinonitrile (5.42 g) was added to toluene (189.6 ml). The obtained mixture was cooled to −65° C., and a 1.5 M solution (20 ml) of diisobutylaluminum hydride in toluene was dropwise added. The mixture was stirred at the same temperature for 1 hr and 45 min. A saturated ammonium chloride solution (54 ml) was dropwise added to the reaction solution and the mixture was stirred at room temperature. Insoluble materials were filtered off, the solution was washed with ethyl acetate (27 ml) and partitioned. The organic layer was washed with 10% Rochelle salt solution and water and concentrated under reduced pressure. The residue was dissolved in toluene/ethyl acetate=5/1 (54 ml) and silica gel (16 g) was added. The mixture was stirred for 1 hr. Silica gel was filtrated off, and washed with toluene/ethyl acetate=5/1 (54 ml). The filtrates were combined and concentrated under reduced pressure. The residue was dissolved in tetrahydrofuran (32 ml) and a solution of sodium hydrogensulfite (1.9 g) in water (3.2 ml) was added to the mixture, and the mixture was stirred at room temperature for 45 min. A solution of sodium hydrogensulfite (630 mg) in water (1 ml) was added to the reaction solution and the mixture was stirred at room temperature for 13 hrs. To the reaction solution was added isopropyl ether (6.4 ml) and the mixture was stirred at room temperature for 30 min. and under ice-cooling for 1 hr. The crystallized crystals were filtrated off and washed with ice-cooled tetrahydrofuran/isopropyl ether=1/1 (12 ml) to give sodium hydroxy[2-({4-[(5-methyl-2-phenyl-4-oxazolyl)methoxy]benzyl}oxy)pyridin-3-yl]methanesulfonate.

This compound was added to a mixture of ethyl acetate (54 ml) and 10% sodium carbonate (54 ml) and the mixture was stirred for 30 min. and partitioned. The organic layer was washed with 10% brine (54 ml), and then with 5% brine (54 ml) and concentrated under reduced pressure. To the residue was added ethyl acetate (5.4 ml) and the residue was dissolved under reflux. The obtained solution was stirred for 1 hr. and n-hexane (16.2 ml) was added to the solution. The mixture was stirred at room temperature for 1 hr, and then under ice-cooling for 1 hr. The precipitated crystals were filtrated off and washed with ice-cooled ethyl acetate/n-hexane=1/1 (35 ml) and dried under reduced pressure at 40° C. to give 2-({4-[(5-methyl-2-phenyl-4-oxazolyl)methoxy]benzyl}oxy)nicotinaldehyde as white crystals.

$^1$H-NMR (CDCl$_3$, δ, 300 MHz); 2.43 (3H, s), 5.01 (2H, s), 5.47 (2H, s), 7.01-7.06 (3H, m), 7.41-7.45 (5H, m), 7.99-8.03 (2H, m), 8.10-8.13 (1H, m), 8.37-8.40 (1H, m), 10.40 (1H, s).

Reference Example 156

Distilled water (150 ml) was added to Raney-nickel (75 ml), and after stirring, the supernatant was decanted. This step was repeated 3 times and distilled water (50 ml) and pyridine (250 ml) were added to Raney-nickel under a nitrogen stream. The obtained mixture was heated to 40° C. and a solution of sodium phosphinate monohydrate (260 g) in distilled water (200 ml) was dropwise added at 40-60° C. over 30 min. The mixture was stirred at 50-60° C. for 15 min. Formic acid (250 ml) was dropwise added to the reaction solution at 50-60° C. over 30 min and a solution of 2-({4-[(5-methyl-2-phenyl-4-oxazolyl)methoxy]benzyl}oxy)nicotinonitrile (50 g) in pyridine (250 ml) was dropwise added at 50-60° C. over 30 min. The mixture was stirred at the same temperature for 30 min. Ethyl acetate (250 ml) and water (250 ml) were added to the reaction solution and insoluble materials were removed. The resulting mixture was washed with ethyl acetate (500 ml). After cooling the filtrate to 20-25° C., it was partitioned 20% Citric acid (500 ml) was further dropwise added slowly to the organic layer at 20-25° C. and the organic layer was separated. Water (50 ml) was added to the organic layer and 20% aqueous citric acid solution was further added dropwise slowly at 20-25° C. to adjust its pH to 3.5. The mixture was partitioned and the organic layer was washed successively with 5% brine, saturated aqueous sodium hydrogencarbonate and 5% brine and concentrated under reduced pressure. The residue was dissolved in tetrahydrofuran (75 ml).

Separately, to a solution of sodium hydrogensulfite (26.18 g) in water (75 ml) were added tetrahydrofuran (350 ml) and isopropyl ether (150 ml) to give a mixed solution. To the mixed solution was added a half amount of the aforementioned tetrahydrofuran solution, and after stirring at room temperature for 1.5 hrs., a ¼ amount of the aforementioned tetrahydrofuran solution was added and the mixture was stirred at room temperature for 30 min. Then, a ¼ amount of the aforementioned tetrahydrofuran solution was added and the mixture was stirred at room temperature for 2 hrs. The obtained mixture was cooled to 0-10° C. and stirred for 2 hrs. the precipitated crystals were filtrated and washed with tetrahydrofuran/isopropyl ether=3/1 (200 ml) cooled to 0-10° C. to give sodium hydroxy[2-({4-[(5-methyl-2-phenyl-4-oxazolyl)methoxy]benzyl}oxy)pyridin-3-yl]methanesulfonate.

This compound was suspended in ethyl acetate (400 ml) and 10% aqueous sodium carbonate solution (400 ml) and the mixture was stirred at 20-30° C. for 1 hr. The organic layer was washed with water (400 ml×3) and concentrated under reduced pressure to give white crystals. Ethyl acetate (50 ml) was added to the crystals, and after heating to 50-60° C., the mixture was stirred for 2 hrs. n-Hexane (100 ml) was dropwise added to the obtained mixture, and after stirring at 20-30° C. for 1 hr., the mixture was cooled to 0-10° C. and stirred for 2 hrs. The precipitated crystals were filtrated, washed with n-hexane/ethyl acetate=2/1 (100 ml) cooled to 0-10° C. in advance and dried (40° C.) under reduced pressure to give 2-({4-[(5-methyl-2-phenyl-4-oxazolyl)methoxy]benzyl}oxy)nicotinaldehyde as white crystals.

$^1$H-NMR (CDCl$_3$, δ, 300 MHz); 2.43 (3H, s), 5.01 (2H, s), 5.47 (2H, s), 7.01-7.06 (3H, m), 7.41-7.45 (5H, m), 7.99-8.03 (2H, m), 8.10-8.13 (1H, m), 8.37-8.40 (1H, m), 10.40 (1H, s).

Reference Example 157

To a mixture of acetonitrile (80 ml) and water (135 mg) were added trimethylsulfonium iodide (6.12 g) and then potassium hydroxide (3.36 g) with stirring 2-({4-[(5-Methyl-2-phenyl-4-oxazolyl)methoxy]benzyl}oxy)nicotinaldehyde (6.0 g) was added to the mixture, and after heating, the mixture was stirred at 40-50° C. for 4 hrs. The mixture was cooled to 0-10° C. and water (32 ml) and then 20% citric acid were dropwise added to the mixture at the same temperature to adjust to pH=7.1. The reaction solution was concentrated under reduced pressure, and after evaporation of acetonitrile, extracted with t-butylmethyl ether (60 ml). The organic layer was washed with water and concentrated under reduced pressure t-Butylmethyl ether (4 ml) was added to the residue and the mixture was stirred at room temperature for 30 min. and n-hexane (12 ml) was added. The mixture was stirred at room temperature for 30 min., and t-butylmethyl ether/n-hexane=1/3 (8 ml) was added. The mixture was stirred at room temperature for 15 min. and than under ice-cooling for 40 min. The obtained crystals were filtrated, washed with t-butylmethyl ether/n-hexane=1/3 (8 ml) ice-cooled in advance and dried under reduced pressure to give 2-({4-[(5-methyl-2-phenyl-4-oxazolyl)methoxy]benzyl}oxy)-3-oxyran-2-ylpyridine as white crystals.

$^1$H-NMR (CDCl$_3$, δ, 300 MHz); 2.45 (3H, s), 2.67 (1H, dd, J=2.6, 5.7 Hz), 3.15 (1H, dd, J=4.2, 5.7 Hz), 4.15 (1H, dd, J=2.6, 4.2 Hz), 5.02 (2H, s), 5.41 (2H, s), 6.88-7.07 (3H, m), 7.41-7.4.7 (6H, m), 8.02-8.13 (3H, m).

Example 1

To a mixture of 4-[(5-methyl-2-phenyl-4-oxazolyl)methoxy]benzyl 2-[3-4-[(5-methyl-2-phenyl-4-oxazolyl)methoxy]benzyloxy]phenyl]acetate (2.40 g), tetrahydrofuran (7 mL) and ethanol (7 mL) was added 1N aqueous sodium hydroxide solution (7.0 mL) and the mixture was stirred overnight at room temperature. The reaction mixture was concentrated, and water and diethyl ether were added to the residue. Dilute hydrochloric acid was added to acidify the aqueous layer, and the precipitated solid was collected by filtration, and dried with air to give crystals (1.24 g, 85%) of 2-[3-[4-[(5-methyl-2-phenyl-4-oxazolyl)methoxy]benzyloxy]phenyl]acetic acid. Recrystallization from acetone-hexane gave colorless prism crystals. melting point: 159-160° C.

Example 2

A mixture of 4-(4-chloromethylphenoxymethyl)-5-methyl-2-phenyloxazole (2.42 g), ethyl 3-(3-hydroxyphenyl)propionate (1.35 g), anhydrous potassium carbonate (0.97 g) and N,N-dimethylformamide (30 mL) was stirred at 90° C. for 15 hrs. The reaction mixture was poured into water and extracted with ethyl acetate. The organic layer was washed with saturated brine, dried over anhydrous magnesium sulfate, and concentrated. The obtained residue was subjected to silica gel column chromatography to give crystals (1.82 g, 55%) of ethyl 3-[3-[4-[(5-methyl-2-phenyl-4-oxazolyl)methoxy]benzyloxy]phenyl]propionate from a fraction eluted with ethyl acetate-hexane (1:6, v/v). Recrystallization from ethyl acetate-hexane gave colorless prism crystals. melting point: 90-91° C.

Example 3

To a mixture of ethyl 3-[3-[4-[(5-methyl-2-phenyl-4-oxazolyl)methoxy]benzyloxy]phenyl]propionate (1.00 g), tetrahydrofuran (3 mL) and ethanol (3 mL) was added a 1N aqueous sodium hydroxide solution (4.2 mL) and the mixture was stirred at 50° C. for 1 hr. 1N Hydrochloric acid and water were added to acidify the reaction mixture and the mixture was extracted with ethyl acetate. The organic layer was washed with saturated brine, dried over anhydrous magnesium sulfate, and concentrated to give crystals (0.61 g, 66%) of 3-[3-[4-[(5-methyl-2-phenyl-4-oxazolyl)methoxy]benzyloxy]phenyl]propionic acid. Recrystallization from ethyl acetate-hexane gave colorless prism crystals. melting point: 157-158° C.

Example 4

To a mixture of 4-(4-chloromethylphenoxymethyl)-5-methyl-2-phenyloxazole (1.00 g), methyl 2-(2-ethoxy-5-hydroxyphenyl)acetate (0.60 g) and N, N-dimethylformamide (30 mL) was added sodium hydride (60%, oil, 0.14 g) under ice-cooling, and the mixture was stirred at room temperature for 2 hrs. The reaction mixture was poured into water and extracted with ethyl acetate. The organic layer was washed with saturated brine, and dried over anhydrous magnesium sulfate. After concentration of the organic layer, the residue was subjected to silica gel column chromatography to give crystals (0.70 g, 70%) of methyl-2-[2-ethoxy-5-[4-[(5-methyl-2-phenyl-4-oxazolyl)methoxy]benzyloxy]phenyl]acetate from a fraction eluted with ethyl acetate-hexane (1:4, v/v). Recrystallization from ethyl acetate-hexane gave colorless prism crystals. melting point: 82-83° C.

Example 5

To a mixture of methyl 2-[2-ethoxy-5-[4-[(5-methyl-2-phenyl-4-oxazolyl)methoxy]benzyloxy]phenyl]acetate (0.56 g), tetrahydrofuran (2 mL) and methanol (2 mL) was added 1N aqueous sodium hydroxide solution (2.2 mL) and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate, and concentrated to give crystals (0.45 g, 87%) of 2-[2-ethoxy-5-[4-[(5-methyl-2-phenyl-4-oxazolyl)methoxy]benzyloxy]phenyl]acetic acid. Recrystallization from ethyl acetate-hexane gave colorless prism crystals. melting point: 122-123° C.

Example 6

A mixture of 4-(4-chloromethylphenoxymethyl)-5-methyl-2-phenyloxazole (1.44 g), ethyl 3-(2-ethoxy-5-hydroxyphenyl)propionate (1.0 g), anhydrous potassium carbonate (0.58 g) and N,N-dimethylformamide (50 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give ethyl 3-[2-ethoxy-5-[4-[(5-methyl-2-phenyl-4oxazolyl)methoxy]benzyloxy]phenyl]propionate as an oil (1.57 g, 72%) from a fraction eluted with ethyl acetate-hexane (1:6, v/v).
$^1$H-NMR (CDCl$_3$) δ: 1.22 (3H, t, J=7.0 Hz), 1.38 (3H, t, J=7.0 Hz), 2.44 (3H, s), 2.56-2.64 (2H, m), 2.90-2.98 (2H, m), 3.96 (2H, q, J=7.0 Hz), 4.11 (2H, q, J=7.0 Hz), 4.97 (2H, s), 5.01 (2H, s), 6.65-6.84 (3H, m), 7.00-7.06 (2H, m), 7.26-7.47 (5H, m), 7.99-8.05 (2H, m).

Example 7

To a mixture of ethyl 3-[2-ethoxy-5-[4-[(5-methyl-2-phenyl-4-oxazolyl)methoxy]benzyloxy]phenyl]propionate (0.58 g), tetrahydrofuran (2 mL) and ethanol (2 mL) was added 1N aqueous sodium hydroxide solution (2.2 mL) and the mixture was stirred at room temperature for 2 hrs. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.46 g, 85%) of 3-[2-ethoxy-5-[4-[(5-methyl-2-phenyl-4-oxazolyl)methoxy]benzyloxy]phenyl]propionic acid. Recrystallization from ethyl acetate-hexane gave colorless prism crystals. melting point: 129-130° C.

Example 8

A mixture of 4-(4-chloromethylphenoxymethyl)-5-methyl-2-phenyloxazole (0.80 g), methyl 4-hydroxyphenylacetate (0.42 g), anhydrous potassium carbonate (0.35 g) and N,N-dimethylformamide (20 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give crystals (0.70 g, 63%) of methyl 2-[4-[4-[(5-methyl-2-phenyl-4-oxazolyl)methoxy]benzyloxy]phenyl]acetate from a fraction eluted with ethyl acetate-hexane (1:6, v/v). Recrystallization from ethyl acetate-hexane gave colorless prism crystals. melting point: 93-94° C.

Example 9

To a mixture of methyl 2-[4-[4-[(5-methyl-2-phenyl-4-oxazolyl)methoxy]benzyloxy]phenyl]acetate (0.55 g), tetrahydrofuran (3 mL) and methanol (3 mL) was added a 1N aqueous sodium hydroxide solution (2.5 mL) and the mixture was stirred at room temperature for 2 hrs. 1N Hydrochloric acid and water were added to acidify the reaction mixture, and the mixture was extracted with ethyl acetate. The organic layer was washed with saturated brine, dried over anhydrous magnesium sulfate, and concentrated to give crystals (0.45 g, 87%) of 2-[4-[4-[(5-methyl-2-phenyl-4-oxazolyl)methoxy]benzyloxy]phenyl]acetic acid. Recrystallization from tetrahydrofuran-hexane gave colorless prism crystals. melting point: 166-167° C.

Example 10

A mixture of 4-(4-chloromethylphenoxymethyl)-5-methyl-2-phenyloxazole (1.91 g), ethyl 2-(2-hydroxyphenyl)acetate (1.00 g), anhydrous potassium carbonate (0.76 g) and N,N-dimethylformamide (20 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give ethyl 2-[2-[4-[(5-methyl-2-phenyl-4-oxazolyl)methoxy]benzyloxy]phenyl]acetate as an oil (1.35 g, 54%) from a fraction eluted with ethyl acetate-hexane (1:4, v/v).
$^1$H-NMR (CDCl$_3$) δ: 1.19 (3H, t, J=7.0 Hz), 2.44 (3H, s), 3.65 (2H, s), 4.10 (2H, q, J=7.0 Hz), 5.00 (2H, s), 5.02 (2H, s), 6.89-7.04 (4H, m), 7.18-7.46 (7H, m), 7.99-8.04 (2H, m).

Example 11

To a mixture of ethyl 2-[2-[4-[(5-methyl-2-phenyl-4-oxazolyl)methoxy]benzyloxy]phenyl]acetate (1.35 g), tetrahydrofuran (5 mL) and ethanol (5 mL) was added 1N aqueous sodium hydroxide solution (6 mL) and the mixture was stirred at room temperature for 2 hrs. 1N Hydrochloric acid and water were added to acidify the reaction mixture, and the mixture was extracted with ethyl acetate. The organic layer was washed with saturated brine, dried over anhydrous magnesium sulfate, and concentrated to give crystals (0.98 g, 76%) of 2-[2-[4-[(5-methyl-2-phenyl-4-oxazolyl)methoxy]benzyloxy]phenyl]acetic acid. Recrystallization from ethyl acetate-hexane gave colorless prism crystals. melting point: 153-154° C.

Example 12

A mixture of 4-(4-chloromethylphenoxymethyl)-5-methyl-2-phenyloxazole (0.60 g), methyl 3-(2-hydroxyphenyl)propionate (0.345 g), anhydrous potassium carbonate (0.529 g) and N,N-dimethylformamide (7 mL) was stirred at room temperature for 18 hrs., and further at 70° C. for 5 hrs. The reaction mixture was poured into water and extracted with ethyl acetate. The organic layer was washed with saturated brine, dried over anhydrous magnesium sulfate and concentrated. The obtained residue was subjected to silica gel column chromatography to give methyl 3-[2-[4-[(5-methyl-2-phenyl-4-oxazolyl)methoxy]benzyloxy]phenyl]propionate as an oil (0.61 g, 70%) from a fraction eluted with ethyl acetate-hexane (1:3, v/v).
NMR (CDCl$_3$) δ: 2.45 (3H, s), 2.59-2.68 (2H, m), 2.94-3.03 (2H, m), 3.64 (3H, s), 5.01 (2H, s), 5.03 (2H, s), 6.84-6.93 (2H, m), 7.03 (2H, d, J=8.6 Hz), 7.13-7.23 (2H, m), 7.34-7.48 (5H, m), 7.99-8.05 (2H, m).

Example 13

A mixture of methyl 3-[2-[4-[(5-methyl-2-phenyl-4-oxazolyl)methoxy]benzyloxy]phenyl]propionate (0.54 g), lithium hydroxide monohydrate (0.0743 g), tetrahydrofuran (6 mL), water (4 mL) and methanol (4 mL) was stirred at room temperature for 1.5 hrs. 1N Hydrochloric acid (1.8 mL) was added to acidify the reaction mixture and the mixture was extracted with ethyl acetate. The organic layer was washed with saturated brine, dried over anhydrous magnesium sulfate and concentrated to give crystals of 3-[2-[4-[(5-methyl-2-phenyl-4-oxazolyl)methoxy]benzyloxy]phenyl]propionic acid. Recrystallization from ethyl acetate-hexane gave colorless prism crystals (0.49 g, 94%). melting point: 98-99° C.

Example 14

Methyl 2-[5-bromo-2-[4-[(5-methyl-2-phenyl-4-oxazolyl)methoxy]benzyloxy]phenyl]acetate (1.00 g), tetramethyltin (0.73 g), tetrakis(triphenylphosphine)palladium (0.11 g) and toluene (50 mL) were stirred with heating under reflux under an argon atmosphere for 40 hrs. The reaction mixture was concentrated and the residue was subjected to silica gel column chromatography to give crystals (0.28 g, 32%) of methyl 2-[5-methyl-2-[4-[(5-methyl-2-phenyl-4-oxazolyl)methoxy]benzyloxy]phenyl]acetate from a fraction eluted with ethyl acetate-hexane (1:6, v/v). Recrystallization from ethyl acetate-hexane gave colorless prism crystals. melting point: 80-81° C.

Example 15

To a mixture of methyl 2-[5-methyl-2-[4-[(5-methyl-2-phenyl-4-oxazolyl)methoxy]benzyloxy]phenyl]acetate (0.22 g), tetrahydrofuran (1 mL) and methanol (1 mL) was added a 1N aqueous sodium hydroxide solution (1 mL) and the mixture was stirred at 50° C. for 1.5 hrs. 1N Hydrochloric acid (1 mL) and water were added to the reaction mixture and the mixture was extracted with ethyl acetate. The organic layer was washed with saturated brine, dried over anhydrous magnesium sulfate and concentrated to give crystals (0.16 g, 76%) of 2-[5-methyl-2-[4-[(5-methyl-2-phenyl-4-oxazolyl)methoxy]benzyloxy]phenyl]acetic acid. Recrystallization from ethyl acetate-hexane gave colorless prism crystals. melting point: 115-116° C.

Example 16

To a mixture of 2-[5-hydroxy-2-[4-[(5-methyl-2-phenyl-4-oxazolyl)methoxy]benzyloxy]phenyl]acetonitrile (0.30 g) and ethanol (3 mL) was added a 4N aqueous potassium hydroxide solution (1 mL) and the mixture was stirred with heating under reflux for 24 hrs. 1N Hydrochloric acid and water were added to acidify the reaction mixture, and the mixture was extracted with ethyl acetate-tetrahydrofuran. The organic layer was washed with saturated brine, dried over anhydrous magnesium sulfate and concentrated. The obtained residue was subjected to silica gel column chromatography to give crystals (0.05 g, 16%) of 2-[5-hydroxy-2-[4-[(5-methyl-2-phenyl-4-oxazolyl)methoxy]benzyloxy]phenyl]acetic acid from a fraction eluted with ethyl acetate-hexane (5:1, v/v). Recrystallization from tetrahydrofuran-hexane gave pale-brown prism crystals. melting point: 194-195° C.

Example 17

To a mixture of [4-[(5-methyl-2-phenyl-4-oxazolyl)methoxy]phenyl]methanol (1.0 g), methyl 2-(5-chloro-2-hydroxyphenyl)acetate (0.74 g), triphenylphosphine (1.08 g) and tetrahydrofuran (50 mL) was dropwise added a solution (40%, 1.79 g) of diethyl azodicarboxylate in toluene at room temperature, and the mixture was stirred for 15 hrs. The reaction mixture was concentrated and the residue was subjected to silica gel column chromatography to give methyl 2-[5-chloro-2-[4-[(5-methyl-2-phenyl-4-oxazolyl)methoxy]benzyloxy]phenyl]acetate as an oil (0.68 g, 42%) from a fraction eluted with ethyl acetate-hexane (1:6, v/v).

$^1$H-NMR (CDCl$_3$) δ: 2.44 (3H, s), 3.61 (2H, s), 3.63 (3H, s), 4.99 (2H, s), 5.00 (2H, s), 6.82-6.87 (1H, m), 7.00-7.04 (2H, m), 7.17-7.22 (2H, m), 7.29-7.33 (2H, m), 7.42-7.47 (3H, m), 7.99-8.04 (2H, m).

Example 18

To a mixture of methyl 2-[5-chloro-2-[4-[(5-methyl-2-phenyl-4-oxazolyl)methoxy]benzyloxy]phenyl]acetate (0.68 g), tetrahydrofuran (2 mL) and methanol (2 mL) was added a 1N aqueous sodium hydroxide solution (2.8 mL) and the mixture was stirred at 50° C. for 1 hr. 1N Hydrochloric acid (3 mL) and water were added to the reaction mixture, and the precipitated solid was collected by filtration, and dried with air to give crystals (0.63 g, 97%) of 2-[5-chloro-2-[4-[(5-methyl-2-phenyl-4-oxazolyl)methoxy]benzyloxy]phenyl]acetic acid. Recrystallization from ethyl acetate-hexane gave colorless prism crystals. melting point: 160-161° C.

Example 19

To a mixture of 4-(4-chloromethylphenoxymethyl)-5-methyl-2-phenyloxazole (4.58 g), methyl 2-(5-bromo-2-hydroxyphenyl)acetate (3.0 g) and N,N-dimethylformamide (100 mL) was added sodium hydride (60%, oil, 0.54 g) under ice-cooling, and the mixture was stirred at room temperature for 15 hrs. The reaction mixture was poured into water and extracted with ethyl acetate. The organic layer was washed with saturated brine, and dried over anhydrous magnesium sulfate. After concentration of the organic layer, the residue was subjected to silica gel column chromatography to give crystals (4.46 g, 70%) of methyl 2-[5-bromo-2-[4-[(5-methyl-2-phenyl-4-oxazolyl)methoxy]benzyloxy]phenyl]acetate from a fraction eluted with ethyl acetate-hexane (1:6, v/v). Recrystallization from ethyl acetate-hexane gave colorless prism crystals. melting point: 100-101° C.

Example 20

To a mixture of methyl 2-[5-bromo-2-[4-[(5-methyl-2-phenyl-4-oxazolyl)methoxy]benzyloxy]phenyl]acetate (0.80 g), tetrahydrofuran (3 mL) and methanol (3 mL) was added a 1N aqueous sodium hydroxide solution (3 mL) and the mixture was stirred at 50° C. for 1.5 hrs. 1N Hydrochloric acid (3 mL) and water were added to the reaction mixture, and the precipitated solid was collected by filtration and dried with air to give crystals (0.63 g, 83%) of 2-[5-bromo-2-[4-[(5-methyl-2-phenyl-4-oxazolyl)methoxy]benzyloxy]phenyl]acetic acid. Recrystallization from ethyl acetate-hexane gave colorless prism crystals. melting point: 162-163° C.

Example 21

Methyl 2-[5-bromo-2-[4-[(5-methyl-2-phenyl-4-oxazolyl)methoxy]benzyloxy]phenyl]acetate (1.20 g), phenylboronic acid (0.30 g), tetrakis(triphenylphosphine)palladium (0.14 g), 2M aqueous sodium carbonate solution (3.7 mL), methanol (5 mL), and toluene (20 mL) were stirred with heating under reflux for 24 hrs under an argon atmosphere. The reaction mixture was diluted with ethyl acetate, washed with saturated brine and dried over anhydrous magnesium sulfate. After concentration of the organic layer, the residue was subjected to silica gel column chromatography to give crystals (0.89 g, 74%) of methyl 2-[2-[4-[(5-methyl-2-phenyl-4-oxazolyl)methoxy]benzyloxy]-5-phenylphenyl]acetate from a fraction eluted with ethyl acetate-hexane (1:6, v/v). Recrystallization from ethyl acetate-hexane gave colorless prism crystals. melting point: 111-112° C.

Example 22

To a mixture of methyl 2-[2-[4-[(5-methyl-2-phenyl-4-oxazolyl)methoxy]benzyloxy]-5-phenylphenyl]acetate (0.65 g), tetrahydrofuran (3 mL) and methanol (3 mL) was added a 1N aqueous sodium hydroxide solution (2.8 mL) and the mixture was stirred at 50° C. for 1.5 hrs. 1N Hydrochloric acid (3 mL) and water were added to the reaction mixture, and the precipitated solid was collected by filtration and dried with air to give crystals (0.65 g, 92%) of 2-[2-[4-[(5-methyl-2-phenyl-4-oxazolyl)methoxy]benzyloxy]-5-phenylphenyl]acetic acid. Recrystallization from ethyl acetate-hexane gave colorless prism crystals. melting point: 102-103° C.

Example 23

To a mixture of 4-(4-chloromethylphenoxymethyl)-5-methyl-2-phenyloxazole (1.54 g), methyl 2-(2-hydroxy-5-methoxyphenyl)acetate (0.80 g) and N,N-dimethylformamide (20 mL) was added sodium hydride (60%, oil, 0.18 g) under ice-cooling, and the mixture was stirred at room temperature for 15 hrs. The reaction mixture was poured into water and extracted with ethyl acetate. The organic layer was washed with saturated brine and dried over anhydrous magnesium sulfate. After concentration of the organic layer, the residue was subjected to silica gel column chromatography to give crystals (1.22 g, 63%) of methyl 2-[5-methoxy-2-[4-[(5-methyl-2-phenyl-4-oxazolyl)methoxy]benzyloxy]phenyl]acetate from a fraction eluted with ethyl acetate-hexane (1:6, v/v). Recrystallization from ethyl acetate-hexane gave colorless prism crystals. melting point: 160-161° C.

Example 24

To a mixture of methyl 2-[5-methoxy-2-[-4-[(5-methyl-2-phenyl-4-oxazolyl)methoxy]benzyloxy]phenyl]acetate (0.98 g), tetrahydrofuran (4 mL) and methanol (4 mL) was added a 1N aqueous sodium hydroxide solution (4.2 mL) and the mixture was stirred at 50° C. for 15 hrs. 1N Hydrochloric acid (4.2 mL) and water were added to the reaction mixture, and the precipitated solid was collected by filtration and dried with air to give crystals (0.90 g, 94%) of 2-[5-methoxy-2-[4-[(5-methyl-2-phenyl-4-oxazolyl)methoxy]benzyloxy]phenyl]acetic acid. Recrystallization from ethyl acetate-hexane gave colorless prism crystals. melting point: 134-136° C.

Example 25

To a mixture of 4-(4-chloromethylphenoxymethyl)-5-methyl-2-phenyloxazole (0.72 g), methyl 2-(5-ethoxy-2-hydroxyphenyl)acetate (0.40 g) and N,N-dimethylformamide (20 mL) was added sodium hydride (60%, oil, 0.08 g) under ice-cooling and the mixture was stirred at room temperature for 15 hrs. The reaction mixture was poured into water and extracted with ethyl acetate. The organic layer was washed with saturated brine and dried over anhydrous magnesium sulfate. After concentration of the organic layer, the residue was subjected to silica gel column chromatography to give methyl 2-[5-ethoxy-2-[4-[(5-methyl-2-phenyl-4-oxazolyl)methoxy]benzyloxy]phenyl]acetate as an oil (0.56 g, 60%) from a fraction eluted with ethyl acetate-hexane (1:4, v/v).

NMR (CDCl$_3$) δ: 1.38 (3H, t, J=7.0 Hz), 2.44 (3H, s), 3.62 (5H, s), 3.98 (2H, q, J=7.0 Hz), 4.95 (2H, s), 5.00 (2H, s), 6.73-6.89 (3H, m), 6.99-7.04 (2H, m), 7.25-7.47 (5H, m), 7.99-8.04 (2H, m).

Example 26

To a mixture of methyl 2-[5-ethoxy-2-[4-[(5-methyl-2-phenyl-4-oxazolyl)methoxy]benzyloxy]phenyl]acetate (0.56 g), tetrahydrofuran (2 mL) and methanol (2 mL) was added a 1N aqueous sodium hydroxide solution (2.2 mL) and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.45 g, 87%) of 2-[5-ethoxy-2-[4-[(5-methyl-2-phenyl-4-oxazolyl)methoxy]benzyloxy]phenyl]acetic acid. Recrystallization from ethyl acetate-hexane gave colorless prism crystals. melting point: 122-123° C.

Example 27

To a mixture of 2-[5-benzyloxy-2-[4-[(5-methyl-2-phenyl-4-oxazolyl)methoxy]benzyloxy]phenyl]acetonitrile (0.18 g), tetrahydrofuran (0.5 mL) and ethanol (3 mL) was added a 4N aqueous potassium hydroxide solution (1 mL), and the mixture was stirred with heating under reflux for 1 hr. 1N Hydrochloric acid and water were added to acidify the reaction mixture, and the mixture, was extracted with ethyl acetate-tetrahydrofuran. The organic layer was washed with saturated brine, dried over anhydrous magnesium sulfate and concentrated. The obtained residue was subjected to silica gel column chromatography to give crystals (0.03 g, 17%) of 2-[5-benzyloxy-2-[4-[(5-methyl-2-phenyl-4-oxazolyl)methoxy]benzyloxy]phenyl]acetic acid from a fraction eluted with ethyl acetate-hexane (2:3, v/v). Recrystallization from tetrahydrofuran-hexane gave colorless prism crystals. melting point: 140-141° C.

Example 28

A mixture of 4-(4-chloromethylphenoxymethyl)-5-methyl-2-phenyloxazole (1.44 g), ethyl 3-(5-ethoxy-2-hydroxyphenyl)propionate (1.0 g), anhydrous potassium carbonate (0.58 g) and N,N-dimethylformamide (50 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give ethyl 3-[5-ethoxy-2-[4-[(5-methyl-2-phenyl-4-oxazolyl)methoxy]

benzyloxy]phenyl]propionate as an oil (1.57 g, 72%) from a fraction eluted with ethyl acetate-hexane (1:6, v/v).

¹H-NMR (CDCl₃) δ: 1.22 (3H, t, J=7.0 Hz), 1.38 (3H, t, J=7.0 Hz), 2.44 (3H, s), 2.56-2.64 (2H, m), 2.90-2.98 (2H, m), 3.96 (2H, q, J=7.0 Hz), 4.11 (2H, q, J=7.0 Hz), 4.97 (2H, s), 5.01 (2H, s), 6.65-6.84 (3H, m), 7.00-7.06 (2H, m), 7.26-7.47 (5H, m), 7.99-8.05 (2H, m).

Example 29

To a mixture of ethyl 3-[5-ethoxy-2-[4-[(5-methyl-2-phenyl-4-oxazolyl)methoxy]benzyloxy]phenyl]propionate (1.56 g), tetrahydrofuran (5 mL) and ethanol (5 mL) was added a 1N aqueous sodium hydroxide solution (6.0 mL), and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate and concentrated to give crystals (1.14 g, 78%) of 3-[5-ethoxy-2-[4-[(5-methyl-2-phenyl-4-oxazolyl)methoxy]benzyloxy]phenyl]propionic acid. Recrystallization from ethyl acetate-hexane gave colorless prism crystals. melting point: 115-116° C.

Example 30

To a mixture of 4-(3-chloromethylphenoxymethyl)-5-methyl-2-phenyloxazole (0.70 g), methyl 2-(2-hydroxyphenyl)acetate (0.33 g) and N,N-dimethylformamide (10 mL) was added sodium hydride (60%, oil, 0.09 g) under ice-cooling and the mixture was stirred at room temperature for 15 hrs. The reaction mixture was poured into water and extracted with ethyl acetate. The organic layer was washed with saturated brine, and dried over anhydrous magnesium sulfate. After concentration of the organic layer, the residue was subjected to silica gel column chromatography to give methyl 2-[2-[3-[(5-methyl-2-phenyl-4-oxazolyl)methoxy]benzyloxy]phenyl]acetate as an oil (0.50 g, 56%) from a fraction eluted with ethyl acetate-hexane (1:4, v/v).

¹H-NMR (CDCl₃) δ: 2.44 (3H, s), 3.65 (3H, s), 3.69 (2H, s), 5.02 (2H, s), 5.08 (2H, s), 6.88-7.34 (8H, m), 7.41-7.45 (3H, m), 7.99-8.04 (2H, m).

Example 31

To a mixture of methyl 2-[2-[3-[(5-methyl-2-phenyl-4-oxazolyl)methoxy]benzyloxy]phenyl]acetate (0.50 g), tetrahydrofuran (2 mL) and methanol (2 mL) was added a 1N aqueous sodium hydroxide solution (2.0 mL) and the mixture was stirred at 50° C. for 1 hr. 1N Hydrochloric acid (2 mL) and water were added to acidify the reaction mixture and the mixture was extracted with ethyl acetate. The organic layer was washed with saturated brine, dried over anhydrous magnesium sulfate and concentrated: to give crystals (0.41 g, 87%) of 2-[2-[3-[(5-methyl-2-phenyl-4-oxazolyl)methoxy]benzyloxy]phenyl]acetic acid. Recrystallization from methyl acetate-hexane gave colorless prism crystals. melting point: 117-118° C.

Example 32

A mixture of 4-(3-chloromethylphenoxymethyl)-5-methyl-2-phenyloxazole (1.21 g), methyl 2-(3-hydroxyphenyl)acetate (0.60 g), anhydrous potassium carbonate (0.65 g) and N,N-dimethylformamide (10 mL) was stirred at 80° C. for 5 hrs. The reaction mixture was poured into water and extracted with ethyl acetate. The organic layer was washed successively with dilute hydrochloric acid and saturated brine, dried over anhydrous magnesium sulfate and concentrated. The obtained residue was subjected to silica gel column chromatography to give an oil from a fraction eluted with ethyl acetate-hexane (1:4, v/v). To a mixture of the obtained oil, tetrahydrofuran (5 mL) and methanol (5 mL) was added a 1N aqueous sodium hydroxide solution (5 mL), and the mixture was stirred at room temperature for 2 hrs. The reaction mixture was concentrated, and dilute hydrochloric acid was added to acidify the residue. The precipitated solid was collected by filtration and dried with air to give crystals (1.40 g, 90%) of 2-[[3-[3-(5-methyl-2-phenyl-4-oxazolyl)methoxy]benzyloxy]phenyl]acetic acid. Recrystallization from acetone-hexane gave colorless prism crystals. melting point: 101-102° C.

Example 33

A mixture of 4-(3-chloromethylphenoxymethyl)-5-methyl-2-phenyloxazole (0.65 g), ethyl 3-(2-ethoxy-5-hydroxyphenyl)propionate (0.46 g), anhydrous potassium carbonate (0.30 g) and N,N-dimethylformamide (10 mL) was stirred at 80° C. for 5 hrs. The reaction mixture was poured into water and extracted with ethyl acetate. The organic layer was washed successively with dilute hydrochloric acid and saturated brine, dried over, anhydrous magnesium sulfate and concentrated. The obtained residue was subjected to silica gel column chromatography to give an oil from a fraction eluted with ethyl acetate-hexane (1:4, v/v). To a mixture of the obtained oil, tetrahydrofuran (5 mL) and ethanol (5 mL) was added a 1N aqueous sodium hydroxide solution (5 mL) and the mixture was stirred at room temperature for 2 hrs. The reaction mixture was concentrated, and dilute hydrochloric acid was added to acidify the residue. The precipitated solid was collected by filtration and dried with air to give crystals (0.89 g, 95%) of 3-[2-ethoxy-5-[3-[(5-methyl-2-phenyl-4-oxazolyl)methoxy]benzyloxy]phenyl]propionic acid. Recrystallization from ethyl acetate-hexane gave colorless prism crystals. melting point: 136-137° C.

Example 34

A mixture of 4-(2-chloromethylphenoxymethyl)-5-methyl-2-phenyloxazole (1.21 g), methyl 2-(3-hydroxyphenyl)acetate (0.60 g), anhydrous potassium carbonate (0.65 g) and N,N-dimethylformamide (10 mL) was stirred at 80° C. for 5 hrs. The reaction mixture was poured into water and extracted with ethyl acetate. The organic layer was washed successively with dilute hydrochloric acid and saturated brine, dried over anhydrous magnesium sulfate and concentrated. The obtained residue was subjected to silica gel column chromatography to give an oil from a fraction eluted with ethyl acetate-hexane (1:4, v/v). To a mixture of the obtained oil, tetrahydrofuran (5 mL) and ethanol (5 mL) was added a 1N aqueous sodium hydroxide solution (5 mL) and the mixture was stirred at room temperature for 2 hrs. The reaction mixture was concentrated, and dilute hydrochloric acid was added to acidify the residue. The precipitated solid was collected by filtration and dried with air to give crystals (1.37 g, 88%) of 2-[3-[2-[(5-methyl-2-phenyl-4-oxazolyl)methoxy]benzyloxy]phenyl]acetic acid. Recrystallization from ethyl acetate-hexane gave colorless prism crystals. melting point: 104-105° C.

Example 35

A mixture of 4-(2-chloromethylphenoxymethyl)-5-methyl-2-phenyloxazole (0.65 g), ethyl 3-(2-ethoxy-5-hydroxyphenyl)propionate (0.46 g), anhydrous potassium carbonate (0.30 g) and N,N-dimethylformamide (10 mL) was stirred at 80° C. for 5 hrs. The reaction mixture was poured into water and extracted with ethyl acetate. The organic layer was washed successively with dilute hydrochloric acid and saturated brine, dried over anhydrous magnesium sulfate and concentrated. The obtained residue was subjected to silica gel column chromatography to give an oil from a fraction eluted with ethyl acetate-hexane (1:4, v/v). To a mixture of the obtained oil, tetrahydrofuran (5 mL) and ethanol (5 mL) was added a 1N aqueous sodium hydroxide solution (5 mL) and the mixture was stirred at room temperature for 2 hrs. The reaction mixture was concentrated, and dilute hydrochloric acid was added to acidify the residue. The precipitated solid was collected by filtration and dried with air to give crystals (0.89 g, 95%) of 3-[2-ethoxy-5-[2-[(5-methyl-2-phenyl-4-oxazolyl)methoxy]benzyloxy]phenyl]propionic acid. Recrystallization from acetone-hexane gave colorless prism crystals. melting point: 146-147° C.

Example 36

To a mixture of 2-[2-[4-[(5-methyl-2-phenyl-4-oxazolyl)methoxy]benzyloxy]-3-pyridyl]acetonitrile (0.20 g), tetrahydrofuran (0.5 mL) and ethanol (1 mL) was added a 2N aqueous sodium hydroxide solution (1.5 mL) and the mixture was stirred with heating under reflux for 10 hrs. 1N Hydrochloric acid (3 mL) and water were added to the reaction mixture, the mixture was extracted with ethyl acetate. The organic layer was washed with saturated brine, dried over anhydrous magnesium sulfate and concentrated. The obtained residue was subjected to silica gel column chromatography to give crystals (0.08 g, 38%) of 2-[2-[4-[(5-methyl-2-phenyl-4-oxazolyl)methoxy]benzyloxy]-3-pyridyl]acetic acid from a fraction eluted with ethyl acetate-hexane (1:1, v/v). Recrystallization from ethyl acetate-hexane gave colorless prism crystals. melting point: 144-145° C.

Example 37

To a mixture of 2-[3-[4-[(5-methyl-2-phenyl-4-oxazolyl)methoxy]benzyloxy]-2-pyridyl]acetonitrile (0.55 g), tetrahydrofuran (1 mL) and ethanol (4 mL) was added a 2N aqueous sodium hydroxide solution (4 mL) and the mixture was stirred with heating under reflux for 12 hrs. 1N Hydrochloric acid (8 mL) and water were added to the reaction mixture, and the precipitated solid was collected by filtration and dried with air to give crystals (0.35 g, 47%) of 2-[3-[4-[(5-methyl-2-phenyl-4-oxazolyl)methoxy]benzyloxy]-2-pyridyl]acetic acid. Recrystallization from tetrahydrofuran-hexane gave colorless prism crystals. melting point: 115-116° C. (dec.)

Example 38

To a mixture of 2-[5-[4-[(5-methyl-2-phenyl-4-oxazolyl)methoxy]benzyloxy]-3-pyridyl]acetonitrile (0.66 g), tetrahydrofuran (1 mL) and ethanol (5 mL) was added a 2N aqueous sodium hydroxide solution (5 mL) and the mixture was stirred with heating under reflux for 8 hrs. 1N Hydrochloric acid (10 mL) and water were added to the reaction mixture, and the precipitated solid was collected by filtration and dried with air to give crystals (0.67 g, 97%) of 2-[5-[4-[(5-methyl-2-phenyl-4-oxazolyl)methoxy]benzyloxy]-3-pyridyl]acetic acid. Recrystallization from tetrahydrofuran-hexane gave pale-brown prism crystals. melting point: 139-140° C.

Example 39

To a mixture of 2-[2-[4-[(5-methyl-2-phenyl-4-oxazolyl)methoxy]benzyloxy]-1-naphthyl]acetonitrile (0.96 g), tetrahydrofuran (5 mL) and ethanol (15 mL) was added a 4N aqueous sodium hydroxide solution (7 mL), and the mixture was stirred with heating under reflux for 4.5 days. 1N Hydrochloric acid and water were added to acidify the reaction mixture, and the mixture was extracted with ethyl acetate-tetrahydrofuran. The organic layer was washed with saturated brine, dried over anhydrous magnesium sulfate and concentrated. The obtained residue was subjected to silica gel column chromatography to give crystals (0.52 g, 51%) of 2-[2-[4-[(5-methyl-2-phenyl-4-oxazolyl)methoxy]benzyloxy]-1-naphthyl]acetic acid from a fraction eluted with ethyl acetate-hexane (1:1, v/v). Recrystallization from ethyl acetate-hexane gave pale-yellow prism crystals. melting point: 187-188° C.

Example 40

To a mixture of 5-chloromethyl-2-(5-methyl-2-phenyl-4-oxazolyl)methoxypyridine (0.91 g), methyl 2-(2-hydroxyphenyl)acetate (0.44 g) and N,N-dimethylformamide (20 mL) was added sodium hydride (60%, oil, 0.12 g) under ice-cooling, and the mixture was stirred at room temperature for 15 hrs. The reaction mixture was poured into water and extracted with ethyl acetate. The organic layer was washed with saturated brine and dried over anhydrous magnesium sulfate. After concentration of the organic layer, the residue was subjected to silica gel column chromatography to give methyl 2-[2-[[6-[(5-methyl-2-phenyl-4-oxazolyl)methoxy]-3-pyridyl]methoxy]phenyl]acetate as an oil (0.81 g, 70%) from a fraction eluted with ethyl acetate-hexane (1:4, v/v).
$^1$H-NMR (CDCl$_3$) δ: 2.49 (3H, s), 3.62 (3H, s), 3.64 (2H, s), 5.02 (2H, s), 5.32 (2H, s), 6.85 (1H, d, J=8.6 Hz), 6.92-6.99 (2H, m), 7.19-7.31 (2H, m), 7.39-7.46 (3H, m), 7.65 (1H, dd, J=8.6, 2.2 Hz), 8.01-8.06 (2H, m), 8.21 (1H, d, J=2.2 Hz).

Example 41

To a mixture of methyl 2-[2-[[6-[(5-methyl-2-phenyl-4-oxazolyl)methoxy]-3-pyridyl]methoxy]phenyl]acetate (0.81 g), tetrahydrofuran (4 mL) and methanol (4 mL) was added a 1N aqueous sodium hydroxide solution (3.6 mL) and the mixture was stirred at 50° C. for 1 hr. 1N Hydrochloric acid (3.7 mL) and water were added to the reaction mixture, and the precipitated solid was collected by filtration and dried with air to give crystals (0.75 g, 97%) of 2-[2-[[6-[(5-methyl-2-phenyl-4-oxazolyl)methoxy]-3-pyridyl]methoxy]phenyl]acetic acid. Recrystallization from ethyl acetate-hexane gave colorless prism crystals. melting point: 123-125° C.

Example 42

To a mixture of [5-(5-methyl-2-phenyl-4-oxazolyl)methoxy-3-pyridyl]methanol (1.50 g), methyl 2-(2-hydroxyphenyl)acetate (0.76 g), triphenylphosphine (1.44 g) and tetrahydrofuran (50 mL) was dropwise added a solution (40%, 2.39 g) of diethyl azodicarboxylate in toluene at room temperature, and the mixture was stirred for 15 hrs. The reaction mixture was concentrated and the residue was subjected to silica gel column chromatography to give crude crystals from a fraction eluted with ethyl acetate-hexane (1:1, v/v) which crude crystals were further subjected to silica gel column chromatography to give crystals (1.24 g, 61%) of methyl 2-[2-[[5-[(5-methyl-2-phenyl-4-oxazolyl) methoxy]-3-pyridyl]methoxy]phenyl]acetate from a fraction eluted with tetrahydrofuran-hexane (3:2, v/v). Recrystallization from ethyl acetate-hexane gave colorless prism crystals. melting point: 77-78° C.

Example 43

To a mixture of methyl 2-[2-[[5-[(5-methyl-2-phenyl-4-oxazolyl)methoxy]-3-pyridyl]methoxy]phenyl]acetate (1.05 g), tetrahydrofuran (5 mL) and methanol (5 mL) was added a 1N aqueous sodium hydroxide solution (5 mL) and the mixture was stirred at 50-60° C. for 1.5 hrs. 1N Hydrochloric acid (5 mL) and water were added to the reaction mixture, and the precipitated solid was collected by filtration and dried with air to give crystals (1.00 g, 97%) of 2-[2-[[5-[(5-methyl-2-phenyl-4-oxazolyl)methoxy]-3-pyridyl] methoxy]phenyl]acetic acid. Recrystallization from tetrahydrofuran-hexane gave colorless prism crystals. melting point: 207-208° C.

Example 44

A mixture of 4-(4-chloromethylphenoxymethyl)-5-methyl-2-phenyloxazole (0.50 g), ethyl 3-(4-hydroxyphenyl) propionate (0.31 g), anhydrous potassium carbonate (0.22 g) and N,N-dimethylformamide (15 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give crystals (0.38 g, 51%) of ethyl 3-[4-[4-[(5-methyl-2-phenyl-4-oxazolyl) methoxy]benzyloxy]phenyl]propionate from a fraction eluted with ethyl acetate-hexane (1:6, v/v). Recrystallization from ethyl acetate-hexane gave colorless prism crystals. melting point: 105-106° C.

Example 45

To a mixture of ethyl 3-[4-[4-[(5-methyl-2-phenyl-4-oxazolyl)methoxy]benzyloxy]phenyl]propionate (0.30 g), tetrahydrofuran (2 mL) and ethanol (2 mL) was added a 1N aqueous sodium hydroxide solution (1.3 mL) and the mixture was stirred at room temperature for 2 hrs. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.25 g, 89%) of 3-[4-[4-[(5-methyl-2-phenyl-4-oxazolyl)methoxy]benzyloxy]phenyl]propionic acid. Recrystallization from tetrahydrofuran-hexane gave colorless prism crystals. melting point: 177-178° C.

Example 46

A mixture of ethyl 3-[2-[4-[(5-methyl-2-phenyl-4-oxazolyl)methoxy]benzyloxy]-1-naphthyl]-2-propenoate (1.51 g), platinum oxide (0.18 g), ethanol (5 mL) and tetrahydrofuran (10 mL) was stirred at room temperature overnight under a hydrogen atmosphere. The catalyst was filtered off, and the filtrate was concentrated to give crystals (1.36 g, 90%) of ethyl 3-[2-[4-[(5-methyl-2-phenyl-4-oxazolyl) methoxy]benzyloxy]-1-naphthyl]propionate. Recrystallization from acetone-hexane gave colorless needle crystals. melting point: 86-87° C.

Example 47

To a mixture of ethyl 3-[2-[4-[(5-methyl-2-phenyl-4-oxazolyl)methoxy]benzyloxy]-1-naphthyl]propionate (1.16 g), tetrahydrofuran (5 mL) and ethanol (5 mL) was added a 1N aqueous sodium hydroxide solution (5 mL) and the mixture was stirred at room temperature for 2 hrs. The reaction mixture was concentrated, and dilute hydrochloric acid was added to acidify the residue. The precipitated solid was collected by filtration and dried with air to give crystals (1.03 g, 94%) of 3-[2-[4-[(5-methyl-2-phenyl-4-oxazolyl) methoxy]benzyloxy]-1-naphthyl]propionic acid. Recrystallization from acetone-hexane gave colorless prism crystals. melting point: 161-162° C.

Example 48

A mixture of 4-(4-chloromethyl-3-methoxyphenoxymethyl)-2-phenyl-5-methyloxazole (2.08 g), methyl 2-(2-hydroxyphenyl)acetate (1.00 g), anhydrous potassium carbonate (1.65 g) and N,N-dimethylformamide (15 mL) was stirred overnight at room temperature. The reaction mixture was poured into dilute hydrochloric acid and extracted with ethyl acetate. The organic layer was washed with saturated brine, dried over anhydrous magnesium sulfate and concentrated. To a mixture of the obtained residue, tetrahydrofuran (10 mL) and methanol (10 mL) was added a 1N aqueous sodium hydroxide solution (10 mL) and the mixture was stirred at room temperature for 2 hrs. The reaction mixture was concentrated, and dilute hydrochloric acid was added to the residue. The precipitated solid was collected by filtration and dried with air to give crystals (1.36 g, 49%) of 2-[2-[3-methoxy-4-[(2-phenyl-5-methyl-4-oxazolyl)methoxy]benzyloxy]phenyl]acetic acid. Recrystallization from acetone-hexane gave colorless needle crystals. melting point: 165-166° C.

Example 49

To a mixture of [4-methoxy-3-[(5-methoxy-2-phenyl-4-oxazolyl)methoxy]phenyl]methanol (0.95 g), methyl 2-(2-hydroxyphenyl)acetate (0.50 g), triphenylphosphine (0.95 g) and tetrahydrofuran (15 mL) was dropwise added a solution (40%, 1.74 g) of diethyl azodicarboxylate in toluene at room temperature, and the mixture was stirred overnight. The reaction mixture was concentrated and the residue was subjected to silica gel column chromatography to give an oil from a fraction eluted with ethyl acetate-hexane (1:3, v/v). To a mixture of the obtained oil, tetrahydrofuran (10 mL) and ethanol (10 mL) was added a 1N aqueous sodium hydroxide solution (5 mL) and the mixture was stirred overnight at room temperature. The reaction mixture was neutralized with 1N hydrochloric acid (5 mL), extracted with ethyl acetate. The organic layer was washed with saturated brine, dried over anhydrous magnesium sulfate and concentrated. The residue was subjected to silica gel column chromatography to give 2-[2-[4-methoxy-3-[(5-methyl-2-phenyl-4-oxazolyl)methoxy]benzyloxy]phenyl]acetic acid from a fraction eluted with ethyl acetate-hexane (1:1, v/v). Recrystallization with ethanol-hexane gave colorless plate crystals (0.52 g, 37%). melting point: 154-155° C.

Example 50

A mixture of 4-(4-chloromethylphenoxymethyl)-2-(2-furyl)-5-methyloxazole (1.84 g), methyl 2-(2-hydroxyphenyl)acetate (1.00 g), anhydrous potassium carbonate (1.66 g) and N,N-dimethylformamide (15 mL) was stirred at room temperature overnight. The reaction mixture was poured into dilute hydrochloric acid and extracted with ethyl acetate. The organic layer was washed with saturated brine, dried over anhydrous magnesium sulfate and concentrated. To a mixture of the obtained residue, tetrahydrofuran (10 mL) and methanol (10 mL) was added a 1N aqueous sodium hydroxide solution (10 mL) and the mixture was stirred at room temperature for 2 hrs. The reaction mixture was concentrated, and dilute hydrochloric acid was added to the residue. The precipitated solid was collected by filtration and dried with air to give crystals (2.08 g, 82%) of 2-[2-[4-[[2-(2-furyl)-5-methyl-4-oxazolyl]methoxy]benzyloxy]phenyl]acetic acid. Recrystallization from acetone-hexane gave colorless prism crystals. melting point: 167-168° C.

Example 51

A mixture of 4-(4-chloromethylphenoxymethyl)-2-phenylthiazole (1.95 g), methyl 2-(2-hydroxyphenyl)acetate (1.00 g), anhydrous potassium carbonate (0.85 g) and N,N-dimethylformamide (15 mL) was stirred overnight at room temperature. The reaction mixture was poured into dilute hydrochloric acid and extracted with ethyl acetate. The organic layer was washed with saturated brine, dried over anhydrous magnesium sulfate and concentrated. To a mixture of the obtained residue, tetrahydrofuran (10 mL) and methanol (10 mL) was added a 1N aqueous sodium hydroxide solution (10 mL) and the mixture was stirred at room temperature for 2 hrs. The reaction mixture was concentrated, and dilute hydrochloric acid was added to the residue. The precipitated solid was collected by filtration and dried with air to give crystals (0.76 g, 29%) of 2-[2-[4-[(2-phenyl-4-thiazolyl)methoxy]benzyloxy]phenyl]acetic acid. Recrystallization from ethyl acetate-hexane gave colorless prism crystals. melting point: 115-116° C.

Example 52

A mixture of 4-(4-chloromethylphenoxymethyl)-5-methyl-2-phenylthiazole (2.13 g), methyl 2-(2-hydroxyphenyl)acetate (1.00 g), anhydrous potassium carbonate (1.65 g) and N,N-dimethylformamide (15 mL) was stirred overnight at room temperature. The reaction mixture was poured into dilute hydrochloric acid and extracted with ethyl acetate. The organic layer was washed with saturated brine, dried over anhydrous magnesium sulfate and concentrated. To a mixture of the obtained residue, tetrahydrofuran (10 mL) and methanol (10 mL) was added a 1N aqueous sodium hydroxide solution (10 mL) and the mixture was stirred at room temperature for 2 hrs. The reaction mixture was concentrated, and dilute hydrochloric acid was added to the residue. The precipitated solid was collected by filtration and dried with air to give crystals (1.19 g, 44%) of 2-[2-[4-[(5-methyl-2-phenyl-4-thiazolyl)methoxy]benzyloxy]phenyl]acetic acid. Recrystallization from ethyl acetate-hexane gave colorless prism crystals. melting point: 122-123° C.

Example 53

A mixture of 4-(2-chloromethylphenoxymethyl)-5-methyl-2-phenyloxazole (8.37 g), 2-(3-hydroxyphenyl)acetic acid (2.02 g), anhydrous potassium carbonate (7.39 g) and N,N-dimethylformamide (30 mL) was stirred overnight at room temperature. The reaction mixture was poured into dilute hydrochloric acid and extracted with ethyl acetate. The organic layer was washed with saturated brine dried over anhydrous magnesium sulfate and concentrated. The obtained residue was subjected to silica gel column chromatography to give crystals (8.37 g, 89%) of 4-[(5-methyl-2-phenyl-4-oxazolyl)methoxy]benzyl 2-[3-[4-[(5-methyl-2-phenyl-4-oxazolyl)methoxy]benzyloxy]phenyl]acetate from a fraction eluted with ethyl acetate-hexane (1:9, v/v). Recrystallization from acetone-hexane gave colorless prism crystals. melting point: 90-91° C.

Example 54

To a mixture of 2-[4-[(5-methyl-2-phenyl-4-oxazolyl)methoxy]benzyloxy]-1-naphthaldehyde (5.48 g), triethyl phosphonoacetate (2.98 g) and N,N-dimethylformamide (50 ml) was added sodium hydride (0.51 g) under ice-cooling. The reaction mixture was stirred at room temperature for 2 hrs. The reaction mixture was poured into iced water, and the precipitated solid was collected by filtration and dried with air to give crystals (5.54 g, 88%) of ethyl 3-(2-(4-((5-methyl-2-phenyl-4-oxazolyl)methoxy)benzyloxy)-1-naphthyl)-2-propenoate. Recrystallization from ethyl acetate-hexane gave colorless prism crystals. melting point: 73-74° C.

Example 55

To a mixture of 4-(2-chloromethylphenoxymethyl)-5-methyl-2-phenyloxazole (1.04 g), methyl 2-(2-hydroxyphenyl)acetate (0.50 g) and N,N-dimethylformamide (30 mL) was added sodium hydride (60%, oil, 0.13 g) under ice-cooling, and the mixture was stirred at room temperature for 15 hrs. The reaction mixture was poured into water and extracted with ethyl acetate. The organic layer was washed with saturated brine, and dried over anhydrous magnesium sulfate. After concentration of the organic layer, the residue was subjected to silica gel column chromatography to give methyl 2-[2-[2-[(5-methyl-2-phenyl-4-oxazolyl)methoxy]benzyloxy]phenyl]acetate as an oil (0.71 g, 53%) from a fraction eluted with ethyl acetate-hexane (1:6, v/v).

$^1$H-NMR (CDCl$_3$) δ: 2.40 (3H, s), 3.63 (3H, s), 3.70 (2H, s), 5.06 (2H, s), 5.16 (2H, s), 6.86-7.34 (7H, m), 7.42-7.49 (4H, m), 7.98-8.03 (2H, m).

Example 56

To a mixture of methyl 2-[2-[2-[(5-methyl-2-phenyl-4-oxazolyl)methoxy]benzyloxy]phenyl]acetate (0.71 g), tetrahydrofuran (3.0 mL) and methanol (3.0 mL) was added a 1N aqueous sodium hydroxide solution (3.2 mL) and the mixture was stirred at 50° C. for 1.5 hrs. 1N Hydrochloric acid (3.2 mL) and water were added to the reaction mixture, and the mixture was extracted with ethyl acetate. The organic layer was washed with saturated brine, dried over anhydrous magnesium sulfate and concentrated to give crystals (0.62 g, 90%) of 2-[2-[2-[(5-methyl-2-phenyl-4-oxazolyl)methoxy]benzyloxy]phenyl]acetic acid. Recrystallization from ethyl acetate-hexane gave colorless prism crystals. melting point: 145-146° C.

Example 57

To a mixture of 4-[2-(4-chloromethylphenoxy)ethyl]-5-methyl-2-phenyloxazole (0.85 g), methyl 2-(2-hydroxyphenyl)acetate (0.40 g) and N,N-dimethylformamide (30 mL) was added sodium hydride (60%, oil, 0.11 g) under ice-cooling, and the mixture was stirred at room temperature for 15 hrs. The reaction mixture was poured into water and extracted with ethyl acetate. The organic layer was washed with saturated brine and dried over anhydrous magnesium sulfate. After concentration of the organic layer, the residue was subjected to silica gel column chromatography to give methyl 2-[2-[4-[2-(5-methyl-2-phenyl-4-oxazolyl)ethoxy]benzyloxy]phenyl]acetate as an oil (0.57 g, 57%) from a fraction eluted with ethyl acetate-hexane (1:6, v/v).

$^1$H-NMR (CDCl$_3$) δ: 2.38 (3H, s), 2.99 (2H, t, J=6.6 Hz), 3.62 (3H, s), 3.65 (2H, s), 4.25 (2H, t, J=6.6 Hz), 4.99 (2H, s), 6.87-6.96 (4H, m), 7.17-7.36 (4H, m), 7.40-7.48 (3H, m), 7.93-8.00 (2H, m).

Example 58

To a mixture of methyl 2-[2-[4-[2-(5-methyl-2-phenyl-4-oxazolyl)ethoxy]benzyloxy]phenyl]acetate (0.57 g), tetrahydrofuran (3.0 mL) and methanol (3.0 mL) was added a 1N aqueous sodium hydroxide solution (2.4 mL) and the mixture was stirred at 50° C. for 1.5 hrs. 1N Hydrochloric acid (2.4 mL) and water were added to the reaction mixture, and the precipitated solid was collected by filtration and dried with air to give crystals (0.51 g, 96%) of 2-[2-[4-[2-(5-methyl-2-phenyl-4-oxazolyl)ethoxy]benzyloxy]phenyl]acetic acid. Recrystallization from ethyl acetate-hexane gave colorless prism crystals. melting point: 141-142° C.

Example 59

To a mixture of t-butyl 4-(hydroxymethyl)phenyl[(5-methyl-2-phenyl-4-oxazolyl)methyl]carbamate (1.0 g), triethylamine (1.01 g) and ethyl acetate (50 mL) was added methanesulfonyl chloride (1.15 g) at 0° C. The reaction mixture was stirred at room temperature for 20 hrs., diluted with ethyl acetate and washed successively with a saturated aqueous sodium hydrogencarbonate and saturated brine. The mixture was dried over anhydrous magnesium sulfate and concentrated to give pale-yellow crystals. To a mixture of the obtained crystals, methyl 2-(2-hydroxyphenyl)acetate (0.55 g) and N,N-dimethylformamide (30 mL) was added sodium hydride (60%, oil, 0.14 g) at 0° C. The mixture was stirred at room temperature for 3 hrs. To the reaction mixture was added water and the mixture was extracted with ethyl acetate. The organic layer was washed successively with water, 2N aqueous sodium hydroxide solution and saturated brine, and dried over anhydrous magnesium sulfate. After concentration of the organic layer, the residue was subjected to silica gel column chromatography to give crystals (0.82 g, 60%) of methyl 2-[2-[4-[(t-butoxycarbonyl)[(5-methyl-2-phenyl-4-oxazolyl)methyl]amino]benzyloxy]phenyl]acetate from a fraction eluted with ethyl acetate-hexane (1:3, v/v). Recrystallization from ethyl acetate-hexane gave colorless prism crystals. melting point: 85-86° C.

Example 60

To a mixture of methyl 2-[2-[4-[(t-butoxycarbonyl)[(5-methyl-2-phenyl-4-oxazolyl)methyl]amino]benzyloxy]phenyl]acetate (0.30 g), tetrahydrofuran (1.0 mL) and methanol (1.0 mL) was added a 1N aqueous sodium hydroxide solution (1.0 mL) and the mixture was stirred at 50° C. for 1 hr. 1N Hydrochloric acid (1.0 mL) and water were added to the reaction mixture and the mixture was extracted with ethyl acetate. The organic layer was washed with saturated brine, dried over anhydrous magnesium sulfate and concentrated to give 2-[2-[4-[(t-butoxycarbonyl)[(5-methyl-2-phenyl-4-oxazolyl)methyl]amino]benzyloxy]phenyl]acetic acid as a colorless amorphous compound (0.19 g, 66%).

$^1$H-NMR (CDCl$_3$) δ: 1.41 (9H, s), 2.38 (3H, s), 3.57 (2H, s), 4.70 (2H, s), 5.09 (2H, s), 6.98-7.26 (8H, m), 7.40-7.42 (3H, m), 7.90-8.00 (2H, m). Elemental analysis: for C$_{31}$H$_{32}$N$_2$O$_6$ Calculated, C: 70.44; H, 6.10; N, 5.30. Found, C: 70.22; H, 6.24; N, 5.06.

Example 61

A mixture of 4-(chloromethyl)-2-[(5-methyl-2-phenyl-4-oxazolyl)methoxy]pyridine (0.472 g), methyl 2-(3-hydroxyphenyl)acetate (0.249 g), anhydrous potassium carbonate (0.415 g) and N,N-dimethylformamide (10 mL) was stirred at 60° C. for 3 hrs. The reaction mixture was poured into water and extracted with ethyl acetate. The organic layer was washed with saturated brine, dried over anhydrous magnesium sulfate and concentrated. The obtained residue was subjected to silica gel column chromatography to give methyl 2-[3-[2-[(5-methyl-2-phenyl-4-oxazolyl)methoxy]-4-pyridylmethoxy]phenyl]acetate as a colorless oil (0.597 g, 90%) from a fraction eluted with ethyl acetate-hexane (1:2, v/v).

$^1$H-NMR (CDCl$_3$) δ: 2.47 (3H, s), 3.59 (2H, s), 3.68 (3H, s), 5.02 (2H, s), 5.31 (2H, s), 6.79-6.84 (4H, m), 6.94 (1H, d, J=5.2 Hz), 7.23 (1H, t, J=8.0 Hz), 7.39-7.45 (3H, m), 7.98-8.05 (2H, m), 8.16 (1H, d, J=5.2 Hz).

Example 62

To a mixture of methyl 2-[3-[2-[(5-methyl-2-phenyl-4-oxazolyl)methoxy]-4-pyridylmethoxy]phenyl]acetate (0.596 g), tetrahydrofuran (6.0 mL) and methanol (6.0 mL) was added a 1N aqueous sodium hydroxide solution (3.0 mL), and the mixture was stirred at room temperature for 1 hr. 1N Hydrochloric acid (3.0 mL) and water were added to the reaction mixture, and the mixture was extracted with ethyl acetate. The organic layer was washed with saturated brine, dried over anhydrous magnesium sulfate and concentrated to give crystals of 2-[3-[2-[(5-methyl-2-phenyl-4-oxazolyl)methoxy]-4-pyridylmethoxy]phenyl]acetic acid. Recrystallization from ethanol-hexane gave colorless prism crystals (0.566 g, 98%). melting point: 148-149° C.

Example 63

A mixture of 2-(chloromethyl)-6-[(5-methyl-2-phenyl-4-oxazolyl)methoxy]pyridine (0.96 g), methyl 2-(3-hydroxyphenyl)acetate (0.50 g), anhydrous potassium carbonate (0.52 g) and N,N-dimethylformamide (15 mL) was stirred at 80° C. for 5 hrs. The reaction mixture was poured into water and extracted with ethyl acetate. The organic layer was washed with saturated brine, dried over anhydrous magnesium sulfate and concentrated. The obtained residue was subjected to silica gel column chromatography to give methyl 2-[3-[5-[(5-methyl-2-phenyl-4-oxazolyl)methoxy]-2-pyridylmethoxy]phenyl]acetate as a colorless oil (1.17 g, 87%) from a fraction eluted with ethyl acetate-hexane (1:1, v/v).

$^1$H-NMR (CDCl$_3$) δ: 2.50 (3H, s), 3.61 (2H, s), 3.69 (3H, s), 5.11 (2H, s), 5.32 (2H, s), 6.70-6.80 (1H, m), 6.84-6.98

(3H, m), 7.04-7.12 (1H, m), 7.17-7.32 (1H, m), 7.36-7.48 (3H, m), 7.52-7.65 (1H, m), 7.96-8.10 (2H, m).

Example 64

To a mixture of methyl 2-[3-[[6-[(5-methyl-2-phenyl-4-oxazolyl)methoxy]-2-pyridyl]methoxy]phenyl]acetate (1.10 g), tetrahydrofuran (5 mL) and methanol (5 mL) was added a 1N aqueous sodium hydroxide solution (5.0 mL) and the mixture was stirred at room temperature for 3 hrs. The reaction mixture was concentrated, and water and dilute hydrochloric acid were added to acidify the residue. The precipitated solid was collected by filtration and dried with air to give crystals (0.85 g, 80%) of 2-[3-[[6-[(5-methyl-2-phenyl-4-oxazolyl)methoxy]-2-pyridyl]methoxy]phenyl]acetic acid. Recrystallization from ethyl acetate-hexane gave colorless prism crystals. melting point: 97-98° C.

Example 65

A mixture of 4-(4-chloromethylphenoxymethyl)-5-methyl-2-phenyloxazole (1.19 g), ethyl 3-(2-ethoxy-4-hydroxyphenyl)propionate (0.76 g), anhydrous potassium carbonate (0.44 g) and N,N-dimethylformamide (30 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give crystals (1.35 g, 82%) of ethyl 3-[2-ethoxy-4-[4-[(5-methyl-2-phenyl-4-oxazolyl)methoxy]benzyloxy]phenyl]propionate from a fraction eluted with ethyl acetate-hexane (1:6, v/v). Recrystallization from ethyl acetate-hexane gave colorless prism crystals. melting point: 64-65° C.

Example 66

To a mixture of ethyl 3-[2-ethoxy-4-[4-[(5-methyl-2-phenyl-4-oxazolyl)methoxy]benzyloxy]phenyl]propionate (1.20 g), tetrahydrofuran (5 mL) and ethanol (5 mL) was added a 1N aqueous sodium hydroxide solution (5.0 mL) and the mixture was stirred at room temperature for 2 hrs. 1N Hydrochloric acid and water were added to acidify the reaction mixture, and the mixture was extracted with ethyl acetate. The organic layer was washed with saturated brine, dried over anhydrous magnesium sulfate and concentrated to give crystals (1.09 g, 97%) of 3-[2-ethoxy-4-[4-[(5-methyl-2-phenyl-4-oxazolyl)methoxy]benzyloxy]phenyl]propionic acid. Recrystallization from ethyl acetate-hexane gave colorless prism crystals. melting point: 135-136° C.

Example 67

A mixture of 4-(4-chloromethylphenoxymethyl)-5-methyl-2-phenyloxazole (1.73 g), 3-(4-mercaptophenyl)propionic acid (1.00 g), triethylamine (1.22 g) and N,N-dimethylformamide (20 mL) was stirred at room temperature for 2 hrs. The reaction mixture was poured into water, acidified with 2N hydrochloric acid and extracted with ethyl acetate. The organic layer was washed with water, dried over anhydrous magnesium sulfate and concentrated to give crystals of 3-[4-[[4-[(5-methyl-2-phenyl-4-oxazolyl)methoxy]benzyl]sulfanyl]phenyl]propionic acid. Recrystallization from ethyl acetate gave colorless prism crystals (1.85 g, 73%). melting point: 157-158° C.

Example 68

A mixture of 4-(3-chloromethylphenoxymethyl)-5-methyl-2-phenyloxazole (0.89 g), methyl 2-(4-hydroxyphenyl)acetate (0.50 g), anhydrous potassium carbonate (0.49 g) and N,N-dimethylformamide (15 mL) was stirred at room temperature for 3 hrs. The reaction mixture was poured into water and extracted with ethyl acetate. The organic layer was washed successively with dilute hydrochloric acid and saturated brine, dried over anhydrous magnesium sulfate and concentrated. The obtained residue was subjected to silica gel column chromatography to give colorless crystals from a fraction eluted with ethyl acetate-hexane (1:4, v/v). To a mixture of the obtained crystal, tetrahydrofuran (6 mL) and methanol (6 mL) was added a 1N aqueous sodium hydroxide solution (6 mL) and the mixture was stirred at room temperature for 2 hrs. Dilute hydrochloric acid was added to acidify the reaction mixture, and the mixture was extracted with ethyl acetate. The organic layer was washed with saturated brine, dried over anhydrous magnesium sulfate and concentrated to give crystals (1.13 g, 93%) of 2-[4-[3-[(5-methyl-2-phenyl-4-oxazolyl)methoxy]benzyloxy]phenyl]acetic acid. Recrystallization from acetone-hexane gave colorless prism crystals. melting point: 179-180° C.

Example 69

A mixture of 4-(2-chloromethylphenoxymethyl)-5-methyl-2-phenyloxazole (0.98 g), methyl 2-(4-hydroxyphenyl)acetate (0.51 g), anhydrous potassium carbonate (0.52 g), and N,N-dimethylformamide (10 mL) was stirred at room temperature for 3 hrs. The reaction mixture was poured into water and extracted with ethyl acetate. The organic layer was washed successively with dilute hydrochloric acid and saturated brine, dried over anhydrous magnesium sulfate and concentrated. The obtained residue was subjected to silica gel column chromatography to give an oil from a fraction eluted with ethyl acetate-hexane (1:4, v/v). To a mixture of the obtained oil, tetrahydrofuran (6 mL), and methanol (6 mL) was added a 1N aqueous sodium hydroxide solution (6 mL) and the mixture was stirred at room temperature for 2 hrs. Dilute hydrochloric acid was added to acidify the reaction mixture, and the mixture was extracted with ethyl acetate. The organic layer was washed with saturated brine, dried over anhydrous magnesium sulfate and concentrated to give crystals (1.00 g, 76%) of 2-[4-[2-[(5-methyl-2-phenyl-4-oxazolyl)methoxy]benzyloxy]phenyl]acetic acid. Recrystallization from acetone-hexane gave colorless prism crystals. melting point: 173-174° C.

Example 70

A mixture of 4-(3-chloromethylphenoxymethyl)-5-methyl-2-phenyloxazole (0.78 g), ethyl 3-(2-ethoxy-4-hydroxyphenyl)propionate (0.50 g), anhydrous potassium carbonate (0.29 g) and N,N-dimethylformamide (20 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give ethyl 3-[2-ethoxy-4-[3-[(5-methyl-2-phenyl-4-oxazolyl)methoxy]benzyloxy]phenyl]propionate as a colorless oil (0.94 g, 87%) from a fraction eluted with ethyl acetate-hexane (1:6, v/v).

$^1$H-NMR (CDCl$_3$) δ: 1.23 (3H, t, J=7.0 Hz), 1.40 (3H, t, J=7.0 Hz), 2.43 (3H, s), 2.52-2.60 (2H, m), 2.82-2.91 (2H, m), 3.98 (2H, q, J=7.0 Hz), 4.11 (2H, q, J=7.0 Hz), 5.01 (4H, s), 6.41-6.49 (2H, m), 6.94-7.11 (4H, m), 7.26-7.47 (4H, m), 7.98-8.04 (2H, m).

Example 71

To a mixture of ethyl 3-[2-ethoxy-4-[3-[(5-methyl-2-phenyl-4-oxazolyl)methoxy]benzyloxy]phenyl]propionate (0.94 g), tetrahydrofuran (4 mL) and ethanol (4 mL) was added a 1N aqueous sodium hydroxide solution (3.6 mL) and the mixture was stirred at 50° C. for 2 hrs. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.75 g, 85%) of 3-[2-ethoxy-4-[3-[(5-methyl-2-phenyl-4-oxazolyl)methoxy]benzyloxy]phenyl]propionic acid. Recrystallization from ethyl acetate-hexane gave colorless prism crystals. melting point: 122-123° C.

Example 72

A mixture of 4-(2-chloromethylphenoxymethyl)-5-methyl-2-phenyloxazole (0.50 g), ethyl 3-(2-ethoxy-4-hydroxyphenyl)propionate (0.31 g), anhydrous potassium carbonate (0.18 g) and N,N-dimethylformamide (10 mL) was stirred at 90° C. for 2 hrs. The reaction mixture was poured into water and extracted with ethyl acetate. The organic layer was washed with saturated brine, dried over anhydrous magnesium sulfate and concentrated. The obtained residue was subjected to silica gel column chromatography to give ethyl 3-[2-ethoxy-4-[2-[(5-methyl-2-phenyl-4-oxazolyl)methoxy]benzyloxy]phenyl]propionate as a colorless oil (0.62 g, 93%) from a fraction eluted with ethyl acetate-hexane (1:6, v/v).
$^1$H-NMR (CDCl$_3$) δ: 1.23 (3H, t, J=7.0 Hz), 1.37 (2H, t, J=7.0 Hz), 2.38 (3H, s), 2.51-2.59 (2H, m), 2.80-2.88 (2H, m), 3.96 (2H, q, J=7.0 Hz), 4.11 (2H, q, J=7.0 Hz), 5.07 (2H, s), 5.09 (2H, s), 6.42-6.50 (2H, m), 6.96-7.09 (3H, m), 7.26-7.48 (5H, m), 7.97-8.02 (2H, m).

Example 73

To a mixture of ethyl 3-[2-ethoxy-4-[2-[(5-methyl-2-phenyl-4-oxazolyl)methoxy]benzyloxy]phenyl]propionate (0.62 g), tetrahydrofuran (3 mL) and ethanol (3 mL) was added a 1N aqueous sodium hydroxide solution (2.4 mL) and the mixture was stirred at 50° C. for 2 hrs. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.50 g, 85%) of 3-[2-ethoxy-4-[2-[(5-methyl-2-phenyl-4-oxazolyl)methoxy]benzyloxy]phenyl]propionic acid. Recrystallization from ethyl acetate-hexane gave colorless prism crystals. melting point: 112-113° C.

Example 74

A mixture of [5-[(5-methyl-2-phenyl-4-oxazolyl)methoxy]-3-pyridyl]methanol (1.20 g), thionyl chloride (0.6 mL), tetrahydrofuran (20 mL) and toluene (20 mL) was stirred at room temperature for 2 hrs. The precipitated crystals were collected by filtration and washed with diisopropyl ether to give crude crystals. A mixture of the obtained crystals, methyl 2-(4-hydroxyphenyl)acetate (0.70 g), anhydrous potassium carbonate (0.92 g) and N,N-dimethylformamide (20 mL) was stirred overnight at 80° C. The reaction mixture was poured into water and extracted with ethyl acetate. The organic layer was washed with saturated brine, dried over anhydrous magnesium sulfate and concentrated. The obtained residue was subjected to silica gel column chromatography to give methyl 2-[4-[5-[(5-methyl-2-phenyl-4-oxazolyl)methoxy]-3-pyridylmethoxy]phenyl]acetate as a pale-yellow oil (1.52 g, 0.84%) from a fraction eluted with ethyl acetate-hexane (1:1, v/v).
$^1$H-NMR (CDCl$_3$) δ: 2.45 (3H, s), 3.57 (2H, s), 3.69 (3H, s), 5.06 (2H, s), 5.07 (2H, s), 6.86-6.98 (2H, m), 7.14-7.26 (2H, m), 7.40-7.54 (4H, m), 7.96-8.08 (2H, m), 8.30 (1H, d, J=1.4 Hz), 8.39 (1H, d, J=3.0 Hz).

Example 75

To a mixture of methyl 2-[4-[5-[(5-methyl-2-phenyl-4-oxazolyl)methoxy]-3-pyridylmethoxy]phenyl]acetate (1.50 g), tetrahydrofuran (6 mL) and methanol (6 mL) was added a 1N aqueous sodium hydroxide solution (6 mL) and the mixture was stirred at room temperature for 2 hrs. Dilute hydrochloric acid was added to acidify the reaction mixture, and the mixture was extracted with ethyl acetate. The organic layer was washed with saturated brine, dried over anhydrous magnesium sulfate and concentrated to give crystals (1.36 g, 94%) of 2-[4-[5-[(5-methyl-2-phenyl-4-oxazolyl)methoxy]-3-pyridylmethoxy]phenyl]acetic acid. Recrystallization from acetone-hexane gave colorless prism crystals. melting point: 141-142° C.

Example 76

A mixture of 2-[5-[3-[(5-methyl-2-phenyl-4-oxazolyl)methoxy]benzyloxy]-3-pyridyl]acetonitrile (2.90 g), a 4N aqueous sodium hydroxide solution (15 mL) and ethanol (15 mL) was heated under reflux for 4 hrs. Water was added to the reaction mixture, and the reaction mixture was neutralized with 1N hydrochloric acid and extracted with ethyl acetate. The organic layer was washed with saturated brine, dried over anhydrous magnesium sulfate and concentrated to give crystals (2.58 g, 85%) of 2-[5-[3-[(5-methyl-2-phenyl-4-oxazolyl)methoxy]benzyloxy]-3-pyridyl]acetic acid. Recrystallization from tetrahydrofuran-hexane gave colorless prism crystals. melting point: 158-159° C.

Example 77

A mixture of [5-(5-methyl-2-phenyl-4-oxazolylmethoxy)-3-pyridyl]methanol (1.50), thionyl chloride (0.80 mL) and toluene (30 mL) was stirred at room temperature for 2 hrs. The reaction mixture was concentrated and the obtained crystals were collected by filtration using isopropyl ether. A mixture of the crystals, methyl 2-(3-hydroxyphenyl)acetate (0.70 g), anhydrous potassium carbonate (1.35 g) and N,N-dimethylformamide (20 mL) was stirred at 50° C. for 15 hrs. The reaction mixture was poured into water and extracted with ethyl acetate. The organic layer was washed with saturated brine, dried over anhydrous magnesium sulfate and, concentrated. The obtained residue was subjected to silica gel column chromatography to give methyl 2-[3-[5-[(5-methyl-2-phenyl-4-oxazolyl)methoxy]-3-pyridylmethoxy]phenyl]acetate as a colorless oil (1.40 g, 75%) from a fraction eluted with ethyl acetate-hexane (2:1, v/v).
$^1$H-NMR (CDCl$_3$) δ: 2.45 (3H, s), 3.60 (2H, s), 3.69 (3H, s), 5.06 (2H, s), 5.08 (2H, s), 6.82-6.94 (3H, m), 7.18-7.32 (2H, m), 7.38-7.50 (4H, m), 7.96-8.08 (2H, m), 8.26-8.32 (1H, m), 8.36-8.42 (1H, m).

Example 78

To a mixture of methyl 2-[3-[5-[(5-methyl-2-phenyl-4-oxazolyl)methoxy]-3-pyridylmethoxy]phenyl]acetate (1.35 g), tetrahydrofuran (6 mL) and methanol (6 mL) was added a 1N aqueous sodium hydroxide solution (6 mL) and the mixture was stirred at room temperature for 3 hrs. The reaction mixture was concentrated, and water and dilute hydrochloric acid were added to acidify the residue. The precipitated solid was collected by filtration to give crystals (1.25 g, 95%) of 2-[3-[5-[(5-methyl-2-phenyl-4-oxazolyl)methoxy]-3-pyridylmethoxy]phenyl]acetic acid. Recrystallization from acetone-hexane gave colorless prism crystals. melting point: 143-144° C.

Example 79

To a mixture of 3-(5 methyl-2-phenyl-4-oxazolylmethoxy)-5-isoxazolylmethanol (0.859 g), methyl 2-(2-hydroxyphenyl)acetate (0.499 g), triphenylphosphine (0.944 g) and tetrahydrofuran (15 mL) was dropwise added a solution (40%, 1.74 g) of diethyl azodicarboxylate in toluene at room temperature, and the mixture was stirred for 15 hrs. The reaction mixture was concentrated and the residue was subjected to silica gel column chromatography to give methyl 2-[2-[3-(5-methyl-2-phenyl-4-oxazolylmethoxy)-5-isoxazolylmethoxy]phenyl]acetate as an oil from a fraction eluted with ethyl acetate-hexane (1:2, v/v). This oil was dissolved in methanol-tetrahydrofuran (1:1, 20 mL) and a 1N aqueous sodium hydroxide solution (10 mL) was added. The mixture was stirred at room temperature for 15 hrs. The reaction mixture was poured into water, 1N hydrochloric acid (10 mL) was added, and the mixture was extracted with ethyl acetate. The organic layer was washed with saturated brine, dried over anhydrous magnesium sulfate and concentrated to give crystals of 2-[2-[3-(5-methyl-2-phenyl-4-oxazolylmethoxy)-5-isoxazoly]methoxylphenyl]acetic acid. Recrystallization from ethanol-hexane gave colorless needle crystals (0.651 g, 52%). melting point: 152-153° C.

Example 80

A mixture of 5-chloromethyl-3-(5-methyl-2-phenyl-4-oxazolylmethoxy)isoxazole (457 mg), methyl 2-(3-hydroxyphenyl)acetate (249 mg), anhydrous potassium carbonate (415 mg) and N,N-dimethylformamide (10 mL) was stirred at 60° C. for 3 hrs. The reaction mixture was poured into water and extracted with ethyl acetate. The organic layer was washed with saturated brine, dried over anhydrous magnesium sulfate and concentrated. The obtained residue was subjected to silica gel column chromatography to give methyl 2-[3-[3-(5-methyl-2-phenyl-4-oxazolylmethoxy)-5-isoxazolylmethoxy]phenyl]acetate as a colorless oil (604 mg, 93%) from a fraction eluted with ethyl acetate-hexane (1:1, v/v).

$^1$H-NMR (CDCl$_3$) δ: 2.47 (3H, s), 3.60 (2H, s), 3.69 (3H, s), 5.04 (2H, s), 5.20 (2H, s), 6.01 (1H, s), 6.80-6.93 (3H, m), 7.25 (1H, t, J=8 Hz), 7.40-7.47 (3H, m), 7.97-8.06 (2H, m).

Example 81

Methyl 2-[3-[3-(5-methyl-2-phenyl-4-oxazolylmethoxy)-5-isoxazolylmethoxy]phenyl]acetate (604 mg) was dissolved in methanol-tetrahydrofuran (1:1, 12 mL) and a 1N aqueous sodium hydroxide solution (3 mL) was added. The mixture was stirred at room temperature for 1 hr. The reaction mixture was poured into water, 1N hydrochloric acid (3 mL) was added, and the mixture was extracted with ethyl acetate. The organic layer was washed with saturated brine, dried over anhydrous magnesium sulfate and concentrated to give crystals of 2-[3-[3-(5-methyl-2-phenyl-4-oxazolylmethoxy)-5-isoxazolylmethloxy]phenyl]acetic acid. Recrystallization from ethanol-hexane gave colorless needle crystals (522 mg, 89%). melting point: 128-129° C.

Example 82

To a mixture of 4-(4-chloromethylphenoxymethyl)-5-methyl-2-phenyloxazole (0.82 g), methyl 2-(2-hydroxy-5-propyl)phenylacetate (0.50 g) and N,N-dimethylformamide (30 mL) was added sodium hydride (60%, oil, 0.12 g) under ice-cooling, and the mixture was stirred at room temperature for 15 hrs. The reaction mixture was poured into water and extracted with ethyl acetate. The organic layer was washed successively with water and saturated brine, dried over anhydrous magnesium sulfate and concentrated. The obtained residue was subjected to silica gel column chromatography to give methyl 2-[2-[4-[(5-methyl-2-phenyl-4-oxazolyl)methoxy]benzyloxy]-5-propylphenyl]acetate as a colorless oil (0.70 g, 60%) from a fraction eluted with ethyl acetate-hexane (1:5, v/v).

$^1$H-NMR (CDCl$_3$) δ: 0.93 (3H, t, J=7.2 Hz), 1.51-1.67 (2H, m), 2.44 (3H, s), 2.51 (2H, t, J=7.6 Hz), 3.62 (3H, s), 3.63 (2H, s), 4.98 (2H, s), 5.00 (2H, s), 6.84 (1H, d, J=8.0 Hz), 6.99-7.06 (4H, m), 7.31-7.36 (2H, d, J=8.8 Hz), 7.42-7.46 (3H, m), 7.99-8.05 (2H, m).

Example 83

To a mixture of methyl 2-[2-[4-[(5-methyl-2-phenyl-4-oxazolyl)methoxy]benzyloxy]-5-propylphenyl]acetate (0.70 g), tetrahydrofuran (3 mL) and methanol (3 mL) was added a 1N aqueous sodium hydroxide solution (3 mL) and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.60 g, 91%) of 2-[2-[4-[(5-methyl-2-phenyl-4-oxazolyl)methoxy]benzyloxy]-5-propylphenyl]acetic acid. Recrystallization from ethyl acetate-hexane gave colorless prism crystals. melting point: 116-117° C.

Example 84

To a mixture of [4-[(2-phenyl-5-propyl-4-oxazolyl)methoxy]phenyl]methanol (0.50 g), methyl 2-(2-hydroxyphenyl)acetate (0.30 g), triphenylphosphine (0.60 g) and tetrahydrofuran (30 mL) was dropwise added a solution (40%, 1.00 g) of diethyl azodicarboxylate in toluene at room temperature, and the mixture was stirred for 15 hrs. To the reaction mixture was added ethyl acetate, and washed successively with water, a 2N aqueous sodium hydroxide solution and saturated brine, dried over anhydrous magnesium sulfate and concentrated. The residue was subjected to silica gel column chromatography to give methyl 2-[2-[4-[(2-phenyl-5-propyl-4-oxazolyl)methoxy]benzyloxy]phenyl]acetate as an oil (0.40 g, 56%) from a fraction eluted with ethyl acetate-hexane (1:4, v/v).

$^1$H-NMR (CDCl$_3$) δ: 0.99 (3H, t, J=7.4 Hz), 1.63-1.80 (2H, m), 2.76 (2H, t, J=7.2 Hz), 3.62 (3H, s), 3.66 (2H, s), 5.00 (2H, s), 5.02 (2H, s), 6.89-7.05 (4H, m), 7.18-7.48 (7H, m), 8.00-8.05 (2H, m).

Example 85

To a mixture of methyl 2-[2-[4-[(2-phenyl-5-propyl-4-oxazolyl)methoxy]benzyloxy]phenyl]acetate (0.40 g), tetrahydrofuran (2 mL) and ethanol (2 mL) was added a 1N aqueous sodium hydroxide solution (1.7 mL) and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.30 g, 77%) of 2-[2-[4-[(2-phenyl-5-propyl-4-oxazolyl)methoxy]benzyloxy]phenyl]acetic acid. Recrystallization from ethyl acetate-hexane gave colorless prism crystals. melting point: 129-130° C.

Example 86

To a mixture of [4-[(2-phenyl-5-propyl-4-oxazolyl)methoxy]phenyl]methanol (0.50 g), methyl 2-(3-hydroxyphenyl) acetate (0.30 g), triphenylphosphine. (0.60 g) and tetrahydrofuran (30 mL) was dropwise added a solution (40%, 1.00 g) of diethyl azodicarboxylate in toluene at room temperature, and the mixture was stirred for 15 hrs. To the reaction mixture was added ethyl acetate, and the mixture was washed successively with water, a 2N aqueous sodium hydroxide solution and saturated brine. The mixture was dried over anhydrous magnesium sulfate and concentrated. The residue was subjected to silica gel column chromatography to give methyl 2-[3-[[4-[(2-phenyl-5-propyl-4-oxazolyl)methoxy]benzyloxy]phenyl]acetate as an oil (0.44 g, 62%) from a fraction eluted with ethyl acetate-hexane (1:4, v/v).

$^1$H-NMR (CDCl$_3$) δ: 0.99 (3H, t, J=7.2 Hz), 1.63-1.82 (2H, m), 2.57 (2H, t, J=7.4 Hz), 3.60 (2H, s), 3.69 (3H, s), 4.98 (2H, s), 5.00 (2H, s), 6.85-6.91 (3H, m), 7.21-7.06 (2H, m), 7.20-7.48 (6H, m), 7.99-8.06 (2H, m).

Example 87

To a mixture of methyl 2-[3-[4-[(2-phenyl-5-propyl-4-oxazolyl)methoxy]benzyloxy]phenyl]acetate (0.44 g), tetrahydrofuran (2 mL) and ethanol (2 mL) was added a 1N aqueous sodium hydroxide solution (2 mL) and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.35 g, 81%) of 2-[3-[4-[(2-phenyl-5-propyl-4-oxazolyl)methoxy]benzyloxy]phenyl]acetic acid. Recrystallization from ethyl acetate-hexane gave colorless prism crystals. melting point: 115-116° C.

Example 88

To a mixture of 2-[2-[[6-[(5-methyl-2-phenyl-4-oxazolyl)methoxy]-3-pyridyl]methoxy]-3-pyridyl]acetonitrile (1.70 g) and ethanol (10 mL) was added a 2N aqueous sodium hydroxide solution (10 mL) and the mixture was heated under reflux for 17 hrs. 1N Hydrochloric acid (20 mL) and water were added to the reaction mixture and the mixture was extracted with ethyl acetate. The organic layer was washed with saturated brine, dried over anhydrous magnesium sulfate and concentrated to give crystals (1.60 g, 90%) of 2-[2-[[6-[(5-methyl-2-phenyl-4-oxazolyl)methoxy]-3-pyridyl]methoxy]-3-pyridyl]acetic acid. Recrystallization from ethyl acetate gave colorless prism crystals. melting point: 147-148° C.

Example 89

A mixture of 4-chloromethyl-2-[[2-(2-furyl)-5-methyl-4-oxazolyl]methoxy]pyridine (457 mg), methyl 3-hydroxyphenylacetate (249 mg), potassium carbonate (415 mg) and N,N-dimethylformamide (10 mL) was stirred at 60° C. for 4 hrs. The reaction mixture was poured into water and extracted with ethyl acetate. The organic layer was washed with saturated brine, dried over anhydrous magnesium sulfate and concentrated. The residue was subjected to silica gel column chromatography to give methyl 3-[2-[[2-(2-furyl)-5-methyl-4-oxazolyl]methoxy]-4-pyridyl]methoxy]phenylacetate as a colorless oil (524 mg, 80%) from a fraction eluted with ethyl acetate-hexane (1:1, v/v).

$^1$H-NMR (CDCl$_3$) δ: 2.46 (3H, s), 3.59 (2H, br s), 3.68 (3H, s), 5.02 (2H, s), 5.29 (2H, s), 6.51 (1H, dd, J=3.6, 1.8 Hz), 6.79-6.96 (5H, m), 6.98 (1H, dd, J=3.6, 0.8 Hz), 7.19-7.27 (1H, m), 7.53 (1H, dd, J=1.8, 0.6 Hz), 8.15 (1H, dd, J=5.2, 0.6 Hz).

Example 90

To a solution of methyl 3-[2-[[2-(2-furyl)-5-methyl-4-oxazolyl]methoxy]-4-pyridyl]methoxy]phenylacetate (521 mg) in tetrahydrofuran-methanol (1:1, 12 mL) was dropwise added a 1N aqueous sodium hydroxide solution (3 mL) at room temperature, and the mixture was stirred for 1 hr. The reaction mixture was poured into water, and the reaction mixture was neutralized with 1N hydrochloric acid (3 mL) and extracted with ethyl acetate. The organic layer was washed with saturated brine, dried over anhydrous magnesium sulfate and concentrated to give crystals of 3-[2-[[2-(2-furyl)-5-methyl-4-oxazolyl]methoxy]-4-pyridyl]methoxy]phenylacetic acid. Recrystallization from ethanol-hexane gave colorless needle crystals (473 mg, 94%). melting point: 136-137° C.

Example 91

A mixture of 2-[2-[3-methoxy-4-[(2-phenyl-5-methyl-4-oxazolyl)methoxy]benzyloxy]-3-pyridyl]acetonitrile (350 mg), ethanol (5 mL) and a 4N aqueous potassium hydroxide solution (5 mL) was heated under reflux for 4 hrs. Water was added to the reaction mixture, and the reaction mixture was neutralized with 2N hydrochloric acid and extracted with ethyl acetate. The organic layer was washed with saturated brine, dried over anhydrous magnesium sulfate and concentrated to give crystals (236 mg, 65%) of 2-[2-[3-methoxy-4-[(2-phenyl-5-methyl-4-oxazolyl)methoxy]benzyloxy]-3-pyridyl]acetic acid. The crystals were recrystallized from ethyl acetate-hexane to give colorless prism crystals. melting point: 145-146° C.

Example 92

To a mixture of 2-[2-[4-[[2-(2-furyl)-5-methyl-4-oxazolyl]methoxy]benzyloxy]-3-pyridyl]acetonitrile (0.60 g) and 2-methoxyethanol (2 mL) was added a 4N aqueous potassium hydroxide solution (2 mL) and the mixture was heated under reflux for 4 hrs. 1N Hydrochloric acid (8 mL) and water were added to the reaction mixture and the mixture was extracted with ethyl acetate. The organic layer was washed with saturated brine, dried over anhydrous magnesium sulfate and concentrated to give crystals (0.40 g, 63%) of 2-[2-[4-[[2-(2-furyl)-5-methyl-4-oxazolyl]methoxy]benzyloxy]-3-pyridyl]acetic acid. Recrystallization from ethyl acetate-hexane gave colorless prism crystals. melting point: 151-152° C.

Example 93

To a mixture of 2-[2-[4-[(5-methyl-2-phenyl-4-thiazolyl)methoxy]benzyloxy]-3-pyridyl]acetonitrile (0.94 g) and 2-methoxyethanol (8 mL) was added a 4N aqueous potassium hydroxide solution (4 mL) and the mixture was heated under reflux for 5 hrs. 1N Hydrochloric acid (16 mL) and water were added to the reaction mixture and the mixture was extracted with ethyl acetate. The organic layer was washed with saturated brine, dried over anhydrous magnesium sulfate and concentrated. The obtained residue was subjected to silica gel column chromatography to give crystals (0.58 g, 59%) of 2-[2-[4-[(5-methyl-2-phenyl-4-thiazolyl)methoxy]benzyloxy]-3-pyridyl]acetic acid from a fraction eluted with acetone-hexane (1:2, v/v). Recrystallization from ethyl acetate-hexane gave colorless prism crystals. melting point: 128-129° C.

Example 94

To a mixture of [4-[(E)-2-(5-methyl-2-phenyl-4-oxazolyl)ethenyl]phenyl]methanol (0.50 g), methyl 2-(2-hydroxyphenyl)acetate (0.27 g), triphenylphosphine (0.63 g) and tetrahydrofuran (30 mL) was dropwise added a solution (40%, 1.04 g) of diethyl azodicarboxylate in toluene at room temperature, and the mixture was stirred for 15 hrs. To the reaction mixture was added ethyl acetate, the mixture was washed successively with water, a 2N aqueous sodium hydroxide solution and saturated brine, dried over anhydrous magnesium sulfate and concentrated. The residue was subjected to silica gel column chromatography to give methyl 2-[2-[4-[(E)-2-(5-methyl-2-phenyl-4-oxazolyl)ethenyl]benzyloxy]phenyl]acetate as a pale-yellow oil (0.4-6 g, 66%) from a fraction eluted with ethyl acetate-hexane (1:6, v/v).

$^1$H-NMR (CDCl$_3$) δ: 2.50 (3H, s), 3.65 (3H, s), 3.70 (2H, s), 5.09 (2H, s), 6.87-6.95 (3H, m), 7.20-7.53 (11H, m), 8.04-8.10 (1H, m).

Example 95

To a mixture of methyl 2-[2-[4-[(E)-2-(5-methyl-2-phenyl-4-oxazolyl)ethenyl]benzyloxy]phenyl]acetate (0.44 g), tetrahydrofuran (2 mL) and ethanol (2 mL) was added a 1N aqueous sodium hydroxide solution (2 mL) and the mixture was stirred at room temperature for 15 hrs. 1N Hydrochloric acid and water were added to acidify the reaction mixture, and the, mixture was extracted with ethyl acetate. The organic layer was washed with saturated brine, dried over anhydrous magnesium sulfate and concentrated to give crystals (0.31 g, 72%) of 2-[2-[4-[(E)-2-(5-methyl-2-phenyl-4-oxazolyl)ethenyl]benzyloxy]phenyl]acetic acid. Recrystallization from ethyl acetate-hexane gave pale-yellow prism crystals. melting point: 189-190° C.

Example 96

To a mixture of [4-[2-(5-methyl-2-phenyl-4-oxazolyl)ethyl]phenyl]methanol (0.60 g), methyl 2-(2-hydroxyphenyl)acetate (0.35 g), triphenylphosphine (0.79 g) and tetrahydrofuran (50 mL) was dropwise added a solution (40%, 1.39 g) of diethyl azodicarboxylate in toluene at room temperature, and the mixture was stirred for 15 hrs. To the reaction mixture was added ethyl acetate, the mixture was washed successively with water, a 2N aqueous sodium hydroxide solution and saturated brine, dried over anhydrous magnesium sulfate and concentrated. The residue was subjected to silica gel column chromatography to give methyl 2-[2-[4-[2-(5-methyl-2-phenyl-4-oxazolyl)ethyl]benzyloxy]phenyl]acetate as a colorless oil (0.54 g, 58%) from a fraction eluted with ethyl acetate-hexane (1:6, v/v).

$^1$H-NMR (CDCl$_3$) δ: 2.06 (3H, s), 2.73-2.81 (2H, m), 2.94-3.02 (2H, m), 3.63 (3H, s), 3.68 (2H, s), 5.06 (2H, s), 6.89-6.97 (2H, m), 7.15-7.45 (9H, m), 7.99-8.03 (2H, m).

Example 97

To a mixture of methyl 2-[2-[4-[2-(5-methyl-2-phenyl-4-oxazolyl)ethyl]benzyloxy]phenyl]acetate (0.54 g), tetrahydrofuran (3 mL) and ethanol (3 mL) was added a 1N aqueous sodium hydroxide solution (3 mL) and the mixture was stirred at room temperature for 15 hrs. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.40 g, 78%) of 2-[2-[4-[2-(5-methyl-2-phenyl-4-oxazolyl)ethyl]benzyloxy]phenyl]acetic acid. Recrystallization from ethyl acetate-hexane gave colorless prism crystals. melting point: 130-131° C.

Example 98

To a mixture of 4-[2-(4-chloromethyl-2-oxazolyl)ethyl]-5-methyl-2-phenyloxazole (0.50 g), methyl 2-(2-hydroxyphenyl)acetate (0.25 g) and N,N-dimethylformamide (20 mL) was added sodium hydride (60%, oil, 0.07 g) under ice-cooling, and the mixture was stirred at room temperature for 15 hrs. The reaction mixture was poured into water and extracted with ethyl acetate. The organic layer was washed successively with water, 2N aqueous sodium hydroxide solution and saturated brine, dried over anhydrous magnesium sulfate and concentrated. The obtained residue was subjected to silica gel column chromatography to give methyl 2-[2-[[2-[2-(5-methyl-2-phenyl-4-oxazolyl)ethyl]-4-oxazolyl]methoxy]phenyl]acetate as a colorless oil (0.43 g, 66%) from a fraction eluted with ethyl acetate-hexane (1:2, v/v).

$^1$H-NMR (CDCl$_3$) δ: 2.27 (3H, s), 2.93-3.01 (2H, m), 3.11-3.20 (2H, m), 3.66 (5H, s), 5.01 (2H, d, J=1.2 Hz), 6.91-6.99 (2H, m), 7.18-7.30 (2H, m), 7.40-7.46 (3H, m), 7.59 (1H, t, J=1.2 Hz), 7.94-8.00 (2H, m).

Example 99

To a mixture of methyl 2-[2-[[2-[2-(5-methyl-2-phenyl-4-oxazolyl)ethyl]-4-oxazolyl]methoxy]phenyl]acetate (0.44 g), tetrahydrofuran (2 mL) and methanol (2 mL) was added a 1N aqueous sodium hydroxide solution (2 mL) and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.34 g, 81%) of 2-[2-[[2-[2-(5-methyl-2-phenyl-4-oxazolyl)ethyl]-4-oxazolyl]methoxy]phenyl]acetic acid. Recrystallization from ethyl acetate-hexane gave colorless prism crystals. melting point: 109-110° C.

Example 100

To a mixture of 4-[2-(4-chloromethyl-2-oxazolyl)ethyl]-5-methyl-2-phenyloxazole (0.50 g), methyl 2-(3-hydroxyphenyl)acetate (0.25 g) and N,N-dimethylformamide (20 mL) was added sodium hydride (60%, oil, 0.07 g) under ice-cooling, and the mixture was stirred at room temperature for 15 hrs. The reaction mixture was poured into water and extracted with ethyl acetate. The organic layer was washed successively with water, 2N aqueous sodium hydroxide solution and saturated brine, dried over anhydrous magnesium sulfate and concentrated. The obtained residue was subjected to silica gel column chromatography to give, methyl 2-[3-[[2-[2-(5-methyl-2-phenyl-4-oxazolyl)ethyl]-4-oxazolyl]methoxy]phenyl]acetate as a colorless oil (0.35 g, 54%) from a fraction eluted with ethyl acetate-hexane (1:2, v/v).

$^1$H-NMR (CDCl$_3$) δ: 2.27 (3H, s), 2.94-3.02 (2H, m), 3.12-3.21 (2H, m), 3.60 (2H, s), 3.69 (3H, s), 4.97 (2H, s), 6.87-6.91 (3H, m), 7.20-7.28 (1H, m), 7.39-7.46 (3H, m), 7.60 (1H, s), 7.94-8.60 (2H, m).

Example 101

To a mixture of methyl 2-[3-[[2-[2-(5-methyl-2-phenyl-4-oxazolyl)ethyl]-4-oxazolyl]methoxy]phenyl]acetate (0.34 g), tetrahydrofuran (2 mL) and methanol (2 mL) was added a 1N aqueous sodium hydroxide solution (2 mL) and the mixture was stirred at 50° C. for 1 hr. 1N Hydrochloric acid and water were added to acidify the reaction mixture, and the mixture was extracted with ethyl acetate. The organic layer was washed with saturated brine, dried over anhydrous magnesium sulfate and concentrated to give crystals (0.26 g, 79%) of 2-[3-[[2-[2-(5-methyl-2-phenyl-4-oxazolyl)ethyl]-4-oxazolyl]methoxy]phenyl]acetic acid. Recrystallization from ethyl acetate-hexane gave colorless prism crystals. melting point: 127-128° C.

Example 102

To a mixture of 4-[2-(4-chloromethyl-2-thiazolyl)ethyl]-5-methyl-2-phenyloxazole (0.64 g), methyl 2-(2-hydroxyphenyl)acetate (0.30 g) and N,N-dimethylformamide (20 mL) was added sodium hydride (60%, oil, 0.09 g) under ice-cooling, and the mixture was stirred at room temperature for 15 hrs. The reaction mixture was poured into water and extracted with ethyl acetate. The organic layer was washed successively with water, 2N aqueous sodium hydroxide solution and saturated brine, dried over anhydrous magnesium sulfate and concentrated. The obtained residue was subjected to silica gel column chromatography to give methyl 2-[2-[[2-[2-(5-methyl-2-phenyl-4-oxazolyl)ethyl]-4-thiazolyl]methoxy]phenyl]acetate as a colorless oil (0.49 g, 60%) from a fraction eluted with ethyl acetate-hexane (1:3, v/v).

$^1$H-NMR (CDCl$_3$) δ: 2.22 (3H, s), 2.99 (2H, t, J=7.2 Hz), 3.40 (2H, t, J=7.2 Hz), 3.66 (3H, s), 3.71 (2H, s), 5.22 (2H, d, J=1.2 Hz), 6.90-6.99 (2H, m), 7.19-7.30 (3H, m), 7.41-7.46 (3H, m), 7.96-8.01 (2H, m).

Example 103

To a mixture of methyl 2-[2-[[2-[2-(5-methyl-2-phenyl-4-oxazolyl)ethyl]-4-thiazolyl]methoxy]phenyl]acetate (0.49 g), tetrahydrofuran (3 mL) and methanol (3 mL) was added a 1N aqueous sodium hydroxide solution (3 mL) and the mixture was stirred at 50° C. for 1 hr. 1N Hydrochloric acid (3 mL) and water were added to the reaction mixture, and the mixture was extracted with ethyl acetate. The organic layer was washed with saturated brine, dried over anhydrous magnesium sulfate, and concentrated to give crystals (0.38 g, 79%) of 2-[2-[[2-[2-(5-methyl-2-phenyl-4-oxazolyl)ethyl]-4-thiazolyl]methoxy]phenyl]acetic acid. Recrystallization from ethyl acetate-hexane gave colorless prism crystals. melting point: 152-153° C.

Example 104

To a mixture of 4-[2-(4-chloromethyl-2-thiazolyl)ethyl]-5-methyl-2-phenyloxazole (0.64 g), methyl 2-(3-hydroxyphenyl)acetate (0.30 g) and N,N-dimethylformamide (20 mL) was added sodium hydride (60%, oil, 0.09 g) under ice-cooling, and the mixture was stirred at room temperature for 15 hrs. The reaction mixture was poured into water and extracted with ethyl acetate. The organic layer was washed successively with water, 2N aqueous sodium hydroxide solution and saturated brine, dried over anhydrous magnesium sulfate and concentrated. The obtained residue was subjected to silica gel column chromatography to give methyl 2-[3-[[2-[2-(5-methyl-2-phenyl-4-oxazolyl)ethyl]-4-thiazolyl]methoxy]phenyl]acetate as a colorless oil (0.31 g, 38%) from a fraction eluted with ethyl acetate-hexane (1:3, v/v).

$^1$H-NMR (CDCl$_3$) δ: 2.21 (3H, s), 2.99 (2H, t, J=7.4 Hz), 3.40 (2H, t, J=7.4 Hz), 3.60 (2H, s), 3.69 (3H, s), 5.16 (2H, s), 6.86-6.93 (3H, m), 7.16-7.28 (2H, m), 7.38-7.46 (3H, m), 7.96-8.01 (2H, m).

Example 105

To a mixture of methyl 2-[3-[[2-[2-(5-methyl-2-phenyl-4-oxazolyl)ethyl]-4-thiazolyl]methoxy]phenyl]acetate (0.31 g), tetrahydrofuran (3 mL) and methanol (3 mL) was added a 1N aqueous sodium hydroxide solution (3 mL) and the mixture was stirred at 50° C. for 1 hr. 1N Hydrochloric acid (3 mL) and water were added to the reaction mixture, and the precipitated crystals were collected by filtration and air-dried to give crystals (0.23 g, 77%) of 2-[3-[[2-[2-(5-methyl-2-phenyl-4-oxazolyl)ethyl]-4-thiazolyl]methoxy]phenyl]acetic acid. Recrystallization from ethyl acetate-hexane gave colorless prism crystals. melting point: 153-154° C.

Example 106

To a mixture of 5-chloromethyl-3-[2-(5-methyl-2-phenyl-4-oxazolyl)ethyl]-1,2,4-oxadiazole (0.61 g), methyl 2-(2-hydroxyphenyl)acetate (0.30 g) and N,N-dimethylformamide (20 mL) was added sodium hydride (60%, oil, 0.09 g) under ice-cooling, and the mixture was stirred at room temperature for 15 hrs. The reaction mixture was poured into water and extracted with ethyl acetate. The organic layer was washed successively with water, 2N aqueous sodium hydroxide solution and saturated brine, dried over anhydrous magnesium sulfate and concentrated. The obtained residue was subjected to silica gel column chromatography to give crystals (0.38 g, 44%) methyl 2-[2-[[3-[2-(5-methyl-2-phenyl-4-oxazolyl)ethyl]-1,2,4-oxadiazol-5-yl]methoxy]phenyl]acetate from a fraction eluted with ethyl acetate-hexane (1:3, v/v). Recrystallization from ethyl acetate-hexane gave colorless prism crystals. melting point: 109-110° C.

Example 107

To a mixture of methyl 2-[2-[[3-[2-(5-methyl-2-phenyl-4-oxazolyl)ethyl]-1,2,4-oxadiazol-5-yl]methoxy]phenyl]acetate (0.30 g), tetrahydrofuran (3 mL) and methanol (3 mL) was added a 1N aqueous sodium hydroxide solution (3 mL) and the mixture was stirred at 50° C. for 1 hr. 1N Hydrochloric acid (3 mL) and water were added to the reaction mixture, and the mixture was extracted with ethyl acetate. The organic layer was washed with saturated brine, dried over anhydrous magnesium sulfate and concentrated to give crystals (0.22 g, 76%) of 2-[2-[[3-[2-(5-methyl-2-phenyl-4-oxazolyl)ethyl]-1,2,4-oxadiazol-5-yl]methoxy]phenyl]acetic acid. Recrystallization from ethyl acetate-hexane gave colorless prism crystals. melting point: 120-121° C.

Example 108

To a mixture of 5-chloromethyl-3-[2-(5-methyl-2-phenyl-4-oxazolyl)ethyl]-1,2,4-oxadiazole (0.61 g), methyl 2-(3-hydroxyphenyl)acetate (0.30 g) and N,N-dimethylformamide (20 mL) was added sodium hydride (60%, oil, 0.09 g) under ice-cooling, and the mixture was stirred at room temperature for 15 hrs. The reaction mixture was poured into water and extracted with ethyl acetate. The organic layer was washed successively with water, 2N aqueous sodium hydroxide solution and saturated brine, dried over anhydrous magnesium sulfate and concentrated. The obtained residue was subjected to silica gel column chromatography to give crystals (0.37 g, 43%) of methyl 2-[3-[[3-[2-(5-methyl-2-phenyl-4-oxazolyl)ethyl]-1,2,4-oxadiazol-5-yl]methoxy]phenyl]acetate from a fraction eluted with ethyl acetate-hexane (1:3, v/v).

Recrystallization from ethyl acetate-hexane gave colorless prism crystals. melting point: 76-77° C.

Example 109

To a mixture of methyl 2-[3-[[3-[2-(5-methyl-2-phenyl-4-oxazolyl)ethyl]-1,2,4-oxadiazol-5-yl]methoxy]phenyl]acetate (0.30 g), tetrahydrofuran (3 mL) and methanol (3 mL) was added a 1N aqueous sodium hydroxide solution (3 mL) and the mixture was stirred at 50° C. for 1 hr. 1N Hydrochloric acid (3 mL) and water were added to the reaction mixture, the mixture was extracted with ethyl acetate. The organic layer was washed with saturated brine, dried over anhydrous magnesium sulfate and concentrated to give crystals (0.28 g, 97%) of 2-[3-[[3-[2-(5-methyl-2-phenyl-4-oxazolyl)ethyl]-1,2,4-oxadiazol-5-yl]methoxy]phenyl]acetic acid. Recrystallization from ethyl acetate-hexane gave colorless prism crystals. melting point: 93-94° C.

Example 110

To a mixture of 2-[6-methyl-2-[4-[(5-methyl-2-phenyl-4-oxazolyl)methoxy]benzyloxy]-3-pyridyl]acetonitrile. (0.58 g), ethanol (10 mL) was added a 2N aqueous sodium hydroxide solution (10 mL) and the mixture was heated under reflux for 24 hrs. 1N Hydrochloric acid (20 mL) and water were added to the reaction mixture and the mixture was extracted with ethyl acetate. The organic layer was washed with saturated brine, dried over anhydrous magnesium sulfate and concentrated to give crystals (0.51 g, 82%) of 2-[6-methyl-2-[4-[(5-methyl-2-phenyl-4-oxazolyl)methoxy]benzyloxy]-3-pyridyl]acetic acid. Recrystallization from ethyl acetate-hexane gave colorless prism crystals. melting point: 138-139° C.

Example 111

To a mixture of [4-[2-(5-methyl-2-phenyl-4-oxazolyl)ethyl]phenyl]methanol (0.87 g), methyl 2-(2-oxo-1,2-dihydro-3-pyridyl)acetate (0.36 g), triphenylphosphine (0.87 g) and tetrahydrofuran (50 mL) was dropwise added a solution (40%, 1.47 g) of diethyl azodicarboxylate in toluene at room temperature, and the mixture was stirred for 15 hrs. The reaction mixture was concentrated and the residue was subjected to silica gel column chromatography to give an oil from a fraction eluted with ethyl acetate-hexane (1:3, v/v). To a mixture of the obtained oil, tetrahydrofuran (3 mL) and methanol, (3 mL) was added an 1N aqueous sodium hydroxide solution (3 mL) and the mixture was stirred at room temperature for 2 hrs. 1N Hydrochloric acid (3 mL) and water were added to the reaction mixture and the mixture was extracted with ethyl acetate. The organic layer was washed with saturated brine, dried over anhydrous magnesium sulfate and concentrated. The residue was subjected to silica gel column chromatography to give crystals (0.14 g, 14%) of 2-[2-[4-[2-(5-methyl-2-phenyl-4-oxazolyl)ethoxy]benzyloxy]-3-pyridyl]acetic acid from a fraction eluted with ethyl acetate-hexane (1:1, v/v). Recrystallization from ethyl acetate-hexane gave colorless prism crystals. melting point: 134-135° C.

Example 112

To a mixture of 4-[[3-methyl-1-(2-pyridyl)-1H-pyrazol-4-yl]methoxy]benzyl alcohol (0.69 g), methyl 2-(2-hydroxyphenyl)acetate (0.40 g), triphenylphosphine (0.65 g) and tetrahydrofuran (10 mL) was dropwise added a solution (40%, 1.18 g) of diethyl azodicarboxylate in toluene at room temperature, and the mixture was stirred overnight. The reaction mixture was concentrated and the residue was subjected to silica gel column chromatography to give an oil from a fraction eluted with ethyl acetate-hexane (1:1, v/v). This oil was dissolved in methanol-tetrahydrofuran (1:1, 10 mL), a 1N aqueous sodium hydroxide solution (5 mL) was added to the mixture, and the mixture was stirred at room temperature for 4 hrs. Water was added to the reaction mixture, and the mixture was neutralized with 1N hydrochloric acid. The precipitated crystals (0.80 g, 80%) of 2-[2-[4-[[3-methyl-1-(2-pyridyl)-1H-pyrazol-4-yl]methoxy]benzyloxy]phenyl]acetic acid were collected by filtration. Recrystallization from acetone-hexane gave colorless prism crystals. melting point: 160-161° C.

Example 113

To a mixture of 3-(5-methyl-2-phenyl-4-thiazolylmethoxy)-5-isoxazolylmethanol (0.80 g), methyl 2-(2-hydroxyphenyl)acetate (0.45 g), tributylphosphine (1.05 g) and tetrahydrofuran (100 mL) was added 1,1'-(azodicarbonyl)dipiperidine (1.31 g) at room temperature and the mixture was stirred for 3 days. The precipitated crystals were filtered off. The filtrate was concentrated and the residue was subjected to silica gel column chromatography to give crystals (0.55 g, 47%) of methyl 2-[2-[[3-[(5-methyl-2-phenyl-4-thiazolyl)methoxy]-5-isoxazolyl]methoxy]phenyl]acetate from a fraction eluted with ethyl acetate-hexane (1:3, v/v). Recrystallization from ethyl acetate-hexane gave colorless prism crystals. melting point: 108-109° C.

Example 114

To a mixture of methyl 2-[2-[[3-[(5-methyl-2-phenyl-4-thiazolyl)methoxy]-5-isoxazolyl]methoxy]phenyl]acetate (0.44 g), tetrahydrofuran (3 mL) and methanol (3 mL) was added a 1N aqueous sodium hydroxide solution (3 mL) and the mixture was stirred at 50° C. for 1 hr. 1N Hydrochloric acid (3 mL) and water were added to the reaction mixture, and the precipitated crystals were collected by filtration and dried with air to give crystals (0.40 g, 93%) of 2-[2-[[3-[(5-methyl-2-phenyl-4-thiazolyl)methoxy]-5-isoxazolyl]methoxy]phenyl]acetic acid. Recrystallization from ethyl acetate-hexane gave colorless needle crystals. melting point: 147-148° C.

Example 115

To a mixture of 2-[2-[[3-[(5-methyl-2-phenyl-4-thiazolyl)methoxy]-5-isoxazolyl]methoxy]-3-pyridyl]acetonitrile (0.35 g) and ethanol (10 mL) was added a 2N aqueous sodium hydroxide solution (10 mL) and the mixture was heated under reflux for 5 hrs. 1N Hydrochloric acid (20 mL) and water were added to the reaction mixture and the mixture was extracted with ethyl acetate. The organic layer was washed with saturated brine, dried over anhydrous magnesium sulfate and concentrated to give crystals (0.30 g, 81%) of 2-[2-[[3-[(5-methyl-2-phenyl-4-thiazolyl)methoxy]-5-isoxazolyl]methoxy]-3-pyridyl]acetic acid. Recrystallization from ethyl acetate-hexane gave colorless prism crystals. melting point: 109-110° C.

Example 116

To a mixture of [3-[2-(5-methyl-2-phenyl-4-oxazolyl)ethoxy]-5-isoxazolyl]methanol (1.00 g), methyl 2-(2-hydroxyphenyl)acetate (0.58 g), tributylphosphine (1.42 g) and tetrahydrofuran (100 mL) was added 1,1'-(azodicarbonyl)dipiperidine (1.77 g) at room temperature and the mixture was stirred for 15 hrs. The precipitated crystals were filtered off. The filtrate was concentrated and the residue was subjected to silica gel column chromatography to give crystals (0.87 g, 59%) of methyl 2-[2-[[3-[2-(5-methyl-2-phenyl-4-thiazolyl)ethoxy]-5-isoxazolyl]methoxy]phenyl]acetate from a fraction eluted with ethyl acetate-hexane (1:3, v/v). Recrystallization from ethyl acetate-hexane gave colorless prism crystals. melting point: 80-81° C.

Example 117

To a mixture of methyl 2-[2-[[3-[2-(5-methyl-2-phenyl-4-thiazolyl)ethoxy]-5-isoxazolyl]methoxy]phenyl]acetate (0.77 g), tetrahydrofuran (5 mL) and methanol (5 mL) was added a 1N aqueous sodium hydroxide solution (5 mL) and the mixture was stirred at room temperature for 3 hrs. 1N Hydrochloric acid (5 mL) and water were added to the reaction mixture and the precipitated crystals were collected by filtration and dried with air to give crystals (0.71 g, 96%) of 2-[2-[[3-[2-(5-methyl-2-phenyl-4-thiazolyl)ethoxy]-5-isoxazolyl]methoxy]phenyl]acetic acid. Recrystallization from ethyl acetate-hexane gave colorless prism crystals. melting point: 159-160° C.

Example 118

To a mixture of [6-[2-[(5-methyl-2-phenyl-4-oxazolyl)ethoxy]-3-pyridyl]methanol (0.60 g), methyl 2-(2-hydroxyphenyl)acetate (0.38 g), tributylphosphine (0.77 g) and tetrahydrofuran (50 mL) was added 1,1'-(azodicarbonyl)dipiperidine (0.96 g) at room temperature and the mixture was stirred for 3 days. The precipitated crystals were filtered off. The filtrate was concentrated and the residue was subjected to silica gel column chromatography to give crystals (0.70 g, 80%) of methyl 2-[2-[[6-[2-(5-methyl-2-phenyl-4-oxazolyl)ethoxy]-3-pyridyl]methoxy]phenyl]acetate from a fraction eluted with ethyl acetate-hexane (1:3, v/v). Recrystallization from ethyl acetate-hexane gave colorless prism crystals. melting point: 78-79° C.

Example 119

To a mixture of methyl 2-[2-[[6-[2-(5-methyl-2-phenyl-4-oxazolyl)ethoxy]-3-pyridyl]methoxy]phenyl]acetate (0.60 g), tetrahydrofuran (3 mL) and methanol (3 mL) was added a 1N aqueous sodium hydroxide solution (3 mL), and the mixture was stirred at room temperature for 4 hrs. 1N Hydrochloric acid (3 mL) and water were added to the reaction mixture and the precipitated crystals were collected by filtration and dried with air to give crystals (0.50 g, 86%) of 2-[2-[[6-[2-(5-methyl-2-phenyl-4-oxazolyl)ethoxy]-3-pyridyl]methoxy]phenyl]acetic acid. Recrystallization from ethyl acetate-hexane gave colorless prism crystals. melting point: 159-160° C.

Example 120

To a mixture of 5-(5-methyl-2-phenyl-4-oxazolylmethoxy)-2-pyridylmethanol (1.00 g), methyl 2-(2-hydroxyphenyl)acetate (0.60 g), triphenylphosphine (0.96 g) and tetrahydrofuran (15 mL) was dropwise added a solution (40%, 1.68 g) of diethyl azodicarboxylate in toluene at room temperature, and the mixture was stirred overnight. The reaction mixture was concentrated and the residue was subjected to silica gel column chromatography to give an oil from a fraction eluted with ethyl acetate-hexane (1:1, v/v). This oil was dissolved in methanol-tetrahydrofuran (1:1, 12 mL), and a 1N aqueous sodium hydroxide solution (6 mL) was added to the mixture. The mixture was stirred at room temperature for 3 hrs. Water was added to the reaction mixture, and the mixture was neutralized with 1N hydrochloric acid. The precipitated crystals (0.69 g, 47%) of 2-[2-[[5-[(5-methyl-2-phenyl-4-oxazolyl)methoxy]-2-pyridyl]methoxy]phenyl]acetic acid were collected by filtration. Recrystallization from acetone-hexane gave colorless leaflet crystals. melting point: 180-181° C.

Example 121

To a mixture of [6-[(5-methyl-2-phenyl-4-thiazolyl)methoxy]-3-pyridyl]methanol (1.00 g), methyl 2-(2-hydroxyphenyl)acetate (0.50 g), tributylphosphine (1.21 g) and tetrahydrofuran (100 mL) was added 1,1'-(azodicarbonyl)dipiperidine (1.51 g) at room temperature and the mixture was stirred for 15 hrs. The precipitated crystals were filtered off. The filtrate was concentrated and the residue was subjected to silica gel column chromatography to give crystals (1.20 g, 87%) of methyl 2-[2-[[6-[(5-methyl-2-phenyl-4-thiazolyl)methoxy]-3-pyridyl]methoxy]phenyl]acetate from a fraction eluted with ethyl acetate-hexane (1:6, v/v). Recrystallization from ethyl acetate-hexane gave colorless prism crystals. melting point: 119-120° C.

Example 122

To a mixture of methyl 2-[2-[[6-[(5-methyl-2-phenyl-4-thiazolyl)methoxy]-3-pyridyl]methoxy]-phenyl]acetate (1.05 g), tetrahydrofuran (5 mL) and methanol (5 mL) was added a 1N aqueous sodium hydroxide solution (5 mL) and the mixture was stirred at 50° C. for 2 hrs. 1N Hydrochloric acid (5 mL) and water were added to the reaction mixture, and the precipitated crystals were collected by filtration and dried with air to give crystals (0.91 g, 88%) of 2-[2-[[6-[(5-methyl-2-phenyl-4-thiazolyl)methoxy]-3-pyridyl]methoxy]phenyl]acetic acid. Recrystallization from ethyl acetate-hexane gave colorless prism crystals. melting point: 173-174° C.

Example 123

To a mixture of [6-[[2-(2-furyl)-5-methyl-4-oxazolyl]methoxy]-3-pyridyl]methanol (1.36 g), methyl 2-(2-hydroxyphenyl)acetate (0.45 g), tributylphosphine (1.09 g) and tetrahydrofuran (100 mL) was added 1,1'-(azodicarbonyl)dipiperidine (1.36 g) at room temperature and the mixture was stirred for 15 hrs. The precipitated crystals were filtered off and the filtrate was concentrated. The residue was subjected to silica gel column chromatography to give crystals (0.83 g, 71%) of methyl 2-[2-[[6-[2-(2-furyl)-5-methyl-4-oxazolyl]methoxy]-3-pyridyl]methoxy]phenyl]acetate from a fraction eluted with ethyl acetate-hexane (1:2, v/v). Recrystallization from ethyl acetate-hexane gave colorless prism crystals. melting point: 84-85° C.

Example 124

To a mixture of methyl 2-[2-[[6-[2-(2-furyl)-5-methyl-4-oxazolyl]methoxy]-3-pyridyl]methoxy]phenyl]acetate (0.65 g), tetrahydrofuran (5 mL) and methanol (5 mL) was added a 1N aqueous sodium hydroxide solution (5 mL) and the mixture was stirred at room temperature for 3 hrs. 1N Hydrochloric acid (5 mL) and water were added to the reaction mixture, and the precipitated crystals were collected by filtration and dried with air to give crystals (0.60 g, 95%) of 2-[2-[[6-[2-(2-furyl)-5-methyl-4-oxazolyl]methoxy]-3-pyridyl]methoxy]phenyl]acetic acid. Recrystallization from ethyl acetate-hexane gave colorless prism crystals. melting point: 119-120° C.

Example 125

To a mixture of 2-[2-[[4-[(5-methyl-2-phenyl-4-oxazolyl)methoxy]phenoxy]methyl]-3-pyridyl]acetonitrile (1.19 g) and ethanol (15 mL) was added a 2N aqueous sodium hydroxide solution (15 mL) and the mixture was heated under reflux for 5 hrs. 1N Hydrochloric acid (30 mL) and water were added to the reaction mixture and the mixture was extracted with ethyl acetate. The organic layer was washed with saturated brine, dried over anhydrous magnesium sulfate and concentrated to give crystals (1.08 g, 86%) of 2-[2-[[4-[(5-methyl-2-phenyl-4-oxazolyl)methoxy]phenoxy]methyl]-3-pyridyl]acetic acid. Recrystallization from ethyl acetate-hexane gave colorless prism crystals. melting point: 126-127° C.

Example 126

To a mixture of 2-[2-[4-[[3-methyl-1-(2-pyridyl)-1H-pyrazol-4-yl]methoxy]benzyloxy]-3-pyridyl]acetonitrile (0.30 g) and ethanol (15 mL) was added a 2N aqueous sodium hydroxide solution (10 mL) and the mixture was heated under reflux for 24 hrs. 1N Hydrochloric acid (20 mL) and water were added to the reaction mixture. The precipitated crystals were collected by filtration and dried with air to give crystals (0.23 g, 74%) of 2-[2-[4-[[3-methyl-1-(2-pyridyl)-1H-pyrazol-4-yl]methoxy]benzyloxy]-3-pyridyl]acetic acid. Recrystallization from ethyl acetate-hexane gave colorless prism crystals. melting point: 150-151° C.

Example 127

To a mixture of 4-[methyl(4-phenyl-2-thiazolyl)aminomethyl]benzyl alcohol (1.00 g), methyl 2-(4-hydroxyphenyl)acetate (643 mg), tributylphosphine (1.30 g) and tetrahydrofuran (30 mL) was added 1,1'-(azodicarbonyl)dipiperidine (1.62 g) at room temperature and the mixture was stirred for 16 hrs. The precipitated crystals were filtered off. The filtrate was concentrated and the residue was subjected to silica gel column chromatography to give methyl 4-[4-[methyl(4-phenyl-2-thiazolyl)aminomethyl]benzyloxy]phenylacetate (1.48 g, quantitative) as a yellow oil from a fraction eluted with ethyl acetate-hexane (1:4, v/v).
$^1$H-NMR (CDCl$_3$) δ: 3.08 (3H, s), 3.56 (2H, s), 3.68 (3H, s), 4.78 (2H, s), 5.03 (2H, s), 6.73 (1H, s), 6.92 (2H, d, J=8.4 Hz), 7.11-7.42 (9H, m), 7.85-7.89 (2H, m).

Example 128

A mixture of methyl 4-[4-[methyl(4-phenyl-2-thiazolyl)aminomethyl]benzyloxy]phenylacetate (510 mg), a 1N aqueous sodium hydroxide solution (2.5 mL), methanol (5 mL) and tetrahydrofuran (10 mL) was stirred at 60° C. for 1 hr. Water was added to the reaction mixture, 1N hydrochloric acid (3 mL) was added to the mixture, and then the mixture was extracted with ethyl acetate. The organic layer was washed with saturated brine, dried over anhydrous magnesium sulfate and concentrated to give crystals of 4-[4-[methyl(4-phenyl-2-thiazolyl)aminomethyl]benzyloxy]phenylacetic acid. The crystals were recrystallized from diethyl ether-hexane to give colorless prism crystals (427 mg, 87%). melting point: 116-118° C.

Example 129

A mixture of 2-[2-[[3-[(5-methyl-2-phenyl-4-oxazolyl)methoxy]-5-isoxazolyl]methoxy]-3-pyridyl]acetonitrile (1.02 g), a 2N aqueous sodium hydroxide solution (10 mL) and ethanol (20 mL) was heated under reflux for 5 hrs. Water was added to the reaction mixture, and the mixture was neutralized with 2N hydrochloric acid and extracted with ethyl acetate. The organic layer was washed with water, dried over anhydrous magnesium sulfate and concentrated to give crystals (820 mg, 77%) of 2-[2-[[3-[(5-methyl-2-phenyl-4-oxazolyl)methoxy]-5-isoxazolyl]methoxy]-3-pyridyl]acetic acid. Recrystallization from ethyl acetate-isopropyl ether gave colorless needle crystals. melting point: 129-130° C.

Example 130

A mixture of 2-[2-[4-[5-methyl-2-(2-naphthyl)-4-oxazolylmethoxy]benzyloxy]-3-pyridyl]acetonitrile (700 mg), a 2N aqueous sodium hydroxide solution (20 mL) and ethanol (40 mL) was heated under reflux for 18 hours. Water was added to the reaction mixture, and the mixture was neutralized with 2N hydrochloric acid and extracted with ethyl acetate. The organic layer was washed with water, dried over anhydrous magnesium sulfate and concentrated. The residue was subjected to silica gel column chromatography to give crystals (420 mg, 58%) of 2-[2-[4-[5-methyl-2-(2-naphthyl)-4-oxazolylmethoxy]benzyloxy]-3-pyridyl]

acetic acid from a fraction eluted with acetone-hexane (2:3, v/v). Recrystallization from ethyl acetate-hexane gave colorless prism crystals. melting point: 155-156° C.

Example 131

A mixture of 4-(5-chloromethyl-2-methoxyphenoxymethyl)-5-methyl-2-phenyloxazole (400 mg), methyl 3-hydroxyphenylacetate (195 mg), potassium carbonate (320 mg) and N,N-dimethylformamide (10 mL) was stirred at 90° C. for 2 hrs. The reaction mixture was poured into water and extracted with ethyl acetate. The organic layer was washed with water, dried over anhydrous magnesium sulfate and concentrated. The residue was subjected to silica gel column chromatography to give crystals of methyl 3-[4-methoxy-3-[(2-phenyl-5-methyl-4-oxazolyl)methoxy]benzyloxy]phenylacetate from a fraction eluted with ethyl acetate-hexane (1:3, v/v). Recrystallization from ethyl acetate-hexane gave colorless prism crystals (470 mg, 85%). melting point: 88-89° C.

Example 132

A mixture of methyl 3-[4-methoxy-3-[(2-phenyl-5-methyl-4-oxazolyl)methoxy]benzyloxy]phenylacetate (420 mg), 1N sodium hydroxide (2 mL), methanol (5 mL) and tetrahydrofuran (5 mL) was stirred at room temperature for 3 hrs. The reaction mixture was poured into water, and the mixture was neutralized with 2N hydrochloric acid to give crystals of 3-[4-methoxy-3-[(2-phenyl-5-methyl-4-oxazolyl)methoxy]benzyloxy]phenylacetic acid. Recrystallization from ethyl acetate gave colorless prism crystals (350 mg, 86%). melting point: 114-115° C.

Example 133

To a mixture of 2-[4-[(5-methyl-2-phenyl-4-oxazolyl)methoxy]benzyloxy]-3-pyridinecarbaldehyde (2.00 g), triethyl phosphonoacetate (1.17 g) and N,N-dimethylformamide (15 ml) was added sodium hydride (0.19 g) at room temperature and the mixture was stirred for 3 hrs. The reaction mixture was poured into water and extracted with ethyl acetate. The organic layer was washed with saturated brine, dried over anhydrous magnesium sulfate and concentrated. The residue was subjected to silica gel column chromatography to give ethyl 3-[2-[4-[(5-methyl-2-phenyl-4-oxazolyl)methoxy]benzyloxy]-3-pyridyl]propenoate as a colorless oil (2.19 g, yield 93%) from a fraction eluted with ethyl acetate-hexane (1:4, v/v).

$^1$H-NMR (CDCl$_3$) δ: 1.32 (3H, t, J=7.0 Hz), 2.44 (3H, s), 4.25 (2H, q, J=7.0 Hz), 5.01 (2H, s), 5.44 (2H, s), 6.59 (1H, d, J=16.2 Hz), 6.93 (1H, dd, J=7.8, 5.0 Hz), 6.98-7.08 (2H, m), 7.36-7.52 (5H, m), 7.76 (1H, dd, J=7.8, 1.8 Hz), 7.84 (1H, d, J=16.2 Hz), 7.96-8.08 (2H, m), 8.18 (1H, dd, J=5.0, 1.8 Hz).

Example 134

To a mixture of ethyl 3-[2-[4-[(5-methyl-2-phenyl-4-oxazolyl)methoxy]benzyloxy]-3-pyridyl]propenoate (2.00 g), tetrahydrofuran (10 mL) and ethanol (10 mL) was added a 1N aqueous sodium hydroxide solution (7 mL) and the mixture was stirred at 70° C. for 3 hrs. The reaction mixture was concentrated, and dilute hydrochloric acid was added to acidify the residue. The precipitated solid was collected by filtration and dried with air to give crystals (1.77 g, yield 94%) of 3-[2-[4-[(5-methyl-2-phenyl-4-oxazolyl)methoxy]benzyloxy]-3-pyridyl]propenoic acid. Recrystallization from tetrahydrofuran-diisopropyl ether gave colorless prism crystals. melting point: 174-175° C.

Example 135

To a mixture of 2-[4-[[2-(2-furyl)-5-methyl-4-oxazolyl]methoxy]-3-methoxybenzyloxy]-3-pyridinecarbaldehyde (0.30 g), triethyl phosphonoacetate. (0.18 g) and N,N-dimethylformamide (15 ml) was added sodium hydride (0.04 g) at room temperature and the mixture was stirred for 15 hrs. The reaction mixture was poured into water and extracted with ethyl acetate. The organic layer was washed with saturated brine, dried over anhydrous magnesium sulfate and concentrated to give crystals (0.28 g, yield 80%) of ethyl 3-[2-[4-[[2-(2-furyl)-5-methyl-4-oxazolyl]methoxy]-3-methoxy benzyloxy]-3-pyridyl]propenoate. Recrystallization from ethyl acetate-hexane gave colorless prism crystals. melting point: 85-87° C.

Example 136

2-[2-[4-[(5-Methyl-2-phenyl-4-oxazolyl)methoxy]benzyloxy]-3-pyridyl]acetic acid (0.20 g) was added to a mixture of lithium hydroxide monohydrate (19 mg), methanol (5 mL) and tetrahydrofuran (5 mL) at room temperature, and the mixture was stirred for 30 min. The reaction mixture was concentrated, and the residue was crystallized from methanol and diethyl ether to give crystals (0.18 g, yield 90%) of lithium 2-[2-[4-[(5-methyl-2-phenyl-4-oxazolyl)methoxy]benzyloxy]-3-pyridyl]acetate. Recrystallization from methanol-diethyl ether gave colorless prism crystals. melting point: 207-209° C.

Example 137

2-[2-[4-[(5-Methyl-2-phenyl-4-oxazolyl)methoxy]benzyloxy]-3-pyridyl]acetic acid (0.30 g) was added to a mixture of a 1N aqueous sodium hydroxide solution (0.7 mL), methanol (5 mL) and tetrahydrofuran (5 mL) at room temperature, and the mixture was stirred for 1 hr. The reaction mixture was concentrated and water (5 mL) was added to the residue. Further, an aqueous solution (3 mL) of calcium chloride (78 mg) was added at room temperature. The precipitated crystals were collected by filtration, washed with water to give crystals (0.24 g, yield 77%) of calcium 2-[2-[4-[(5-methyl-2-phenyl-4-oxazolyl)methoxy]benzyloxy]-3-pyridyl]acetate dihydrate. Recrystallization from tetrahydrofuran-hexane gave colorless prism crystals. melting point: 140-145° C.

Example 138

2-[2-[4-[(5-Methyl-2-phenyl-4-oxazolyl)methoxy]benzyloxy]-3-pyridyl]acetic acid (0.20 g) was added to a mixture of a 1N aqueous potassium hydroxide solution (0.46 mL), methanol (5 mL) and tetrahydrofuran (5 mL) at 0° C., and the mixture was stirred at room temperature for 1 hr. The reaction mixture was concentrated, and the residue was washed with diethyl ether to give crystals (0.19 g, yield 86%) of potassium 2-[2-[4-[(5-methyl-2-phenyl-4-oxazolyl) methoxy]benzyloxy]-3-pyridyl]acetate. Recrystallization from methanol-diethyl ether gave colorless prism crystals. melting point: 157-159° C.

Example 139

A mixture of 2-[3-[3-[(5-methyl-2-phenyl-4-oxazolyl)methoxy]benzylthio]phenyl]acetonitrile (1.03 g), a 4N aqueous potassium hydroxide solution (30 mL), tetrahydrofuran (10 mL) and ethanol (30 mL) was stirred with heating under reflux for 14 hrs. The reaction mixture was concentrated and water was added to the residue. The mixture was acidified with 2N hydrochloric acid and extracted with ethyl acetate. The organic layer was washed with water, dried over anhydrous magnesium sulfate and concentrated. The residue was subjected to silica gel column chromatography to give crystals (0.87 g, yield 81%) of 2-[3-[3-[(5-methyl-2-phenyl-4-oxazolyl)methoxy]benzylthio]phenyl]acetic acid from a fraction eluted with ethyl acetate-methanol (50:1, v/v). Recrystallization from acetone-hexane gave colorless needle crystals. melting point: 81-82° C.

Example 140

A mixture of diethyl 2-[3-[3-[(5-methyl-2-phenyl-4-oxazolyl)methoxy]benzylthio]benzyl]malonate (0.70 g), a 4N aqueous potassium hydroxide solution (10 mL), tetrahydrofuran (20 mL) and ethanol (20 mL) was stirred at 60° C. for 1 hr. The reaction mixture was concentrated and water was added to the residue. The mixture was neutralized with 2N hydrochloric acid, and the precipitated crystals were collected by filtration. The obtained crystals were dissolved in pyridine (40 mL) and this mixture was stirred with heating under reflux for 1 hr. The reaction mixture was concentrated, 2N hydrochloric acid was added to the mixture and the mixture was extracted with ethyl acetate. The organic layer was washed with water, dried over anhydrous magnesium sulfate and concentrated to give crystals (0.44 g, yield 77%) of 3-[3-[3-[(5-methyl-2-phenyl-4-oxazolyl)methoxy]benzylthio]phenyl]propionic acid. Recrystallization from acetone-hexane gave colorless prism crystals. melting point: 120-121° C.

Example 141

A mixture of methyl [3-chloro-4-[(dimethylamino)carbonylthio]phenyl]acetate (0.80 g), a 28% solution of sodium methoxide in methanol (0.75 g) and methanol (20 mL) was stirred with heating under reflux for 2 hrs. 4-(3-Chloromethylphenoxymethyl)-5-methyl-2-phenyloxazole (0.87 g) was added to the reaction mixture at room temperature and the mixture was further stirred for 12 hrs. The reaction mixture was poured into 0.1N hydrochloric acid and the mixture was extracted with ethyl acetate. The organic layer was washed with water, dried over anhydrous magnesium sulfate and concentrated. The residue was subjected to silica gel column chromatography to give methyl 2-[3-chloro-4-[3-[(5-methyl-2-phenyl-4-oxazolyl)methoxy]benzylthio]phenyl]acetate as a colorless oil (0.48 g, yield 35%), from a fraction eluted with ethyl acetate-hexane (1:3, v/v).

$^1$H-NMR (CDCl$_3$) δ: 2.43 (3H, s), 3.55 (2H, s), 3.69 (3H, s), 4.12 (2H, s), 4.96 (2H, s), 6.88-7.08 (4H, m), 7.16-7.31 (3H, m), 7.41-7.47 (3H, m), 7.99-8.04 (2H, m).

Example 142

A mixture of methyl 2-[3-chloro-4-[3-[(5-methyl-2-phenyl-4-oxazolyl)methoxy]benzylthio]phenyl]acetate. (0.47 g), a 1N aqueous sodium hydroxide solution (3 mL), tetrahydrofuran (5 mL) and methanol (5 mL) was stirred at room temperature for 1 hr. The reaction mixture was poured into water and acidified with 1N hydrochloric acid. The precipitated solid was collected by filtration and dried with air to give crystals (0.43 g, yield 94%) of 2-[3-chloro-4-[3-[(5-methyl-2-phenyl-4-oxazolyl)methoxy]benzylthio]phenyl]acetic acid. Recrystallization from ethyl acetate-methanol gave colorless prism crystals. melting point: 150-151° C.

Example 143

Triethylamine (0.195 g) was added to a mixture of 4-(5-chloromethyl-2-methoxyphenoxymethyl)-5-methyl-2-phenyloxazole (0.30 g), 3-(4-mercaptophenyl)propionic acid (0.16 g) and N,N-dimethylformamide (10 mL) with stirring at room temperature and the mixture was further stirred for 2 hrs. The reaction mixture was poured into water and acidified with 2N hydrochloric acid. The precipitated crystals were collected by filtration and the obtained crystals were subjected to silica gel column chromatography to give crystals (0.21 g, yield 49%) of 3-[4-[3-[4-methoxy-3-(5-methyl-2-phenyl-4-oxazolyl)methoxy]benzylthio]phenyl]propionic acid from a fraction eluted with acetone-hexane (1:1, v/v). Recrystallization from acetone-diisopropyl ether gave colorless prism crystals. melting point: 181-182° C.

Example 144

Triethylamine (0.305 g) was added to a mixture of 4-(3-chloromethylphenoxymethyl)-5-methyl-2-phenyloxazole (0.43 g), 3-(4-mercaptophenyl)propionic acid (0.25 g) and N,N-dimethylformamide (10 mL) with stirring at room temperature, and the mixture was further stirred for 2 hrs. The reaction mixture was poured into water, acidified with 2N hydrochloric acid and extracted with ethyl acetate. The organic layer was washed with water, dried over anhydrous magnesium sulfate and concentrated. The residue was subjected to silica gel column chromatography to give crystals (0.37 g, yield 59%) of 3-[4-[3-[3-(5-methyl-2-phenyl-4-oxazolyl)methoxy]benzylthio]phenyl]propionic acid from a fraction eluted with acetone-hexane (1:1, v/v). Recrystallization from acetone-diisopropyl ether gave colorless prism crystals. melting point: 128-129° C.

Example 145

Sodium t-butoxide (2.86 g) was added to dimethyl sulfoxide (20 ml), and after stirring at room temperature for 50 min., tetrahydrofuran (30 ml) was added and ice-cooled. Trimethylsulfonium iodide (4.04 g) was added to the mixture, and after stirring under ice-cooling for 10 min., a solution of sodium hydroxy[2-({4-[(5-methyl-2-phenyl-4-oxazolyl)methoxy]benzyl}oxy)pyridin-3-yl]methanesulfonate (5 g) in dimethyl sulfoxide (15 ml) was dropwise added under ice-cooling and the mixture was stirred under ice-cooling for 1 hr. and at room temperature for 1 hr. The reaction solution was poured into iced water (100 ml) and extracted twice with t-butylmethyl ether (50 ml). The organic layers were combined, washed 4 times with water (50 ml) and concentrated under reduced pressure to give 2-({4-[(5-methyl-2-phenyl-4-oxazolyl)methoxy]benzyl}oxy)-3-oxiran-2-ylpyridine.

The compound was dissolved in tetrahydrofuran (37 ml) under an argon stream and after cooling to −10° C., a 1.5 M solution (7.1 ml) of diisobutylaluminum hydride in toluene was dropwise added at −5° C.--10° C. The reaction solution was stirred at the same temperature for 40 min., and a 20% Rochelle salt solution (37 ml) was dropwise added while maintaining the mixture at not higher than 5° C. The temperature of the reaction solution was elevated to 20-30° C. and t-butylmethyl ether (74 ml) was added. The organic layer was separated and washed with 20% Rochelle salt and water and dried over anhydrous sodium sulfate. The organic layer was concentrated under reduced pressure, t-Butylmethyl ether (4.5 ml) was added to the residue and the mixture was stirred at room temperature for 50 min. and n-heptane (2 ml) was added. The mixture was stirred at room temperature for 55 min., and the precipitated crystals were collected by filtration, washed with t-butylmethyl ether/n-heptane=2/1 (5 ml) ice-cooled in advance and dried under reduced pressure to give 2-[2-({4-[(5-methyl-2-phenyl-4-oxazolyl)methoxy]benzyl}oxy)pyridin-3-yl]ethanol as white crystals.

$^1$H-NMR (CDCl$_3$, δ, 300 MHz); 1.91 (1H, t, J=5.4 Hz), 2.50 (3H, s), 2.93 (2H, t, J=6.4 Hz), 3.90 (2H, m), 5.06 (2H, s), 5.41 (2H, s), 7.70 (2H, d, J=8.6 Hz), 7.32-7.53 (6H, m), 8.06-8.13 (3H, m).

Example 146

Sodium dihydrogenphosphate dihydrate (10.45 g) was dissolved in water (80 ml) and the mixture was adjusted to pH=6.70 with 6N-sodium hydroxide. Water (13 ml) was added to give a phosphate buffer.

2-[2-({4-[(5-Methyl-2-phenyl-4-oxazolyl)methoxy] benzyl}oxy)pyridin-3-yl]ethanol (10.0 g) was suspended in acetonitrile (100 ml) and the aforementioned phosphate buffer (70 ml) and 2,2,6,6-tetramethyl-1-piperidinyloxyradical (131.2 mg) was added at 25° C. To the obtained mixture were simultaneously added dropwise a solution of 5% sodium hypochlorite (355 mg) in water (5 ml) and a solution of sodium chlorite (5.43 g) in water (15 ml) at 25° C. and the mixture was stirred for 1 hr. 0.2N-Sodium hydroxide was added to adjust the reaction solution to pH 8, and a solution of sodium sulfite (7.260 g) in water (100 ml) was dropwise added. The reaction solution was stirred for 20 min. and acetonitrile was evaporated under reduced pressure. Toluene (100 ml), tetrahydrofuran (50 ml) and 2N-sodium hydroxide (12 ml) were added to the residue to partition the mixture. The organic layer was extracted with water (50 ml), and aqueous layers were combined and washed with a mixture of toluene (100 ml) and tetrahydrofuran (50 ml). 6N Hydrochloric acid was dropwise added to adjust the aqueous layer to pH 7.0, and toluene (150 ml) and tetrahydrofuran (70 ml) were added 6N Hydrochloric acid was added to adjust the mixture to pH 6.5 and the mixture was partitioned. The organic layer was washed with 5% brine, dried over anhydrous sodium sulfate and concentrated under reduced pressure. Tetrahydrofuran (20 ml) was added to the obtained crystals and the mixture was refluxed. Isopropyl ether (20 ml) was added to the obtained solution, and after stirring for 1 hr., the mixture was stirred under ice-cooling for 2 hrs. The obtained crystals were filtrated, washed with isopropyl ether (20 ml) ice-cooled in advance, and dried under reduced pressure at 40° C. to give 2-[2-[4-[(5-methyl-2-phenyl-4-oxazolyl)methoxy]benzyloxy]-3-pyridyl]acetic acid as white crystals.

$^1$H-NMR (CDCl$_3$, δ, 300 MHz); 2.40 (3H, s), 3.63 (2H, s), 4.95 (2H, s), 5.31 (2H, s), 6.84-6.87 (1H, m), 6.93 (2H, d, J=8.7 Hz), 7.32-7.50 (6H, m), 8.00-8.15 (3H, m).

Example 147

1N Sodium hydroxide-methanol solution (2.4 ml) was added to 2-[2-[4-[(5-methyl-2-phenyl-4-oxazolyl)methoxy] benzyloxy]-3-pyridyl]acetic acid (1.0 g) and the mixture was heated to 40° C. The obtained solution was allowed to cool and acetone (10 ml) was added. The mixture was stirred at room temperature for 30 min and acetone (5 ml) was further added. The mixture was stirred at room temperature for 1 hr, and under ice-cooling for 1 hr. The precipitated crystals were collected by filtration, washed with acetone (10 ml) ice-cooled in advance, and dried under reduced pressure to give sodium 2-[2-[4-[(5-methyl-2-phenyl-4-oxazolyl)methoxy]benzyloxy]-3-pyridyl]acetate as white crystals.

$^1$H-NMR (DMSO-d$_6$, δ, 300 MHz); 2.43 (3H, s), 3.20 (2H, s), 4.98 (2H, s), 5.25 (2H, s), 6.83-6.87 (1H, m), 7.01 (2H, d, J=8.6 Hz), 7.39 (2H, d, J=8.6 Hz), 7.50-7.54 (4H, m), 7.90-7.96 (3H, m).

Preparation Example 1

Production of Capsules

| | |
|---|---|
| 1) Compound of Example 4 | 30 mg |
| 2) Cellulose (fine powder) | 10 mg |
| 3) Lactose | 19 mg |
| 4) Magnesium stearate | 1 mg |
| Total | 60 mg |

1), 2), 3) and 4) are admixed and filled into a gelatin capsule.

Preparation Example 2

Production of Tablets

| | |
|---|---|
| 1) Compound of Example 4 | 30 g |
| 2) Lactose | 50 g |
| 3) Corn starch | 15 g |
| 4) Carboxymethylcellulose calcium | 44 g |
| 5) Magnesium stearate | 1 g |
| 1000 tablets total | 140 g |

The whole amounts of 1), 2) and 3) and 30 g of 4) are kneaded together with water and the mixture, after drying in vacuo, is granulated. The granular mixture is admixed with 14 g of 4) and 1 g of 5) and the resulting mixture is tableted using a tableting machine to give 1000 tablets each containing 30 mg of compound of Example 4.

INDUSTRIAL APPLICABILITY

The compound of the present invention is of low toxicity and can be used as, for example, a prophylactic or therapeutic agent of diabetes mellitus (e.g. type 1 diabetes mellitus, type 2 diabetes mellitus, gestational diabetes mellitus, etc.); a prophylactic or therapeutic agent of hyperlipidemia (e.g., hypertriglyceridemia, hypercholesterolemia, hypo-high-density lipoproteinemia, postprandial hyperlipemia etc.); an insulin sensitivity enhancing agent; a retinoid-related receptor function regulating agent; an insulin sensitizer; a prophylactic or therapeutic agent of impaired glucose tolerance (IGT); and an agent for preventing progress from impaired glucose tolerance to diabetes mellitus.

The compound of the present can be used also as, for example, a prophylactic or therapeutic agent of diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, inferior limb infection, etc.), diabetic gangrene, xerostomia, lowered sense of hearing, cerebrovascular disease, peripheral circulatory disturbance, etc.), obesity, osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disease etc.), muscular dystrophy, myocardiac infarction, angina pectoris, cerebrovascular disease (e.g., cerebral infarction, cerebral apoplexy), insulin resistant syndrome, syndrome X, hyperinsulinemia, hyperinsulinemia-induced sensory disorder, tumor (e.g., leukemia, breast cancer, prostate cancer, skin cancer, etc.), irritable intestinal syndrome, acute or chronic diarrhea, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, pancreatitis, inflammatory colonic disease, ulcerative colitis, etc.), visceral obesity syndrome, arteriosclerosis (e.g., atherosclerosis, etc.), etc.

Also, the compound of the present invention can be used for ameliorating conditions such as bellyache, nausea, vomiting, or dysphoria in epigastrium and the like, each of which is accompanied by gastrointestinal ulcer, acute or chronic gastritis, biliary dyskinesia, cholecystitis, etc., and the like.

Further, the compound of the present invention can control (enhance or inhibit) appetite and food intake, and therefore, can be used as an agent for treating, for example, leanness and cibophobia (the weight increase in administration, subjects suffering from leanness or cibophobia) or an agent for treating obesity.

According to the present invention, moreover, a production method of the compound of the present invention can be provided.

This application is based on patent application No. 2000-402648 filed in Japan, the contents of which are all hereby incorporated by reference.

What is claimed is:

1. A compound represented by the formula

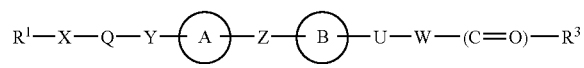

(I)

wherein
  $R^1$ is an oxazolyl group which may have 1 to 4 substituents selected from the group consisting of
  (1) halogen atom,
  (2) nitro group,
  (3) an aliphatic hydrocarbon group having 1 to 15 carbon atoms,
  (4) an alicyclic hydrocarbon group having 3 to 12 carbon atoms,
  (5) an aromatic hydrocarbon group having 6 to 14 carbon atoms,
  (6) an acyl group which may have 1 to 3 substituents selected from the group consisting of a $C_{1-6}$ alkyl group optionally substituted by 1 to 3 halogen atoms, a $C_{1-6}$ alkoxy group optionally substituted by 1 to 3 halogen atoms, a halogen atom, nitro, hydroxy, and amino,
  (7) an amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms or acyl group having 1 to 13 carbon atoms,
  (8) a hydroxy group which is optionally substituted by alkyl group having 1 to 10 carbon atoms, alkenyl group having 2 to 10 carbon atoms, aralkyl group having 7 to 13 carbon atoms, acyl group having 1 to 13 carbon atoms or aryl group having 6 to 14 carbon atoms, each of which group may have 1 or 2 substituents selected from the group consisting of a halogen atom and an alkoxy group having 1 to 3 carbon atoms, and
  (9) a thiol group which is optionally substituted by alkyl group having 1 to 10 carbon atoms, cycloalkyl group having 3 to 10 carbon atoms, aralkyl group having 7 to 13 carbon atoms, acyl group having 2 to 13 carbon atoms or aryl group having 6 to 14 carbon atoms, wherein the above (3) may have 1 to 3 substituents selected from the group consisting of
1) a cycloalkyl group having 3 to 10 carbon atoms,
2) an aryl group having 6 to 14 carbon atoms,
3) an aralkyl group having 7 to 9 carbon atoms,
4) an amino group,
5) an amino group mono- or di-substituted by alkyl group having 1 to 4 carbon atoms or acyl group having 2 to 8 carbon atoms,
6) an amidino group,
7) an acyl group having 2 to 8 carbon atoms,
8) a carbamoyl group,
9) a carbamoyl group mono- or di-substituted by alkyl group having 1 to 4 carbon atoms,
10) a sulfamoyl group,
11) a sulfamoyl group mono- or di-substituted by alkyl group having 1 to 4 carbon atoms,
12) a carboxyl group,
13) an alkoxycarbonyl group having 2 to 8 carbon atoms,
14) a hydroxy group,
15) a $C_{1-6}$ alkoxy group optionally substituted by 1 to 3 halogen atoms,
16) a $C_{2-5}$ alkenyloxy group optionally substituted by 1 to 3 halogen atoms,
17) a cycloalkyloxy group having 3 to 7 carbon atoms,
18) an aralkyloxy group having 7 to 9 carbon atoms,
19) an aryloxy group having 6 to 14 carbon atoms,
20) a thiol group,
21) a $C_{1-6}$ alkylthio group optionally substituted by 1 to 3 carbon atoms,
22) an aralkylthio group having 7 to 9 carbon atoms,
23) an arylthio group having 6 to 14 carbon atoms,
24) a sulfo group,
25) a cyano group,
26) an azide group,
27) a nitro group,
28) a nitroso group, and
29) a halogen atom,
    wherein the above (4) and (5) may have 1 to 3 substituents selected from the group consisting of
1) a $C_{1-6}$ alkyl group optionally substituted by 1 to 3 halogen atoms,
2) a $C_{2-6}$ alkenyl group optionally substituted by 1 to 3 halogen atoms,
3) a cycloalkyl group having 3 to 10 carbon atoms,
4) an aromatic hydrocarbon group having 6 to 14 carbon atoms,
5) an aralkyl group having 7 to 9 carbon atoms,
6) an amino group,
(7) an amino group mono- or di-substituted by alkyl group having 1 to 4 carbon atoms or acyl group having 2 to 8 carbon atoms,
8) an amidino group,
9) an acyl group having 2 to 8 carbon atoms,
10) a carbamoyl group,
11) a carbamoyl group mono- or di-substituted by alkyl group having 1 to 4 carbon atoms,
12) a sulfamoyl group,
13) a sulfamoyl group mono- or di-substituted by alkyl group having 1 to 4 carbon atoms,
14) a carboxyl group,
15) an alkoxycarbonyl group having 2 to 8 carbon atoms,
16) a hydroxy group,
17) a $C_{1-6}$ alkoxy group optionally substituted by 1 to 3 halogen atoms,
18) a $C_{2-5}$ alkenyloxy group optionally substituted by 1 to 3 halogen atoms,
19) a cycloalkyloxy group having 3 to 7 carbon atoms,
20) an aralkyloxy group having 7 to 9 carbon atoms,
21) an aryloxy group having 6 to 14 carbon atoms,
22) a thiol group,
23) a $C_{1-6}$ alkylthio group optionally substituted by 1 to 3 halogen atoms,
24) an aralkylthio group having 7 to 9 carbon atoms,
25) an arylthio group having 6 to 14 carbon atoms,
26) a sulfo group,
27) a cyano group,
28) an azide group,
29) a nitro group,
30) a nitroso group, and
31) a halogen atom;
X is a bond;
Q is an alkylene group having 1 to 20 carbon atoms;
Y is an oxygen atom;
ring A is a benzene ring optionally further having 1 to 3 substituents selected from the group consisting of
(1) an aliphatic hydrocarbon group having 1 to 15 carbon atoms which may have 1 to 3 substituents selected from the group consisting of
   1) a cycloalkyl group having 3 to 10 carbon atoms,
   2) an aryl group having 6 to 14 carbon atoms,
   3) an aralkyl group having 7 to 9 carbon atoms,
   4) an amino group,
   5) an amino group mono- or di-substituted by alkyl group having 1 to 4 carbon atoms or acyl group having 2 to 8 carbon atoms,
   6) an amidino group,
   7) an acyl group having 2 to 8 carbon atoms,
   8) a carbamoyl group,
   9) a carbamoyl group mono- or di-substituted by alkyl group having 1 to 4 carbon atoms,
   10) a sulfamoyl group,
   11) a sulfamoyl group mono- or di-substituted by alkyl group having 1 to 4 carbon atoms,
   12) a carboxyl group,
   13) an alkoxycarbonyl group having 2 to 8 carbon atoms,
   14) a hydroxy group,
   15) a $C_{1-6}$ alkoxy group optionally substituted by 1 to 3 halogen atoms,
   16) a $C_{2-5}$ alkenyloxy group optionally substituted by 1 to 3 halogen atoms,
   17) a cycloalkyloxy group having 3 to 7 carbon atoms,
   18) an aralkyloxy group having 7 to 9 carbon atoms,
   19) an aryloxy group having 6 to 14 carbon atoms,
   20) a thiol group,
   21) a $C_{1-6}$ alkylthio group optionally substituted by 1 to 3 carbon atoms,
   22) an aralkylthio group having 7 to 9 carbon atoms,
   23) an arylthio group having 6 to 14 carbon atoms,
   24) a sulfo group,
   25) a cyano group,
   26) an azide group,
   27) a nitro group,
   28) a nitroso group, and
   29) a halogen atom,
(2) a hydroxy group which is optionally substituted by alkyl group having 1 to 10 carbon atoms, alkenyl group having 2 to 10 carbon atoms, aralkyl group having 7 to 13 carbon atoms, acyl group having 1 to 13 carbon atoms or aryl group having 6 to 14 carbon atoms, each of which group may have 1 to 2 substituents selected from the group consisting of a halogen atom and an alkoxy group having 1 to 3 carbon atoms,
(3) halogen atom,
(4) an acyl group which may have 1 to 3 substituents selected from the group consisting of a $C_{1-6}$ alkyl group optionally substituted by 1 to 3 halogen atoms, a $C_{1-6}$ alkoxy group optionally substituted by 1 to 3 halogen atoms, a halogen atom, nitro, hydroxy, and amino,
(5) nitro group, and
(6) an amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms or acyl group having 1 to 13 carbon atoms;

Z is —$(CH_2)_n$—O— (n is an integer of 1 to 8);

ring B is a pyridine ring which optionally further has 1 to 3 substituents selected from the group consisting of
(1) an aliphatic hydrocarbon group having 1 to 15 carbon atoms which may have 1 to 3 substituents selected from the group consisting of
  1) a cycloalkyl group having 3 to 10 carbon atoms,
  2) an aryl group having 6 to 14 carbon atoms,
  3) an aralkyl group having 7 to 9 carbon atoms,
  4) an amino group,
  5) an amino group mono- or di-substituted by alkyl group having 1 to 4 carbon atoms or acyl group having 2 to 8 carbon atoms,
  6) an amidino group,
  7) an acyl group having 2 to 8 carbon atoms,
  8) a carbamoyl group,
  9) a carbamoyl group mono- or di-substituted by alkyl group having 1 to 4 carbon atoms,
  10) a sulfamoyl group,
  11) a sulfamoyl group mono- or di-substituted by alkyl group having 1 to 4 carbon atoms,
  12) a carboxyl group,
  13) an alkoxycarbonyl group having 2 to 8 carbon atoms,
  14) a hydroxy group,
  15) a $C_{1-6}$ alkoxy group optionally substituted by 1 to 3 halogen atoms,
  16) a $C_{2-5}$ alkenyloxy group optionally substituted by 1 to 3 halogen atoms,
  17) a cycloalkyloxy group having 3 to 7 carbon atoms,
  18) an aralkyloxy group having 7 to 9 carbon atoms,
  19) an aryloxy group having 6 to 14 carbon atoms,
  20) a thiol group,
  21) a $C_{1-6}$ alkylthio group optionally substituted by 1 to 3 carbon atoms,
  22) an aralkylthio group having 7 to 9 carbon atoms,
  23) an arylthio group having 6 to 14 carbon atoms,
  24) a sulfo group,
  25) a cyano group,
  26) an azide group,
  27) a nitro group,
  28) a nitroso group, and
  29) a halogen atom,
(2) an aromatic hydrocarbon group having 6 to 14 carbon atoms which may have 1 to 3 substituents selected from the group consisting of
  1) a $C_{1-6}$ alkyl group optionally substituted by 1 to 3 halogen atoms,
  2) a $C_{2-6}$ alkenyl group optionally substituted by 1 to 3 halogen atoms,
  3) a cycloalkyl group having 3 to 10 carbon atoms,
  4) an aromatic hydrocarbon group having 6 to 14 carbon atoms,
  5) an aralkyl group having 7 to 9 carbon atoms,
  6) an amino group,
  7) an amino group mono- or di-substituted by alkyl group having 1 to 4 carbon atoms or acyl group having 2 to 8 carbon atoms,
  8) an amidino group,
  9) an acyl group having 2 to 8 carbon atoms,
  10) a carbamoyl group,
  11) a carbamoyl group mono- or di-substituted by alkyl group having 1 to 4 carbon atoms,
  12) a sulfamoyl group,
  13) a sulfamoyl group mono- or di-substituted by alkyl group having 1 to 4 carbon atoms,
  14) a carboxyl group,
  15) an alkoxycarbonyl group having 2 to 8 carbon atoms,
  16) a hydroxy group,
  17) a $C_{1-6}$ alkoxy group optionally substituted by 1 to 3 halogen atoms,
  18) a $C_{2-5}$ alkenyloxy group optionally substituted by 1 to 3 halogen atoms,
  19) a cycloalkyloxy group having 3 to 7 carbon atoms,
  20) an aralkyloxy group having 7 to 9 carbon atoms,
  21) an aryloxy group having 6 to 14 carbon atoms,
  22) a thiol group,
  23) a $C_{1-6}$ alkylthio group optionally substituted by 1 to 3 halogen atoms,
  24) an aralkylthio group having 7 to 9 carbon atoms,
  25) an arylthio group having 6 to 14 carbon atoms,
  26) a sulfo group,
  27) a cyano group,
  28) an azide group,
  29) a nitro group,
  30) a nitroso group, and
  31) a halogen atom,
(3) a hydroxy group which is optionally substituted by alkyl group having 1 to 10 carbon atoms, alkenyl group having 2 to 10 carbon atoms, aralkyl group having 7 to 13 carbon atoms, acyl group having 1 to 13 carbon atoms or aryl group having 6 to 14 carbon atoms, each of which group may have 1 to 2 substituents selected from the group consisting of a halogen atom and an alkoxy group having 1 to 3 carbon atoms,
(4) halogen atom,
(5) an acyl group which may have 1 to 3 substituents selected from the group consisting of a $C_{1-6}$ alkyl group optionally substituted by 1 to 3 halogen atoms, a $C_{1-6}$ alkoxy group optionally substituted by 1 to 3 halogen atoms, a halogen atom, nitro, hydroxy, and amino,
(6) nitro group, and
(7) an amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms or acyl group having 1 to 13 carbon atoms;

U is a bond;

W is an alkylene group having 1 to 20 carbon atoms; and $R^3$ is —$OR^8$ ($R^8$ is a hydrogen atom, alkyl group having 1 to 4 carbon atoms, or $C_{6-10}$ aryl group optionally having 1 to 3 substituents selected from alkyl group having 1 to 4 carbon atoms and halogen atom); or a salt thereof.

2. The compound of claim 1, wherein Q is $C_{1-6}$ alkylene.

3. The compound of claim 1, wherein n is an integer of 1 to 3.

4. The compound of claim 1, wherein W is a $C_{1-6}$ alkylene.

5. The compound of claim 1, wherein $R^1$ is an oxazolyl group which optionally has 1 to 3 substituents selected from
1) a $C_{1-10}$ alkyl group optionally having 1 to 3 substituents selected from a $C_{1-6}$ alkoxy group optionally substituted by 1 to 3 halogen atoms, a halogen atom, a nitro group, a hydroxy group and an amino group;
2) a $C_{3-10}$ cycloalkyl group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group; and
3) a $C_{6-14}$ aromatic hydrocarbon group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group;

Q is a $C_{1-6}$ alkylene;

ring A is a benzene ring which optionally further has 1 to 3 substituents selected from an alkyl group having 1 to 4 carbon atoms, a hydroxy group, an alkoxy group having 1 to 4 carbon atoms, an aralkyloxy group having 7 to 10 carbon atoms and a halogen atom;

Z is —(CH$_2$)$_n$—O— wherein n is an integer of 1 to 3;

ring B is a pyridine ring which optionally further has 1 to 3 substituents selected from an alkyl group having 1 to 4 carbon atoms, an aryl group having 6 to 14 carbon atoms, a hydroxy group, an alkoxy group having 1 to 4 carbon atoms, an aralkyloxy group having 7 to 10 carbon atoms and a halogen atom;

W is a $C_{1-6}$ alkylene; and $R^3$ is —OR$^8$ wherein $R^8$ is a hydrogen atom or an alkyl group having 1 to 4 carbon atoms.

6. The compound of claim 1, which is 2-[2-[4-[(5-methyl-2-phenyl-4-oxazolyl)methoxy]benzyloxy]-3-pyridyl]acetic acid or a salt thereof.

7. A pharmaceutical composition comprising the compound of claim 1 or a salt thereof and a pharmacologically acceptable carrier.

8. A method for treating diabetes mellitus in a mammal, which comprises administering an effective amount of the compound of claim 1 or a salt thereof to said mammal.

9. A production method of a compound represented by the formula

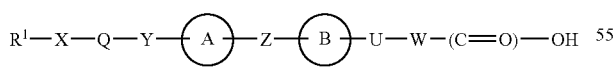

(I-6)

wherein
$R^1$ is an oxazolyl group which may have 1 to 4 substituents selected from the group consisting of
(1) halogen atom,
(2) nitro group,
(3) an aliphatic hydrocarbon group having 1 to 15 carbon atoms,
(4) an alicyclic hydrocarbon group having 3 to 12 carbon atoms,
(5) an aromatic hydrocarbon group having 6 to 14 carbon atoms,
(6) an acyl group which may have 1 to 3 substituents selected from the group consisting of a $C_{1-6}$ alkyl group optionally substituted by 1 to 3 halogen atoms, a $C_{1-6}$ alkoxy group optionally substituted by 1 to 3 halogen atoms, a halogen atom, nitro, hydroxy, and amino,
(7) an amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms or acyl group having 1 to 13 carbon atoms,
(8) a hydroxy group which is optionally substituted by alkyl group having 1 to 10 carbon atoms, alkenyl group having 2 to 10 carbon atoms, aralkyl group having 7 to 13 carbon atoms, acyl group having 1 to 13 carbon atoms or aryl group having 6 to 14 carbon atoms, each of which group may have 1 or 2 substituents selected from the group consisting of a halogen atom and an alkoxy group having 1 to 3 carbon atoms, and
(9) a thiol group which is optionally substituted by alkyl group having 1 to 10 carbon atoms, cycloalkyl group having 3 to 10 carbon atoms, aralkyl group having 7 to 13 carbon atoms, acyl group having 2 to 13 carbon atoms or aryl group having 6 to 14 carbon atoms,
wherein the above (3) may have 1 to 3 substituents selected from the group consisting of
1) a cycloalkyl group having 3 to 10 carbon atoms,
2) an aryl group having 6 to 14 carbon atoms,
3) an aralkyl group having 7 to 9 carbon atoms,
4) an amino group,
5) an amino group mono- or di-substituted by alkyl group having 1 to 4 carbon atoms or acyl group having 2 to 8 carbon atoms,
6) an amidino group,
7) an acyl group having 2 to 8 carbon atoms,
8) a carbamoyl group,
9) a carbamoyl group mono- or di-substituted by alkyl group having 1 to 4 carbon atoms,
10) a sulfamoyl group,
11) a sulfamoyl group mono- or di-substituted by alkyl group having 1 to 4 carbon atoms,
12) a carboxyl group,
13) an alkoxycarbonyl group having 2 to 8 carbon atoms,
14) a hydroxy group,
15) a $C_{1-6}$ alkoxy group optionally substituted by 1 to 3 halogen atoms,
16) a $C_{2-5}$ alkenyloxy group optionally substituted by 1 to 3 halogen atoms,
17) a cycloalkyloxy group having 3 to 7 carbon atoms,
18) an aralkyloxy group having 7 to 9 carbon atoms,
19) an aryloxy group having 6 to 14 carbon atoms,
20) a thiol group,
21) a $C_{1-6}$ alkylthio group optionally substituted by 1 to 3 carbon atoms,
22) an aralkylthio group having 7 to 9 carbon atoms,
23) an arylthio group having 6 to 14 carbon atoms,
24) a sulfo group,
25) a cyano group,
26) an azide group,
27) a nitro group,
28) a nitroso group, and
29) a halogen atom, wherein the above (4) and (5) may have 1 to 3 substituents selected from the group consisting of
1) a $C_{1-6}$ alkyl group optionally substituted by 1 to 3 halogen atoms,
2) a $C_{2-6}$ alkenyl group optionally substituted by 1 to 3 halogen atoms,
3) a cycloalkyl group having 3 to 10 carbon atoms,
4) an aromatic hydrocarbon group having 6 to 14 carbon atoms,
5) an aralkyl group having 7 to 9 carbon atoms,
6) an amino group,
(7) an amino group mono- or di-substituted by alkyl group having 1 to 4 carbon atoms or acyl group having 2 to 8 carbon atoms,
8) an amidino group,
9) an acyl group having 2 to 8 carbon atoms,
10) a carbamoyl group,
11) a carbamoyl group mono- or di-substituted by alkyl group having 1 to 4 carbon atoms,
12) a sulfamoyl group,
13) a sulfamoyl group mono- or di-substituted by alkyl group having 1 to 4 carbon atoms,
14) a carboxyl group,
15) an alkoxycarbonyl group having 2 to 8 carbon atoms,
16) a hydroxy group,
17) a $C_{1-6}$ alkoxy group optionally substituted by 1 to 3 halogen atoms,
18) a $C_{2-5}$ alkenyloxy group optionally substituted by 1 to 3 halogen atoms,
19) a cycloalkyloxy group having 3 to 7 carbon atoms,
20) an aralkyloxy group having 7 to 9 carbon atoms,
21) an aryloxy group having 6 to 14 carbon atoms,
22) a thiol group,
23) a $C_{1-6}$ alkylthio group optionally substituted by 1 to 3 halogen atoms,
24) an aralkylthio group having 7 to 9 carbon atoms,
25) an arylthio group having 6 to 14 carbon atoms,
26) a sulfo group,
27) a cyano group,
28) an azide group,
29) a nitro group,
30) a nitroso group, and
31) a halogen atom;
X is a bond;
Q is an alkylene group having 1 to 20 carbon atoms;
Y is an oxygen atom;
ring A is a benzene ring optionally further having 1 to 3 substituents selected from the group consisting of
(1) an aliphatic hydrocarbon group having 1 to 15 carbon atoms which may have 1 to 3 substituents selected from the group consisting of
  1) a cycloalkyl group having 3 to 10 carbon atoms,
  2) an aryl group having 6 to 14 carbon atoms,
  3) an aralkyl group having 7 to 9 carbon atoms,
  4) an amino group,
  5) an amino group mono- or di-substituted by alkyl group having 1 to 4 carbon atoms or acyl group having 2 to 8 carbon atoms,
  6) an amidino group,
  7) an acyl group having 2 to 8 carbon atoms,
  8) a carbamoyl group,
  9) a carbamoyl group mono- or di-substituted by alkyl group having 1 to 4 carbon atoms,
  10) a sulfamoyl group,
  11) a sulfamoyl group mono- or di-substituted by alkyl group having 1 to 4 carbon atoms,
  12) a carboxyl group,
  13) an alkoxycarbonyl group having 2 to 8 carbon atoms,
  14) a hydroxy group,
  15) a $C_{1-6}$ alkoxy group optionally substituted by 1 to 3 halogen atoms,
  16) a $C_{2-5}$ alkenyloxy group optionally substituted by 1 to 3 halogen atoms,
  17) a cycloalkyloxy group having 3 to 7 carbon atoms,
  18) an aralkyloxy group having 7 to 9 carbon atoms,
  19) an aryloxy group having 6 to 14 carbon atoms,
  20) a thiol group,
  21) a $C_{1-6}$ alkylthio group optionally substituted by 1 to 3 carbon atoms,
  22) an aralkylthio group having 7 to 9 carbon atoms,
  23) an arylthio group having 6 to 14 carbon atoms,
  24) a sulfo group,
  25) a cyano group,
  26) an azide group,
  27) a nitro group,
  28) a nitroso group, and
  29) a halogen atom,
(2) a hydroxy group which is optionally substituted by alkyl group having 1 to 10 carbon atoms, alkenyl group having 2 to 10 carbon atoms, aralkyl group having 7 to 13 carbon atoms, acyl group having 1 to 13 carbon atoms or aryl group having 6 to 14 carbon atoms, each of which group may have 1 to 2 substituents selected from the group consisting of a halogen atom and an alkoxy group having 1 to 3 carbon atoms,
(3) halogen atom,
(4) an acyl group which may have 1 to 3 substituents selected from the group consisting of a $C_{1-6}$ alkyl group optionally substituted by 1 to 3 halogen atoms, a $C_{1-6}$ alkoxy group optionally substituted by 1 to 3 halogen atoms, a halogen atom, nitro, hydroxy, and amino,
(5) nitro group, and
(6) an amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms or acyl group having 1 to 13 carbon atoms;
Z is —$(CH_2)_n$—O— (n is an integer of 1 to 8);
ring B is a pyridine ring which optionally further has 1 to 3 substituents selected from the group consisting of
(1) an aliphatic hydrocarbon group having 1 to 15 carbon atoms which may have 1 to 3 substituents selected from the group consisting of
  1) a cycloalkyl group having 3 to 10 carbon atoms,
  2) an aryl group having 6 to 14 carbon atoms,
  3) an aralkyl group having 7 to 9 carbon atoms,
  4) an amino group,
  5) an amino group mono- or di-substituted by alkyl group having 1 to 4 carbon atoms or acyl group having 2 to 8 carbon atoms,
  6) an amidino group,
  7) an acyl group having 2 to 8 carbon atoms,
  8) a carbamoyl group,
  9) a carbamoyl group mono- or di-substituted by alkyl group having 1 to 4 carbon atoms,
  10) a sulfamoyl group,
  11) a sulfamoyl group mono- or di-substituted by alkyl group having 1 to 4 carbon atoms,
  12) a carboxyl group,
  13) an alkoxycarbonyl group having 2 to 8 carbon atoms,
  14) a hydroxy group, 15) a $C_{1-6}$ alkoxy group optionally substituted by 1 to 3 halogen atoms,
16) a $C_{2-5}$ alkenyloxy group optionally substituted by 1 to 3 halogen atoms,
17) a cycloalkyloxy group having 3 to 7 carbon atoms,
18) an aralkyloxy group having 7 to 9 carbon atoms,
19) an aryloxy group having 6 to 14 carbon atoms,
20) a thiol group,
21) a $C_{1-6}$ alkylthio group optionally substituted by 1 to 3 carbon atoms,
22) an aralkylthio group having 7 to 9 carbon atoms,
23) an arylthio group having 6 to 14 carbon atoms,
24) a sulfo group,
25) a cyano group,
26) an azide group,
27) a nitro group,
28) a nitroso group, and
29) a halogen atom, (2) an aromatic hydrocarbon group having 6 to 14 carbon atoms which may have 1 to 3 substituents selected from the group consisting of
1) a $C_{1-6}$ alkyl group optionally substituted by 1 to 3 halogen atoms,
2) a $C_{2-6}$ alkenyl group optionally substituted by 1 to 3 halogen atoms,
3) a cycloalkyl group having 3 to 10 carbon atoms,
4) an aromatic hydrocarbon group having 6 to 14 carbon atoms,
5) an aralkyl group having 7 to 9 carbon atoms,
6) an amino group,
(7) an amino group mono- or di-substituted by alkyl group having 1 to 4 carbon atoms or acyl group having 2 to 8 carbon atoms,
8) an amidino group,
9) an acyl group having 2 to 8 carbon atoms,
10) a carbamoyl group,
11) a carbamoyl group mono- or di-substituted by alkyl group having 1 to 4 carbon atoms,
12) a sulfamoyl group,
13) a sulfamoyl group mono- or di-substituted by alkyl group having 1 to 4 carbon atoms,
14) a carboxyl group,
15) an alkoxycarbonyl group having 2 to 8 carbon atoms,
16) a hydroxy group,
17) a $C_{1-6}$ alkoxy group optionally substituted by 1 to 3 halogen atoms,
18) a $C_{2-5}$ alkenyloxy group optionally substituted by 1 to 3 halogen atoms,
19) a cycloalkyloxy group having 3 to 7 carbon atoms,
20) an aralkyloxy group having 7 to 9 carbon atoms,
21) an aryloxy group having 6 to 14 carbon atoms,
22) a thiol group,
23) a $C_{1-6}$ alkylthio group optionally substituted by 1 to 3 halogen atoms,
24) an aralkylthio group having 7 to 9 carbon atoms,
25) an arylthio group having 6 to 14 carbon atoms,
26) a sulfo group,
27) a cyano group,
28) an azide group,
29) a nitro group,
30) a nitroso group, and
31) a halogen atom, (3) a hydroxy group which is optionally substituted by alkyl group having 1 to 10 carbon atoms, alkenyl group having 2 to 10 carbon atoms, aralkyl group having 7 to 13 carbon atoms, acyl group having 1 to 13 carbon atoms or aryl group having 6 to 14 carbon atoms, each of which group may have 1 to 2 substituents selected from the group consisting of a halogen atom and an alkoxy group having 1 to 3 carbon atoms, (4) halogen atom, (5) an acyl group which may have 1 to 3 substituents selected from the group consisting of a $C_{1-6}$ alkyl group optionally substituted by 1 to 3 halogen atoms, a $C_{1-6}$ alkoxy group optionally substituted by 1 to 3 halogen atoms, a halogen atom, nitro, hydroxy, and amino, (6) nitro group, and (7) an amino group optionally mono- or di-substituted by alkyl group having 1 to 10 carbon atoms, alkenyl group having 2 to 10 carbon atoms, cycloalkyl group having 3 to 10 carbon atoms, cycloalkenyl group having 3 to 10 carbon atoms, aryl group having 6 to 14 carbon atoms or acyl group having 1 to 13 carbon atoms;

U is a bond; and

W is an alkylene group having 1 to 20 carbon atoms;

or a salt thereof, which comprises subjecting a compound represented by the formula

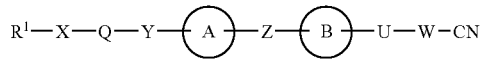

(XII)

wherein each symbol is as defined above, or a salt thereof, to a hydrolysis reaction in the presence of an acid or a base in an aqueous solvent.

* * * * *